US008362220B2

(12) United States Patent
Girolami et al.

(10) Patent No.: US 8,362,220 B2
(45) Date of Patent: Jan. 29, 2013

(54) METAL COMPLEX COMPOSITIONS AND METHODS FOR MAKING METAL-CONTAINING FILMS

(75) Inventors: Gregory S. Girolami, Urbana, IL (US); Do Young Kim, Albany, CA (US); John R. Abelson, Urbana, IL (US); Navneet Kumar, Urbana, IL (US); Yu Yang, Urbana, IL (US); Scott Daly, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 377 days.

(21) Appl. No.: 12/595,384

(22) PCT Filed: Apr. 9, 2008

(86) PCT No.: PCT/US2008/059728
§ 371 (c)(1),
(2), (4) Date: Mar. 11, 2010

(87) PCT Pub. No.: WO2008/127935
PCT Pub. Date: Oct. 23, 2008

(65) Prior Publication Data
US 2010/0168404 A1 Jul. 1, 2010

Related U.S. Application Data

(60) Provisional application No. 60/911,619, filed on Apr. 13, 2007, provisional application No. 60/914,948, filed on Apr. 30, 2007.

(51) Int. Cl.
*C07F 5/02* (2006.01)
*C08F 10/00* (2006.01)

(52) U.S. Cl. .......... 534/15; 526/133; 526/160; 526/161; 526/348

(58) Field of Classification Search .................. 534/15; 526/126, 133, 160, 161, 348
See application file for complete search history.

(56) References Cited

U.S. PATENT DOCUMENTS

| 3,355,261 | A | 11/1967 | Miller |
| 5,464,656 | A | 11/1995 | Verkade |
| 6,420,507 | B1 | 7/2002 | Kale et al. |
| 6,445,023 | B1 | 9/2002 | Vaartstra et al. |
| 6,797,341 | B2 | 9/2004 | Zeng et al. |
| 6,872,639 | B2 | 3/2005 | DeBoer et al. |
| 7,592,254 | B2 | 9/2009 | Abelson et al. |

FOREIGN PATENT DOCUMENTS

| WO | WO 03/082482 | 10/2003 |
| WO | WO 2005/014669 | 2/2005 |
| WO | WO 2008/127935 | 1/2008 |

OTHER PUBLICATIONS

Heinrich Noth et al. Metal Tetrahydridoborates and Tetrahydroborato Metallates, 24[+] Solvates of sodium Bis (borane) dimethylamide, Eur. J. Inorg. Chem. 1999, 1373-1379.*
Abelson et al. (Oct. 2004) "Superconductor Integrated Circuit Fabrication Technology," *Proc. IEEE* 92(10):1517-1533.
Agrestini et al. (2004) "Substitution of Sc for Mg in $MgB_2$: Effect on Transition Temperature and Kohn Anomaly," *Phys. Rev. B* 70:134514.
Aouadi et al. (2004) "Titanium Boron Nitride Films Grown by Ion Beam Assisted Deposition: Chemical and Optical Characterization," *Surf. Coat. Technol.* 183:369-377.
Au, R. J. P. (2007) "Highly Ordered Macroporous Gold Film Formed by CVD Using Monodisperse Polystyrene Spheres as Templates," *Chem. Vap. Deposition* 13:20-22.
Auday et al. (Oct. 15, 2000) "Secondary Emission of Dielectrics Used in Plasma Display Panels," *J. Appl Phys.* 88(8):4871-4874.
Babcock et al. (2000) "Polydentate Amines as CVD Precursor Ancillary Ligands. Epitaxial MgO Thin-Film Growth Using a Highly Volatile, Thermally and Air-Stable Magnesium Precursor," *Chem. Vapor Dep.* 6(4):180-183.
Babcock et al. (2001) "Transparent Conducting CdO Thin Film Growth Using a Highly Volatile, Thermally and Air-Stable Cadmium Precursor," *Chem. Vap. Dep.* 7(6):239-242.
Baker et al. (May/Jun. 1995) "Auger Electron Spectroscopy/X-Ray Photoelectron Spectroscopy Study of To-B Thin Films," *J. Vac. Sci. Technol. A* 13(3):1633-1638.
Bauer et al. (Jun. 1999) "YBCO Films on Metal Substrates with Biaxially Aligned MgO Buffer Layers," *IEEE Trans. App. Superconduc.* 9(2):1502-1505.
Bazhin et al. (2006) "Magnetron Sputtering of a Vanadium-Diboride Target in $Ar+N_2$ Gaseous Mixtures," *Vacuum* 80:918-922.
Becker et al. (1965) "Reaction of Grignard Compounds with Diborane : Characterization of Chloromagnesium Borohydride," *Inorg. Chem.* 4:1816-1818.
Beckett et al. (2003) "Synthesis and Characterization of a Series of Group 7 Metal 2,2,2,2-dicarbonylbis(triorganophosphine)-*arachno*-2-metallatetraboranes, $[M(CO)_2L_2(B_3H_8)]$ (M = Re, Mn); Crystal and Molecular Structrues of $[Re(CO)_2(dppf)(B_3H_8)]$ and $[Mn(CO)_2(dppe)(B_3H_8)]$," *Polyhedron* 22:1627-1632.
Beckloff et al. (1999) "Process-Structure-Reflectance Correlations for $TiB_2$ Films Prepared by Chemical Vapor Deposition," *J. Am. Ceramic Soc.* 82(3):503-512.
Blom et al. (Mar./Apr. 1989) "Reactively Sputtered Titanium Boride Thin Films," *J. Vac. Sci. Technol.* 7(2):162-165.
Boeuf, J.P. (Feb. 26, 2003) "Plasma Display Panels: Physics, Recent Developments and Key Issues," *J. of Phys. D App. Phys.* 36:R53-R79.
Boo et al. (1999) "Growth of Magnesium Oxide Thin Films Using Single Molecular Precursors by Metal-Organic Chemical Vapor Deposition," *Thin Solid Films* 341:63-37.

(Continued)

*Primary Examiner* — Michael G Hartley
*Assistant Examiner* — Jagadishwar Samala
(74) *Attorney, Agent, or Firm* — Greenlee Sullivan P.C.

(57) ABSTRACT

The present invention provides compositions of matter useful as deposition agents for making structures, including thin film structures and hard coatings, on substrates and features of substrates. In an embodiment, for example, the present invention provides metal complexes having one or more diboranamide or diboranaphosphide ligands that are useful as chemical vapor deposition (CVD) and/or atomic layer deposition (ALD) precursors for making thin film structures and coatings. Metal complex CVD precursors are provided that possess volitilities sufficiently high so as to provide dense, smooth and homogenous thin films and coatings.

9 Claims, 43 Drawing Sheets

OTHER PUBLICATIONS

Boo et al. (Mar. 1996) "Preparation of MgO Films on GaAs by Metalorganic Chemical Vapor Deposition," *Mater. Lett.* 26:233-236.

Bremer et al. (2005) "Metal Tetrahydroborates and Tetrahydroborato Metalates. 30 [1] Solvates of Alcoholato-, Phenolato-, and Bis(trimeethylsilyl)amido-Magnesium Tetrahydroborates $XMgBH_4(L_n)$," *Z. Anorg. Allg. Chem.* 631:683-697.

Bremer et al. (2003) "The Structure of Some Amine Solvates of Magnesium Bis(tetrahydroborate) and DFT Calculations on Solvates of Lithium Tetrahydroborate," *Eur. J. Inorg. Chem.* :111-119.

Brock et al. (Dec. 2000) "Superconductor ICs: The 100-Ghz Second Generation," *IEEE Spectrum* 37:40-46.

Brumaghim et al. (Web Release Apr. 15, 1999) "Synthesis of Hydride and Alkyl Compounds Containing the Cp*Os(NO) Fragment. Crystal Structure of [Cp*Os(μ-NO)]$_2$," *Organometallics* 18:2139-2144.

Bunshah, R.F. (1977) "Structure and Properties of Refractory Compounds Deposited by Direct Evaporation," *Thin Solid Films* 40:169-182.

Burg et al. (Oct. 1965) "Lewis Acid-Based Reactions Among Dimethylaminoboron Hydrides," *Inorg. Chem.* 4(10):1467-1472.

Calabrese et al. (1976) "The Low Temeprature Crystal and Molecular Structure of Beryllium Bis(octahydrotriborate), $Be(B_3H_8)_2$," *J. Am. Chem. Soc.* 98:5489-5492.

Chen et al. (Jun. 1999) "Rapid Single Flux Quantum T-Flip Flop Operating up to 770 GHz," *Appl. Supercon. IEEE Trans.* 9(2):3212-3215.

Chi et al. (1997) "51. Lewis Base Adducts of 1,1,1,5,5,5-Hexafluoro-2,4-Pentandionato-Copper(I) Comounds," *Inorg. Synth.* 31:289-294.

Choi et al. (Aug. 18, 1997) "Epitaxial Growth of $Y_2O_3$ Films on Si9100) Without an Interfacial Oxide Layer," *Appl. Phys. Lett.* 71(7):903-905.

Claeson et al. (1999) "Supersonducting Films and Devices," *Curr. Opin. Solid St. M.* 4:45-52.

Clark et al. (2006) "Homohenous, Titanocene-Catalyzed Dehydrocoupling of Amine-Borane Adducts," *J. Am. Chem. Soc.* 128:9582-9583.

Cramer et al. (1991) "The Crystal and Molecular Structure of Pentamethylcyclopentadienyl Grignard Reagent: [CP*Mg(thf)μ-Cl)$_2$," *J. Organomet. Chem.* 408:131-136.

Dahm et al. (1998) "Magnetron Sputter Deposition of Chromium Diboride Coatings," *Surface & Coatings Technology* 108-109:413-418.

de la Peña et al. (2002) "Effects of Al Doping on the Structural and Electronic Properties of $Mg_{1-x}Al_xB_2$," *Phys. Rev. B* 66:012511.

Denton et al. (1976) "Preparation and Nuclear Magnetic Resonance Studies of Stereochmically Nonrigid Magnesium, Zinc, and Cadmium Derivatives of Hexaborane(10). Crystal and Molecular Structure of $Mg(THF)_2(B_6H_9)_2$," *Inorg. Chem.* 15(3):541-548.

de Rouffignac et al. (Web Release Aug. 17, 2005) "Atomic Layer Deposition of $Y_2O_3$ Thin Films from Yttrium Tris(N, N'-diisopropylacetamidinate) and Water," *Chem. Mater.* 17:4808.

Doy et al. (1999) "New Precision Contouring Process of Lanthanum Hexaboride ($LaB_6$) Crystals Used for Electron Guns," *J. Ceram. Soc. Jpn.* 107(6):502-509.

Edleman et al. (Web Release Sep. 10, 2002) "Synthesis and Characterization of Volatile, Fluorine-Free β-Ketoiminate Lanthanide MOCVD Precursors and Their Implementation in Low-Temperature Growth of Epitaxial $CeO_2$ Buffer Layers for Superconducting Electronics," *J. Inorg. Chem.* 41(20):5005-5023.

El-Kaderi et al. (Web Release May 28, 2004) "Factors that Influence I- Versus $\eta^2$—Coordination of β-Diketiminato Ligands in Magnesium Complexes," *Organometallics* 23:3488-3495.

Ephritikhine, M. (1997) "Synthesis, Structure, and Reactions of Hydride, Borohydride and Aluminohydride Compounds of the f-Elements," *Chem. Rev.* 97:2193-2242.

Fagan et al. (1981) "Synthesis and Properties of Bis(pentamethylcyclopentadienyl) Actinide Hydrocarbyls and Hydrides. A New Class of Highly Reactive f-Element Organometallic Compounds," *J. Am. Chem. Soc.* 103:6650-6667.

Fan et al. (2001) "Growth of Atomically Flat Homoepitaxial Magnesium Oxide Thin Films by Metal-Organic Chemical Vapor Deposition," *Mater. Chem. Phys.* 70:191-196.

Fan et al. (Jul. 2, 2001) "Experimental Study of $MgB_2$ Decomposition," *Appl. Phys. Lett.* 79(1)87-89.

Ferrando et al. (2003) "Pulsed Laser Deposition of Epitaxial Titanium Diboride Thin Films," *Thin Solid Films* 444:91-94.

Foster, et al. (Aug. 15, 1995) "Substrate Effects on the Structure of Epitaxial $PbTiO_3$ Thin Films Prepared on MgO, $LaAlO_3$, and $SrTiO_3$ by Metalorganic Chemical-Vapor Deposition," *J. Appl. Phys.* 78:2607-2622.

Fujii et al. (1999) "Preffered Orientations and Microstructure of MgO Films Prepared by Plasma-Enhanced Metalorganic Chemical Vapor Deposition," *Thin Solid Films* 352:85-90.

Fujii et al. (Nov. 1994) "Crystallographic Orientations of MgO Films Prepared by Plasma-Enhanced Metalorganic Chemical Vapor Deposition," *Jpn. J. Appl. Phys.* 33(11):6331-6335.

Gaines et al. (1975) "Synthesis and Intramoleculat Exchange Characteristics of Beryllium Bis(octahydrotriborate), $Be(B_3H_8)_2$," *J. Chem. Soc., Chem. Commun.* :626-627.

Gaines et al. (1978) "Synthesis and Properties of Some Neutral Octahydrotriborate(1-) Complexes of CHromium-, Manganese-, and Iron-Group Metals," *Inorg. Chem.* 17(4):794-806.

Gao et al. (Jan. 1993) "Microstructure of $PbTiO_3$ Thin Films Deposited on (001)mgO by MOCVD," *J. of Mater. Res.* 8(1):145-153.

Garg et al. (Web Release Jan. 14, 2004) "Core Level Photoemission Study of Polycrystalline $MgB_2$," *Solid State Commun.* 131:343-347.

Gesley et al. (1984) "A Determination of the Low Work Function Planes of $LaB_6$," *Surf. Sci.* 146:583-599.

Girolami et al. (1987) "Organometallic Route to the Chemical Vapor Deposition of Titanium Carbide Films at Exceptionally Low Temperatures," *J. Am. Chem. Soc.* 109:1579-1580.

Goedde et al. (2004) "A New Class of CVD Precursors to Metal Borides: $Cr(B_3H_8)_2$ and Related Octahydrotriborate Complexes," *J. Am. Chem. Soc.* 126:12230-12231.

Gordon et al. (Web Release Jul. 10, 2001) "Vapor Deposition of Metal Oxides and Silicates: Possible Gate Insulators for Future Microelectronics," *Chem. Mater.* 13:2463-2464.

Grebenik et al. (1998) "Transition Metal Mediated Homologation of $BH_3$•THF : Synthesis and Crystal Structure of $\{WH_3(Pme_3)_3B_3H_8\}$," *J. Organomet. Chem.* 345 :C31-C34.

Greenwood (Jul. 1983) "Metalloboranes," *Pre Appl. Chem.* 55(9):1416-1430.

Guggenberger, L. J. (Feb. 1970) "The Crystal Structure of the Tettramethylammonium Salt of the Octahydrotriborotetracarbonylchromium Anion, $(CO)_4CrB_3H_8$-," *Inorg. Chem.* 9:367-373.

Hagimura et al. (1980) "Catalytic Effecs of Various Materials on the Growth of Lanthanum Hexaboride Whiiskers by Chemical Vapor Deposition," *Nippon Kagaku Kaishi* :1108-1113.

Hatanpaa et al. (Web Release Jun. 29, 1999) "Properties of $[Mg_2(thd)_4]$ as a Precursor for Atomic Layer Deposition of MgO Thin Films and Crystal Structures of $[Mg_2(thd)_4]$ and $[Mg(thd)_2(EtOH)_2]$," *Chem. Mater.* 11:1846-1852.

Hatanpaa et al. (Web Release Jan. 19, 2001) "Ancillary Ligand Effect on the Properties of ,MG(thd)$_2$' and Crystal Structures of $[Mg(thd)_2(ethylenediamine)]_2$, $[Mg(thd)_2(tmeda)]$, and $[Mg(thd)_2(trien)]^1$," *Inorg. Chem.* 40:788-794.

He et al. (1986) "Epitaxial and Electronic Structures of Ultra-Thin Copper Films on MgO Crystal Surfaces," *Surf. Sci.* 178:934-942.

Heřmánek et al. (1966) "Chemie Der Borhydride I. Herstellung Von Magnesiumoktahydrotriboraten," *Collect. Czech. Chem. Commun.* 31:177-89.

Hermann et al. (1957) "39. Uranium(IV) Chloride," *Inorg. Synth.* 5:143-145.

Hough et al. (1958) "The Sodium-Diborane Reaction," *J. Am. Chem. Soc.* 80:1828-1829.

Huang et al. (1993) "Preparation and Characterization of Thin Films of MgO, $Al_2O_3$ and $MgAl_2O_4$ by Atomic Layer Deposition," *J. Elec. Mater.* 22(2):215-220.

Huang et al. (Sep. 21, 1992) "Temperature-Dependence of the Growth Orientation of Atomic Layer Growth MgO," *Appl. Phys. Lett.* 61(12):1450-1452.

Hung et al. (Jun. 22, 1992) "Epitaxial Growth of MgO on (100)GaAs Using Ultrahigh Vacuum Electron-Beam Evaporation," *Appl. Phys. Lett.* 60(25):3129-3131.

International Search Reportand Written Opinion, Corresponding to International Application No. PCT/US08/59728, Mailed Jul. 14, 2008.

Inumaru et al. (2000) "Pulsed Laser Deposition of Epitaxial Titanium Nitride on MgO(001) Monitored by RHEED Oscillation," *Appl. Surf. Sci.* 158:375-377.

Jaska et al. (Web Release May 10, 2001) "Rhodium-Catalyzed Formation of Boron-Nitrogen Bonds," A M<ild Route to Cyclic AMinoboranes and Borazines, *Chem. Commun.* :962-963.

Jaska et al. (2003) "Transistion Metal-Catalyzed Formation of Boron-Nitrogen Bonds: Catalytic Dehysrocoupling of Amine-Borane Adducts to Form AMinoboranes and Borazines," *J. Am. Chem. Soc.* 125(31):9424-9434.

Jaska et al. (2004) "Heterogenous of Homogenous Catalysis? Mechanistic Studies of the Rhodium-Catalyzed Dehydrocoupling of Amine-Borane and Phosphine-Borane Adducts," *J. Am. Chem. Soc.* 126(31):9776-9785.

Jaska et al. (2004) "Catalytic Dehydration of Amine-Borane and Phosphine-Borane Adducts: The Mechanism is Heterogenous in One Case and Homogenous in the Other," *J. Am. Chem. Soc.* 126(5):1334-1335.

Jayaraman et al. (Nov./Dec. 2005) "Hafnium Diboride Thin Films by Chemical Vapor Deposition from a Single Source Precursor," *J. Vac. Sci. Technol A* 23(6):1619-1625.

Jayaraman et al. (Jul./Aug. 2005) "Chromium Diboride Thin Films by Low Temperature Chemical Vapor Deposition," *J. Vac. Sci. Technol. A* 23(4):631-633.

Jeffries et al. (1992) "Metal-Organic Chemical Vapor Deposition of Copepr and Copper(i) Oxide from Copper(I) tert0Butoxide," *Chem. Mater.* 4)6):1169-1175.

Jensen et al. (1988) "Titanium, Zirconium, and Hafnium Tetrahydroborates as 'Taiored' CVD Precursors for Metal Diboride Thin Films," *J. Am. Chem. Soc.* 110(5):1643-1644.

Jensen et al. (1989) "Synthesis, Characterization, and X-Ray Crystal Structures of the Divalent Titanium Complex $Ti(\eta^2-BH_4)_2(dmpe)_2$ and the Unidentate Tetrahydroborate Complex $V(\eta^1-BH_4)2(dmpe)_2$," *Inorg. Chem.* 28(11):2107-2113.

Just et al. (2000) "Metal Amides: Versatile Dopant Precursors for Electronic Materials," *Adv. Mater. Opt. Electr.* 10:213-221.

Kang et al. (May 25, 2001) "$MgB_2$ Superconducting Thin Films with a Transition Temperature of 39 Kelvin," *Science* 292:1521-1523.

Kelesoglu et al. (1999) "Microstructure and Properties of Nitride and Diboride Hard Coatings Deposited Under Intense Mild-Energy Ion Bombardment," *Surface and Coatings Technology* 116-119:133-140.

Keller et al. (1971) "The Chemistry of Sodium Bis(borane)dimethylamide(1-)," *Inorg. Chem.* 10(10):2256-2259.

Kher et al. (1998) "Chemical Vapor Deposition of Metal Borides 7. The Relatively Low Temp;erature Formation of Crystalline Lanthanum Hexaboride Thin Films from Boron Hydride Cluster Compounds by Chemical Vapor Deposition," *J. Phys. Chem. Solids* 59(8):1343-1351.

Kitaguchi et al. (Oct. 4, 2004) "$MgB_2$ Films with Very High Critical Current Densities Due to Strong Grain Boundary Pinning," *Appl. Phys. Lett.* 85(14):2842-2844.

Klein, N. (Aug. 23, 2002) "High-Frequency Applications of High-Temperature Superconductor Thin Films," *Rep. Prog. Phys.* 65:1387-1425.

Klie et al. (Jan. 17, 2006) "Electron Doping in $MgB_2$ Studies by Electron Energy-Loss Spectroscopy," *Phys. Rev. B Condens. Matter Mater. Phys.* 73:014513-10.

Kühberger et al. (2002) "Effects of Sn, CO and Fe on $MgB_2$," *Physica C* 370:39-43.

Kwak et al. (Jun. 19, 1989) "Metalorganic Chemical Vapor Deposition of [100]Textured MgO Thin Films," *Appl. Phys. Lett.* 54(25):2542-2544.

Lafferty, J. M. (Mar. 1951) "Boride Cathodes," *J. Appl. Phys.* 22(3):299-309.

Lairson et al. (Feb. 8, 1993) "Epitaxial PtFe(001) Thin Films on MgO(001) With Perpendicular Magnetic Anisotrophy," *Appl. Phys. Lett.* 62(6):639-641.

Lairson et al. (Sep. 21, 1992) "Epitaxial Pt(110), and Pt(111) Films on MgO(001), MgO(110), MgO(111), and $Al_2O_3(0001)$," *Appl. Phys. Lett.* 61(12):1390-1392.

Laske et al. (Dec. 14, 1993) "Synthesis of New Bis(cyclopentadienyl)yttrium Complexes with Ether Functionalized Cyclopentadienyl Ligands. Crystal Structure of $[(C_5H_4CH_2OMe)2Y(\mu-H)_2BH_2]$," *J. Organomet. Chem.* 462(1-2):149-153.

Late et al. (Web Release Sep. 22, 2006) "Field Emission Studies on Well Adhered Pulsed Laser Deposited $LaB_6$ on W tip," *Appl. Phys. Lett.* 89:123510.

Lee et al. (Jul. 22, 2002) "Tungstein Nanowires and Their Filed Electron Emission Poperties," *Appl. Phys. Lett.* 81(4):745-747.

Lettieri et al. (Jul. 2002) "Critical Issues in the Heteroepitaxial Growth of Alkaline-Earth Oxides on Silicon," *J. Vac. Sci. Technol. A* 20(4):1332-1340.

Leutkens et al. (1989) "3. Trimethyohosphine," *Inorg. Synth.* 26:7-12.

Li et al. (Dec. 23, 2002) "Field Emission From $MoO_3$ Nanobelts," *Appl. Phys. Lett.* 81(26):5048-5050.

Likharev et al. (Mar. 1991) "RSFQ Logic/Memory Family:A New Josephson-Junction Technology for Sub-Terahertz-Clock-Frequency Digital Systems," *Appl. Supercon. IEEE Trans.* 1(1):3-28.

Lin et al. (Aug. 14, 2003) "Growth of Tantalm Boride Films by RF Magnetron Sputtering," *J. Electrochem. Soc.* 150(10):G607-G611.

Lippard et al. (Jun. 1968) "Transition MNetal Borohydride Complexes. II. The Reaction of Copper (I) Compounds with Boron Hydride Anions," *Inorg. Chem.* 7(6):1051-1056.

Liu et al. (Jun. 4, 2001) "Thermodynamics of the Mg-B System: Implications for the Deposition of $MgB_2$ Thin Films," *Appl. Phys. Lett.* 78(23):3678-3680.

Lobkovskii et al. (1982) "X-Ray Crystallographic Investigation of Crystals of Bis(tetrahydroborato)tris(tetrahydrofuranato)magnesium," *J. Struct. Chem.* 23:644-646.

Lobkovskii et al. (1990) "Crystsal and Molecular Structure of Magnesium Borohydride Diglymate," *J. Struct. Chem.* 31:506-508.

Lo Nigro et al. (Mar. 2006) "An MOCVD Approach to High-k Praseodymium-Based Films," *Chem. Vap. Deposition* 12(2):109-124.

Lu et al. (Mar. 1, 1993) "Solid Source MOCVD for the Epitaxial Growth of Thin Oxide Films," *J. Cryst. Growth* 128(1-4):788-792.

Marks et al. (Mar. 1972) "Structure and Dynamics in Metal Tetrahydroborates. I. Nuclear Magnetic Resonance tudies of Zirconium and Hafnium Tatrahydroborates," *J. Am. Chem. Soc.* 94(5):1542-1550.

Marks et al. (Apr. 1977) "Covalent Transition Metal, Lanthanide, and Actinide Tetrahydroborate Complexes," *Chem. Rev.* 77(2):263-293.

Matero et al. (Jun. 2000) "Effect of Water Dose on the Atomic Layer Deposition Rate of Oxide Thin Films," *Thin Solid Films* 368(1):1-7.

Mathon et al. (2001) "Theory of Tunneling Magnetoresistance of an Epitaxial Fe/MgO/Fe(001) Junction," *Phys. Rev. B* 63:220403.

Matthews et al. (Jun. 2000) "CVD of MgO from a $Mg((\beta$-ketoiminate)$_2$: Preparation, Characterization, and Utilization of an Intramolecularly Stabolized, Highly Volatile, Thermally Robust Precursor," *Chem. Vapor Deposition* 6(3):129-1321.

Mills et al. (Aug. 23, 2002) "Novel $TiO_2$ CVD Films for Semiconductor Photocatalysis," *J. Photochem. Photobiol. A* 151(1-3):171-179.

Mitterer, C. (1997) "Borides in Thin Film Technology," *Solid State Chem.* 133:279-291.

Moca et al. (2002) "Localized States within the Gap in a Two-Band Superconductor," *Phys. Rev. B* 66:052501.

Moeckly et al. (Oct. 15, 1990) "Growth of $YBa_2Cu_3O_7$ Thin Films on MgO: The Effects of Substrate Preparation," *Appl. Phys. Lett.* 57(16):1687-1689.

Motojima et al. (Aug. 1, 1990) "$ZrB_2$ Coated on Copper Plate by Chemical Vapour Deposition, and its Corrosion and Oxidation Stabolities," *Thin Solid Films* 189(1):73-79.

Mroczkowski, S. J. (May 1991) "Electron Emission Characteristics of Sputtered Lanthanum Hexaboride," *J. Vac. Sci. Technol A* 9(3):586-590.

Mukaida et al. (1990) "Morphology and Deposition Rates of $TiB_2$ Prepared by Chemical Vapour Deposition of $TiCl_4 + B_2H_6$ System," *J. Mater. Sci.* 25:1069-1075.

Musolf et al. (1993) "Deposition of Buffer Layers for MOCVD of $Y_1Ba_2Cu_3O_{7-x}$ on Gas," *J. Alloy Comp.* 195:295-298.

Nagamatsu et al. (Mar. 1, 2001) "Superconductivity at 39 K in Magnesium Diboride," *Nature* 410:63-64.

Naito et al. (May 25, 2004) "$MgB_2$ Thin Films for Superconducting Electronics," *Supercond. Sci. Technol.* 17:R1-R18.

Nakamoto et al. (Dec. 30, 2002) "Field Emission from $LaB_6$ and TiN Emitter Arrays Fabricated by Transfer Mold Technique," *Appl. Surf. Sci.* 202(3-4):289-294.

Nashimoto et al. (Mar. 9, 1992) "Epitaxial Growth of MgO on GaAs(001) for Growing Epitaxial $BaTiO_3$ Thin Films by Pulsed Laser Deposition," *Appl. Phys. Lett.* 60(10):1199-1201.

Niemer et al. (Oct. 12, 1992) "Organometallic Chemical Vapor Deposition of Tungsten Metal, and Suppression of Carbon Incorporation by Codeposition of Platinum," *Appl. Phys. Lett.* 61(15):1793-1795.

Niinistö et al. (Web Release Jul. 2, 2004) "Processing of $Y_2O_3$ Thin Films by Atomic Layer Deposition from Cyclopentadienyl-Type Compounds and Water as precursors," *Chem. Mater.* 16(15):2953-2958.

Niu et al. (Jul. 2000) "Epitaxial Thin Films of MgO on Si Using Metalorganic Molecular Beam Epitaxy," *J. Vac. Sci. Technol. B* 18(4):2146-2152.

Noth et al. (1999) "Metal tetrahydridoborates and tetrahydroboratometalates. Part 24. Solvates of sodium bis(borane)dimethylamide," *Eur. J. Inorg. Chem.* (8):1373-1379.

Ohta et al. (Jan. 2001) "Static Vapor Pressure Measurement of Low Volatility Precursors for Molecular Vapor Deposition Below Ambient Temperature," *Chem. Vapor Deposition* 7(1):33-37.

Okamoto et al. (Oct. 1987) "DC Gas Discharge Display Panel with $LaB_6$ Thin-Film Cathode," *Jpn. J. Appl. Phys.* 26(10):1722-1726.

Päivasaari et al. (Oct. 2005) "High Growth of Erbium Oxide Thin Films in Atomic Layer Deposition from (CpMe)3Er and Water Precursors," *Chem. Vap. Deposition* 11(10):415-419.

Park et al. (Nov. 2002) "Heteroepitaxial Growth of MgO Thin Films on $Al_2O_3$(0001) by Metalorganic Chemical Vapor Deposition," *Jpn. J. Appl. Phys.* 41(11B):6919-6921.

Pelleg et al. (May 1, 2002) "Diffusion Barrier Properties of Amorphous $TiB_2$ for Application in Cu Metallization," *J. Appl. Phys.* 91(9):6099-6104.

Pierson et al. (2001) "Structural and Electrical Properties of Sputtered Titanium Boronitride Films," *Surface & Coatings Technology* 142:906-910.

Prust et al. (2001) "Synthesis and Structures of β-Diketoiminate Complexes of Magnesium," *Z. Anorg. Allg. Chem.* 627:2032-2037.

Putkonen et al. (Web Release Jun. 29, 2000) "Enhanced Growth Rate in Atomic Layer Epitaxy Deposition of Magnesium Oxide Thin Films," *J. Mater. Chem.* 10:1857-1861.

Putkonen et al. (Web Release May 6, 2004) "Magnesium Aluminate Thin Films by Atomic Layer Deposition from Organometallic Precursors and Water," *Thin Solid Films* 466:103-107.

Qian et a. (2000) "Stereoselective Synthesis and Structural Characterization of *rac*-Planar Chiral Bis(2-methoxyethylindenyl-)lanthanum and Yttrium Tetrahydroborates," *Polyhedron* 19:1955-1959.

Ramesh et al. (May 28, 1990) "Epitaxy of Y-Ba-Cu-O Thin Films Grown on Single-Crystal MgO," *Appl. Phys. Lett.* 56(22):2243-2245.

Randich, E. (1980) "Low Temperature Chemical Vapor Deposition of $TaB_2$," *Thin Solid Films* 72:517-522.

Rees et al. (1999) "Molecular Design of Dopant Precursors for Atomic Layer Epitaxy of SrS:Ce," *J. Mater. Chem.* 9:249-252.

Rinzler et al. (Sep. 15, 1995) "Unraveling Nanotubes: Field Emission From an Atomic Wire," *Science* 269:1550-1553.

Rogacki et al. (2006) "Strong Magnetic Pair Breaking in Mn-Substituted $MgB_2$ Single Crystals," *Phys. Rev. B Condens. Matter Mater. Phys.* 73:174520-8.

Roy et al. (Dec. 1996) "Study of a Laser Heated Electron Gun," *Rev. Sci. Instrum.* 67(12):4098-4102.

Sadique et al. (Web Release Nov. 26, 2001) "Monomeric and Dimeric Amidinate Complexes of Magnesium," *Inorg. Chem.* 40:6349-6355.

Sandstrom et al. (1999) "Structure and Surface Morphology of Epitaxial Ni Films Grown on MgO(1 1 1) Substrates: Growth of High Quality Single Domain Films," *J. Cryst. Growth* 197:849-857.

Schelm et al. (2005) "Tuning the Surface-Plasmon Resonance in Nanoparticles for Glazing Applications," *J. Appl. Phys.* 97:124314-124318.

Schmidt et al. (Jul./Aug. 1978) "Design and Optimization of Directly Heated $LaB_6$ Cathode Assemblies for Electron-Beam Instruments," *J. Vac. Sci. Technol.* 15(4):1554-1560.

Schmidt et al. (Mar. 25, 2002) "Evidence for Two-Band Superconductivity from Break-Junction Tunneling on $MgB_2$," *Phys. Rev. Lett.* 88(12):127002.

Schumann et al. (1998) "Organic Compounds of the Lanthanides. 127," *Z. Anorg. Allg. Chem.* 624:1811-1818.

Schwarberg et al. (Dec. 1970) "Gas Chromatographic and Related Properties of the Alkaline Earth with 2,2,6,6-Tetramethyl-3,5-Heptanedione," *Anal Chem.* 42(14):1828-1830.

Segal et al. (1978) "Transition Metal Hydroborate Complexes. 10. Crystal and Molecular Structure of Tris(tetrahydroborato)tris(tetrahydrofuran)yttrium(III)," *Inorg. Chem.* 17:844-850.

Seo et al. (2005) "Epitaxial and Polycrystalline $HfN_x$ ($0.8 \leq x \leq 1.5$) Layers on MgO(001): Film Growth and Physical Properties," *J. Appl. Phys.* 97:083521.

Sharma et al. (Nov./Dec. 1999) "Growth of Single Crystal MgO on TiN/Si Heterostructure by Pulsed Laser Deposition," *J. Vac. Sci. Technol. A* 17(6):3393-3396.

Shikama et al. (1988) "Deposition of $TiB_2$ Films by a Co-Sputtering Method," *Thin Solid Films* 156:287-293.

Shim et al. (2002) "Bottom-Up Filling of Submicrometer Features in Catalyst-Enhanced Chemical Vapor Deposition of Copper," *J. Electrochem. Soc.* 149(2):G109-G113.

Shin et al. (Jan. 1, 2004) "Growth, Surface Morphology, and Electrical Resistivity of Fully Strained Substoichiometric Epitaxial $TiN_x$ ($0.67 \leq x < 1.0$) Layers on MgO(001)," *J. Appl. Phys.* 95(1):356-362.

Slusky et al. (Mar. 15, 2001) "Loss of Superconductivity With the Addition of Al to MgB2 and a Structural Transition in $Mg_{1-x}Al_xB_2$," *Nature* 2001, 410:343-345.

Srivastava et al. (1991) "Reactivity of $\mu$-$Me_2NB_2H_5$ Toward the As-N Bond," *Inorg. Chem.* 30:2441-2444.

Sung et al. (2000) "Epitaxial Growth of MgO Films on Si(1 1 1) by Metal Organic Chemical Vapor Deposition," *J. Cryst. Growth* 210:651-654.

Sung et al. (Web Release Jan. 11, 2002) "Chemical Beam Deposition of MgO Films on Si Substrates Using Methylmaggnesium *tert*-Butoxide," *Chem. Mater.* 14:826-831.

Sung et al. (Mar. 15, 2002) "Remote-Plasma Chemical Vapor Deposition of Conformal $ZrB_2$ Films at Low Temperatuure: A Promising Diffusion Barrier for Ultralarge Scale Integrated Electronics," *J. Appl. Phys.* 91(6):3904-3911.

Talapatra et al. (2005) "X-Ray Photolelectron Spectroscopy Studies of $MgB_2$ for Valence State of Mg," *Physica C* 419:141-147.

Tampieri et al. (2002) "Effects of Copper Doping in $MgB_2$ Superconductor," *Solid State Commun.* 121:497-500.

Tatsuno et al. (1979) "51. ($\eta^3$-Allyl)Palladium(II) Complexes," *Inorg. Synth.* 19:220-223.

Tennant et al. (Jan./Feb. 1989) "The Effect of $LaB_6$ Cathode Shape on its Performance in JBX 5DII Electron Beam Lithography Systems," *J. Vac. Sci. Technol. B* 7(1):93-97.

Tiitta et al. (1997) "Volatile Metal β-Diketonates: ALE and CVD Precursors for Electroluminescent Device Thin Films," *Chem. Vap. Deposition* 3(4):167-182.

Tonouchi et al. (2005) "Recent Topics in High $T_c$ Superconductive Electronics," *Jpn. J. Appl. Phys.* 44(11):7735-7749.

Tsuda et al. (Oct. 22, 2001) "Evidence for a Multiple Superconducting Gap in MgB2 from High-Resolution Photoemission Spectroscopy," *Phys. Rev. Lett* 87(17):177006.

Ueda et al. (2006) "Low-Temperature Growth of $MgB_2$ Thin Films with $T_c$ Above 38K," *Jpn. J. Appl. Phys. Part 1* 45(7):5738-5741.

Ueda et al. (Feb. 15, 2003) "In Situ Growth of Superconducting $MgB_2$ Thin Films y Molecular-Beam Epitaxy," *Journal of Applied Physics* 93(4):2113-2120.

Ueda et al. (2002) "Synthesis and Photoemission Study of As-Grown Superconducting $MgB_2$ Thin Films," *Physica C* 378:225-228.

Vasquez et al. (Jul. 16, 2001) "X-Ray Photoemission Study of $MgB_2$," *Phys. Rev. B* 64:052510.

Verhoeven et al. (Nov. 1976) "Influence of Crystallography and Purity on Brightness of $LaB_6$ Cathodes," *J. Appl. Phys.* 47(11):5105-5106.

Waldhauser et al. (1998) "Sputteredd Thermionic Hexaboride Coatings," *Surf. Coat. Technol.* 98:1315-1323.

Wang et al. (Web Release Oct. 14, 2005) "Synthesis and Characterization of Low-Melting, Highly Volatile Magnesium MOCVD Precursors and Their Implementation in MgO Thin Film Growth," *Chem. Mater.* 17:5697-5704.

Wang et al. (2006) "P-Doped *p*-Type Films Deposited on Si Substrate by Radio-Frequency Magnetron Sputtering," *Appl. Phys. Lett.* 88(15):152-102.

Wang et al. (Sep. 9, 2002) "High Critical Current Density and Improved Irreversibility Filed in Bulk $MgB_2$ Made by a Scaleable, Nanoparticle Addition Route," *Appl. Phys. Lett.* 81(11):2026-2028.

Weber et al. (1990) "Thin Yttrium and Rare Oxide Films Priduced by Plasma Enhanced CVD of Novel Organometallic π-COMplexes," *Appl. Phys. A: Mater. Sci. Process.* 51:520-525.

Wilke et al. (Web Release Dec. 15, 2005) "Superconductivity in $MgB_2$ Doped with Ti and C," *Physica C* 418:160-167.

Wong et al. (Nov. 8, 1999) "Field-Emission Characteristics of SiC Nanowires Prepared by Chemical-Vapor Deposition," *Appl. Phys. Lett.* 75(19):2918-2920.

Xia et al. (2003) "Synthesis, Structure, and Properties of Magnesium Complexes Containing Cyclopentadienyl and Amidinate Ligand Sets," *J. Organomet. Chem.* 682:224-232.

Xu et al. (Jul. 2001) "Mn-Substitution Effects on $MgB_2$ Superconductor," *J. Phys. Soc. Jpn.* 70(7):1889-1891.

Xu et al. (Oct. 22, 2001) "Anisotropy of Superconductivity from MgB2 Single Crystals," *Appl. Phys. Lett.* 79(17):2779-2781.

Yamabe et al. (1984) "Electron Emission from <100> $LaB_6$ Cathodes with Large Cone Angles and Flat Tips," *J. Vac. Sci. Technol. A* 2(3):1361-1364.

Yan et al. (Apr. 16, 2001) "Highly Conductive Epitaxial CdO Thin Films Prepared by Pulsed Laser Deposition," *Chang, Appl. Phys. Lett.* 78(16):2342-2344.

Yuasa et al. (2004) "High Tunnel Magnetoresistance at Room Temperature in Fully Epitaxial Fe/MgO/Fe Tunnel Junctions Due to Coherent Spin-Polarized Tunneling," *Jpn. J. Appl. Phys. Part 2 Lett. Exp. Lett*, 43(4B):L588-L590.

Yutani et al. (1993) "Work Functions of Thin $LaB_6$ Films," *Appl. Surf. Sci.* 70-71:737-741.

Zeng et al. (1996) "Preparation and Characterization of Epitaxial MgO Thin Film by Atmospheric-Pressure Metalorganic Chemical Vapor Deposition," *J. Cryst. Growth* 169:474-479.

Zeng et al. (Sep. 2002) "In Situ Epitaxial $MgB_2$ Thin Films for Superconducting Electronics," *Nature Materials* 1:35-38.

Zhang et al. (2005) "Single-Cryatalline $LaB_6$ Nanowires," *J. Am. Chem. Soc.* 127(9):2862-2863.

Zhang et al. (2006) "Field Emission of Electrons from Single $LaB_6$ Nanowires," *Adv. Mater.* 18:87-91.

Zhang et al. (2005) "Single-Crystalline $GdB_6$ Nanowire Field Emitters," *J. Am. Chem. Soc.* 127(38):13120-13121.

Zhang et al. (2005) "Single-Crystalline $CeB_6$ Nanowires," *J. Am. Chem. Soc.* 127(22):8002-8003.

Zhang et al. (Web Release Dec. 5, 1998) "Catalyst-Enhanced Chemical Vapor Deposition of Yttrium Oxide," *Chem. Mater.* 11:148-153.

Zhang et al. (1997) "Catalyst Enhanced Chemical Vapor Deposition: Effects on Chemical Vapor Deposition Temperature and Film Purity," *J. Am. Chem. Soc.* 119(39):9295-9296.

Zhao et al. (Aug. 20, 2001) "High Critical Current Density of $MgB_2$ Bulk Superconductor Doped with Ti and Sintered at Ambient Pressure," *Appl. Phys. Lett.* 79(8):1154-1156.

Zhao et al. (1992) "Thin Films of Magnesium Oxide {repared by Plasma-Enhanced Chemical Vapour Deposition," *Appl. Phys. A-Mater. Sci. Process.* 54:451-454.

Zinn et al. (1992) "Reaction Pathways in Organometallic Chemical Vapor Deposition (OMCVD)," *Adv. Mater.* 4(5):375-378.

Akzo Nobel Polymer Chemicals LLC, Material Safety Data Sheet for CP2MG SSG (BIS Cyclopentadienyl Magnesium), Product Code 11-090024; Date of last issue Oct. 20, 2000.

Goedde (2001) "Transition Metal Hydroborate Complexes: Structures, Syntheses, and Use as Chemical Vapor Deposition Precursors," *Doctoral Thesis*, University of Illinois.

Levicheva et al. (1987) "The Preparation and Thermal Decomposition of $[Mg(NH_3)_6](B_3H_8)_2$," *Russsian Journal of Inorganic Chemistry*, 32:510-512.

Noth (1982) "Metal Tetrahydridoborates and Tetrahydridoborato Metallates, 11[1] The Crystal and Molecular Structure of Magnesium Tetrahydridoborate $Mg(BH_4)_2$ • 3 THF," *Z. Naturforsch*, 37b:1499-1503.

Yang (Jan. 2008) "Chemical Vapor Deposition of Metal Diboride and Metal Oxide Thin Films from Borohydride-Bonded Precursors," *Doctoral Thesis*, University of Illinois.

Kim (Dec. 2007) "Part I. Synthesis of Metal Hydroborates as Potential Chemical Vapor Deposition Precursors. Part II. Chemical Vapor Deposition of Titanium-Doped Magnesium Diboride Thin Films," *Doctoral Thesis*, University of Illinois.

Daly and Girolami (2010) "Uranium-hydrogen interactions: synthesis and crystal structures of tris(N,N-dimethylaminodiboranato)uranium(III)," *Chem. Commun.* 46:407-408.

Daly et al. (2010) "Lanthanide N,N-Dimethylaminodiboranates: Highly Volatile Precursors for the Deposition of Lanthanide-Containing Thin Films," *J. Am. Chem. Soc.* 132:2106-2107.

Gaines and Hildebrant (1974) "New Transition Metal Derivatives of the Triborohydride Ion and the First Example of Reversible Bidentate-Tridentate Borane Ligand Functionality," *J. Am. Chem. Soc.* 96: 5574-5576.

Kim and Girolami (2006) "Synthesis and Characterization of the Octahydrotriborate Complexes Cp*V(B3 H8)2 and Cp*Cr(B3H8)2, and the Unusual Cobaltaborane Cluster Cp* 2Co2(B6H14)," *J. Am. Chem. Soc.* 28(33): 10969-10977.

Titov et al. (1984) "Synthesis and Thermal Decomposition of Magnesium, Calcium, and Strontium Octahydrotriborates Solvated with Diglyme," *Zh. Neorg. Kim.* 29:668-673.

Titov et al. (1984) "Synthesis and Thermal Decomposition of Magnesium, Calcium, and Strontium Octahydrotriborates Solvated with Diglyme," *Russian Journal of Inorganic Chemistry*, 29(3):386-389 (English Translation of *Zh. Neorg. Kim.* 29:668-673).

The Dow Chemical company (2010) Product Data Sheet for $Cp_2Mg$.

\* cited by examiner

A

B

METAL COMPLEX COMPOSITIONS AND METHODS FOR MAKING METAL-CONTAINING FILMS

CROSS-REFERENCE TO RELATED APPLICATIONS

This application is a national stage application under 35 U.S.C. §371 of PCT/US08/59728, filed Apr. 9, 2008, which claims the benefit of priority to U.S. provisional Patent Applications 60/911,619 filed Apr. 13, 2007 and 60/914,948 filed Apr. 30, 2007, which are hereby incorporated by reference in their entirety.

STATEMENT REGARDING FEDERALLY SPONSORED RESEARCH OR DEVELOPMENT

This invention was made with United States government support awarded by the following agencies: NSF DMR03-15428. The United States has certain rights in this invention.

BACKGROUND OF INVENTION

Metal diborides ($MB_2$) possess outstanding properties for thin film applications in microelectronics and hard coatings: metal diborides such as $TiB_2$, $ZrB_2$ and $HfB_2$ have melting points often exceeding 3000° C., electrical resistivities as low as 15 μΩ-cm, and hardnesses approaching 30 GPa. In addition, they are chemically robust. Some metal borides are attractive as potential replacements for TiN as electrically conductive diffusion barriers in integrated circuits, preventing the interdiffusion of copper and silicon in interconnects (See, S. Jayaraman et al. *J. Vac. Sci. Technol.*, A 2005, 23, 1619-1625, J. W. Sung, *J. Appl. Phys.* 2002, 91, 3904-3911, U.S. Pat. No. 6,445,023 B1 and 6,872,639 B2). Moreover, magnesium diboride ($MgB_2$), which becomes superconducting below ca. 40 K, is potentially useful for the fabrication of superconductor-based integrated circuits. (See, M. Naito et al. *Supercond. Sci. Technol.* 2004, 17, R1-R18, U.S. Pat. No. 6,797,341).

Physical vapor deposition (PVD) and chemical vapor deposition (CVD) methods are primarily employed in preparing thin films of metal diborides. In general, the PVD process deposits thin films of the desired composition by generating highly reactive particles from pure bulk targets by evaporation or sputtering followed by transporting them onto the substrate on which the films grow. In CVD, a molecular precursor that contains some or all of the elements in the desired thin film, is vaporized and delivered onto a hot substrate, sometimes in combination with other precursors. Subsequent chemical reactions afford thin films of the desired material on the substrate. CVD methods can produce uniform coatings on high aspect-ratio trenches and holes, which is difficult to accomplish by PVD methods, which tend to be "line of sight" owing to its use of highly reactive particles.

Atomic layer deposition (ALD), which is a variant of the CVD method, is based on self-limiting reactions. A substrate is exposed to a precursor, which reacts to coat the substrate with a monolayer (or less) of material. The excess precursor is then pumped away, and the substrate is exposed to a second precursor, which reacts with the thin layer generated by the first reactant. Then, the excess of this second reactant is removed. By repeating this cycle, or variants in which more than two precursors are employed, the desired thin film can be grown layer by layer. One feature of ALD is that it can provide highly conformal coatings in extremely narrow, deep holes.

The PVD processes that have been performed for the deposition of transition metal diboride thin films include sputtering, co-sputtering, reactive sputtering, pulsed-laser ablation and evaporation. Sputtering from $MB_2$ targets is the most frequently employed method for $MB_2$ deposition among PVD methods; thin films of $TiB_2$, $ZrB_2$, $HfB_2$, $VB_2$, $TaB_2$, and $CrB_2$ have been deposited from each $MB_2$ target.[1-5] $TiB_2$ thin films have been prepared by a co-sputtering method that uses separate Ti and B targets (See, J. Pelleg et al. *J. Appl. Phys.* 2002, 91, 6099-6104; T. Shikama et al. *Thin Solid Films* 1988, 156, 287-293). Reactive sputtering method using $B_2H_6$ gas as a boron source has also been employed to deposit $TiB_2$ thin films. (See, H. O. Blom et al. *J. Vac. Sci. Technol.*, A 1989, 7, 162-165). In all these sputtering methods, the fluxes of metal and boron must be precisely controlled to produce stoichiometric $MB_2$ deposits: different sputter yields, different angular emission profiles, and different gas scattering effects can cause there to be excess metal or excess boron in the films. (See C. Mitterer, *J. Solid State Chem.*, 133, (1997) 279) Failure to produce stoichiometric $MB_2$ films often results in films with less useful properties. Although sputtering itself can be performed at moderate substrate temperatures, high temperature annealing processes are often necessary to obtain films with desired properties. An alternative to sputtering, pulsed-laser ablation, has been employed to produce $TiB_2$ films (See, V. Ferrando, et al. *Thin Solid Films* 2003, 444, 91-94). One disadvantage of this PVD technique is that a high deposition temperature of 720° C. was necessary. Thin films of $TiB_2$ and $ZrB_2$ have also been prepared by evaporation; the films were, however, nonstoichiometric and required high deposition temperatures of above 1000° C. (See, R. F. Bunshah, *Thin Solid Films* 1977, 40, 169-182). Although high-quality $MB_2$ films have often been prepared by PVD methods, all these PVD approaches have limited abilities to deposit uniform coatings onto non-flat surfaces.

CVD methods for thin films of transition metal diborides can be divided into two processes in terms of precursor types: 1) processes using metal halide precursors and 2) processes using single sources of metal hydroborate complexes. In the former, metal halides are reduced in the presence of a boron source to metal borides and hydrohalic acids (HX). $TiB_2$ and $ZrB_2$, for example, have been prepared from the reaction of $BCl_3$ and $H_2$ with $TiCl_4$ and $ZrCl_4$, respectively.[6,7] Diborane can be used in place of boron halides and $H_2$: the reaction between $B_2H_6$ and $TiCl_4$ and $TaCl_5$ produced $TiB_2$ and $TaB_2$ thin films, respectively.[8,9] However, CVD processes using halogen-based precursors require high deposition temperatures of 600-1200° C. and often leave behind traces of halogen contaminants both of these features are detrimental for many microelectronic applications. Another disadvantage of this method is that few metal halides are volatile below their decomposition temperatures.

Single source precursors to metal diborides have been described that have the general stoichiometry $MB_xH_y$; these bear tetrahydroborate ($BH_4^-$) or octahydrotriborate ($B_3H_8^-$) groups. The precursors $Zr(BH_4)_4$, $Hf(BH_4)_4$, and $Cr(B_3H_8)_2$ have afforded the corresponding $MB_2$ thin films at temperatures as low as 150° C.[10-12] The single source precursors are free of heteroatoms such as halogens that could contaminate the films, and the deposition temperatures are often lower than 400° C.

For many metal boride phases, it is not possible to use single source CVD precursors to grow films because no precursor of stoichiometry $MB_xH_y$ exists. Volatile $M(BH_4)_n$ complexes of d-block transition metals are rare because the $BH_4^-$ ligand is sterically small and strongly reducing, and in fact only $Ti(BH_4)_3$, $Zr(BH_4)_4$, and $Hf(BH_4)_4$ are known.

Because $BH_4^-$ is sterically small, three or four $BH_4^-$ ligands are required to saturate the coordination sphere of a transition metal center and form a volatile complex, which accordingly means a +3 or +4 oxidation state for the metal center. Many transition metals, however, are not stable in these oxidation states in the presence of strongly reducing $BH_4^-$ groups. By employing the sterically more demanding hydroborate ligand, $B_3H_8^-$, the highly volatile chromium(II) complex of $Cr(B_3H_8)_2$ has been prepared and have demonstrated its excellence as single source precursor to very high quality $CrB_2$ thin films.[12,13] However, although the $B_3H_8^-$ group is sterically larger than the $BH_4^-$ ligand, so far only chromium has been shown to form a highly volatile transition metal species suitable as a CVD precursor.

The lattice structure of $MgB_2$ is identical with that of the transition metal diborides, but the deposition of $MgB_2$ thin films is complicated by one major challenge: loss of Mg from the $MgB_2$ phase at growth temperatures above ca. 400° C.[14] If enough Mg is lost, the $MgB_2$ films become non-superconducting. Several reports of the deposition of $MgB_2$ by PVD methods have appeared. Kang and co-workers have produced $MgB_2$ films by depositing amorphous boron followed by reaction with Mg vapor at 900° C. in sealed tantalum tube.[15] Although this method has produced high-quality $MgB_2$ films with a critical temperature $T_c$ of 39 K, the ex-situ high temperature annealing process must be conducted in a sealed tube, which makes this method impractical for producing multilayer thin films on a large scale. Ueda et al. have produced $MgB_2$ thin films with a $T_c$ of ca. 38 K by co-evaporation at 240 to 270° C.[16,17] Zeng et al. have grown $MgB_2$ thin films by an in situ hybrid physical-chemical vapor deposition (HP-CVD) method in which $B_2H_6$ reacts with Mg vapor generated from Mg chips placed near the substrate.[18,19] The main obstacle to employing this latter approach in the fabrication of multilayer devices is the high deposition temperature of ca. 750° C., which will promote undesirable interfacial reactions.

A desirable method for incorporating $MgB_2$ into multilayer devices should produce crystalline, conformal films below 400° C. via an in situ deposition process without the need for a subsequent annealing process at an elevated temperature. To date, only the co-evaporation method comes close to this requirement, but this method cannot afford conformal films on topologically complex substrates. Thus, a need exists for designing and synthesizing volatile magnesium-containing compounds for the CVD of $MgB_2$.

SUMMARY OF THE INVENTION

The present invention provides compositions of matter useful as deposition agents for making structures, including thin film structures and hard coatings, on substrates and features of substrates. In an embodiment, for example, the present invention provides metal complexes, including but not limited to transition metal complexes and alkaline earth metal complexes (e.g., magnesium complexes), having one or more diboranamide or diboranaphosphide ligands that are useful as chemical vapor deposition (CVD), atomic layer deposition (ALD) precursors, and/or molecular beam epitaxy (MBE) precursors for making thin film structures and coatings. Metal complex CVD, ALD and MBE precursors are provided that possess volitilities sufficiently high so as to provide dense, smooth and homogenous thin films and coatings. In addition, metal complexes of the present invention useful as CVD, ALD and MBE precursors are capable of accessing a range of useful thin film and coating compositions, including metal oxide and metal boride thin films, such as metal diboride films. In an embodiment, metal complexes of the present invention provide single source CVD precursors for making high purity metal diboride thin films and/or CVD precursors capable of generating high purity thin films and/or coatings on substrates at relative low substrate processing temperatures (e.g., less than about 450 degrees Celsius). The present invention also provides methods of making metal complexes, including but not limited to transition metal complexes and alkaline earth metal complexes (e.g., magnesium complexes), having one or more diboranamide or diboranaphosphide ligands useful as deposition agents. As used herein and throughout this description, the term "metal" includes transition metal elements including the d-block transition metals and f-block metals, including both the lanthanides and the actinides, and also includes metals other than transition and f-block metals, including but not limited to, alkaline earth metals such as magnesium, calcium, strontium and barium.

The present invention provides CVD, ALD and MBE methods and precursor compositions for making thin films exhibiting mechanical and electronic properties useful for a range of electronic device fabrication applications, including applications for making integrated electronic devices and/or thin film electronic devices. For example, the present CVD, ALD and MBE methods and precursor compositions are capable of generating conformal and super conformal thin films, layers and coatings on a range of substrates, including electronic device substrates and substrates having contoured surfaces. Metal complex compositions and CVD methods of the present invention are capable of generating metal boride films and coatings exhibiting a high melting point, good mechanical hardness and large thermal and electrical conductivities. In addition, the present CVD, ALD and MBE methods and precursor compositions are useful for fabricating superconducting structures comprising high purity metal diboride thin films. The present methods are compatible with a wide range of existing materials processing techniques and processing conditions, and are useful for making a wide range of functional devices including, but not limited to, integrated electronic circuits, macroelectronic device arrays, memory devices, sensors, MEMS & NEMS systems, photovoltaic devices, and micro- and nanofluidic systems.

In an aspect, the present invention provides metal complexes having one or more diboranamide or diboranaphosphide ligands, which are particularly useful for making metal-containing structures via deposition techniques, such as CVD, ALD and MBE techniques. In an embodiment, the invention provides a composition of matter comprising a metal complex having the formula:

$$(ML_x)_zD_y \quad (F1)$$

wherein each M, independent of other M, is a metal atom selected from the group consisting of: Be, Mg, Ca, Sr, Ba, Ra, Al, Ga, In, Sc, Y, La, Ti, Zr, Hf, V, Nb, Ta, Cr, Mo, W, Mn, Re, Fe, Ru, Os, Co, Rh, Ir, Ni, Pd, Pt, Cu, Ag, Au, Zn, Hg, Ce, Pr, Nd, Pm, Sm, Eu, Gd, Tb, Dy, Ho, Er, Tm, Yb, Lu, Ac, Th, Pa, U, Np, Pu, Am, and Cm.
wherein each D, independent of other D, is a neutral coordinating ligand;
wherein x is equal to the oxidation state of M;
wherein y is 0, 1, 2, 3 or 4;
wherein z is 1, 2 or 3;
wherein each L, independent of other L, is an anionic ligand,
wherein at least one of L is a monoanionic group comprising a diboranamide or diboranaphosphide group having the formula;

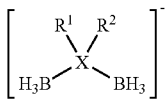
(F2)

wherein: each X is independently N or P;
wherein, independently for each L, $R^1$ and $R^2$ are functional groups independently selected from the group consisting of hydrogen, alkyl, haloalkyl, aryl, heteroaryl, trialkylsilyl, alkenyl, alkynyl, halogen, fluoroalkyl, silylalkyl, alkoxy, hydroxyl, amide, boryl, and thiolate. Optionally, in an embodiment L is has the formula (F3);

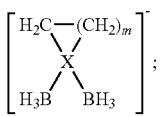
(F3)

wherein m is an integer from 1 to 7. Optionally, in an embodiment $R^1$ and $R^2$ are alkyl groups, such as $C_1$ to $C_{10}$ alkyl groups. Optionally, in an embodiment $R^1$ and $R^2$ are methyl groups.

In an embodiment of this aspect of the present invention, the metal complex comprises a monovalent metal, x is 1 and z is 1. In these embodiments, $(ML_x)_z$ in formula F1 has the formula ML. Monovalent metals useful in compositions of this embodiment of the present invention include, but are not limited to, Cu, Ag, and Au. In an embodiment, the present invention provides a composition having the formula F1 wherein ML has a formula selected from the group consisting of: $M((BH_3)_2NR_1R_2)$ and $M((BH_3)_2PR_1R_2)$. In an embodiment, for example, ML has a formula selected from the group consisting of:

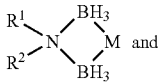
(F4)

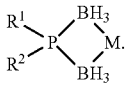
(F5)

Compositions of this embodiment of the present invention include, but are not limited to, metal complexes having a formula selected from the group consisting of:

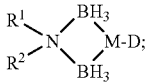
(F6)

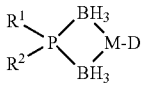
(F7)

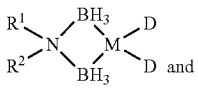
(F8)

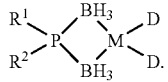
(F9)

In another embodiment of this aspect of the present invention, the metal complex comprises a divalent metal, x is equal to 2 and z is equal to 1. In these embodiments, $(ML_x)_z$ in formula F1 has the formula $ML_2$. Divalent metals useful in compositions of this embodiment of the present invention include, but are not limited to, Be, Mg, Ca, Sr, Ba, Ra, Ti, V, Nb, Cr, Mo, Mn, Re, Fe, Ru, Os, Co, Rh, Ir, Ni, Pd, and Pt. In an embodiment, the present invention provides a composition having the formula F1 wherein $ML_2$ has a formula selected from the group consisting of: $M((BH_3)_2NR_1R_2)_2$ and $M((BH_3)_2PR_1R_2)_2$. In an embodiment, for example, $ML_2$ has a formula selected from the group consisting of:

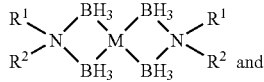
(F10)

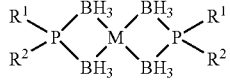
(F11)

Compositions of this embodiment of the present invention include, but are not limited to, metal complexes having a formula selected from the group consisting of:

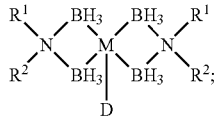
(F12)

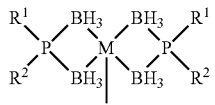
(F13)

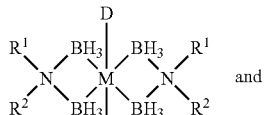
(F14)

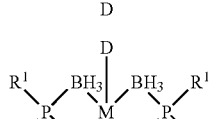
(F15)

In another embodiment of this aspect of the present invention, the metal complex comprises one or more trivalent metals, x is equal to 3 and z is equal to 1 or 2. In these embodiments, $(ML_x)_z$ in formula F1 has the formula $(ML_3)_z$, wherein z is 1 or 2. Trivalent metals useful in compositions of this embodiment of the present invention include, but are not limited to, Al, Ga, In, Sc, Y, La, Ce, Pr, Nd, Pm, Sm, Eu, Gd, Tb, Dy, Ho, Er, Tm, Yb, Lu, Ac, and U. In an embodiment, the present invention provides a composition having the formula F1 wherein $(ML_x)_z$ has a formula selected from the group consisting of: $M((BH_3)_2NR_1R_2)_3$, $M((BH_3)_2PR_1R_2)_3$, $(M((BH_3)_2NR_1R_2)_3)_2$ and $(M((BH_3)_2PR_1R_2)_3)_2$. In an embodiment, for example, $(ML_x)_z$ has the formula $ML_3$ and is selected from the group consisting of:

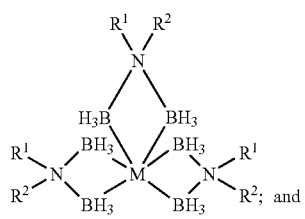
(F16)

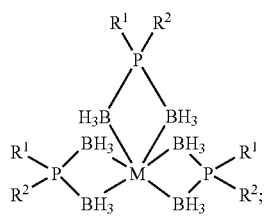
(F17)

In another embodiment, for example, $(ML_x)_z$ has the formula $(ML_3)_2$ and has a dimeric structure selected from the group consisting of:

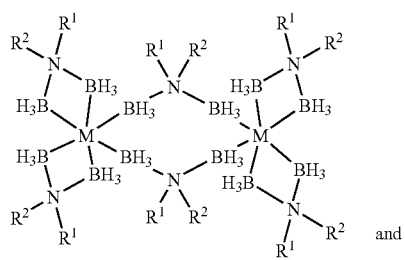
(F18)

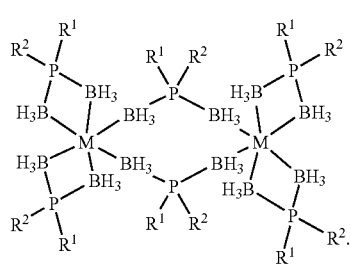
(F19)

Compositions of this embodiment of the present invention include, but are not limited to, metal complexes having a formula selected from the group consisting of:

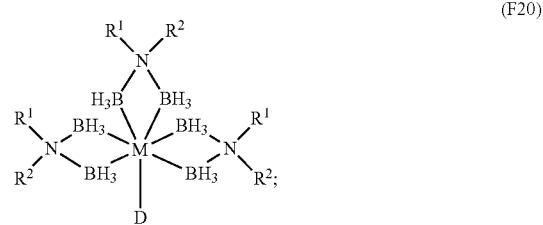
(F20)

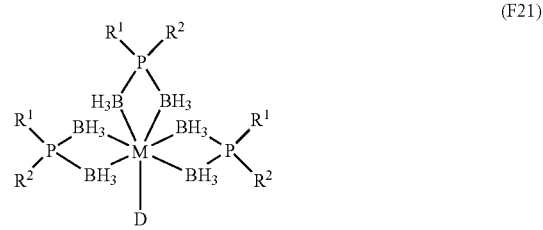
(F21)

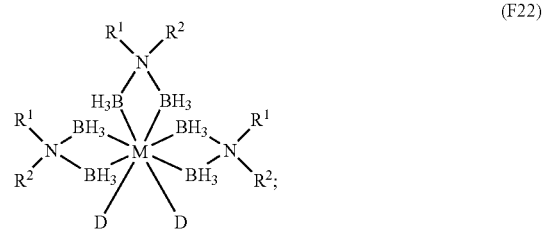
(F22)

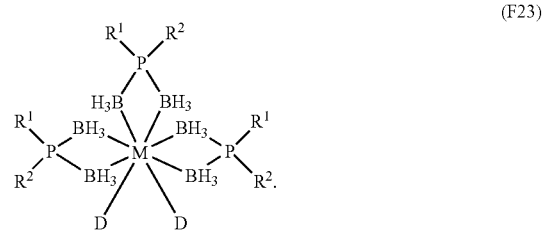
(F23)

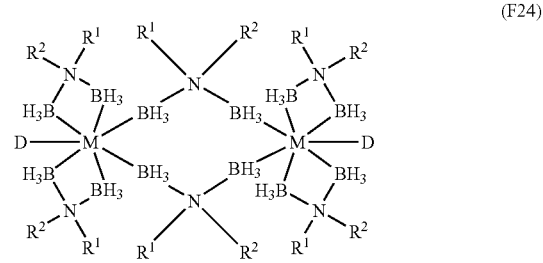
(F24)

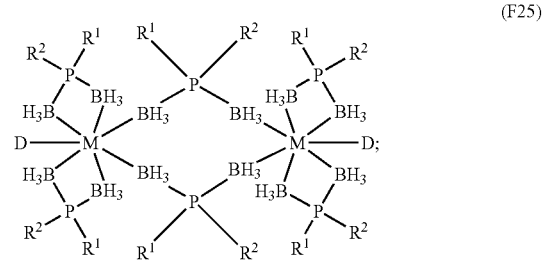
(F25)

-continued

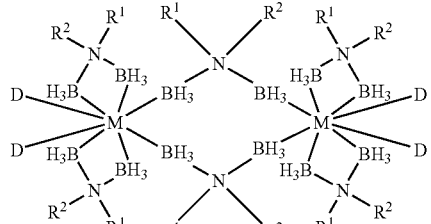
(F26)

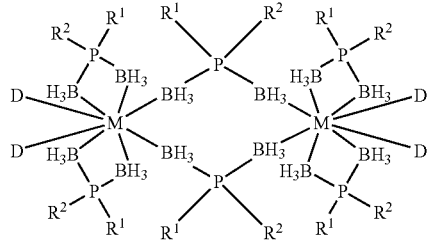
(F27)

Compositions of the present invention also include complexes similar to those illustrated by formula F18-F27 but containing bridging diboranamide or diboranaphosphide ligands with the $BH_3$ groups coordinating to their respective metals in a bidentate fashion via two B—H-M bridges. An example of this embodiment is observed in $Y_2(H_3BNMe_2BH_3)_6$ and $Dy_2(H_3BNMe_2BH_3)_6$.

Compositions of embodiment F18-F27 also include complexes that contain bridging diboranamide or diboranaphosphide ligands with the $BH_3$ groups coordinating to their respective metals in a tridentate fashion via three B—H-M bridges. An example of this embodiment is observed in structural isomer B of $U(H_3BNMe_2BH_3)_3$.

Compositions of embodiment F18-F27 also include, but are not limited to, complexes where the bridging diboranamide or diboranaphosphide ligands are chelating one metal center while simultaneously bridging to the adjacent metal center via a terminal B—H-M bridge. Examples of this embodiment are observed in $Eu_2(H_3BNMe_2BH_3)_4(thf)_4$ and in structural isomer A of $U(H_3BNMe_2BH_3)_3$.

In an embodiment, the present invention provides compositions wherein each L in formula F1 is a diboranamide or diboranaphosphide group. Alternatively, the present invention includes mixed ligand metal complexes wherein at least one L in formula F1 is a diboranamide or diboranaphosphide group, but at least one L in formula F1 is a different anionic group. In an embodiment, for example, the present invention includes mixed ligand metal complexes wherein at least one L in formula F1 is a diboranamide or diboranaphosphide group, and at least one L in formula F1 is an anionic ligand selected from the group consisting of: a cyclopentadienyl, a borohydride, β-diketonate, octahydroborato group, indenyl, β-diketiminate, pyrazolate, triazolate, amidinate, alkyl, alkoxide, thiolate, amide, imide, halide, hydride, sulfide, cyanide, thiocyanate, isothiocyanate, hydroxide, oxide, oxalate, nitrides, nitrite, nitrate, azide, phosphate, phosphite, and cyclooctatetraene dianion. In an embodiment, for example, the present invention includes mixed ligand metal complexes wherein at least one L in formula F1 is a diboranamide or diboranaphosphide group, and at least one L in formula F1 is an anionic ligand selected from the group consisting of: cyclopentadienyl, monomethylcyclopentadienyl, 1,2-dimethylcyclopentadienyl, 1,3-dimethylcyclopentadienyl, 1,2,3-trimethylcyclopentadienyl, 1,2,4-trimethylcyclopentadienyl, tetramethylcyclopentadienyl, pentamethylcyclopentadienyl, (trimethylsilyl)cyclopentadienyl, 1,3 bis(trimethylsilyl)cyclopentadienyl, 1,2,4-tris(trimethylsilyl)cyclopentadienyl, trifluoromethylcyclopentadienyl, tetrahydroborate, trihydrocyanoborate, trihydromethylborate; acetylacetonate (2,4-pentanedione anion), 1,1,1-(trifluoro)acetylacetonate (1,1,1-trifluoro-2,4-pentanedione anion), hexafluoroacetylacetonate (1,1,1,5,5,5-hexafluoro-2,4-pentanedione anion), 1,1,1-trifluoro-5,5-dimethyl-2,4-hexanedione anion, 2,2,4,4-tetramethyl-3,5-heptanedione anion, and octahydroborato ($B_3H_8^-$). As will be generally understood by those having skill in the art, the description above provides specific examples of anionic ligands for metal complexes of the present invention. Compositions having ligands other than those specifically exemplified are within the scope of the present invention.

A wide range of neutral coordinating ligands (D) are useful in the present compositions. In an embodiment, for example, D is a two-electron donor ligand. In an embodiment, neutral coordinating ligands (D) for the present compositions are selected from the group consisting of: alkenes ($R^3R^4C{=}CR^5R^6$), alkynes ($R^3C{\equiv}CR^4$), ethers ($R^3OR^4$), sulfides ($R^3SR^4$), amines ($R^3NR^4R^5$), nitriles ($R^3CN$), isonitriles ($R^3NC$), phosphines ($R^3PR^4R^5$), phosphites (($R^{30}$)P($OR^4$)($OR^5$)), arsines ($R^3AsR^4R^5$), and stibenes ($R^3SbR^4R^5$); wherein $R^3$, $R^4$, $R^5$ and $R^6$ are functional groups independently selected from the group consisting of hydrogen, alkyl, fluoroalkyl, aryl, alkenyl, alkynyl, and trialkylsilyl. In an embodiment, neutral coordinating ligands (D) for the present compositions are selected from the group consisting of: cyclic monoethers, linear polyethers, cyclic polyethers, cyclic monoamines, linear polyamines, cyclic polyamines, cyclic monophosphines, linear polyphosphines, cyclic polyphosphines, cyclic monoalkenes, linear polyenes, linear dienes, linear trienes, linear tetraenes, cyclic polyenes, cyclic dienes, cyclic trienes, cyclic tetraenes, cyclic monoalkynes, cyclic dialkynes, carbonyls, and trifluorophosphines.

In an embodiment, coordinating ligands (D) for the present compositions are selected from the group consisting of: tetrahydrofuran, 1,2-dimethoxyethane, diethylether, and dimethyl ether.

Composition of the present invention particularly attractive for use as a CVD, ALD or MBE precursor include, but are not limited to, $Mg(H_3BNMe_2BH_3)_2$; $Mg(H_3BNMe_2BH_3)_2$(tetrahydrofuran); $Mg(H_3BNMe_2BH_3)_2$(dimethoxyethane); $Ti(H_3BNMe_2BH_3)_2$; $Cr(H_3BNMe_2BH_3)_2$; $Mo(H_3BNMe_2BH_3)_2$; $Mn(H_3BNMe_2BH_3)_2$; $Y_2(H_3BNMe_2BH_3)_6$; $Y(H_3BNMe_2BH_3)_3$(tetrahydrofuran); $La_2(H_3BNMe_2BH_3)_6$; $La(H_3BNMe_2BH_3)_3$(tetrahydrofuran); $Ce_2(H_3BNMe_2BH_3)_6$; $Ce(H_3BNMe_2BH_3)_3$(tetrahydrofuran); $Pr(H_3BNMe_2BH_3)_3$(tetrahydrofuran); $Nd(H_3BNMe_2BH_3)_3$(tetrahydrofuran); $Sm(H_3BNMe_2BH_3)_3$(tetrahydrofuran); $Eu(H_3BNMe_2BH_3)_3$(tetrahydrofuran); $Dy_2(H_3BNMe_2BH_3)_6$; $Dy(H_3BNMe_2BH_3)_3$(tetrahydrofuran); $Er_2(H_3BNMe_2BH_3)_6$; $Er(H_3BNMe_2BH_3)_3$(tetrahydrofuran), and $U(H_3BNMe_2BH_3)_3$(tetrahydrofuran).

In another aspect, the present invention provides methods of making structures via deposition techniques, including chemical vapor deposition, atomic layer deposition, high density plasma (HDP) CVD, hot filament (surface) chemical vapor deposition and/or molecular beam epitaxy (MBE) techniques. In an embodiment of this aspect, the invention provides a method of making a structure comprising the step of contacting a substrate or a feature of a substrate with one or more metal complexes of the present invention having one or more diboranamide or diboranaphosphide ligands. Methods of this aspect of the present invention may further comprise the step of decomposing the metal complex(es) on a surface of the substrate or a surface of the feature of the substrate. Methods of the present invention are capable of generating structures having a wide range of shapes and physical dimensions, including physical dimensions ranging from a few nanometers to 1000s of microns, that comprise device components of an electronic device. Methods of the present invention are capable of generating structures on substrate features comprising prepatterned device components, on relief features of the substrate and recessed features of the substrate, such as a trench, trough, slit, channel, and via.

Metal complexes useful in this aspect of the invention are described above and exemplified in detail throughout the present description. Use of metal complexes having a high volatility is particularly beneficial for generating dense films and coatings having a substantially homogenous composition. Methods of this aspect of the present invention are capable of generating structures comprising metal-containing structures such as metal oxide and/or metal boride films, layers and coatings. In a preferred embodiment, deposition methods of the present invention generate metal diboride films exhibiting useful mechanical, thermal and electronic properties. Methods of this aspect of the present invention are also capable of generating structures comprising conformal or super-conformal films, layer and coatings on a range of substrates including electronic device substrates that are prepatterned with device components. Methods of this aspect of the present invention are also capable of generating structures comprising superconducting materials, such as $MgB_2$ films, useful in high performance electronic devices. Methods of this aspect of the present invention are also capable of generating hard coatings useful in a range of applications.

A method of making a structure of the present invention further comprises the steps of vaporizing one or more metal complexes of the present invention having one or more diboranamide or diboranaphosphide ligands, thereby generating a deposition gas, and contacting the substrate or the feature of a substrate with the deposition gas. In an embodiment, this processing step generates a deposition gas which is a chemical vapor deposition precursor, a MBE precursor or an atomic layer deposition precursor. Methods of this embodiment may optionally comprise the step of heating the substrate or the feature of the substrate during the step of contacting the substrate or the feature of a substrate with the deposition gas. Use of some metal complexes of the present invention having one or more diboranamide or diboranaphosphide ligands enables CVD, ALD and/or MBE methods wherein the substrate or the feature of the substrate is heated to a temperature less than or equal to approximately 450 degrees Celsius during processing. Such lower temperature deposition methods of the present invention are useful for accessing a broad range of thin film and coating compositions, including boron containing films and coatings, having useful mechanical and electronic properties.

In some embodiments, the present deposition methods utilize a metal complex having one or more diboranamide or diboranaphosphide ligands that comprises a single source CVD, ALD or MBE precursor. In these methods, metal-containing structures are generated by exposure of the substrate and/or feature of the substrate to a single CVD, ALD and/or MBE precursor of the present invention. Alternatively, the present invention includes deposition methods using one or more additional deposition gases or additives. In an embodiment, for example, the present methods further comprise the steps of providing one or more additional deposition gases; and contacting the substrate or the feature of the substrate with the one or more additional deposition gases. Additional depositions gases useful in the present invention include CVD, ALD and/or MBE precursors, including but not limited to, metal complexes of the present invention having one or more diboranamide or diboranaphosphide ligands.

The present invention includes deposition methods wherein the substrate and/or deposition gas are contacted with an additive during processing. In an embodiment, for example, the methods of the present invention further comprise the step of contacting the substrate or feature thereon with one or more chemical vapor deposition catalysts during deposition processing. Such embodiments of the present invention include catalyst assisted deposition methods that are particularly useful for accessing a broad range of thin film or coating compositions, including doped thin film/coating compositions. In another embodiment, deposition methods of the present invention further comprise the step of providing one or more deposition additives in contact with the deposition gas during the step of contacting the substrate or the feature of a substrate with the deposition gas. Use of additives in this aspect of the present invention is beneficial for accessing a range of useful thin film or coating compositions. Useful additives for generating metal oxide, metal nitride, boronitrides or borocarbonitrides thin film and/or coating compositions include, but are not limited to, $H_2O$, $O_2$, $O_3$, $NO_2$, $NH_3$, $N_2H_4$, $CO_2$, and $H_2$.

In another aspect, the present invention provides methods of making metal complexes having one or more diboranamide or diboranaphosphide ligands. In an embodiment, for example, the present invention provides a method of synthesizing a metal complex comprising the steps of:
(i) providing a metal salt having a formula selected from the group consisting of $MCl_n$, $MBr_n$, and $MI_n$, wherein M, is a metal selected from the group consisting of: Be, Mg, Ca, Sr, Ba, Ra, Al, Ga, In, Sc, Y, La, Ti, Zr, Hf, V, Nb, Ta, Cr, Mo, W, Mn, Re, Fe, Ru, Os, Co, Rh, Ir, Ni, Pd, Pt, Cu, Ag, Au, Zn, Hg, Ce, Pr, Nd, Pm, Sm, Eu, Gd, Tb, Dy, Ho, Er, Tm, Yb, Lu, Ac, Th, Pa, U, Np, Pu, Am and Cm; wherein n is 1, 2, 3 or 4; and
(ii) contacting the metal salt with an alkali metal diboranamide reagent or alkali metal diboranaphosphide reagent having the formula:

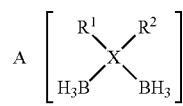
(F28)

wherein A is an alkali metal;
wherein X is N or P;
wherein $R^1$ and $R^2$ are functional groups independently selected from the group consisting of hydrogen, alkyl, haloalkyl, aryl, heteroaryl, trialkylsilyl, alkenyl, alkynyl, halogen, fluoroalkyl, silylalkyl, alkoxy, hydroxyl, aldehyde, amide, nitrile, ether, ester, and thiol.

In an embodiment of this aspect of the present invention $R^1$ and $R^2$ are alkyl groups, such as $C_1$ to $C_{10}$ alkyl groups, for example methyl groups. In an embodiment, the alkali metal diboranamide reagent or alkali metal diboranaphosphide reagent is selected from the group consisting of: $Na(H_3BNMe_2BH_3)$, $K(H_3BNMe_2BH_3)$, $L_1(H_3BNMe_2BH_3)$, $Na(H_3BPMe_2BH_3)$, $K(H_3BPMe_2BH_3)$, $L_1(H_3BPMe_2BH_3)$ and adducts of these reagents with donor molecules such as, adducts of these reagents with tetrahydrofuran, 1,2-dimethoxyethane, diethylether, and dimethyl ether.

Synthetic methods for making metal complexes of the present invention can be carried out in the solid phase or in the solution phase. In an embodiment, for example, methods of the present invention comprise the step of contacting the metal salt and the alkali metal diboranamide reagent or alkali metal diboranaphosphide reagent in the solid phase, for example via mixing solid reagents. Alternatively, methods of the present invention in some embodiments comprise the step of contacting the metal salt and the alkali metal diboranamide reagent or alkali metal diboranaphosphide reagent in a solvent. Solvents for the present synthetic methods may be selected from the group consisting of ethers, polyethers, cyclic ethers, thiothers, amines (aliphatic or aromatic, primary, secondary, or tertiary), polyamines, nitriles, cyanates, isocyanates, thiocyanates, esters, aldehydes, toulene, saturated or unsaturated hydrocarbons (linear, branched, or cyclic), halogenated hydrocarbons, silylated hydrocarbons, amides or compounds containing combinations of any of the above, or mixtures of one or more of the above. Useful solvents in synthetic methods of the present invention include, but are not limited to, tetrahydrofuran, dimethoxyethane, diethylether, and dimethyl ether.

Synthetic methods of the present invention may further comprise one or more purification steps. As will be understood by those having skill in the art a variety of purification methods may be used in the present methods, including sublimation, chromatographic methods, crystallization, vacuum removal of solvent, washing, and solvent extraction. Purification via sublimation is preferred for some applications of the present invention.

In another aspect the present invention comprises a device component or electronic device comprising one or more structures generated by a method comprising the step of contacting a substrate or a feature of a substrate with one or more metal complexes of the present invention having one or more diboranamide or diboranaphosphide ligands.

In another aspect the present invention provides a composition of matter comprising a metal complex having the formula:

$$M(B_3H_8)_xD_y \quad (F29)$$

wherein M is a metal atom selected from the group consisting of: Be, Mg, Ca, Sr, Ba, Ra, Al, Ga, In, Sc, Y, La, Ti, Zr, Hf, V, Nb, Ta, Mo, W, Mn, Re, Fe, Ru, Os, Co, Rh, Ir, Ni, Pd, Pt, Cu, Ag, Au, Zn, Hg, Ce, Pr, Nd, Pm, Sm, Eu, Gd, Tb, Dy, Ho, Er, Tm, Yb, Lu, Ac, Th, Pa, U, Np, Pu, Am, and Cm;
wherein each D, independent of other D, is a neutral coordinating ligand;
wherein x is the oxidation state of M; and
wherein y is 0, 1, 2, 3 or 4.
In an embodiment of this aspect of the invention, M is optionally Mg.

Similar to the compositions described above in the context of formula F1, D can optionally be a two-electron donor ligand. In an embodiment, D is selected from the group consisting of: alkenes ($R^3R^4C=CR^5R^6$), alkynes ($R^3C\equiv CR^4$), ethers ($R^3OR^4$), sulfides ($R^3SR^4$), amines ($R^3NR^4R^5$), nitriles ($R^3CN$), isonitriles ($R^3NC$), phosphines ($R^3PR^4R^5$), phosphites (($R^{30}$)P($OR^4$)($OR^5$)), arsines ($R^3AsR^4R^5$), and stibenes ($R^3SbR^4R^5$); wherein $R^3$, $R^4$, $R^5$ and $R^6$ are functional groups independently selected from the group consisting of hydrogen, alkyl, fluoroalkyl, aryl, alkenyl, alkynyl, and trialkylsilyl. In an embodiment, D is selected from the group consisting of: cyclic monoethers, linear polyethers, cyclic polyethers, cyclic monoamines, linear polyamines, cyclic polyamines, cyclic monophosphines, linear polyphosphines, cyclic polyphosphines, cyclic monoalkenes, linear polyenes, linear dienes, linear trienes, linear tetraenes, cyclic polyenes, cyclic dienes, cyclic trienes, cyclic tetraenes, cyclic monoalkynes and cyclic dialkynes. In an embodiment, D is selected from the group consisting of tetrahydrofuran, 1,2-dimethoxyethane, diethylether, and dimethyl ether.

In an embodiment, the composition of this aspect of the invention has a formula selected from the group consisting of: $Mg(B_3H_8)_2$, $Mg(B_3H_8)_2(Et_2O)_2$, and $Mg(B_3H_8)_2(Me_2O)_2$.

Compositions of this aspect of the present invention (i.e., having the formula F29) are useful as deposition agents in a variety of application including use as CVD ALD and MBE precursors. Similar to the description of uses of the compositions formula F1, compositions having the formula F29 are useful for making a wide range of metal containing structures, including thin films, thin film structures and coatings.

In another aspect, the present invention provides a method of making a structure comprising the step of contacting a substrate or a feature of a substrate with a composition having the formula F29. Optionally, methods of this aspect may further comprise the step of decomposing said composition having formula F29 on a surface of said substrate or a surface of said feature of said substrate. Optionally, methods of this aspect may further comprising the steps of: vaporizing the composition having formula F29, thereby generating a deposition gas; and contacting said substrate or said feature of said substrate with said deposition gas.

In an embodiment, a composition of the invention is isolated or purified. In an embodiment, an isolated or purified compound may be at least partially isolated or purified as would be understood in the art.

Without wishing to be bound by any particular theory, there can be discussion herein of beliefs or understandings of underlying principles or mechanisms relating to the invention. It is recognized that regardless of the ultimate correctness of any explanation or hypothesis, an embodiment of the invention can nonetheless be operative and useful.

BRIEF DESCRIPTION OF THE DRAWINGS

FIG. 28A shows an example of an ultra-conformal MgO film grown on a deep trench structure with depth to width ratio equal to 30:1. FIGS. 28B and 28C demonstrate the trade off in the conformality with growth rate by varying the deposition conditions.

Figure 1:
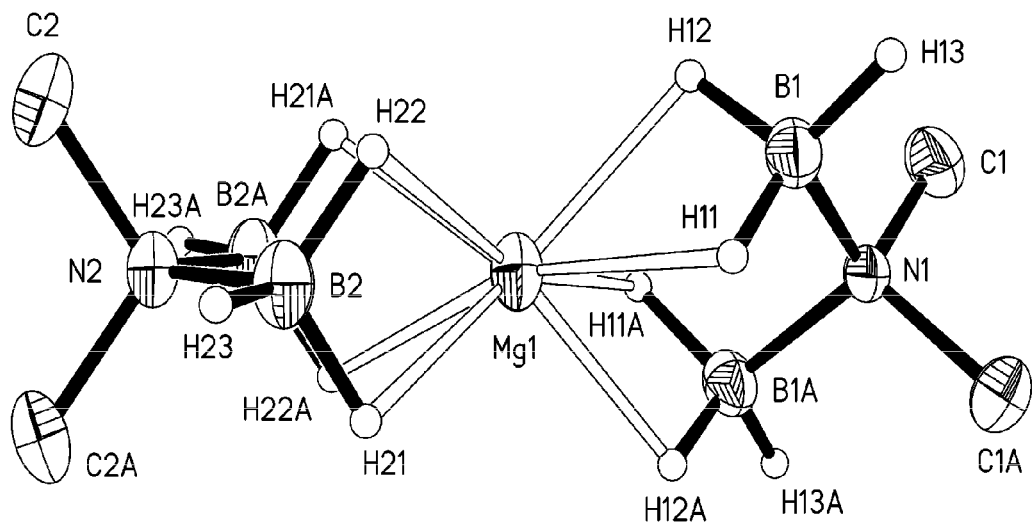
FIG. 1. The molecular structure of $Mg(H_3BNMe_2BH_3)_2$, which was determined by single crystal X-ray crystallography.

Example 12, Table 1. Crystallographic Data for Mg(B$_3$H$_8$)$_2$(Et$_2$O)$_2$ (2), Mg(B$_3$H$_8$)$_2$(Me$_2$O)$_2$ (3).

Example 12, Table 2. Selected Bond Lengths (Å) and Angles (deg) for Mg(B$_3$H$_8$)$_2$(Et$_2$O)$_2$ (2).$^a$ Example 12, Table 3. Selected Bond Lengths (Å) and Angles (deg) for Mg(B$_3$H$_8$)$_2$(Me$_2$O)$_2$ (3).

Example 13, Table 1. Crystallographic Data for Mg(H$_3$BNMe$_2$BH$_3$)$_2$ (1), Mg(H$_3$BNMe$_2$BH$_3$)$_2$(thf) (2), Mg(H$_3$BNMe$_2$BH$_3$)$_2$(dme) (3), and Cp*Mg(H$_3$BNMe$_2$BH$_3$)(thf) (4).

Example 13, Table 2. Selected Bond Lengths (Å) and Angles (deg) for Mg(H$_3$BNMe$_2$BH$_3$)$_2$ (1).$^a$ Example 13, Table 3. Selected Bond Lengths (Å) and Angles (deg) for Mg(H$_3$BNMe$_2$BH$_3$)$_2$(thf) (2).

Example 13, Table 4. Selected Bond Lengths (Å) and Angles (deg) for Mg(H$_3$BNMe$_2$BH$_3$)$_2$(dme) (3).

Example 13, Table 5. Selected Bond Lengths (Å) and Angles (deg) for Cp*Mg(H$_3$BNMe$_2$BH$_3$)(thf) (4).

Example 14, Table 1. Crystallographic Data for Y$_2$(H$_3$BNMe$_2$BH$_3$)$_6$ (1), Y(H$_3$BNMe$_2$BH$_3$)$_3$(thf) (2), Dy$_2$(H$_3$BNMe$_2$BH$_3$)$_6$ (3), and Dy(H$_3$BNMe$_2$BH$_3$)$_3$(thf) (4).

Example 14, Table 2. Selected Bond Lengths (Å) and Angles (deg) for Y$_2$(H$_3$BNMe$_2$BH$_3$)$_6$ (1).

Example 14, Table 3. Selected Bond Lengths (Å) and Angles (deg) for Dy$_2$(H$_3$BNMe$_2$BH$_3$)$_6$ (2).

Example 14, Table 4. Selected Bond Lengths (Å) and Angles (deg) for Y(H$_3$BNMe$_2$BH$_3$)$_3$(thf) (3).

Example 14, Table 5. Selected Bond Lengths (Å) and Angles (deg) for Dy(H$_3$BNMe$_2$BH$_3$)$_3$(thf) (4).

Example 15, Table 1. Compositions of films obtained from Mg(H$_3$BNMe$_2$BH$_3$)$_2$ in the presence of various co-reactants. All films were deposited on Si(100) substrates at 350° C. with a Mg(H$_3$BNMe$_2$BH$_3$)$_2$ line pressure of ~150 mTorr. The film stoichiometries were determined from Auger depth profiles; films that deviate from the MB$_2$ stoichiometry may be compositionally heterogeneous.

Example 16, Table 1. Summary of the magnesium containing precursors used for CVD/ALD growth of MgO thin films.

DETAILED DESCRIPTION OF THE INVENTION

Referring to the drawings, like numerals indicate like elements and the same number appearing in more than one drawing refers to the same element. In addition, hereinafter, the following definitions apply:

The expression "metal complex" refers to a composition comprising one or more metal atoms associated with one or more other groups including ligand groups such as neutral coordinating ligands and ionic coordinating ligands. Metal complexes include coordination compounds comprising one or more metals bound to one or more other groups via coordinate covalent bonds, ionic compounds comprising one or more metals participating in ionic bonding with one or more other groups, and compounds wherein one or more metals are bonded to one or more other groups via covalent and/or ionic bonding. Metal complexes of the present invention include metals bound to one or more ligands selected from the group consisting of diboranamide group ligands, diboranaphosphide group ligands, and optionally anionic ligands other than diboranamide group ligands, diboranaphosphide group ligands, and optionally neutral coordinating ligands. In some embodiments, metal complexes of the present invention include mixed ligand compositions including metals bound to one or more anionic ligands including one or more diboranamide group ligands and/or diboranaphosphide group ligands and one or more anionic ligands other than diboranamide group ligands and/or diboranaphosphide group ligands, and optionally neutral coordinating ligands.

The expression "diboranamide group" refers to a group having a charge of −1, in which two BH$_3$ units and two organic substituents are bound to a central nitrogen atom. The expression "diboranaphosphide group" refers to a group having a charge of −1, in which two BH$_3$ units and two organic substituents are bound to a central phosphorus atom. The diboranamide group and diboranaphosphide group may be illustrate by the formula:

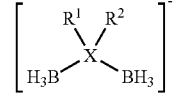

wherein X is N for the diboranamide group and x is P for the diboranaphosphide group. R$^1$ and R$^2$ may be a range of functional groups including, but not limited to, hydrogen, alkyl, haloalkyl, aryl, heteroaryl, trialkylsilyl, alkenyl, alkynyl, halogen, fluoroalkyl, silylalkyl, alkoxy, hydroxyl, amide, boryl, and thiolate. The H$_3$BNMe$_2$BH$_3$ group may be referred to by the abbreviation "DMDBA".

The expression "neutral coordinating ligand" refers to a ligand that does not possess a net electrical charge. Neutral coordinating ligands are not ionic species. Neutral coordinating ligands include, but are not limited to, Lewis bases such as two-electron donor ligands. Neutral coordinating ligands include mondentate, bidentate and polydentate ligands.

Tetrahydrofuran may be referred to by the abbreviation "thf".

Dimethoxyethane may be referred to by the abbreviation "DME".

The expression "oxidation state of a metal" refers to an indicator of the degree of oxidation of a metal atom in a chemical compound. The oxidation state is the hypothetical charge that the metal atom would have if all ligands are assigned closed shell electronic structures. Metal atoms capable of having an oxidation state of +1 include, but are not limited to, Li, Na, K, Rb, Cs, Cu, Ag, Au, Hg, and Tl. Metal atoms capable of having an oxidation state of +2 include, but are not limited to, Be, Mg, Ca, Sr, Ba, Ra, Ti, V, Nb, Cr, Mo, Mn, Re, Eu, Yb, Sm, Ru, Os, Co, Rh, Ir, Ni, Pd, Pt, W, and Fe. Metal atoms capable of having an oxidation state of +3 include, but are not limited to, Al, Ga, In, Sc, Y, La, Ti, V, Nb, Ta, Cr, Mo, W, Mn, Fe, Os, Co, Rh, Ru, Ir, Ce, Pr, Nd, Pm, Sm, Eu, Gd, Tb, Dy, Ho, Er, Tm Yb, Lu, Ac, U, Lu, Ac, Th, Pa, U, Np, Pu, Am, and Cm. Metal atoms capable of having an oxidation state of +4 include, but are not limited to, Ti, Zr, Hf, V, Nb, Ta, Mn, Zr, Mo, Ru, Rh, Pd, Sn, Hf, W, Re, Os, Ir, Pt, Pb, Ce, Pr, Th, U, Pr, Th, Pa, U, Np, and Pu. Metal atoms capable of having an oxidation state of +5 include, but are not limited to, V, Nb, Mo, Ta, W, Pa, U, and Np. Metal atoms capable of having an oxidation state of +6 include, but are not limited to, Mn, Mo, Ru, W, Re, Os, Ir, and U.

"Conformal layer" refers to the physical characteristics of a layer of deposited material on a substrate or a feature of a substrate. Conformal layers preferably lack gaps or voids having a volume larger than about $10^{-6}$ $\mu m^3$ within the bulk phase of the conformal layer or positioned between the layer and the surfaces of a feature coated by the layer. Conformal layers have uniform thickness at any surface of the feature (with variation less than about 20%). Conformal layers in the present invention may have a uniform composition throughout the layer or may have a composition that varies through all or a portion of the layer. The term "superconformal" refers to the result in which the thickness of coating on the sidewall proximate to the bottom of the feature is larger than the thickness of coating on a surface immediately outside of the feature adjacent to its opening.

Alkyl groups include straight-chain, branched and cyclic alkyl groups. Alkyl groups include those having from 1 to 30 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. Cyclic alkyl groups include those having one or more rings. Cyclic alkyl groups include those having a 3-, 4-, 5-, 6-, 7-, 8-, 9- or 10-member carbon ring and particularly those having a 3-, 4-, 5-, 6-, or 7-member ring. The carbon rings in cyclic alkyl groups can also carry alkyl groups. Cyclic alkyl groups can include bicyclic and tricyclic alkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cyclic alkenyl groups include those having one or more rings. Cyclic alkenyl groups include those in which a double bond is in the ring or in an alkenyl group attached to a ring. Cyclic alkenyl groups include those having a 3-, 4-, 5-, 6-, 7-, 8-, 9- or 10-member carbon ring and particularly those having a 3-, 4-, 5-, 6- or 7-member ring. The carbon rings in cyclic alkenyl groups can also carry alkyl groups. Cyclic alkenyl groups can include bicyclic and tricyclic alkyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms.

Aryl groups include groups having one or more 5- or 6-member aromatic or heteroaromatic rings. Aryl groups can contain one or more fused aromatic rings. Heteroaromatic rings can include one or more N, O, or S atoms in the ring. Heteroaromatic rings can include those with one, two or three N, those with one or two O, and those with one or two S, or combinations of one or two or three N, O or S. Aryl groups are optionally substituted. Substituted aryl groups include among others those which are substituted with alkyl or alkenyl groups, which groups in turn can be optionally substituted. Specific aryl groups include phenyl groups, biphenyl groups, pyridinyl groups, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl having one or more hydrogens replaced with one or more fluorine atoms, chlorine atoms, bromine atoms and/or iodine atoms.

Optional substitution of any alkyl, alkenyl and aryl groups includes substitution with one or more of the following substituents: halogens, —CN, —COOR, —OR, —COR, —OCOOR, —CON(R)$_2$, —OCON(R)$_2$, —N(R)$_2$, —NO$_2$, —SR, —SO$_2$R, —SO$_2$N(R)$_2$ or —SOR groups. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for alkyl, alkenyl and aryl groups include among others:

—COOR where R is a hydrogen or an alkyl group or an aryl group and more specifically where R is methyl, ethyl, propyl, butyl, or phenyl groups all of which are optionally substituted;

—COR where R is a hydrogen, or an alkyl group or an aryl groups and more specifically where R is methyl, ethyl, propyl, butyl, or phenyl groups all of which groups are optionally substituted;

—CON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;

—OCON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;

—N(R)$_2$ where each R, independently of each other R, is a hydrogen, or an alkyl group, acyl group or an aryl group and more specifically where R is methyl, ethyl, propyl, butyl, or phenyl or acetyl groups all of which are optionally substituted; or R and R can form a ring which may contain one or more double bonds.

—SR, —SO$_2$R, or —SOR where R is an alkyl group or an aryl groups and more specifically where R is methyl, ethyl, propyl, butyl, phenyl groups all of which are optionally substituted; for —SR, R can be hydrogen;

—OCOOR where R is an alkyl group or an aryl groups;

—SO$_2$N(R)$_2$ where R is a hydrogen, an alkyl group, or an aryl group and R and R can form a ring;

—OR where R=H, alkyl, aryl, or acyl; for example, R can be an acyl yielding —OCOR* where R* is a hydrogen or an alkyl group or an aryl group and more specifically where R* is methyl, ethyl, propyl, butyl, or phenyl groups all of which groups are optionally substituted;

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

As to any of the above groups which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

The compounds of this invention may contain one or more chiral centers. Accordingly, this invention is intended to include racemic mixtures, diasteromers, enantiomers and mixture enriched in one or more stereoisomer. The scope of the invention as described and claimed encompasses the racemic forms of the compounds as well as the individual enantiomers and non-racemic mixtures thereof.

An objective of the current invention is to provide a process for the preparation of volatile metal complexes containing N,N-(disubstituted)diboranamide ("diboranamide") or P,P-(disubstituted)diboranaphosphide ("diboranaphosphide") groups, which are useful for chemical vapor deposition (CVD) of metal diborides or metal-containing films on substrates. The diboranamide group is defined here as a group with the charge of −1, in which two BH$_3$ units and two organic substituents are bound to a central nitrogen atom. The diboranaphosphide group is defined here as a group with the charge of −1, in which two BH$_3$ units and two organic substituents are bound to a central phosphorus atom. In one aspect, the present invention relates to a method of depositing metal-containing layers on substrates by vaporizing and decomposing metal complexes of formula F1.

The present invention provides novel metal complexes containing N,N-(disubstituted)diboranamide ("diboranamide") or P,P-(disubstituted)diboranaphosphide ("diboranaphosphide") groups, which are useful for chemical vapor deposition (CVD) of metal diborides or other metal-containing films on substrates. Novel reactions to prepare the metal complexes of these groups are also provided. The diboranamide group is defined here organic groups with the charge of −1, in which two BH$_3$ groups and two organic substituents are bound to a central nitrogen atom. The diboranaphosphide group is defined here as a group with the charge of −1, in which two BH$_3$ units and two organic substituents are bound to a central phosphorus atom.

Some of the ligands of formula F2 are known to those skilled in the art. For example, the ligand L in the compounds of formula F2, where $R^1$ and $R^2$ are the methyl groups, has been reported by A. B. Burg et. al. (*Inorg, Chem.* 1965, 4, 1467), C. Keller et. al. (*Inorg. Chem.* 1971, 10, 2256) and H. Nöth et. al. (*Eur. J. Inorg. Chem.* 1999, 1373). The compounds of formula I may be prepared in a variety of suitable ways. One method to prepare the compounds of formula I, for example, is treating sodium N,N-dialkyldiboranamides with metal halide compounds followed by subliming the products from the reaction mixtures.

The solvents that are suitable for preparation of the compounds of present invention can be one or more of the followings: no solvent (solventless solid state reaction), ethers, polyethers, cyclic ethers, thiothers, amines (aliphatic or aromatic, primary, secondary, or tertiary), polyamines, nirtiles, cyanates, isocyanates, thiocyanates, esters, aldehydes, toulene, saturated or unsaturated hydrocarbons (linear, branched, or cyclic), halogenated hydrocarbons, silylated hydrocarbons, amides or compounds containing combinations of any of the above, or mixtures of one or more of the above. In a preferred embodiment, the solvent system includes, for example, solventless solid state reaction system, solid state reaction under non-coordinating solvents (e.g. pentane, toluene, or halogenated hydrocarbon), ethers (e.g., diethylether), polyethers (e.g., dimethoxyethane), and cyclic ethers (e.g., tetrahydrofuran). The product may be isolated from the reaction mixture in many different ways including, for example, sublimation, or crystallization from the solution containing products. Typically, highly pure product is isolated by sublimation from crystallized solid product.

Any suitable method using the volatile compound of formula I can be used to prepare metal-containing films. The metal complexes of formula I in the present invention may be introduced onto a substrate as a vapor, decompose and form a layer containing one or more metals in the form of a metal-containing film. A metal complex is preferably delivered and decomposed as a vapor in CVD, ALD, or molecular beam epitaxy (MBE). The decomposition of metal complexes in CVD, ALD, or MBE processes affords layers containing one or more metals on substrates. Metal borides, metal borocarbides, or metal boron-carbonitrides are deposited if the metal complexes are decomposed under inert condition in which no other vapor except the metal complex vapor or inert gas such as argon. If the decomposition is carried out under an oxidizing atmosphere in which gas molecules containing oxygen such as water, oxygen, ozone, carbon dioxide or nitrogen dioxide is present, metal oxides are formed. When amine species such as ammonia or hydrazine are used as gaseous co-reactants, layers containing metals in the form of nitrides, boronitrides, or borocarbo-nitrides are deposited. In one embodiment of the invention, the metal complexes in this invention may be used as dopants in small amounts in other phases: for example, the magnesium compound of formula I may be used as a magnesium dopant in the preparation of p-type semiconductor materials such as GaN and AlGaN.

An apparatus for the deposition of layers from gaseous metal complexes is typically pressure tight and can be evacuated. Thus, deposition processes are typically carried out under reduced pressure and the metal complexes are transported into the apparatus as vapors. Inert or reactive carrier gases, or other gaseous co-reactants can also be introduced into the apparatus. Decomposition of the precursors on a substrate is conducted by known methods such as thermal decomposition, plasma or radiation-induced decomposition, or photolytic decomposition. The principles of processes and apparatus for the deposition of films are well known in the art.

The vaporization of precursors may be carried out by conventional vaporization methods from solid precursors. The vaporization methods may also include the nebulization of solid precursors, where before the nebulization, solid precursors may be dissolved in organic solvents, including hydrocarbons such as decane, dodecane, tetradecane, toluene, xylene and mesitylene, and ethers, esters, ketones, and chlorinated hydrocarbons. The precursor solution may also be delivered onto a substrate by direct injection of the solutions. A carrier gas that is passed through or over the precursor may be used to enhance the vaporization of the precursor especially when higher precursor flux is needed.

The present invention will be further illustrated by the following non-limiting examples. The particular materials, amounts, conditions, and other details in these examples should not be construed to limit the scope of the present invention to their details.

All experiments were carried out under vacuum or under argon by using standard Schlenk techniques. Solvents were distilled under nitrogen from sodium/benzophenone immediately before use. The starting material Na($H_3$BNMe$_2$BH$_3$) was prepared by the method of H Nöth et al., *Eur. J. Inorg. Chem.* 8, 1383 (1999). TiCl$_3$(thf)$_3$, VCl$_3$(thf)$_3$, CrCl$_3$(thf)$_3$, MoCl$_3$(thf)$_3$ were prepared by literature procedures. MnCl$_2$ was dried with thionyl chloride. MgBr$_2$, YCl$_3$, and DyCl$_3$ were used as received from Aldrich. All metal compounds produced by the following procedures are often pyrophoric. They should be handled with strict exclusion of air and moisture in a well-ventilated fume hood. The IR spectra were recorded on a Nicolet Impact 410 instrument as Nujol mulls. The $^1$H and $^{11}$B NMR data were collected on Varian Unity Inova 600 instrument at 599.761 and 192.432 MHz, respectively. Chemical shifts are reported in δ units (positive shifts to high frequency) relative to tetramethylsilane ($^1$H NMR) or BF$_3$.Et$_2$O ($^{11}$B NMR). Field desorption (FD) and field ionization (FI) mass spectra were recorded on a Micromass 70-VSE mass spectrometer; for FD spectra, the samples were loaded as C$_6$H$_6$ solutions and the spectrometer source temperature was slowly warmed to 100° C. while collecting the data. The shapes of all peak envelopes correspond with those calculated from the natural abundance isotopic distributions. Magnetic moments were determined in C$_6$D$_6$ by the Evans NMR method on a Varian Gemini 500 instrument at 499.699 MHz.

Example 1

Synthesis of bis(N,N-dimethyldiboranamido) magnesium(II), Mg(H$_3$BNMe$_2$BH$_3$)$_2$ MgBr$_2$ powder (1.94 g, 10.5 mmol) and sodium dimethyldiboranamide (2.0 g, 21.0 mmol) were combined and mixed with the use of a mortar and pestle. The ground reaction mixture was transferred in a 100 round-bottom Schlenk flask. The Schlenk flask was capped with a water-cooled cold finger and evacuated. Sublimation under static vacuum afforded colorless product over 8 hours.

Yield: 1.13 g (64%). Sublimation: 20-70° C. at 0.05 Torr. Vapor pressure at 20° C.: 0.8±0.1 torr. Mp: 70° C. $^1$H NMR (C$_7$D$_8$, 20° C.): δ 2.04 (s, 12H, NMe$_2$), 1.91 (q, J$_{BH}$=90.0 Hz, 12H, BH$_3$). $^{13}$C{$^1$H} NMR(C$_7$D$_8$, 20° C.): δ 50.98 (s, NMe$_2$). Anal. Calcd for C$_4$H$_{24}$N$_2$B$_4$Mg: C, 28.6; H, 14.4; N, 16.6; B, 25.8; Mg, 14.5. Found: C, 28.6; H, 15.1; N, 16.6, B, 25.7; Mg, 14.1.

The molecular structure of Mg(H$_3$BNMe$_2$BH$_3$)$_2$, which was determined by single crystal X-ray crystallography, is shown in FIG. 1. Mg(H$_3$BNMe$_2$BH$_3$)$_2$ is a monomeric compound in which two [H$_3$BNMe$_2$BH$_3$]$^-$ ligands coordinate to the magnesium center by means of eight Mg to hydrogen bonds. All Mg—H distances are equal within experimental error, averaging 2.02 Å and the two diboranamide ligands describe a dihedral angle of 46.7°

Example 2

Synthesis of bis(N,N-dimethyldiboranamido)(tetrahydrofuran)magnesium(II), Mg(H$_3$BNMe$_2$BH$_3$)$_2$(thf)

To a suspension of MgBr$_2$ (0.51 g, 2.8 mmol) in thf (20 ml) at room temperature was added a solution of Na(H$_3$BNMe$_2$BH$_3$) (0.53 g, 5.6 mmol) in thf (30 ml). After the reaction mixture had been stirred for 8 h at room temperature, the solvent was removed in vacuum. Colorless solid was isolated as a product by sublimation.

Yield: 0.31 g (47%). Sublimation: 70° C. at 0.05 Torr. $^1$H NMR(C$_7$D$_8$, 20° C.): δ 3.57 (m, 4H, OCH$_2$), 2.33 (s, 12H, NMe$_2$), 1.99 (q, J$_{BH}$=84.5 Hz, 12H, BH$_3$), 1.28 (m, 4H, OCH$_2$CH$_2$). $^{13}$C{$^1$H} NMR(C$_7$D$_8$, 20° C.): δ 69.2 (s, OCH$_2$), 52.4 (s, NCH$_3$), 25.5 (s, OCH$_2$CH$_2$). Anal. Calcd for C$_8$H$_{32}$N$_2$B$_4$OMg: C, 40.1; H, 13.4; N, 11.7; B, 18.0; Mg, 10.1. Found: C, 39.5; H, 13.3; N, 11.3; B, 16.0; Mg, 10.5.

Example 3

Synthesis of bis(N,N-dimethyldiboranamido)(1,2-dimethoxyethane)magnesium(II), Mg(H$_3$BNMe$_2$BH$_3$)$_2$(dme)

The synthesis of this compound is similar to that of Mg(H$_3$BNMe$_2$BH$_3$)$_2$(thf) in Example 2, using 1,2-dimethoxyethane instead of thf. Colorless crystals were obtained by sublimation.

Yield: 0.27 g (37%). Sublimation: 80° C. at 0.05 Torr. $^1$H NMR(C$_6$D$_6$, 20° C.): δ 3.00 (s, 6H, OMe), 2.81 (s, 4H, OCH$_2$), 2.48 (s, 12H, NMe$_2$), 2.11 (q, J$_{BH}$=88.5 Hz, 12H, BH$_3$). $^{13}$C{$^1$H} NMR(C$_6$D$_6$, 20° C.): δ 69.6 (s, OCH$_2$), 59.6 (s, OCH$_3$), 52.6 (s, NMe$_2$). Anal. Calcd for $C_8H_{34}N_2B_4O_2Mg$: C, 37.3; H, 13.3; N, 10.9; B, 16.8; Mg, 9.42. Found: C, 36.4; H, 13.2; N, 10.4; B, 17.1; Mg, 9.92.

Example 4

Synthesis of bis(N,N-dimethyldiboranamido)titanium(II), $Ti(H_3BNMe_2BH_3)_2$

To a suspension of $TiCl_3(thf)_3$ (1.31 g, 3.5 mmol) in diethyl ether (20 mL) at 0° C. was added a solution of sodium N,N-dimethyldiboranamide (1.01 g, 10.6 mmol) in diethyl ether (40 mL). The reaction mixture was stirred at 0° C. for 50 min and was allowed to warm to room temperature and stirred for 5 h. Gas slowly evolved. A blue-green solution and a white precipitate formed. The blue-green solution was filtered, concentrated to ca. 10 mL, and cooled to −20° C. to afford blue-green crystals.

Yield: 0.58 g (86%). The product can also be further purified by sublimation at 45° C. and 0.05 Torr. Anal. Calcd for $C_4H_{24}N_2B_4Ti$: C, 25.1; H, 12.6; N, 14.6; B, 22.6; Ti, 25.0. Found: C, 24.4; H, 12.8; N, 13.8; B, 22.0; Ti, 25.0. MS (FI): m/z 192.2 ($M^+$). $^1H$ NMR($C_6D_6$, 20° C.): δ 13.2 (s, fwhm=650 Hz, NMe). Magnetic moment ($C_6D_6$, 20° C.): $2.6\mu_B$.

Figure 2:
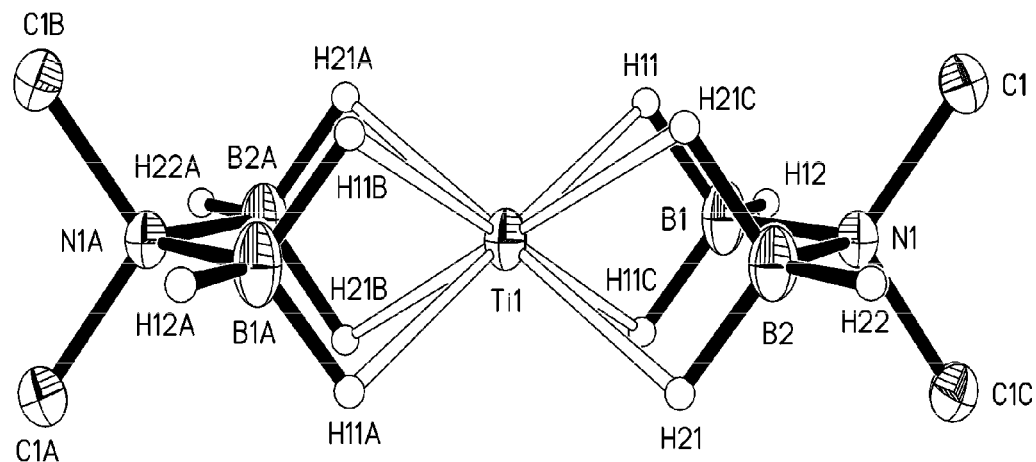
FIG. 2. $Ti(H_3BNMe_2BH_3)_2$, a monomeric compound that contains two $[H_3BNMe_2BH_3]^-$ ligands binding to the titanium center by means of eight Ti—H contacts.

$Ti(H_3BNMe_2BH_3)_2$, shown in FIG. 2, is a monomeric compound that contains two $[H_3BNMe_2BH_3]^-$ ligands binding to the titanium center by means of eight Ti—H contacts. Unlike the $Mg(H_3BNMe_2BH_3)_2$, the two diboranamide ligands are coplanar, describing a dihedral angle of 0°. The Ti—H distances are identical within the experimental error at 2.005 and 2.034 Å.

Example 5

Synthesis of bis(N,N-dimethyldiboranamido)chromium(II), $Cr(H_3BNMe_2BH_3)_2$

Following a similar procedure as described above for the $Ti(H_3BNMe_2BH_3)_2$ complex, but using $CrCl_3(thf)_3$, blue crystalline solids were obtained as a product by the removal of the solvent from the reaction mixture followed by sublimation.

Yield: 0.18 g (34%). Sublimation: 40° C. at 0.05 Torr. Anal. Calcd for $C_4H_{24}N_2B_4Cr$: C, 24.6; H, 12.4; N, 14.3; B, 22.1; Cr, 26.6. Found: C, 24.7; H, 12.2; N, 14.3; B, 22.7; Cr, 25.1. MS (FI): m/z 196.2 ($M^+$). $^1H$ NMR($C_6D_6$, 20° C.): δ 43.6 (s, fwhm=400 Hz, NMe). Magnetic moment ($C_6D_6$, 20° C.): $4.8\mu_B$. The molecular geometry of $Cr(H_3BNMe_2BH_3)_2$ is essentially identical to that of $Ti(H_3BNMe_2BH_3)_2$.

Example 6

Synthesis of bis(N,N-dimethyldiboranamido)molybdenum(II), $Mo(H_3BNMe_2BH_3)_2$

Following a similar procedure as described above for the $Ti(H_3BNMe_2BH_3)_2$, but using $MoCl_3(thf)_3$, green crystalline solids were obtained as a product by the removal of the solvent from the reaction mixture followed by sublimation.

Yield: 0.18 g (28%). Sublimation: 70° C. at 0.05 Torr. MS (FD): m/z 239.2 ($M^+$). Anal. Calcd for $C_4H_{24}N_2B_4Mo$: C, 20.1; H, 10.1; N, 11.7; B, 18.1; Mo, 40.1. Found: C, 20.4; H, 10.1; N, 12.2; B, 17.7; Mo, 39.6. $^1H\{^{11}B\}$ NMR ($CD_2Cl_2$, 20° C.): δ 4.93 (t, $J_{HH}$=9.3 Hz, 4H, BH), 2.68 (s, 12H, NMe$_2$), 6.75 (d, $J_{HH}$=9 Hz, 8H, MoHB). $^{11}B\{^1H\}$ NMR: 25.24 (s). IR ($cm^{-1}$): 2438 vs, 2192 w, 2153 w, 2126 w, 2014 w, 1925 s, 1865 vs, 1765 m, 1731 m, 1335 s, 1306 s, 1241 s, 1217 s, 1152 s, 1092 vs, 1028 s, 975 s, 939 m, 912 m, 807 s.

A second species is present in the solutions, with NMR peak intensities that are 29% of those for the major species. $^1H$ NMR: δ 4.55 (t, $J_{HH}$=9.6 Hz, 4H, BH), 2.72 (s, 12H, NMe$_2$), 6.74 (d, $J_{HH}$=9 Hz, 8H, MoHB). $^{11}B\{^1H\}$ NMR: 24.43 (s).

The molecular geometry of $Mo(DMDBA)_2$ is essentially the same as that for $Ti(H_3BNMe_2BH_3)_2$.

Example 7

Synthesis of bis(N,N-dimethyldiboranamido)manganese(II), $Mn(H_3BNMe_2BH_3)_2$

Following a similar procedure as described above for the $Ti(H_3BNMe_2BH_3)_2$, but using $MnCl_2$, light yellow crystalline solids were obtained as a product by the removal of the solvent from the reaction mixture followed by sublimation.

Yield: 0.25 g (29%). Sublimation: 50° C. at 0.05 Torr. Anal. Calcd for $C_4H_{24}N_2B_4Mn$: C, 24.2; H, 12.2; N, 14.1. Found: C, 24.2; H, 12.3; N, 14.2. MS (FI): m/z 197.2 (($M-2)^+$). $^1H$ NMR($C_6D_6$, 20° C.): δ 46.8 (s, fwhm=3200 Hz, NMe$_2$). Magnetic moment ($C_6D_6$, 20° C.): $5.9\mu_B$. The molecular geometry of the $Mn(H_3BNMe_2BH_3)_2$ is essentially identical to that of $Mn(H_3BNMe_2BH_3)_2$ with a dihedral angle of 46.5° between the two diboranamide ligands.

Example 8

Synthesis of hexa(N,N-dimethyldiboranamido)diyttrium(III), $Y_2(H_3BNMe_2BH_3)_6$ Following a similar procedure as described above for $Mg(H_3BNMe_2BH_3)_2$, but using $YCl_3$, off-white solids were obtained as a product by sublimation.

Figure 3:
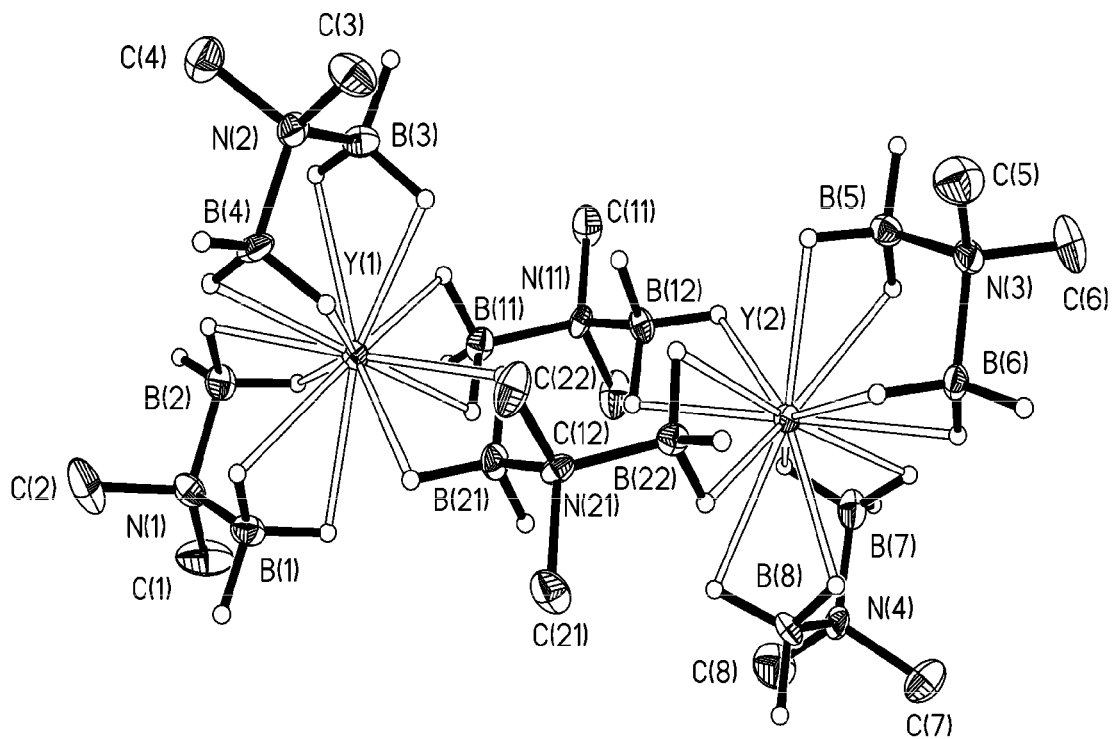
FIG. 3. $Y_2(H_3BNMe_2BH_3)_6$, a dimeric compound in which each yttrium center contains two $[H_3BNMe_2BH_3]^-$ ligands and two $[H_3BNMe_2BH_3]^-$ ligands bridge between two yttrium centers.

Yield: 0.22 g (19%). Sublimation: 100° C. at 0.05 Torr. $^1H$ NMR ($CD_2Cl_2$, 20° C.): δ 2.42 (s, 36H, NMe$_2$), 2.06 (q, $J_{BH}$=84 Hz, 36H, BH$_3$). $^{13}C\{^1H\}$ NMR ($CD_2Cl_2$, 20° C.): δ 51.14 (s, CH$_3$). $^{11}B\{^1H\}$ NMR ($CD_2Cl_2$, 20° C.): δ 50.83 (s, BH$_3$). Anal. Calcd for $C_6H_{36}N_3B_6Y$: C, 23.7; H, 11.9; N, 12.8; B, 21.3; Y, 29.2. Found: C, 22.9; H, 11.1; N, 12.8; B, 19.5; Y, 28.0. $Y_2(H_3BNMe_2BH_3)_6$, shown in FIG. 3, is a dimeric compound in which each yttrium center contains two $[H_3BNMe_2BH_3]^-$ ligands and two $[H_3BNMe_2BH_3]^-$ ligands bridge between two yttrium centers.

Example 9

Synthesis of tris(dimethyldiboranamido)(tetrahydrofuran)yttrium(III), $Y(H_3BNMe_2BH_3)_3(thf)$ Following a similar procedure as described above for the $Ti(H_3BNMe_2BH_3)_2$ complex, but using $YCl_3$ and solvent thf, off-white solids were obtained as a product by the removal of the solvent from the reaction mixture followed by sublimation.

Yield: 0.76 g (37%). Sublimation: 90° C. at 0.05 Torr. $^1H$ NMR ($CD_2Cl_2$, 20° C.): δ 3.98 (m, 4H, OCH$_2$), 2.37 (s, 18H, NMe$_2$), 2.00 (q, $J_{BH}$=84 Hz, 18H, BH$_3$), 1.90 (m, 4H, CH$_2$). Anal. Calcd for $C_{10}H_{44}N_3B_6O_1Y$: C, 31.9; H, 11.8; N, 11.2. Found: C, 30.1; H, 11.8; N, 11.5.

Example 10

Synthesis of hexa(N,N-dimethyldiboranamido) didysprosium(III), $Dy_2(H_3BNMe_2BH_3)_6$ Following a similar procedure as described above for $Mg(H_3BNMe_2BH_3)_2$, but using $DyCl_3$, off-white solids were obtained as a product by sublimation.

Yield: 0.19 g (24%). Sublimation: 90° C. at 0.05 Torr. Anal. Calcd for $C_6H_{36}N_3B_6Dy$: C, 19.1; H, 9.61; N, 11.1. Found: C, 19.0; H, 9.62; N, 10.8. MS (F1): m/z 377.3 (M−1)$^+$. $^1$H NMR($C_6D_6$, 20 (C): δ 97.5 (s, fwhm=250 Hz, $NMe_2$). The molecular geometry of $Dy_2(H_3BNMe_2BH_3)_6$ is the same as that for $Y_2(H_3BNMe_2BH_3)_6$.

Example 11

Synthesis of Tris(dimethyldiboranamido)(thf)dysprosium(III), $Dy(H_3BNMe_2BH_3)_3(thf)$ Following a similar procedure as described above for $Ti(H_3BNMe_2BH_3)_2$, but using $DyCl_3$, colorless crystals were obtained as a product by extraction with pentane followed by crystallization at −20° C.

Yield: 0.47 g (63%). Sublimation: 90° C. at 0.05 Torr. $^1$H NMR($C_6D_6$, 20° C.): δ−19.50 (s, fwhm=250 Hz, 18H, $NMe_2$); −29.07 (s, fwhm=150 Hz, 4H, —$CH_2CH_2$— in thf). Anal. Calcd for $C_{10}H_{44}N_3B_6O_1Dy$: C, 26.7; H, 9.86; N, 9.34; B, 14.4; Dy, 36.1. Found: C, 26.1; H, 10.1; N, 8.73; B, 15.0; Dy, 33.8.

Example 12

Volatile Magnesium Octahydrotriborate Complexes as Potential CVD Precursors to $MgB_2$. Synthesis and Characterization of $Mg(B_3H_8)_2$ and its Etherates Introduction Magnesium diboride ($MgB_2$) has been the subject of considerable interest since the discovery in 2001 that it becomes superconducting at 39 K.[1] $MgB_2$ has highly attractive properties for applications in superconducting electronics: in addition to having the highest critical temperature of all intermetallic superconductors, it has a long coherence length of ca. 5 nm and a high critical current density.[2-4] These properties suggest that $MgB_2$-based superconducting circuits should operate more rapidly, and at a higher temperature, than circuits based on niobium alloys.

Because multilayer tunneling junctions are core elements in integrated circuits, intensive research has been directed toward the development of methods to grow high-quality $MgB_2$ thin films. Successful depositions of such films have been achieved by co-evaporation of Mg and B in extremely clean environments,[5] by boron deposition followed by ex-situ annealing with Mg vapor in a sealed tube,[6] and by a hybrid physical-chemical vapor deposition (HPCVD) technique in which $B_2H_6$ reacts with Mg vapor.[7] Methodological improvements are still required, however, to achieve the large-scale fabrication of multilayer $MgB_2$ tunneling junctions, which require the deposition of stoichiometric, crystalline films via an in-situ process at a low temperature. No purely chemical vapor deposition (CVD) route to $MgB_2$ films has been described. One obstacle is that magnesium tends to evaporate from the growth surface at temperatures above 0.425° C.,[8] leaving behind boron or boron-rich films.

Another obstacle to preparing $MgB_2$ by CVD is that few magnesium compounds are volatile and, of those, none has been shown to be chemically suited as a precursor for this phase. Although magnesium complexes of tetrahydroborate ($BH_4^-$), octahydrotriborate ($B_3H_8^-$), and nonahydrohexaborate ($B_6H_9^-$) groups have been described, all are nonvolatile. Specifically, the binary complex $Mg(BH_4)_2$ is known,[9] as are several Lewis base adducts, $Mg(BH_4)_2L_x$ (L=ethers, amines, or sulfoxides).[10-13] For the higher boron hydrides, ionic species of the form $[Mg(L)_6][B_3H_8]_2$, where L is $NH_3$, thf, or ⅓ diglyme, can be prepared by reaction of $Mg(BH_4)_2L_x$ with diborane,[14-16] and $Mg(B_6H_9)_2(thf)_2$ can be prepared by reaction of $MgMe_2$ or $MeMgBr$ with $B_6H_{10}$ in thf.[17]

We now describe the synthesis of bis(octahydrotriborate) magnesium $Mg(B_3H_8)_2$ and its Lewis base adducts, $Mg(B_3H_8)_2(Et_2O)_2$ and $Mg(B_3H_8)_2(Me_2O)_2$. These molecules are volatile and are the first crystallographically characterized magnesium complexes of the $B_3H_8$ ligand. Owing to their volatility, $Mg(B_3H_8)_2(Et_2O)_2$ and $Mg(B_3H_8)_2(Me_2O)_2$ are potential precursors for the deposition of $MgB_2$ thin films, and we describe preliminary efforts to grow thin films from them under CVD conditions. These new compounds closely resemble other volatile $MB_xH_y$ precursors that are known to afford high qualify films of metal diboride materials such as $TiB_2$, $CrB_2$, $ZrB_2$, and $HfB_2$.[18-22]

Results and Discussion

Synthesis and Characterization of $Mg(B_3H_8)_2$. If the reaction of $MgBr_2$ and $NaB_3H_8$ is carried out in ether solvents (diethyl ether, tetrahydrofuran, or dimethoxyethane), the reaction products are non-volatile. Previous work suggests that the presence of excess solvent results in the formation of ionic magnesium compounds: the reactions of $Mg(BH_4)_2$ with $B_2H_6$ in thf or diglyme afford the salts $[Mg(thf)_6][B_3H_8]_2$[14] and $[Mg(diglyme)_2][B_3H_8]_2$,[15] in which the magnesium dications are exclusively coordinated to ether molecules. The ionic nature of these latter materials is shown by the absence of Mg—H—B stretching bands near 2300 cm$^{-1}$ in their IR spectra. Similarly, Lewis base adducts of $Mg(BH_4)_2$ have different structures depending on the stoichiometry: the 3:1 complexes $Mg(BH_4)_2L_3$ (L=thf, tert-butylamine, or piperidine) and the 4:1 complex $Mg(BH_4)_2(pyridine)_4$ are monomeric, but the 6:1 adducts $[MgL_6][BH_4]_2$ (L=benzylamine or dimethyl sulfoxide) are ionic salts.[10,12]

A key to the synthesis of volatile magnesium $B_3H_8$ complexes is the use of reaction methods that avoid the use of a solvent. Thus, the solid state reaction of $MgBr_2$ and $NaB_3H_8$ at 20° C., followed by sublimation at 80° C. and 0.05 Torr, affords the new compound $Mg(B_3H_8)_2$ (1) as a white solid. Attempts to obtain single crystals of 1 suitable for X-ray diffraction have been unsuccessful.

The infrared spectrum of 1 (FIG. 4) contains two terminal B—H stretches at 2543 and 2479 cm$^{-1}$, one bridging Mg—H—B stretch at 2316 cm$^{-1}$ and a bridging B—H—B stretch at 2175 cm$^{-1}$. All of these bands are consistent with the presence of coordinated $B_3H_8$ groups. The B—H stretching bands for 1 are similar to those observed for transition metal octahydrotriborate complexes[19,23-25] with two exceptions. First, the 2316 cm$^{-1}$ frequency for the M—H—B stretching band is higher than those of 2000-2200 cm$^{-1}$ seen for transition metal $B_3H_8$ complexes;[24,25] The higher frequency seen in 1 reflects the lower mass of the magnesium atom and the less covalent character of the Mg—$B_3H_8$ interaction. Second, the 2316 cm$^{-1}$ band is more intense than the M—H—B stretching bands seen for transition metal complexes.

Further characterization of 1 (for example, by solution NMR spectroscopy) has been precluded by the insolubility of 1 in common organic solvents, including pentane, benzene, toluene, dichloromethane, tetrahydrofuran, and dioxane. Protic solvent such as ethanol and water react with 1, with vigorous evolution of gas.

Figure 4:
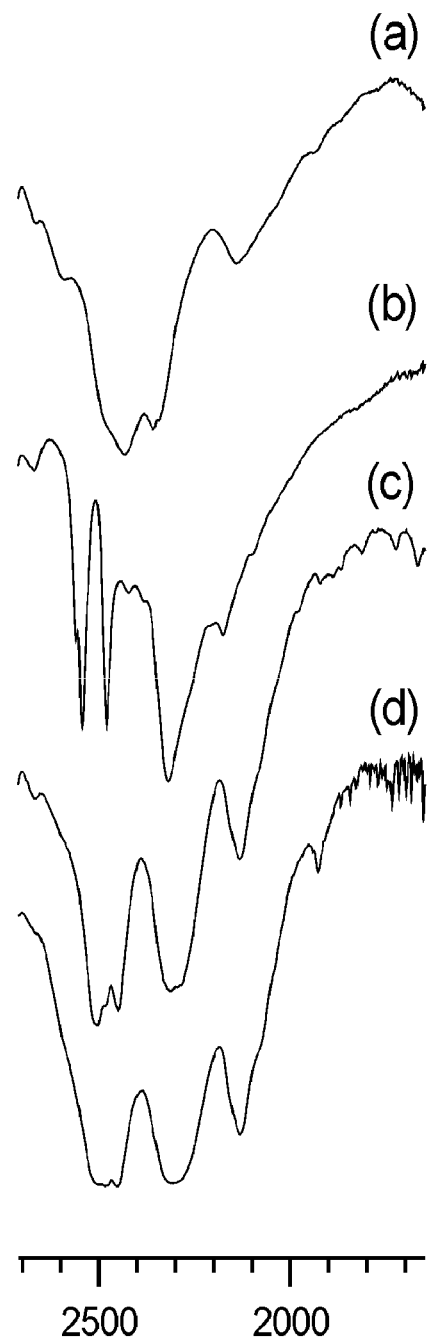
FIG. 4. B—H stretching region in the infrared spectra of (a) $NaB_3H_8$, (b) $Mg(B_3H_8)_2$, (c) $Mg(B_3H_8)_2(Et_2O)_2$, (d) $Mg(B_3H_8)_2(Me_2O)_2$.

Synthesis and Characterization of $Mg(B_3H_8)_2(Et_2O)_2$ and $Mg(B_3H_8)_2(Me_2O)_2$. The solid state reaction of $MgBr_2 \cdot Et_2O$ and $NaB_3H_8$ at 20° C., followed by sublimation at 70° C. and 0.05 Torr, yields the colorless crystalline product, $Mg(B_3H_8)_2(Et_2O)_2$ (2). A similar reaction with $MgBr_2(Me_2O)_{1.6}$ affords the dimethyl ether analogue $Mg(B_3H_8)_2(Me_2O)_2$ (3). The IR spectrum of 2 features strong bands at 2506 and 2448 $cm^{-1}$ due to terminal B—H stretches, a strong broad band at 2302 $cm^{-1}$ for the Mg—H—B stretch, and a medium intensity band at 2129 $cm^{-1}$ due to the B—H—B stretches (FIG. 4). The IR spectrum of 3 in the B—H stretching region is very similar to that of 2.

Like 1, compounds 2 and 3 react with protic solvents and are insoluble in almost all non-protic solvents; we attribute the insolubility in strongly coordinating ethers such as tetrahydrofuran or 1,2-dimethoxyethane to the formation of ionic salts (see above). Compound 2 is, however, soluble in diethyl ether. The weaker Lewis basicity of $Et_2O$ is probably responsible for its ability to dissolve $Mg(B_3H_8)_2(Et_2O)_2$ without forming insoluble ionic salts.

Figure 5:
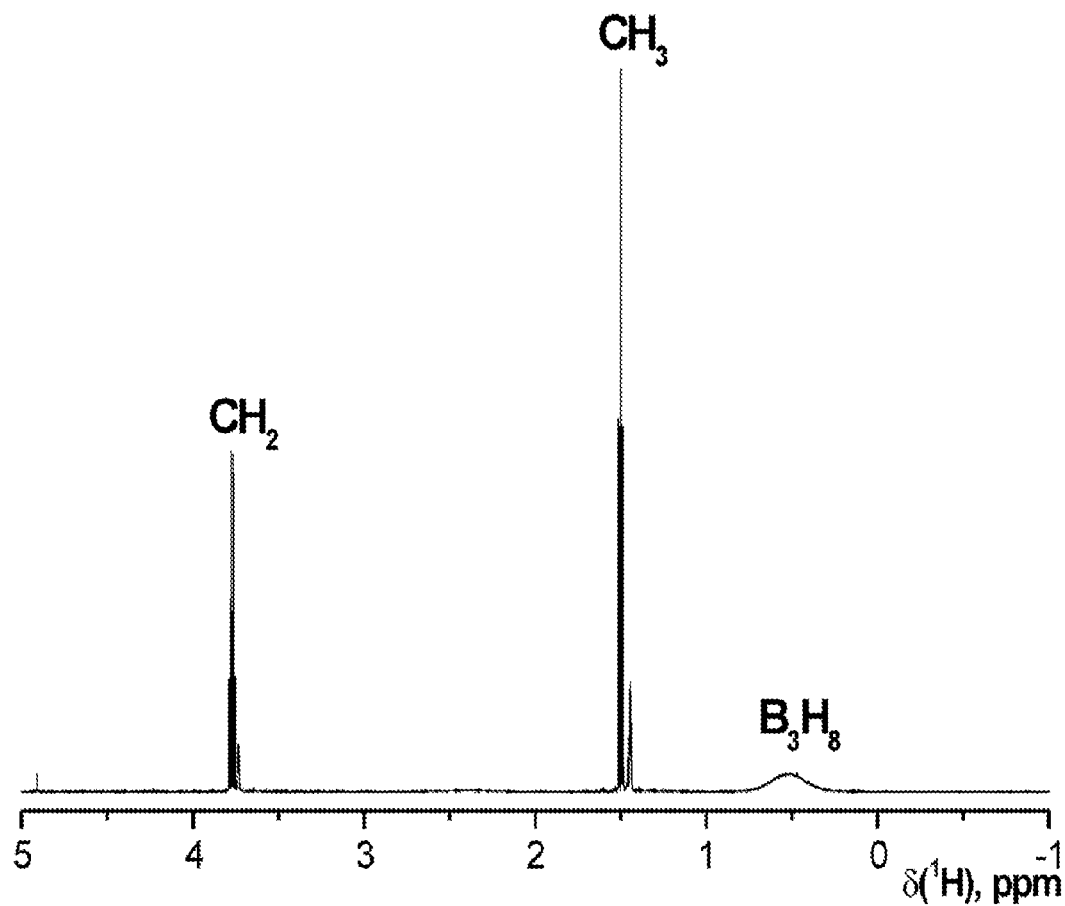
FIG. 5. $^1H$ NMR spectrum of $Mg(B_3H_8)_2(Et_2O)_2$, 2, in $(C_2D_5)_2O$ at 20° C.

The $^1H$ NMR spectrum of 2 in $(C_2D_5)_2O$ at 20° C. (FIG. 5) shows a broad, unresolved signal at δ 0.52 for the $B_3H_8$ groups, and characteristic resonances for the $Et_2O$ protons. The $^{11}B$ NMR spectrum at 20° C. contains a broad, unresolved resonance at δ-31.7. Similar $^1H$ NMR and $^{11}B$ spectra are seen at −80° C., which suggests that the $B_3H_8$ ligand is fluxional on the NMR time scale even at this temperature. The mass spectrum of 2 contains no parent peak (m/z=205); instead, the most intense peak in the spectrum (m/z=318) corresponds to $Mg_2(B_3H_8)_3(Et_2O)_2^+$. The mass spectrum of 3 is similar, the most intense signal (at m/z 262) being due to $Mg_2(B_3H_8)_3(Me_2O)_2^+$.

Figure 6:
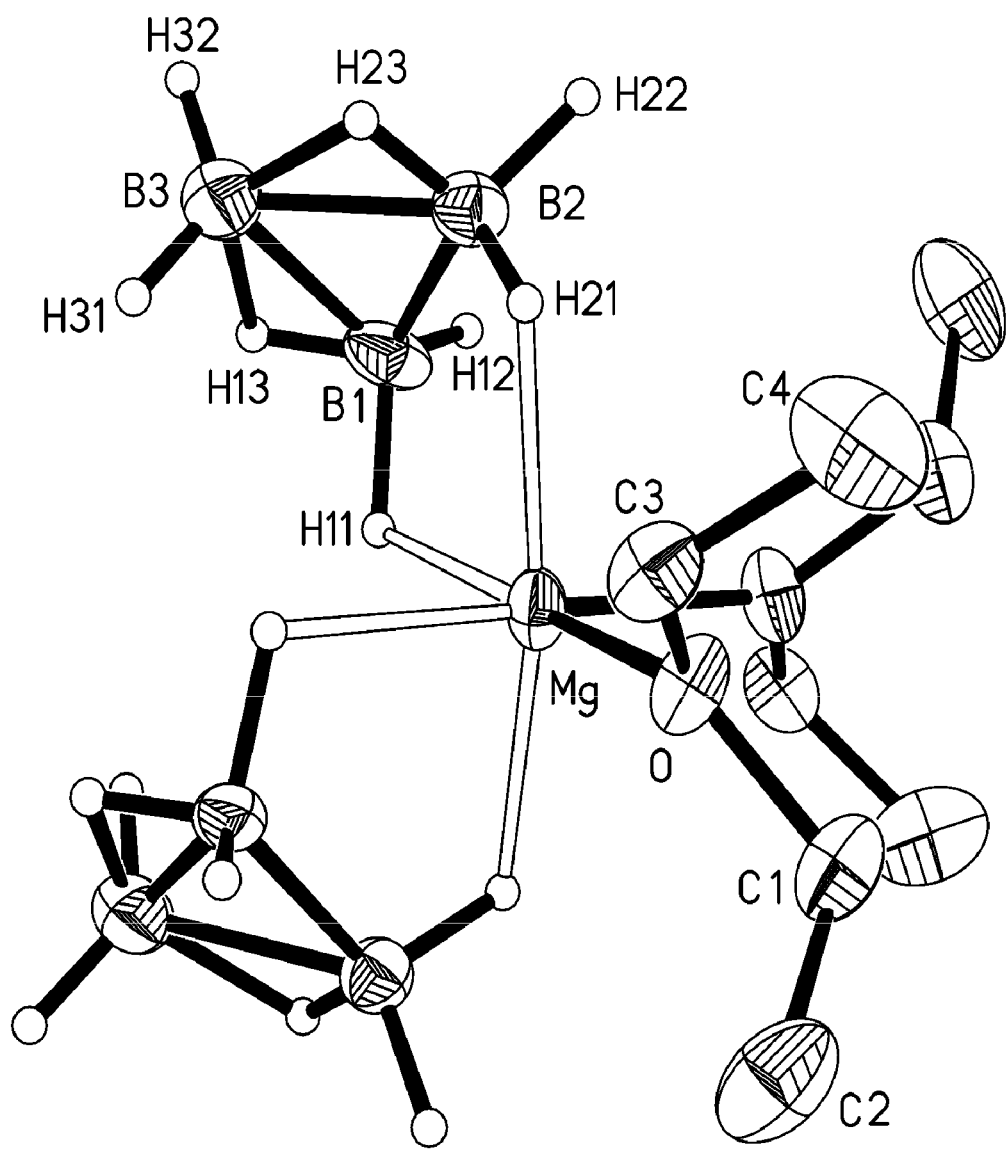
FIG. 6. Molecular structure of $Mg(B_3H_8)_2(Et_2O)_2$, 2. Ellipsoids are drawn at the 35% probability level, except for hydrogen atoms, which are represented as arbitrarily sized spheres. Methyl and methylene hydrogen atoms have been deleted for clarity.
Figure 7:
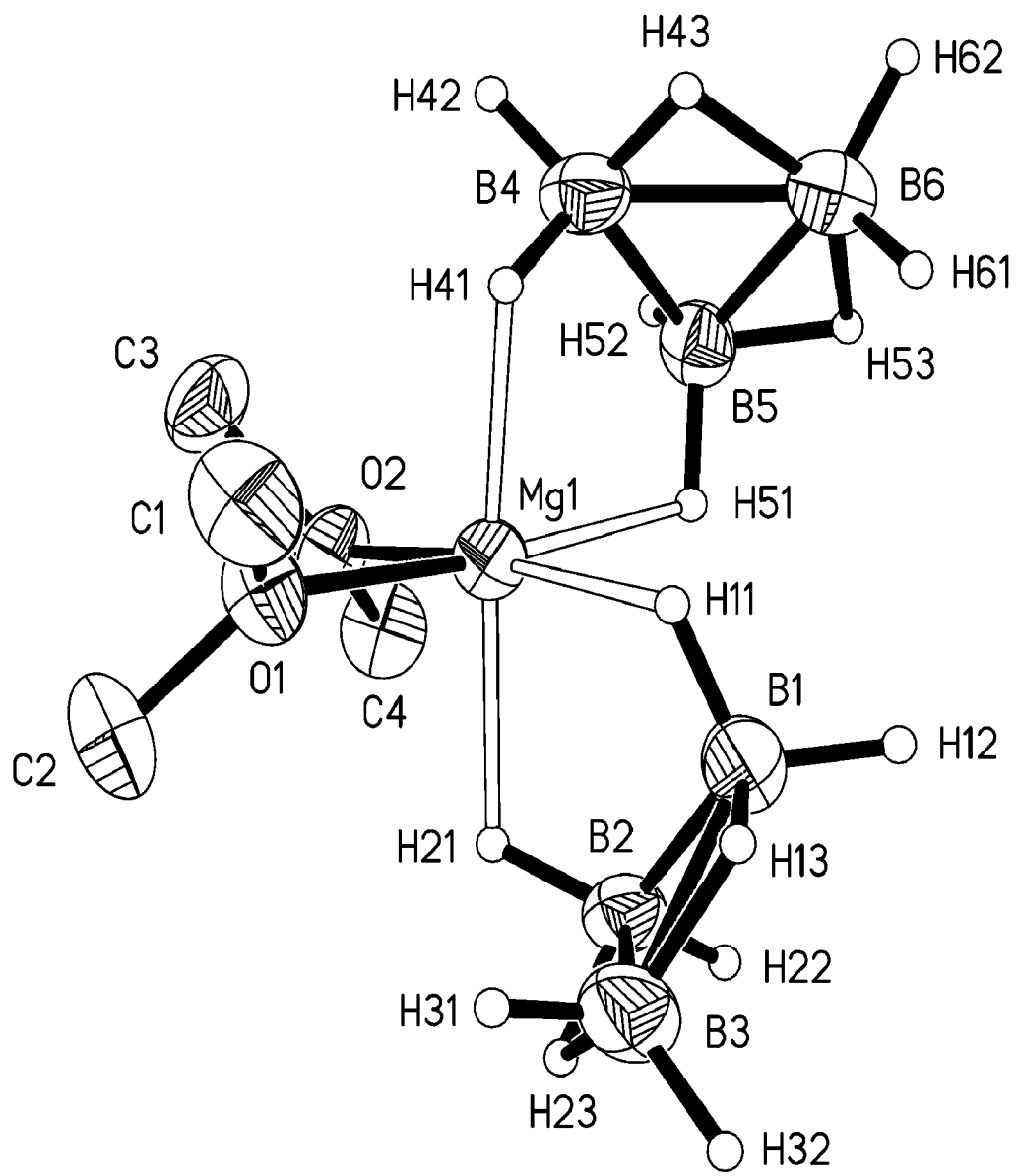
FIG. 7. Molecular structure of $Mg(B_3H_8)_2(Me_2O)_2$, 3. Ellipsoids are drawn at the 35% probability level, except for hydrogen atoms, which are represented as arbitrarily-sized spheres. Methyl hydrogen atoms have been deleted for clarity.

The molecular structures of 2 and 3 are shown in FIGS. 6 and 7; crystallographic data, and selected bond distances and angles are listed in Tables 1-3. The magnesium center in the diethyl ether adduct 2 adopts a distorted cis-octahedral geometry with two bidentate $B_3H_8$ groups and two $Et_2O$ ligands. The Mg—H distances are identical within experimental error at 1.99(3) and 2.01(4) Å, and the Mg...B distances are nearly identical at 2.575(5) and 2.591(5) Å. The B—H distances of 1.17(2) Å within the Mg—H—B units are slightly longer than the terminal B—H distances of 1.12(3) Å, as expected. As seen in other metal complexes of the bidentate $B_3H_8^-$ ligand,[19,26-29] the B—B distance for the non-bridged B—B bond is the shortest at 1.779(7) Å, whereas B—B distances for the two hydrogen bridged B—B bonds are slightly longer at 1.795(7) and 1.809(7) Å.

The Mg—H distances of 1.99(3) and 2.01(4) Å in 2 lie in the range 1.97-2.24 Å seen in magnesium complexes of the $BH_4$ ligand.[9-13,30,31] The Mg...B distances of 2.575(5) and 2.591(5) in 2 are slightly longer than those of 2.40-2.54 Å found in magnesium complexes of bidentate $BH_4$ ligands;[10-13] but are much longer than those of 2.21-2.29 Å seen in magnesium complexes containing tridentate $BH_4$ ligands,[30,31] as expected.

The molecular geometry of the dimethyl ether adduct 3 is very similar to that of 2: the magnesium center is six-coordinate with two bidentate $B_3H_8^-$ ligands and two mutually cis dimethyl ether groups. All Mg—H and Mg...B distances in 3 are also nearly identical to those in 2: the average Mg—H distance is 1.96(4)Å, and the average Mg...B distance is 2.565(6)Å. The dimethyl ether ligand in 3 should be sterically less demanding than the diethyl ether ligand in 2, and this difference may be responsible for a subtle difference in the relative orientations adopted by the coordinated $B_3H_8$ groups. If we focus on the "unbound" $BH_2$ group within each $B_3H_8$ ligand, in 3 one is proximal to the dimethyl ether group and the other is distal, whereas in 2 both "unbound" $BH_2$ groups are distal to the diethyl ether ligands.

Most likely, the ether groups in 2 and 3 occupy mutually cis positions so as to minimize interligand steric repulsions. Interestingly, the molecular structures of 2 and 3 differ from that of the chromium analogue $Cr(B_3H_8)_2(Et_2O)_2$,[19] which adopts a trans-octahedral geometry. Electronic factors relating to the Jahn-Teller effect dominate in determining the structure of the $d^4$ chromium complex: the diethyl ether ligands, which generate the weakest ligand field splitting, are relegated to the axial positions so as to maximize the ligand field stabilization energy. In contrast, no such electronic factors operate in $Mg(B_3H_8)_2(Et_2O)_2$.

Preliminary Attempts to Grow $MgB_2$ Thin Films. Deposition of thin films was carried out in an ultra high vacuum (UHV) chamber equipped with a turbomolecular pump with the base pressure of $5 \times 10^{-9}$ Torr.[22] The $Mg(B_3H_8)_2$ compound 1 is not an ideal precursor for CVD because it sublimes very slowly and with some decomposition; the ether adducts 2 and 3 sublime much more readily. For $Mg(B_3H_8)_2(Et_2O)_2$ (2), the precursor reservoir was heated to 70° C. and delivered to the Si(100) surface by means of an argon carrier gas. The onset temperature for film growth is 400° C. The resulting deposit is non-stoichiometric, exhibiting a B/Mg ratio of 7 as determined by Auger electron spectroscopy. For $Mg(B_3H_8)_2(Me_2O)_2$ (3), the onset temperature is 450° C., and the films deposited under these conditions consist of 70 at. % boron, 20 at. % carbon, 8 at. % oxygen, and essentially no magnesium.

Titov et. al have reported that the solid state decomposition of $[Mg(diglyme)_2][B_3H_8]_2$ at 185° C. yields $Mg(BH_4)_2$, $MgB_{12}H_{12}$, $H_2$, and $B_5H_{9.15}$ The solid state decomposition of $[Mg(NH_3)_6][B_3H_8]_2$ at 120-140° C. is reported by Levicheva to proceed somewhat differently, affording $Mg(BH_4)_2(NH_3)_2$, $B_3N_3H_6$, $(BNH)_n$, and $H_2$.[16] These findings suggest that the thermolysis mechanism depends on the identity of the Lewis base; thus, magnesium octahydrotriborate complexes with other neutral ligands may be more successful in affording $MgB_2$ by CVD (or plasma-assisted CVD) methods.

Experimental Section

All experiments were carried out under vacuum or under argon by using standard Schlenk techniques. Solvents were distilled under nitrogen from sodium/benzophenone immediately before use. $NaB_3H_8$ was prepared by a literature procedure,[32] and $MgBr_2$ and $MgBr_2(Et_2O)$ were used as received (Aldrich). Dimethyl ether was purchased from Matheson. Microanalyses were performed by the University of Illinois Microanalytical Laboratory. The IR spectra were recorded on a Nicolet Impact 410 instrument as Nujol mulls between KBr plates. Field ionization (FI) mass spectra were recorded on a Micromass 70-VSE mass spectrometer. The shapes of all peak envelops correspond with those calculated from the natural abundance isotopic distributions. Melting points were determined in closed capillaries under argon on a Thomas-Hoover Unimelt apparatus.

Bis(octahydrotriborato)magnesium(II), $Mg(B_3H_8)_2$, 1. Solid $MgBr_2$ (2.97 g, 16.1 mmol) and $NaB_3H_8$ (1.02 g, 16.1 mmol) were ground together briefly in a mortar and pestle. The dry mixture was transferred to a 250 mL round-bottomed flask, and 50-60 steel balls (4.5-mm diameter) were added. The flask was gently agitated for 30 min and over this period the solid became slightly damp. Sublimation at 80° C. under vacuum afforded a white product. Yield: 0.16 g (19%). Mp: 120° C. (dec). Anal. Calcd for $B_6H_{16}Mg$: H, 15.3; B, 61.6;

Mg, 23.1. Found: H, 13.0; B, 60.2; Mg, 23.1. IR (cm$^{-1}$): 2543 vs, 2479 vs, 2316 vs, 2175 w, 1298 sh, 1134 vs, 1043 w, 981 vs, 829 s.

Bis(octahydrotriborato)bis(diethylether)magnesium(II), Mg(B$_3$H$_8$)$_2$(Et$_2$O)$_2$, 2. Solid MgBr$_2$·Et$_2$O (4.0 g, 15.5 mmol) and NaB$_3$H$_8$ (1.0 g, 15.8 mmol) were ground together briefly in a mortar and pestle. The mixture was transferred a 250 mL round-bottomed flask, and 50-60 steel balls (4.5-mm diameter) were added. The flask was gently agitated for 30 min and over this period the solid became slightly damp. Sublimation at 70° C. under vacuum afforded white crystals. Yield: 0.82 g (41%). Mp. 40° C. Anal. Calcd for C$_4$H$_{36}$B$_6$O$_2$Mg: C, 37.9; H, 14.3; B, 25.6; Mg, 9.59. Found: C, 37.5; H, 14.1; B, 25.6; Mg, 9.71. MS (FI) (fragment ion, relative abundance): m/z 139 [Mg(B$_3$H$_8$)(Et$_2$O)$^+$, 20], 213 [Mg(B$_3$H$_8$)(Et$_2$O)$_2$$^+$, 25], [Mg$_3$(B$_3$H$_8$)$_2$(Et$_2$O)$_2$$^+$, 20], 318 [Mg$_2$(B$_3$H$_8$)$_3$(Et$_2$O)$_2$$^+$, 100]. $^1$H NMR(O(C$_2$D$_5$)$_2$, 20° C.): δ 3.77 (q, 8H, CH$_2$), 1.50 (t, 12H, CH$_3$), 0.52 (br, fwmh=125 Hz, 16H, B$_3$H$_8$). IR (cm$^{-1}$): 2506 vs, 2448 vs, 2302 vs, 2129 m, 1289 w, 1262 w, 1189 w, 1148 s, 1092 s, 1034 s, 992 s, 891 m, 865 w, 832 m, 778 s, 692 w.

Magnesium Dibromide: 1.6 Dimethylether, MgBr$_2$(Me$_2$O)$_{1.6}$. Solid MgBr$_2$ (6.3 g, 34 mmol) was cooled to −78° C. and Me$_2$O (50 mL) was condensed onto the solid. After the mixture had been stirred for 4 h, the Me$_2$O was removed under vacuum to afford a white solid. Yield: 8.9 g The stoichiometry MgBr$_2$(Me$_2$O)$_{1.6}$ was calculated by assuming that the increase in mass of 2.5 g is contribution of Me$_2$O (54 mmol).

Bis(octahydrotriborato)bis(dimethylether)magnesium (II), Mg(B$_3$H$_8$)$_2$(Me$_2$O)$_2$, 3. Solid MgBr$_2$(Me$_2$O)$_{1.6}$ (1.86 g, 7.22 mmol) and NaB$_3$H$_8$ (0.92 g, 14.5 mmol) were ground together briefly in a mortar and pestle. The mixture was transferred to a 100 mL round-bottomed flask, and 30-40 steel balls (4.5-mm diameter) were added. The flask was gently agitated for 15 min and over this period the solid became slightly damp. Sublimation at 75° C. under vacuum afforded white crystals. Yield: 0.25 g (25%). Mp: 55° C. Anal. Calcd for C$_2$H$_{28}$B$_6$O$_2$Mg: C, 24.3; H, 14.3; B, 32.9; Mg, 12.3. Found: C, 23.9; H, 14.0; B, 33.1; Mg, 13.0. MS (FI) (fragment ion, relative abundance): m/z 111 [Mg(B$_3$H$_8$)(Me$_2$O)$^+$, 40], [Mg(B$_3$H$_8$)(Me$_2$O)$_2$$^+$, 45], 216 [Mg$_2$(B$_3$H$_8$)(Me$_2$O)$^+$, 20], 262 [Mg$_2$(B$_3$H$_8$)$_3$(Me$_2$O)$_2$$^+$, 100], 276 [Mg$_2$(B$_3$H$_8$)$_3$(BH$_4$)(Me$_2$O)$_2$$^+$, 15], 308 [Mg$_2$(B$_3$H$_8$)$_3$(Me$_2$O)$_3$$^+$, 10]. IR (cm$^{-1}$): 2493 vs, 2449 vs, 2301 vs, 2129 s, 1260 s, 1154 s, 1048 s, 973 w, 893 s, 812 m, 757 w.

Crystallographic Studies.[33] Single crystals of both compounds, grown by sublimation, were mounted on glass fibers with Krytox oil (DuPont), and immediately cooled to −80° C. in a cold nitrogen gas stream on the diffractometer. Data for 2 and 3 were collected with an area detector by using the measurement parameters listed in Table 1. The measured intensities were reduced to structure factor amplitudes and their estimated standard deviations by correction for background, and Lorentz and polarization effects. Systematically absent reflections were deleted and symmetry-equivalent reflections were averaged to yield the sets of unique data. The analytical approximations to the scattering factors were used, and all structure factors were corrected for both real and imaginary components of anomalous dispersion. All structures were solved using direct methods (SHELXTL). The correct positions for all non-hydrogen atoms of 2 and 3 were deduced from E-maps. Final refinement parameters for 2 and 3 are given in Table 1. A final analysis of variance between observed and calculated structure factors showed no apparent errors. Subsequent discussions for 2 and 3 will be divided into individual paragraphs.

(a) Mg(B$_3$H$_8$)$_2$(Et$_2$O)$_2$, 2. Although the orthorhombic lattice and systematic absences suggested the space group P222$_1$, the actual space group is P2$_1$2$_1$2 with the second screw axis exhibiting weak violations of the systematic absences, probably owing to Renninger effects. All 1750 unique reflections were used in the least squares refinement. Although corrections for crystal decay were unnecessary, a face-indexed absorption correction was applied. The quantity minimized by the least-squares program was $\Sigma w(F_o^2 - F_c^2)^2$, where $w=\{[\sigma(F_o^2)]^2 + 1.22P\}^{-1}$ and $P=(F_o^2 + 2F_c^2)/3$. Hydrogen atoms were located in the difference maps, and their positions were refined with independent isotropic displacement parameters. Chemically similar B—H and C—H distances were constrained to equal within 0.01 Å. An isotropic extinction parameter was refined to a final value of x=1.37(5)×10$^{-5}$ where $F_c$ is multiplied by the factor $k[1+F_c^2 \times \lambda^3/\sin 2\theta]^{-1/4}$ with k being the overall scale factor. Successful convergence was indicated by the maximum shift/error of 0.000 for the last cycle. The largest peak in the final Fourier difference map (0.20 eÅ$^{-3}$) was located 1.25 Å from H13.

(b) Mg(B$_3$H$_8$)$_2$(Me$_2$O)$_2$, 3. Systematic absences for 0kl (k+l≠2n) and h0l (l≠2n) were consistent with space groups Pca2$_1$ and Pbcm; the non-centrosymmetric Pca2$_1$ was shown to be the correct choice by successful refinement of the proposed model. All 2837 unique reflections were used in the least squares refinement. Although corrections for crystal decay were unnecessary, a face-indexed absorption correction was applied. The quantity minimized by the least-squares program was $\Sigma w(F_o^2 - F_c^2)^2$, where $w=\{[\sigma(F_o^2)]^2 + (0.0386P)^2\}^{-1}$ and $P=(F_o^2 + 2F_c^2)/3$. Boron-bound hydrogen atoms were located in the difference maps and refined without constraints; these hydrogen atoms were each given independent isotropic displacement parameters. Methyl hydrogen atoms were placed in idealized tetrahedral locations with C—H=0.98 Å and optimized by rotation about C—O bonds; their displacement parameters were set equal to 1.5 times U$_{eq}$ for the attached carbon. No correction for isotropic extinction was necessary. Successful convergence was indicated by the maximum shift/error of 0.000 for the last cycle. The largest peak in the final Fourier difference map (0.09 eÅ$^{-3}$) was located 0.87 Å from O1.

REFERENCES

1. Nagamatsu, J.; Nakagawa, N.; Muranaka, T.; Zenitani, Y.; Akimitsu, J. *Nature* 2001, 410, 63-64.
2. Xu, M.; Kitazawa, H.; Takano, Y.; Ye, J.; Nishida, K.; Abe, H.; Matsushita, A.; Tsujii, N.; Kido, G. *Appl. Phys. Lett.* 2001, 79, 2779-2781.
3. Schmidt, H.; Zasadzinski, J. F.; Gray, K. E.; Hinks, D. G. *Phys. Rev. Lett.* 2002, 88.
4. Tsuda, S.; Yokoya, T.; Kiss, T.; Takano, Y.; Togano, K.; Kito, H.; Ihara, H.; Shin, S. *Phys. Rev. Lett.* 2001, 8717.
5. Ueda, K.; Naito, M. *J. Appl. Phys.* 2003, 93, 2113-2120.
6. Kang, W. N.; Kim, H. J.; Choi, E. M.; Jung, C. U.; Lee, S. L. *Science* 2001, 292, 1521-1523.
7. Zeng, X. H.; Pogrebnyakov, A. V.; Kotcharov, A.; Jones, J. E.; Xi, X. X.; Lysczek, E. M.; Redwing, J. M.; Xu, S. Y.; Lettieri, J.; Schlom, D. G.; Tian, W.; Pan, X. Q.; Liu, Z. K. *Nat. Mater.* 2002, 1, 35-38.
8. Fan, Z. Y.; Hinks, D. G.; Newman, N.; Rowell, J. M. *Appl. Phys. Lett.* 2001, 79, 87-89.
9. Becker, W. E.; Ashby, E. C. *Inorg. Chem.* 1965, 4, 1816-1818.
10. Bremer, M.; Noth, H.; Warchhold, M. Eur. *J. Inorg. Chem.* 2003, 111-119.

11. Lobkovskii, E. B.; Titov, L. V.; Psikha, S. B.; Antipin, M. Y.; Struchkov, Y. T. *J. Struct. Chem.* 1982, 23, 644-646.
12. Noeth, H. *Z. Naturforsch. B* 1982, 378, 1499-503.
13. Lobkovskii, E. B.; Titov, L. V.; Levicheva, M. D.; Chekhlov, A. N. *J. Struct. Chem.* 1990, V31, 506-508.
14. Hermanek, S.; Plesek, J. *Collect. Czech. Chem. Commun.* 1966, 31, 177-89.
15. Titov, L. V.; Levicheva, M. D.; Psikha, S. B. *Zh. Neorg. Khim.* 1984, 29, 668-73.
16. Levicheva, M. D.; Titov, L. V.; Psikha, S. B. *Zh. Neorg. Khim.* 1987, 32, 510-12.
17. Denton, D. L.; Clayton, W. R.; Mangion, M.; Shore, S. G.; Meyers, E. A. *Inorg. Chem.* 1976, 15, 541-548.
18. Jensen, J. A.; Gozum, J. E.; Pollina, D. M.; Girolami, G. S. *J. Am. Chem. Soc.* 1988, 110, 1643-1644.
19. Goedde, D. M.; Girolami, G. S. *J. Am. Chem. Soc.* 2004, 126, 12230-12231.
20. Jayaraman, S.; Klein, E. J.; Yang, Y.; Kim, D. Y.; Girolami, G. S.; Abelson, J. R. *J. Vac. Sci. Technol., A* 2005, 23, 631-633.
21. Sung, J.; Goedde, D. M.; Girolami, G. S.; Abelson, J. R. *J. Appl. Phys.* 2002, 91, 3904-3911.
22. For the details of the growth condition, see: J., Sreenivas; Yang, Y.; Kim, D. Y.; Girolami, G. S.; Abelson, J. R. *J. Vac. Sci. Technol., A* 2005, 23, 1619-1625.
23. Gaines, D. F.; Morris, J. H. *J. Chem. Soc., Chem. Commun.* 1975, 626-7.
24. Lippard, S. J.; Ucko, D. *Inorg. Chem.* 1968, 7, 1051-1056.
25. Gaines, D. F.; Hildebrandt, S. J. *Inorg. Chem.* 1978, 17, 794-806.
26. Beckett, M. A.; Brassington, D. S.; Coles, S. J.; Gelbrich, T.; Hursthouse, M. B. *Polyhedron* 2003, 22, 1627-1632.
27. Grebenik, P. D.; Leach, J. B.; Green, M. L. H.; Walker, N. M. *J. Organomet. Chem.* 1988, 345, C31-034.
28. Calabrese, J. C.; Gaines, D. F.; Hildebrandt, S. J.; Morris, J. H. *J. Am. Chem. Soc.* 1976, 98, 5489-5492.
29. Guggenberger, L. J. *Inorg. Chem.* 1970, 9, 367-373.
30. Bremer, M.; Linti, G.; Noth, H.; Thomann-Albach, M.; Wagner, G. *Z. Anorg. Allg. Chem.* 2005, 631, 683-697.
31. Prust, J.; Most, K.; Muller, I.; Alexopoulos, E.; Stasch, A.; Uson, I.; Roesky, H. W. *Z. Anorg. Allg. Chem.* 2001, 627, 2032-2037.
32. Hough, W. V.; Edwards, L. J.; McElroy, A. D. *J. Am. Chem. Soc.* 1958, 80, 1828-9.
33. For details of the crystallographic methods used see: Brumaghim, J. L.; Priepot, J. G.; Girolami, G. S. *Organometallics* 1999, 18, 2139-2144.

Example 13

Highly Volatile Magnesium Complexes with Diboranamide Ligands. Synthesis and Characterization of $Mg(H_3BNMe_2BH_3)_2$ and Related Compounds Introduction The discovery in 2001 of superconductivity in magnesium diboride ($MgB_2$) below 39 K[1] has initiated extensive research into this material. In addition to possessing the highest superconducting transition temperature of all intermetallic superconductors, $MgB_2$ possesses a long coherence length of ca. 5 nm and a large energy gap,[2-4] which make this material an attractive replacement for the niobium-based phases currently used in superconducting circuits. Thin films of $MgB_2$ are of particular interest for the fabrication of Josephson junctions, but a major obstacle is that this phase decomposes with loss of magnesium above 425° C.[5] Overcoming this problem requires either growing the film below 400° C. or using very high Mg partial pressures. $MgB_2$ films have been prepared by co-evaporation of Mg and B at ~300° C.,[6] by boron deposition and subsequent ex-situ annealing under a high Mg pressure in a sealed tube at 900° C.,[7] and by reaction of $B_2H_6$ at 750° C. with Mg vapor that is generated near the substrate.[8] These methods, however, have not yet proven suitable for the in situ growth of crystalline $MgB_2$ required for the large scale fabrication of multilayer tunneling junctions.

It is known that high-quality thin films of several metal diboride phases can be grown by chemical vapor deposition (CVD) from transition metal hydroborates such as $Ti(BH_4)_3$ (dme),[9] $Zr(BH_4)_4$,[10] and $Hf(BH_4)_4$,[11] and $Cr(B_3H_8)_2$.[12,13] As reported herein we synthesized and characterized the new magnesium compound $Mg(B_3H_8)_2$ and derivatives thereof, and our initial studies of their use as CVD precursors to $MgB_2$ thin films.[14] Significantly, $Mg(B_3H_8)_2$ and its etherates are the only volatile magnesium hydroborate complexes known; other Mg compounds that contain tetrahydroborate $(BH_4^-)$,[15-21] octahydrotriborate $(B_3H_8^-)$,[18,22,23] or nonahydrohexaborate $(B_6H_9^-)$[24] groups are all non-volatile.

We now report the synthesis of a new class of remarkably volatile magnesium complexes of the N,N-dimethyldiboranamide ligand $H_3BNMe_2BH_3^-$. Specifically, we describe the preparation and characterization of $Mg(H_3BNMe_2BH_3)_2$, its adducts with ethers, and the mixed ligand complex $Cp^*Mg(H_3BNMe_2BH_3)(thf)$. The homoleptic complex $Mg(H_3BNMe_2BH_3)_2$ has a vapor pressure of 800 mTorr at 25° C., which makes it the most volatile magnesium complex known.

Results and Discussion

Synthesis and Characterization of $Mg(H_3BNMe_2BH_3)_2$. The solid state reaction of $MgBr_2$ and sodium N,N-dimethyldiboranamide, $Na(H_3BNMe_2BH_3)$, at room temperature followed by sublimation at 20-70° C. under a static vacuum affords a colorless crystalline product, $Mg(H_3BNMe_2BH_3)_2$, 1, in good yield. This synthetic method, which involves grinding or milling of the solid starting materials, avoids the use of solvents such as ethers that can coordinate to the magnesium center. This air- and moisture-sensitive magnesium complex sublimes even at room temperature and has an unusually high vapor pressure of 800 mTorr at 25° C. It is thermally stable up to 120° C.

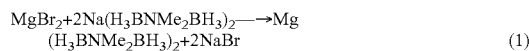

$$MgBr_2 + 2Na(H_3BNMe_2BH_3)_2 \longrightarrow Mg(H_3BNMe_2BH_3)_2 + 2NaBr \qquad (1)$$

The infrared spectrum of 1 features a strong band at 2449 cm$^{-1}$ due to terminal B—H stretches, and a strong, broad band centered at 2195 cm$^{-1}$ due to bridging B—H stretches. These B—H stretching bands are similar to those observed in the IR spectra of transition metal complexes of the diboranamide ligand.[25]

The $^1$H NMR spectrum of 1 at 20° C. shows two signals, a singlet at δ 2.04 for the NMe$_2$ groups and a broad 1:1:1:1 quartet at δ 1.91 for the BH$_3$ groups ($^{11}$B has I=3/2) The $J_{BH}$ coupling constant of 90.0 Hz is nearly identical to the 91 and 92 Hz values observed for the thf and 15-crown-5 solvates of $Na(H_3BNMe_2BH_3)$,[26] respectively, and slightly larger than the 74-83 Hz range found in magnesium tetrahydroborates[17,20] At −80° C., the quartet becomes a broad unresolved signal due to the more rapid spin-lattice relaxation of the $^{11}$B and $^{10}$B nuclei at a lower temperature, as seen in many transition metal tetrahydroborates.[27,28] Exchange of terminal B—H hydrogen atoms with those that bridge to the metal center (see structure below) is evidently fast on the NMR time scale even at −80° C.

Figure 8:
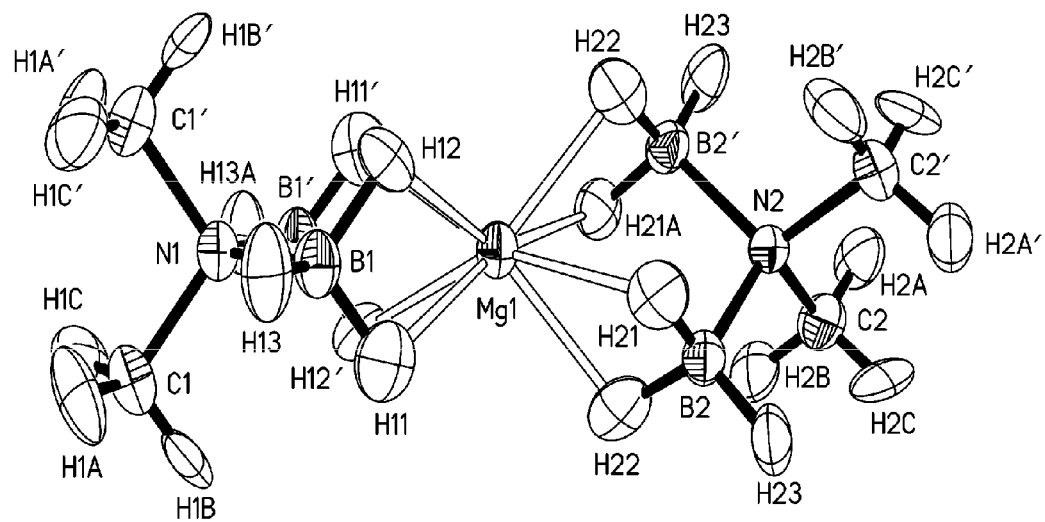
FIG. 8. Molecular structure of $Mg(H_3BNMe_2BH_3)_2$, 1. Ellipsoids are drawn at the 30% probability level, except for hydrogen atoms, which are represented as arbitrarily sized spheres. Methyl hydrogen atoms have been deleted for clarity.

Crystal Structure of $Mg(H_3BNMe_2BH_3)_2$. The molecular structure of 1 is presented in FIG. 8; crystallographic data and selected bond distances and angles are listed in Tables 1 and 2. The magnesium center is coordinated to two chelating [H$_3$BNMe$_2$BH$_3$]$^-$ ligands, which are similar but crystallographically inequivalent. The planes of the two ligands (as defined by the B—N—B backbones) are related by a dihedral angle of 46.7(1)°. If each BH$_3$ unit is considered to occupy one coordination site, the overall geometry about the magnesium center is nearly exactly halfway between square planar (dihedral angle of 0°) and tetrahedral (dihedral angle of 90°). The factors that favor the adoption of this unusual coordination geometry are not immediately obvious, and may be the result of packing forces. A similar dihedral angle of 46.5(2)° has been found for the high-spin d$^5$ manganese analogue Mn(H$_3$BNMe$_2$BH$_3$)$_2$.[25]

Two hydrogen atoms from each BH$_3$ group bridge to the magnesium center to form total eight Mg—H contacts; the Mg—H bond lengths are essentially identical and average 2.02(3) Å. The average B—H distances of 1.14(3) Å within the Mg—H—B bridges is slightly longer than the average terminal B—H distance of 1.05(2) Å, as expected. The dihedral angle between the two Mg(μ-H)$_2$ planes at each end of a dimethyldiboranamide ligand is 93.8°, whereas the average B—Mg—B angle within a diboranamide ligand is 66.0(6)°. The Mg . . . B distances are almost equal at 2.369(1) and 2.386(1) Å, and the B—N distances are identical within experimental error at 1.585(1) and 1.581(1) Å. The geometry about the nitrogen atoms is nearly perfect tetrahedron: the B—N—B, B—N—C, and C—N—C angles of 108.5(1)-110.2(1)° are all within about 1° of the ideal value 109.5°.

The Mg—H and Mg . . . B distances in Mg(H$_3$BNMe$_2$BH$_3$)$_2$ can be profitably compared with those of magnesium complexes containing bidentate BH$_4^-$ ligands, which are electronically and structurally similar. The Mg—H distance of 2.02(3) Å in 1 falls in the 1.97-2.09 Å range observed in magnesium complexes containing bidentate BH$_4$ groups.[15-17,19-21] In contrast, the Mg . . . B distances of 2.369(1) and 2.386(1) Å in 1 are shorter than those of 2.40-2.54 Å seen for magnesium complexes of bidentate BH$_4$ ligands.[17,19-21] This shorter Mg . . . B distance of 1 is a consequence of the chelating nature of the dimethyldiboranamide ligand, which causes the Mg(μ-H)$_2$B units to be non-planar, i.e, folded about the H . . . H axis; in contrast, in Mg—BH$_4$ complexes the Mg(μ-H)$_2$B units are planar, thus maximizing the Mg . . . B distance.

Volatility of Mg(H$_3$BNMe$_2$BH$_3$)$_2$ The 800 mTorr vapor pressure of 1 at 25° C. is remarkably high for a magnesium compound, which in part reflects its low molecular weight. It can be sublimed in vacuum at reasonable rates even at room temperature. This volatility makes 1 an attractive chemical vapor deposition (CVD) precursor for magnesium-containing phases, as is described herein. In comparison, all other magnesium compounds have lower volatilities. The widely used CVD source dicyclopentadienylmagnesium (Cp$_2$Mg) has a vapor pressure described by the equation logP (in Torr)= 10.452−3522/T (in Kelvin), which corresponds to ~45 mTorr at 25° C.[29] The magnesium amidinate complexes bis(N,N'-di-tert-butylacetamidinato)magnesium and bis(N,N'-diisopropylacetamidinato)magnesium sublime readily only when heated under vacuum to 70° C.; although they have been reported to be more volatile than Cp$_2$Mg on the basis of their sublimation temperatures in the same evaporation apparatus, the vapor pressures have not been reported.[30] The volatilities of these amidinate complexes are limited by the need to prevent oligomerization by attaching bulky substituents to the amidinate backbone, thus increasing the molecular weight. Magnesium 2,2,6,6-tetramethyl-3,5-heptanedionate (thd), which is a dimer, Mg$_2$(thd)$_4$,[31] has been used as a CVD or atomic layer deposition (ALD) precursor for MgO thin films.[31-34] This compound evaporates at reasonable rates only above 250° C., as determined by thermogravimetric analyses under a helium flow.[31,35] Monomeric Mg(thd)$_2$L$_x$ complexes can be made with a variety of Lewis bases, but their volatilities are only slightly higher than that of Mg$_2$(thd)$_4$.[36,37] Magnesium complexes of the fluorinated β-diketonate ligand, 1,1,1,5,5,5-hexafluoro-2,4-pentanedionate (hfa), especially those carrying ancillary diamine ligands, are more volatile than Mg$_2$(thd)$_4$ and its related complexes; however, even the most volatile of these complexes, Mg(hfa) (Me$_2$NCH$_2$CH$_2$NMe$_2$), evaporates readily only at ~100° C. under 5 Torr of nitrogen.[38] Finally, the heteroleptic β-diketiminato magnesium complex (cyclopentadienyl)(N,N-di-tert-butyl-2,4-pentanediketiminato)magnesium is nearly as volatile as Cp$_2$Mg, and the binary β-diketiminato magnesium complexes bis(N,N'-di-tert-butyl-2,4-pentanediketiminato)magnesium and bis(N,N'-diisopropyl-2,4-pentanediketiminato)magnesium sublime at 104 and 160° C., respectively, at 0.05 Torr.[39]

Synthesis and Characterization of Mg(H$_3$BNMe$_2$BH$_3$)$_2$ (thf) and Mg(H$_3$BNMe$_2$BH$_3$)$_2$(dme). Treatment of MgBr$_2$ with Na(H$_3$BNMe$_2$BH$_3$) in tetrahydrofuran, followed by sublimation at 70° C., affords white crystals of the thf adduct Mg(H$_3$BNMe$_2$BH$_3$)$_2$(thf), 2. Carrying out this reaction in 1,2-dimethoxyethane affords the related compound Mg(H$_3$BNMe$_2$BH$_3$)$_2$(dme), 3.

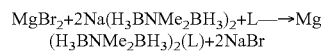

L=thf                                                         (2)

L=dme                                                    (3)

The infrared spectrum of 2 contains three strong bands in the B—H stretch region: a strong terminal B—H stretch at 2391 cm$^{-1}$, and two strong bridging B—H stretches at 2300 and 2241 cm$^{-1}$. Very similar bands are seen for 3. Relative to the features seen for unsolvated 1, the terminal B—H stretch appears at a lower frequency (and thus largely overlaps with the bridging B—H stretches), whereas the bridging B—H stretches appear at higher frequencies. These differences suggest that the Mg-diboranamide interaction is weaker in the ether adducts, a conclusion that is consistent with the longer Mg—H and Mg . . . B bonds seen in their crystal structures (see below). The $^1$H NMR spectrum of 2 at 20° C. shows a broad quartet at δ 1.99 for the BH$_3$ groups, and a similar feature at δ 2.11 is seen for 1.

Figure 9:
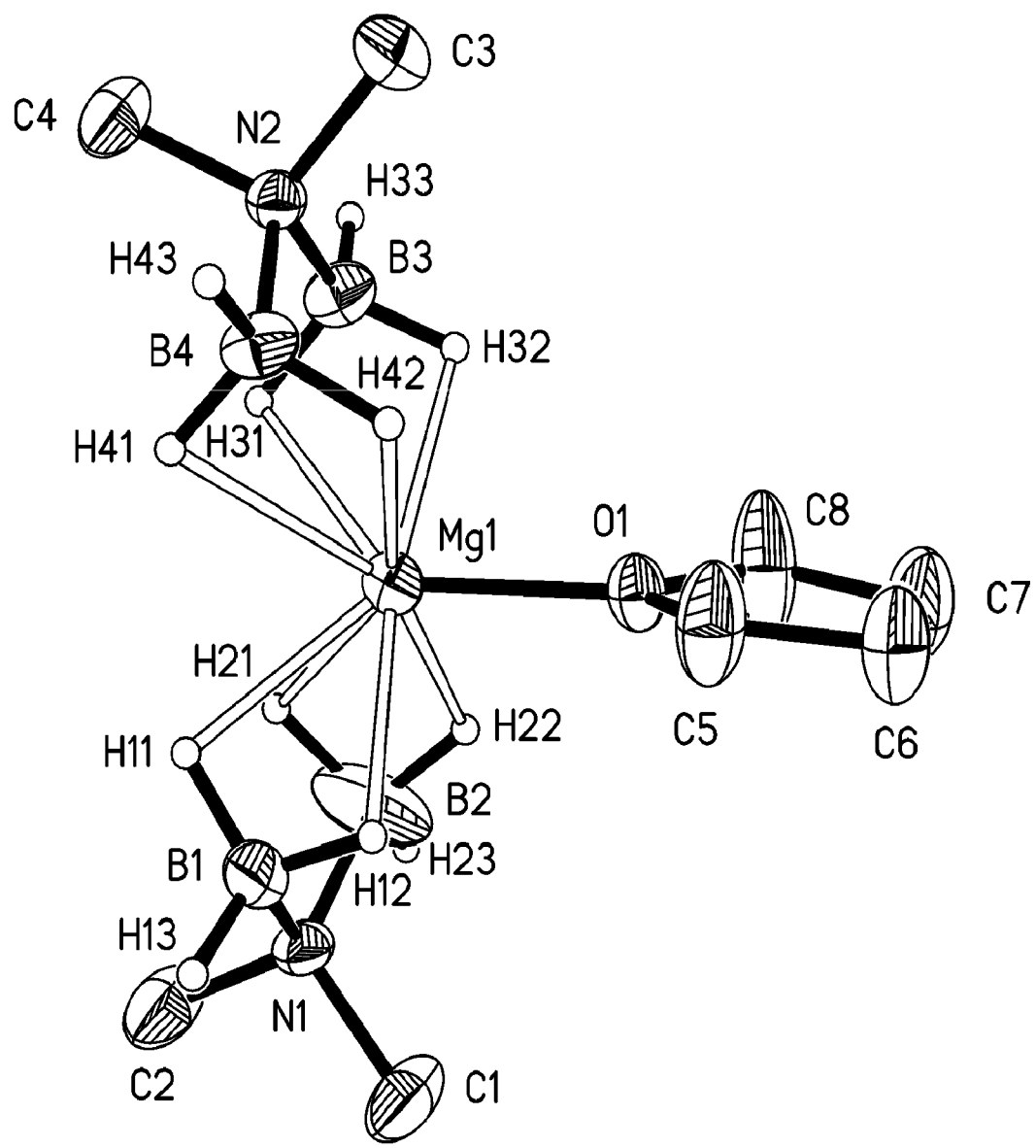
FIG. 9. Molecular structure of Mg(H$_3$BNMe$_2$BH$_3$)$_2$(thf), 2. Ellipsoids are drawn at the 30% probability level, except for hydrogen atoms, which are represented as arbitrarily sized spheres. Methyl and methylene hydrogen atoms have been deleted for clarity.
Figure 10:
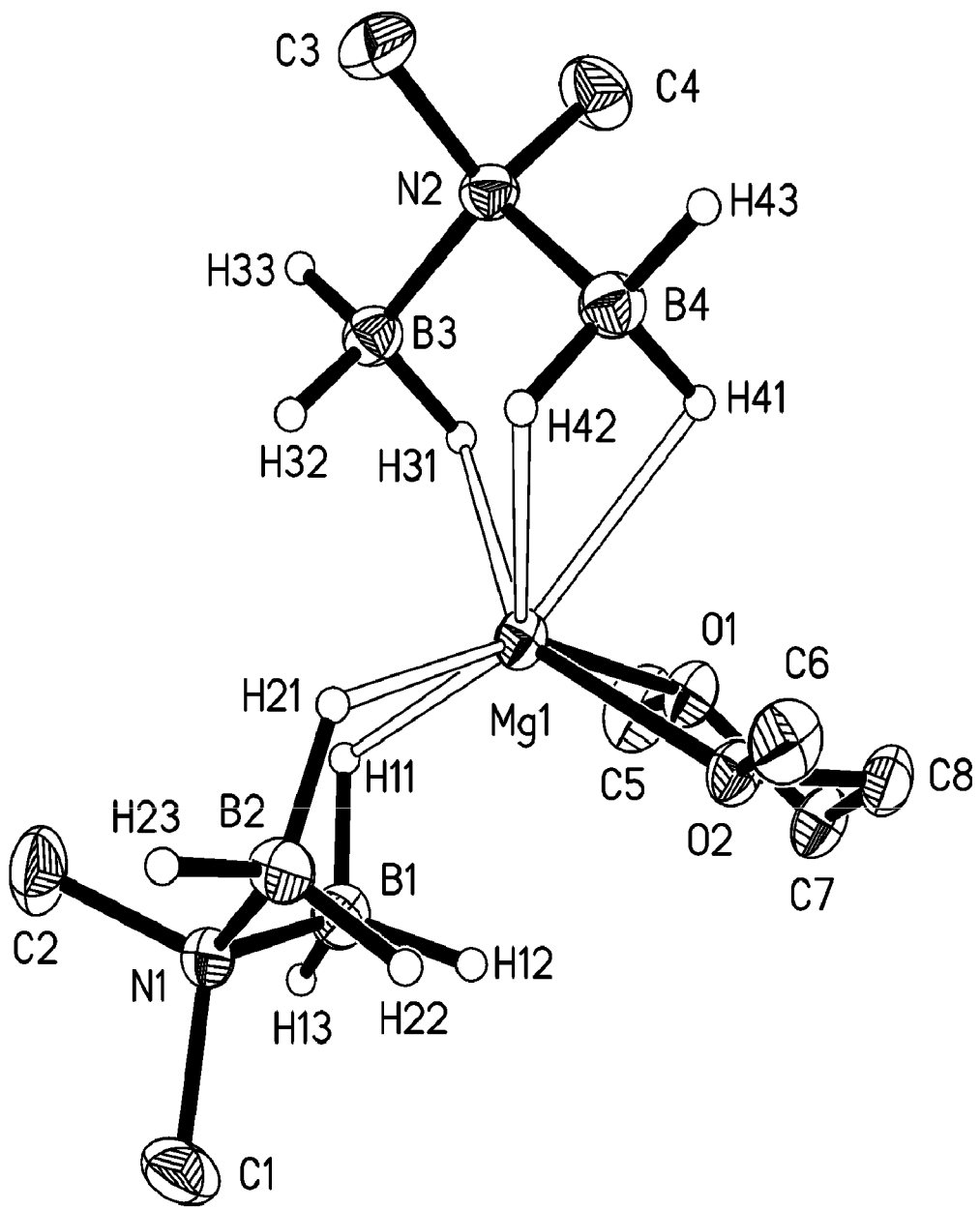
FIG. 10. Molecular structure of Mg(H$_3$BNMe$_2$BH$_3$)$_2$(dme), 3. Ellipsoids are drawn at the 30% probability level, except for hydrogen atoms, which are represented as arbitrarily-sized spheres. Methyl and methylene hydrogen atoms have been deleted for clarity.

Crystal Structures of Mg(H$_3$BNMe$_2$BH$_3$)$_2$(thf) and Mg(H$_3$BNMe$_2$BH$_3$)$_2$(dme). The molecular structure of 2 and 3 are presented in FIGS. 9 and 10; crystallographic data, and selected bond distances and angles are listed in Tables 1, 3, and 4. For the thf adduct 2, the magnesium center adopts a distorted square pyramidal geometry in which four BH$_3$ groups from two chelating diboranamide ligands occupy basal positions and the thf molecule occupies the apical site. Each BH$_3$ group of the diboranamide ligand coordinates to the magnesium center in a bidentate mode like that seen in 1, but the Mg—H distances of 2.13(10) Å are longer by about 0.1 Å than those in 1. Similarly, the Mg . . . B distances of 2.484(4)-2.553(5) Å are 0.1-0.15 Å longer than those in 1. These longer Mg—H and Mg . . . B distances, which suggest a weaker Mg-diboranamide interaction, reflect the higher degree of steric crowding in 2 due to the presence of the additional tetrahydrofuran ligand. In 2, the B—H distances to the bridging hydrogen atoms of 1.11 Å and those to the terminal hydrogen atoms of 1.10 Å are essentially identical.

This pattern differs from that in unsolvated 1, in which the bridging B—H distances were longer by nearly 0.1 Å, which again suggests that the Mg-diboranamide bonding is weaker in the ether adduct than in 1. The average B—Mg—B angle of 60.7° is some 6° smaller than that in 1 owing to the longer M-B distances in 2.

The magnesium center in the dme adduct 3 adopts a distorted octahedral geometry in which two diboranamide groups and one dme group act as chelating ligands. Unlike 1 and 2, in which eight hydrogen atoms form close contacts with the Mg atom, in 3 only five hydrogen atoms (H11, H21, H31, H41, and H42) form short Mg—H—B bridges, which range from 1.98(1) to 2.20(1) Å. The next shortest Mg—H contacts of 2.43(1) and 2.39(1) Å are formed to H12 and H32, respectively; all the other Mg—H distances are greater than 3 Å. The Mg . . . B distances of 2.608(2)-2.868(2) Å are also considerably longer than those in 2 by ~0.4 Å. The large Mg—H and Mg . . . B distances are consistent with the higher degree of steric congestion caused by the bidentate dme ligand. The long M . . . B distances in 3 cause the B—Mg—B angles of 56.11(5) and 59.36(5)° within each diboranamide ligand to be smaller than those in 1 and 2.

Synthesis and Characterization of Cp*Mg(H$_3$BNMe$_2$BH$_3$)(thf). Treatment of the magnesium pentamethylcyclopentadienyl complex [Cp*MgCl(thf)]$_2$ with one equivalent of Na(H$_3$BNMe$_2$BH$_3$) in diethyl ether affords the diboranamide complex Cp*Mg(H$_3$BNMe$_2$BH$_3$)(thf), 4, which can be obtained as white crystals by sublimation at 60° C. and 0.05 Torr.

$$\tfrac{1}{2}[Cp*MgCl(thf)]_2 + Na(H_3BNMe_2BH_3)_2 \longrightarrow Cp*Mg(H_3BNMe_2BH_3)(thf) + NaCl \qquad (4)$$

The B—H stretching modes in the IR spectrum of 4 closely resemble those seen for 2 and 3: there is a strong terminal B—H stretching band at 2393 cm$^{-1}$ and three strong bridging B—H stretching bands at 2297, 2241, and 2185 cm$^{-1}$. The $^1$H NMR spectrum of 4 at 20° C. contains a broad singlet at δ 2.21 for the BH$_3$ groups, a singlet at δ 2.14 for Cp* ring, and a singlet at δ 1.94 for NMe$_2$ groups, and characteristic resonances for the thf protons. Interestingly, based on the solid state structure (see below) there should be two NMe$_2$ environments: one methyl group should be proximal to the Cp* group and the other should be distal. Evidently, there is some exchange process that renders these two groups equivalent; there is also only one signal for the NMe$_2$ group in the $^{13}$C NMR spectrum.

Figure 11:
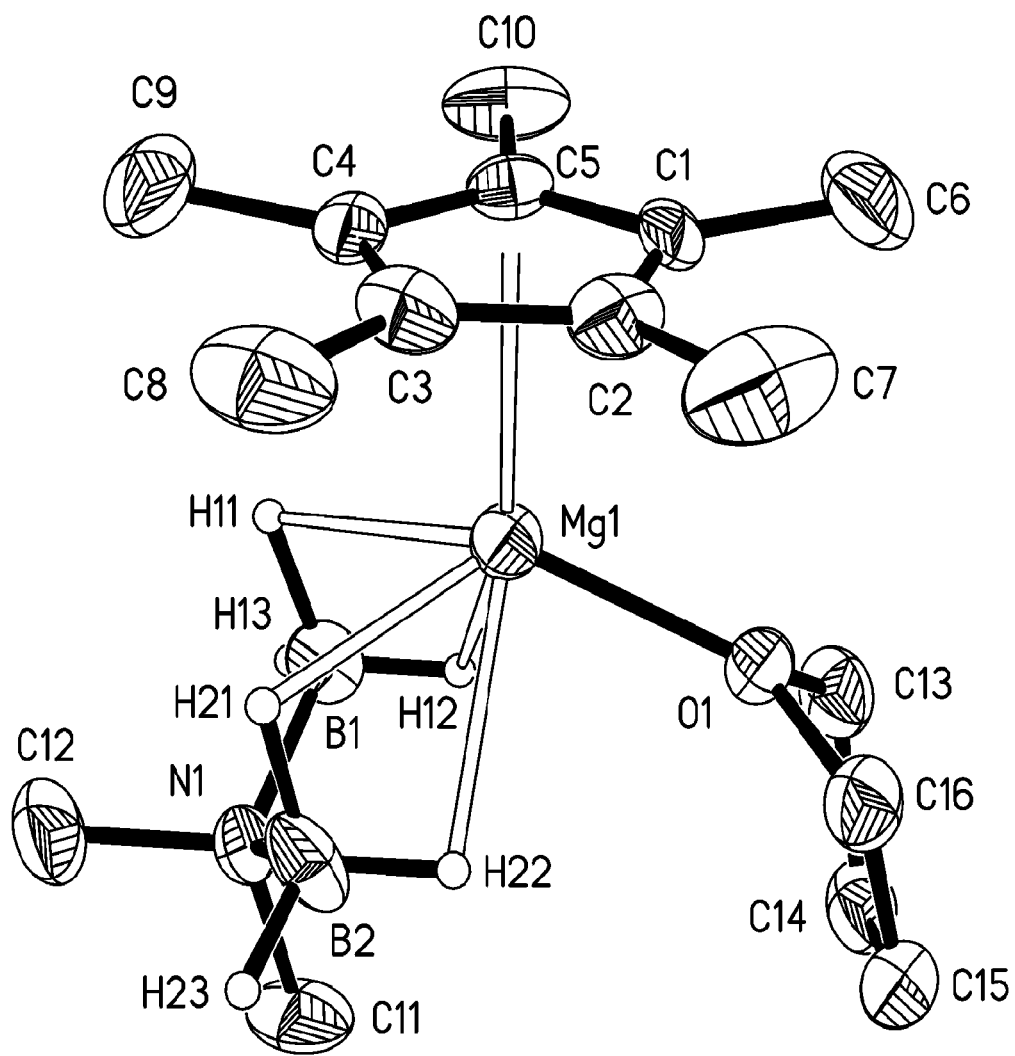
FIG. 11. Molecular structure of Cp*Mg(H$_3$BNMe$_2$BH$_3$)(thf), 4. Ellipsoids are drawn at the 30% probability level, except for hydrogen atoms, which are represented as arbitrarily-sized spheres. Methyl and methylene hydrogen atoms have been deleted for clarity.

Crystal Structure of Cp*Mg(H$_3$BNMe$_2$BH$_3$)(thf). The molecular structure of 4 is shown in FIG. 11; crystallographic data and selected bond distances and angles are listed in Tables 1 and 5. The magnesium center is coordinated to one η$^5$-Cp* ligand, one chelating [H$_3$BNMe$_2$BH$_3$]$^-$ ligand, and one thf molecule. All the BH$_3$ groups are bound to the magnesium center by means of two bridging hydrogen atoms. Three of Mg—H distances are equal, averaging 2.22(8) Å, and one may be slightly longer at 2.30(4) Å. The Mg . . . B distances are nearly identical at 2.534(7) and 2.554(8) Å. Although of marginal significance statistically, the refined B—H distances to the hydrogens that are proximal to the Cp* ring (1.22(4) and 1.18(4) Å) are slightly longer than those to hydrogens that are distal (1.15(3) and 1.15(4) Å). The terminal B—H distances are 1.15(3) and 1.07(4) Å. The Mg—C distances fall in a narrow range 2.360(5)-2.414(6) Å; the average Mg—C distance of 2.38(1) Å is similar to that of 2.38(2) Å seen in [Cp*MgCl(thf)]$_2$[40] but shorter than that of 2.44(3) Å seen in CpMg(η$^2$-t-BuC(NMes)$_2$)(thf), where Mes=2,4,6-C$_6$H$_2$Me$_3$.[41]

Experimental Section

All experiments were carried out under vacuum or under argon by using standard Schlenk techniques. Solvents were distilled under nitrogen from sodium/benzophenone immediately before use. The starting materials Na(H$_3$BNMe$_2$BH$_3$),[26] and Cp*MgCl(thf)[42] were prepared by literature procedures. MgBr$_2$ was used as received from Aldrich. Microanalyses were performed by the University of Illinois Microanalytical Laboratory. The IR spectra were recorded on a Nicolet Impact 410 instrument as Nujol mulls between KBr plates. The $^1$H and $^{13}$C NMR data were collected on a Varian Gemini 500 instrument at 499.699 MHz and 125.663 MHz, respectively. Chemical shifts are reported in δ units (positive shifts to high frequency) relative to tetramethylsilane. Field ionization (FI) mass spectra were recorded on a Micromass 70-VSE mass spectrometer. The shapes of all peak envelops correspond with those calculated from the natural abundance isotopic distributions. Melting points and decomposition temperatures were determined in closed capillaries under argon on a Thomas-Hoover Unimelt apparatus. Vapor pressures were measured by placing samples in a closed vessel equipped with a MKS 627B absolute capacitance manometer. The pressure increase as a function of time was plotted, and the vapor pressure determined from the y-axis intercept obtained by extrapolating the linear portion of the curve at longer times back to t=0.

Bis(N,N-dimethyldiboranamido)magnesium, Mg(H$_3$BNMe$_2$BH$_3$)$_2$, 1. Solid MgBr$_2$ (1.94 g, 10.5 mmol) and Na(H$_3$BNMe$_2$BH$_3$) (2.0 g, 21.0 mmol) were ground together briefly in a mortar and pestle. The dry solid mixture was transferred to a 100 mL round-bottom Schlenk flask, and 30-40 steel balls (4.5-mm diameter) were added. The flask was gently agitated for 30 min. Sublimation at 70° C. under static vacuum afforded white crystals (under a dynamic vacuum, substantial amount of the product can be lost). Yield: 1.13 g (64%). Vapor pressure at 25° C.: 0.8±0.1 torr. Mp: 70° C. $^1$H NMR(C$_7$D$_8$, 20° C.): δ 2.04 (s, 12H, NMe$_2$), 1.91 (q, J$_{BH}$=90.0 Hz, 12H, BH$_3$). $^{13}$C{$^1$H} NMR(C$_7$D$_8$, 20° C.): δ 50.98 (s, NMe$_2$). Anal. Calcd for C$_4$H$_{24}$N$_2$B$_4$Mg: C, 28.6; H, 14.4; N, 16.6; B, 25.8; Mg, 14.5. Found: C, 28.6; H, 15.1; N, 16.6, B, 25.7; Mg, 14.1. IR (cm$^{-1}$): 2449 s, 2355 w, 2294 w, 2195 s, 2149 m, 2078 w, 1312 s, 1239 m, 1219 m, 1178 s, 1142 s, 1022 s, 927 m, 904 m, 810 m, 521 s, 421 s.

Bis(N,N-dimethyldiboranamido)(tetrahydrofuran)magnesium, Mg(H$_3$BNMe$_2$BH$_3$)$_2$(thf), 2. To a suspension of MgBr$_2$ (0.51 g, 2.8 mmol) in tetrahydrofuran (20 mL) at room temperature was added a solution of Na(H$_3$BNMe$_2$BH$_3$) (0.53 g, 5.6 mmol) in tetrahydrofuran (30 mL). After the reaction mixture had been stirred for 8 h at room temperature, the solvent was removed in vacuum. Sublimation at 70° C. and at 0.05 Torr afforded white crystals. Yield: 0.31 g (47%). $^1$H NMR(C$_7$D$_8$, 20° C.): δ 3.57 (m, 4H, OCH$_2$), 2.33 (s, 12H, NMe$_2$), 1.99 (q, J$_{BH}$=84.5 Hz, 12H, BH$_3$), 1.28 (m, 4H, OCH$_2$CH$_2$). $^{13}$C{$^1$H} NMR(C$_7$D$_8$, 20° C.): δ 69.2 (s, OCH$_2$), 52.4 (s, NCH$_3$), 25.5 (s, OCH$_2$CH$_2$). Anal. Calcd for C$_8$H$_{32}$N$_2$B$_4$OMg: C, 40.1; H, 13.4; N, 11.7; B, 18.0; Mg, 10.1. Found: C, 39.5; H, 13.3; N, 11.3; B, 16.0; Mg, 10.5. IR (cm$^{-1}$): 2391 s, 2300 s, 2241 s, 2975 w, 1298 m, 1237 m, 1216 m, 1177 s, 1148 s, 1023 s, 929 m, 873 s, 816 m, 693 w.

Bis(N,N-dimethyldiboranamido)(dimethoxyethane)magnesium, Mg(H$_3$BNMe$_2$BH$_3$)$_2$(dme), 3. To a suspension of MgBr$_2$ (0.51 g, 2.8 mmol) in 1,2-dimethoxyethane (20 mL) at room temperature was added a solution of Na(H$_3$BNMe$_2$BH$_3$) (0.53 g, 5.6 mmol) in 1,2-dimethoxyethane (30 mL). After the reaction mixture had been stirred for 8 h at room temperature, the solvent was removed in vacuum. Sublimation at 70° C. and at 0.05 Torr afforded white crystals. Yield: 0.27 g (37%). $^1$H NMR(C$_6$D$_6$, 20° C.): δ 3.00

(s, 6H, OMe), 2.81 (s, 4H, OCH$_2$), 2.48 (s, 12H, NMe$_2$), 2.11 (q, J$_{BH}$=88.5 Hz, 12H, BH$_3$). $^{13}$C{$^1$H} NMR(C$_6$D$_6$, 20° C.): δ 69.6 (s, OCH$_2$), 59.6 (s, OCH$_3$), 52.6 (s, NMe$_2$). Anal. Calcd for C$_8$H$_{34}$N$_2$B$_4$O$_2$Mg: C, 37.3; H, 13.3; N, 10.9; B, 16.8; Mg, 9.42. Found: C, 36.4; H, 13.2; N, 10.4; B, 17.1; Mg, 9.92. IR (cm$^{-1}$): 2411 w, 2357 s, 2290 s, 2230 s, 2066 w, 1299 w, 1276 w, 1236 w, 1212 w, 1176 s, 1148 s, 1094 m, 1054 s, 1018 s, 925 w, 871 m, 811 w.

(Pentamethylcyclopentadienyl)(N,N-dimethyldiboranamido)(tetrahydrofuran)magnesium(II), Cp*Mg(H$_3$BNMe$_2$BH$_3$)(thf), 4. To a suspension of Cp*MgCl.thf (0.99 g, 3.7 mmol) in Et$_2$O (25 mL) at −78° C. was added a solution of Na(H$_3$BNMe$_2$BH$_3$) (0.38 g, 4.0 mmol) in Et$_2$O (20 mL). The reaction mixture was stirred for 10 min, allowed to warm to room temperature, and stirred for 5 h to give a colorless solution and a white precipitate. The solution was filtered and the filtrate was taken to dryness in vacuum. Sublimation at 60° C. and at 0.05 Torr in vacuum yielded white crystals. Yield: 0.68 g (63%). $^1$H NMR(C$_6$D$_6$, 20° C.): δ 3.42 (m, 4H, OCH$_2$), 2.21 (br, 6H, BH$_3$), 2.14 (s, 15H, C$_5$Me$_5$), 1.94 (s, NMe$_2$), 1.17 (m, 4H, OCH$_2$CH$_2$). $^{13}$C{$^1$H} NMR (C$_6$D$_6$, 20° C.): δ 110.40 (s, C$_5$Me$_5$), 69.55 (s, OCH$_2$), 52.45 (s, NMe$_2$), 25.32 (s, OCH$_2$CH$_2$), 11.16 (s, C$_5$Me$_5$). Anal. Calcd for C$_{16}$H$_{36}$NB$_4$OMg: C, 63.3; H, 11.6; N, 4.62; B, 7.13; Mg, 8.01. Found: C, 62.1; H, 11.7; N, 5.11; B, 9.20; Mg, 8.24. IR (cm$^{-1}$): 2434 sh, 2393 s, 2297 s, 2241 s, 2185 s, 2077 m, 1342 w, 1311 w, 1294 w, 1277 w, 1238 w, 1213 w, 1176 s, 1146 s, 1024 s, 926 m, 910 m, 874 s, 806 m, 681 w.

X-ray Structure Determinations.[43] Single crystals of all four compounds, grown by sublimation, were mounted on glass fibers with Krytox oil (DuPont), and immediately cooled to −80° C. in a cold nitrogen gas stream on the diffractometer. Data for 1-4 were collected with an area detector by using the measurement parameters listed in Table 1. The measured intensities were reduced to structure factor amplitudes and their esd's by correction for background, and Lorentz and polarization effects. Systematically absent reflections were deleted and symmetry-equivalent reflections were averaged to yield the sets of unique data. The analytical approximations to the scattering factors were used, and all structure factors were corrected for both real and imaginary components of anomalous dispersion. All structures were solved using direct methods (SHELXTL). The correct positions for all non-hydrogen atoms of 1-4 were deduced from E-maps. Final refinement parameters for 1-4 are given in Table 1. A final analysis of variance between observed and calculated structure factors showed no apparent errors. Subsequent discussions for 1-4 will be divided into individual paragraphs.

Mg(H$_3$BNMe$_2$BH$_3$)$_2$, 1. Systematic absences for hkl (h+k+l≠2n), and hhl (2h+l≠4n) were consistent with space groups I$\bar{4}$2d and I4$_1$md; the group I$\bar{4}$2d was shown to be the correct choice by successful refinement of the proposed model. All 1542 unique reflections were used in the least squares refinement. Although corrections for crystal decay were unnecessary, a face-indexed absorption correction was applied. The quantity minimized by the least-squares program was Σw(F$_o^2$−F$_c^2$)$^2$, where w={[σ(F$_o^2$)]$^2$ (0.0449P)$^2$}$^{-1}$ and P=(F$_o^2$+2F$_c^2$)/3. The locations of the hydrogen atoms were refined without constraints and each was given an independent anisotropic displacement parameter. An isotropic extinction parameter was refined to a final value of x=2.7(2)× 10$^{-5}$ where F$_c$ is multiplied by the factor k[1+F$_c^2$xλ$^3$/sin 2θ]$^{-1/4}$ with k being the overall scale factor. Successful convergence was indicated by the maximum shift/error of 0.001 for the last cycle. Final refinement parameters are given in Table 1. The largest peak in the final Fourier difference map (0.12 eÅ$^{-3}$) was located 1.27 Å from H(21).

Mg(H$_3$BNMe$_2$BH$_3$)$_2$(thf), 2. Systematic absences for hkl (h+k≠2n) and h0l (l≠2n) were consistent with space groups Cc and C2/c; the non-centrosymmetric Cc was shown to be the correct choice by successful refinement of the proposed model. All 2576 unique reflections were used in the least squares refinement. Although corrections for crystal decay were unnecessary, a face-indexed absorption correction was applied. The quantity minimized by the least-squares program was Σw(F$_o^2$−F$_c^2$)$^2$, where w={[σ(F$_o^2$)]$^2$+(0.0735P)$^2$}$^{-1}$ and P=(F$_o^2$+2F$_c^2$)/3. The B—H distances involving the bridging hydrogen atoms were constrained to equal within 0.05 Å; similar constraints were applied for chemically related B—H distances to the terminal hydrogen atoms. Methyl hydrogen atoms were placed in idealized locations with C—H=0.98 Å and were assigned displacement parameters equal to 1.5 times U$_{eq}$ for the attached carbon atom; the methyl groups were allowed to rotate about the N—C axis to find the best least-squares positions. Methylene hydrogen atoms were also placed in idealized locations with C—H=0.99 Å and their displacement parameters were set equal to 1.2 times U$_{eq}$ for the attached carbon atom. The displacement parameter for B2 was suspiciously large and probably reflects disorder in this site. Successful convergence was indicated by the maximum shift/error of 0.001 for the last cycle. Final refinement parameters are given in Table 1. The largest peak in the final Fourier difference map (0.18 eÅ$^{-3}$) was located 0.97 Å from B(2).

Mg(H$_3$BNMe$_2$BH$_3$)$_2$(dme), 3. Systematic absences for hkl (h+k≠2n) and h0l (l≠2n) were consistent with space groups Cc and C2/c; the centrosymmetric group C2/c was shown to be the correct choice by successful refinement of the proposed model. All 3840 unique reflections were used in the least squares refinement. Although corrections for crystal decay were unnecessary, a face-indexed absorption correction was applied. The quantity minimized by the least-squares program was Σw(F$_o^2$−F$_c^2$)$^2$, where w={[σ(F$_o^2$)]$^2$+(0.0473P)$^2$}$^{-1}$ and P=(F$_o^2$+2F$_c^2$)/3. Hydrogen atoms surfaced in the difference maps and their locations were refined without constraints. Hydrogen atoms attached to boron were each given an independent isotropic displacement parameter; methyl and methylene hydrogens were assigned isotropic displacement parameters equal to 1.5 times U$_{eq}$ and 1.2 times U$_{eq}$ for the attached carbon atom, respectively. Successful convergence was indicated by the maximum shift/error of 0.001 for the last cycle. Final refinement parameters are given in Table 1. The largest peak in the final Fourier difference map (0.18 eÅ$^{-3}$) was located 0.82 Å from B(3).

Cp*Mg(H$_3$BNMe$_2$BH$_3$)(thf), 4. Systematic absences for 0k0 (k≠2n) and h0l (h+l≠2n) were only consistent with space group P2$_1$/n. All 3827 unique data were used in the least squares refinement. Although corrections for crystal decay were unnecessary, a face-indexed empirical absorption correction was applied. The quantity minimized by the least-squares program was Σw(F$_o^2$−F$_c^2$)$^2$, where w={[σ(F$_o^2$)]$^2$+(0.04P)$^2$}$^{-1}$ and P=(F$_o^2$+2F$_c^2$)/3. Late in the refinement, it became clear that the data crystal was twinned by merohedry; the twin law corresponds to reflection through the bc plane (or 180° rotation about c). The calculated intensities were set equal to the formula I$_{calc}$=xI$_{hkl}$+(1−x)I$_{h'k'l'}$, where h'=−h, k'=k, and l'=l, and x is the volume fraction of the major twin individual. The value of x refined to 0.868(2). In the final cycle of least squares, independent anisotropic displacement factors were refined for the non-hydrogen atoms. The locations of the hydrogen atoms attached to boron were refined without constraints; these hydrogen atoms were each given independent isotropic displacement parameters. Hydrogen atoms attached to carbon were placed in idealized positions with C—H=0.98 Å for methyl hydrogens and 0.99 Å for methylene hydrogens; the methyl groups were allowed to rotate about the C—C axis to find the best least-squares positions. The displacement parameters for methyl hydrogens were set to 1.5 times $U_{eq}$ for the attached carbon; those for methylene hydrogens were set equal to 1.2 times $U_{eq}$. Successful convergence was indicated by the maximum shift/error of 0.000 for the last cycle. Final refinement parameters are given in Table 1. The largest peak in the final Fourier difference map (0.17 e Å$^{-3}$) was located 0.64 Å from carbon atom C(6).

REFERENCES

1. Nagamatsu, J.; Nakagawa, N.; Muranaka, T.; Zenitani, Y.; Akimitsu, J. *Nature* 2001, 410, 63-64.
2. Xu, M.; Kitazawa, H.; Takano, Y.; Ye, J.; Nishida, K.; Abe, H.; Matsushita, A.; Tsujii, N.; Kido, G. *Appl. Phys. Lett.* 2001, 79, 2779-2781.
3. Schmidt, H.; Zasadzinski, J. F.; Gray, K. E.; Hinks, D. G. *Phys. Rev. Lett.* 2002, 88.
4. Tsuda, S.; Yokoya, T.; Kiss, T.; Takano, Y.; Togano, K.; Kito, H.; Ihara, H.; Shin, S. *Phys. Rev. Lett.* 2001, 8717.
5. Fan, Z. Y.; Hinks, D. G.; Newman, N.; Rowell, J. M. *Appl. Phys. Lett.* 2001, 79, 87-89.
6. Ueda, K.; Naito, M. J. *Appl. Phys.* 2003, 93, 2113-2120.
7. Kang, W. N.; Kim, H. J.; Choi, E. M.; Jung, C. U.; Lee, S. L. *Science* 2001, 292, 1521-1523.
8. Zeng, X. H.; Pogrebnyakov, A. V.; Kotcharov, A.; Jones, J. E.; Xi, X. X.; Lysczek, E. M.; Redwing, J. M.; Xu, S. Y.; Lettieri, J.; Schlom, D. G.; Tian, W.; Pan, X. Q.; Liu, Z. K. *Nat. Mater.* 2002, 1, 35-38.
9. Jensen, J. A.; Gozum, J. E.; Pollina, D. M.; Girolami, G. S. *J. Am. Chem. Soc.* 1988, 110, 1643-1644.
10. Sung, J.; Goedde, D. M.; Girolami, G. S.; Abelson, J. R. *J. Appl. Phys.* 2002, 91, 3904-3911.
11. Jayaraman, S.; Yang, Y.; Kim, D. Y.; Girolami, G. S.; Abelson, J. R. *J. Vac. Sci. Technol., A* 2005, 23, 1619-1625.
12. Goedde, D. M.; Girolami, G. S. *J. Am. Chem. Soc.* 2004, 126, 12230-12231.
13. Jayaraman, S.; Klein, E. J.; Yang, Y.; Kim, D. Y.; Girolami, G. S.; Abelson, J. R. *J. Vac. Sci. Technol., A* 2005, 23, 631-633.
14. See Example 12.
15. Bremer, M.; Linti, G.; Noth, H.; Thomann-Albach, M.; Wagner, G. *Z. Anorg. Allg. Chem.* 2005, 631, 683-697.
16. Prust, J.; Most, K.; Muller, I.; Alexopoulos, E.; Stasch, A.; Uson, I.; Roesky, H. W. *Z. Anorg. Allg. Chem.* 2001, 627, 2032-2037.
17. Bremer, M.; Noth, H.; Warchhold, M. *Eur. J. Inorg. Chem.* 2003, 111-119.
18. Hermanek, S.; Plesek, J. *Collect. Czech. Chem. Commun.* 1966, 31, 177-89.
19. Lobkovskii, E. B.; Titov, L. V.; Psikha, S. B.; Antipin, M. Y.; Struchkov, Y. T. *J. Struct. Chem.* 1982, 23, 644-646.
20. Noeth, H. *Z. Naturforsch. B* 1982, 378, 1499-503.
21. Lobkovskii, E. B.; Titov, L. V.; Levicheva, M. D.; Chekhlov, A. N. *J. Struct. Chem.* 1990, V31, 506-508.
22. Levicheva, M. D.; Titov, L. V.; Psikha, S. B. *Zh. Neorg. Khim.* 1987, 32, 510-12.
23. Titov, L. V.; Levicheva, M. D.; Psikha, S. B. *Zh. Neorg. Khim.* 1984, 29, 668-73.
24. Denton, D. L.; Clayton, W. R.; Mangion, M.; Shore, S. G.; Meyers, E. A. *Inorg. Chem.* 1976, 15, 541-548.
25. See Example 12.
26. Noth, H.; Thomas, S. *Eur. J. Inorg. Chem.* 1999, 1373-1379.
27. Marks, T. J.; Kolb, J. R. *Chem. Rev.* 1977, 77, 263-93.
28. Marks, T. J.; Shimp, L. A. *J. Am. Chem. Soc.* 1972, 94, 1542-1550.
29. Product data sheet for Cp$_2$Mg (Rohm and Hass Electronic Materials, 2007).
30. Sadique, A. R.; Heeg, M. J.; Winter, C. H. *Inorg. Chem.* 2001, 40, 6349-6355.
31. Hatanpaa, T.; Ihanus, J.; Kansikas, J.; Mutikainen, I.; Ritala, M.; Leskela, M. *Chem. Mater.* 1999, 11, 1846-1852.
32. Kwak, B. S.; Boyd, E. P.; Zhang, K.; Erbil, A.; Wilkins, B. *Appl. Phys. Lett.* 1989, 54, 2542-2544.
33. Zhao, Y. W.; Suhr, H. *Appl. Phys. A: Mater. Sci. Process.* 1992, 54, 451-454.
34. Lu, Z.; Feigelson, R. S.; Route, R. K.; Dicarolis, S. A.; Hiskes, R.; Jacowitz, R. D. *J. Cryst. Growth* 1993, 128, 788-792.
35. Schwarberg, J. E.; Sievers, R. E.; Moshier, R. W. *Anal. Chem.* 1970, 42, 1828-1830.
36. Hatanpaa, T.; Kansikas, J.; Mutikainen, I.; Leskela, M. *Inorg. Chem.* 2001, 40, 788-794.
37. Babcock, J. R.; Wang, A. C.; Metz, A. W.; Edleman, N. L.; Metz, M. V.; Lane, M. A.; Kannewurf, C. R.; Marks, T. J. *Chem. Vap. Deposition* 2001, 7, 239-+.
38. Wang, L.; Yang, Y.; Ni, J.; Stern, C. L.; Marks, T. J. *Chem. Mater.* 2005, 17, 5697-5704.
39. El-Kaderi, H. M.; Xia, A. B.; Heeg, M. J.; Winter, C. H. *Organometallics* 2004, 23, 3488-3495.
40. Cramer, R. E.; Richmann, P. N.; Gilje, J. W. *J. Organomet. Chem.* 1991, 408, 131-136.
41. Xia, A.; El-Kaderi, H. M.; Jane Heeg, M.; Winter, C. H. *J. Organomet. Chem.* 2003, 682, 224-232.
42. Fagan, P. J.; Manriquez, J. M.; Maatta, E. A.; Seyam, A. M.; Marks, T. J. *J. Am. Chem. Soc.* 1981, 103, 6650-6667.
43. For details of the crystallographic methods used see: Brumaghim, J. L.; Priepot, J. G.; Girolami, G. S. *Organometallics* 1999, 18, 2139-2144.

Example 14

Volatile Lanthanide Complexes with Diboranamide Ligands, Synthesis and Characterization of $Y_2(H_3BNMe_2BH_3)_6$, $Dy_2(H_3BNMe_2BH_3)_6$, and their Adducts with Tetrahydrofuran Introduction Of the known metal boride phases, some of the most interesting are the rare earth metal hexaborides (LnB$_6$, Ln=lanthanide elements, including yttrium). These materials have remarkable structures, in which B$_6$ octahedra are linked to one another through their corners by exo B—B bonds to form a Cartesian lattice. The metal atoms are located at the centers of the holes formed by this lattice; they are surrounded by the triangular faces of eight adjacent B$_6$ octahedra, and so have 24 boron atoms as nearest neighbors. The physical properties of metal hexaborides are also of interest: these materials have been used as electron emitters in instruments such as scanning and transmission electron microscopes.[1-6]

The low work functions, low vapor pressures at elevated temperatures, and high mechanical strengths[7-9] make LnB$_6$ phases excellent materials for these applications, which involve strong electric fields, extremely high vacuum, high temperatures, and the presence of highly-reactive ionized gases. Because LnB$_6$ phases are highly absorbing in the near infrared region, but have high transmittance and low reflectance in the visible region, they are also excellent solar radiation shielding materials.[10]

Generation of a strong local electric field is crucial for efficient field emission, and so electron emitters in electron microscopes are best formed into shapes with high curvature.[11-14] Typically, single crystals of $LnB_6$ are employed, but an alternative approach uses physical vapor deposition (PVD) to grow a $LnB_6$ film onto a sharp tungsten, molybdenum, or silicon tip.[15-20] Further improvements may be possible by taking advantage of the very sharp tips of nano-materials. For example, Zhang et al. have demonstrated that nanowires of $LaB_6$, $CeB_6$, and $GdB_6$ can be grown by CVD.[21-24] A drawback of current CVD routes to thin films of $LnB_6$—i.e., the reduction of $LnCl_3$ and $BCl_3$ by $H_2$—is that they require high-temperatures (800-1500° C.).[21-26] Single source CVD routes, which often work well at much lower temperatures, have not been developed. Of the few known compounds that contain both lanthanide and boron—most of which are lanthanide tetrahydroborate complexes such as $Ln(BH_4)_3(thf)_n$, $Ln(BH_4)_2L_2$, $Cp_2Ln(BH_4)(thf)$, and $(C_5H_4CH_2CH_2OMe)_2Ln(BH_4)$[27,28]—none has been described as volatile. Volatile lanthanum-containing molecules that do not contain boron atoms have been extensively studied for the deposition of thin films of lanthanum oxides $(Ln_2O_3)$ that are high-k dielectric materials and high-temperature superconductors $(LnBa_2Cu_3O_{7-\delta})$. None of these precursors, such as lanthanum β-diketonates,[29,30] cyclopentadienyls,[31-33] and amides[34-36] have been used for the CVD of $LnB_6$ phases.

Here we report the synthesis and characterization of lanthanide complexes of the N,N-dimethyldiboranamide ligand $[H_3BNMe_2BH_3]^-$. Among the compounds prepared are the homoleptic compounds $M_2(H_3BNMe_2BH_3)_6$, where M=Y and Dy, and their mononuclear adducts with tetrahydrofuran. These molecules, which possess a boron-to-metal ratio of 6 and are readily volatile below 100° C., are potential CVD precursors for the low-temperature growth of $LnB_6$.

Results and Discussion

Synthesis and Characterization of $Y_2(H_3BNMe_2BH_3)_6$ and $Dy_2(H_3BNMe_2BH_3)_6$. The solid state reaction of $YCl_3$ and sodium N,N-dimethyldiboranamide, $Na(H_3BNMe_2BH_3)$, at room temperature, followed by sublimation at 100° C. in vacuum, affords the dinuclear yttrium complex, $Y_2(H_3BNMe_2BH_3)_6$, 1. A similar reaction with $DyCl_3$ yields the dysprosium analogue $Dy_2(H_3BNMe_2BH_3)_6$, 2. This synthetic method, which involves a solid state reaction of the starting materials at room temperature, perforce avoids the formation of solvated complexes.

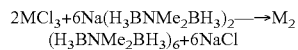

 (1)

 (2)

The infrared spectrum of 1 features a strong band at 2424 $cm^{-1}$ due to terminal B—H stretches, and two strong bands at 2220 and 2166 $cm^{-1}$ due to the bridging B—H stretches. Very similar B—H stretches at 2416, 2216, and 2170 $cm^{-1}$ are observed for the dysprosium analogue 2. These B—H stretching bands closely resemble those seen in homoleptic magnesium and transition metal complexes of the diboranamide ligand.[37]

Figure 12:
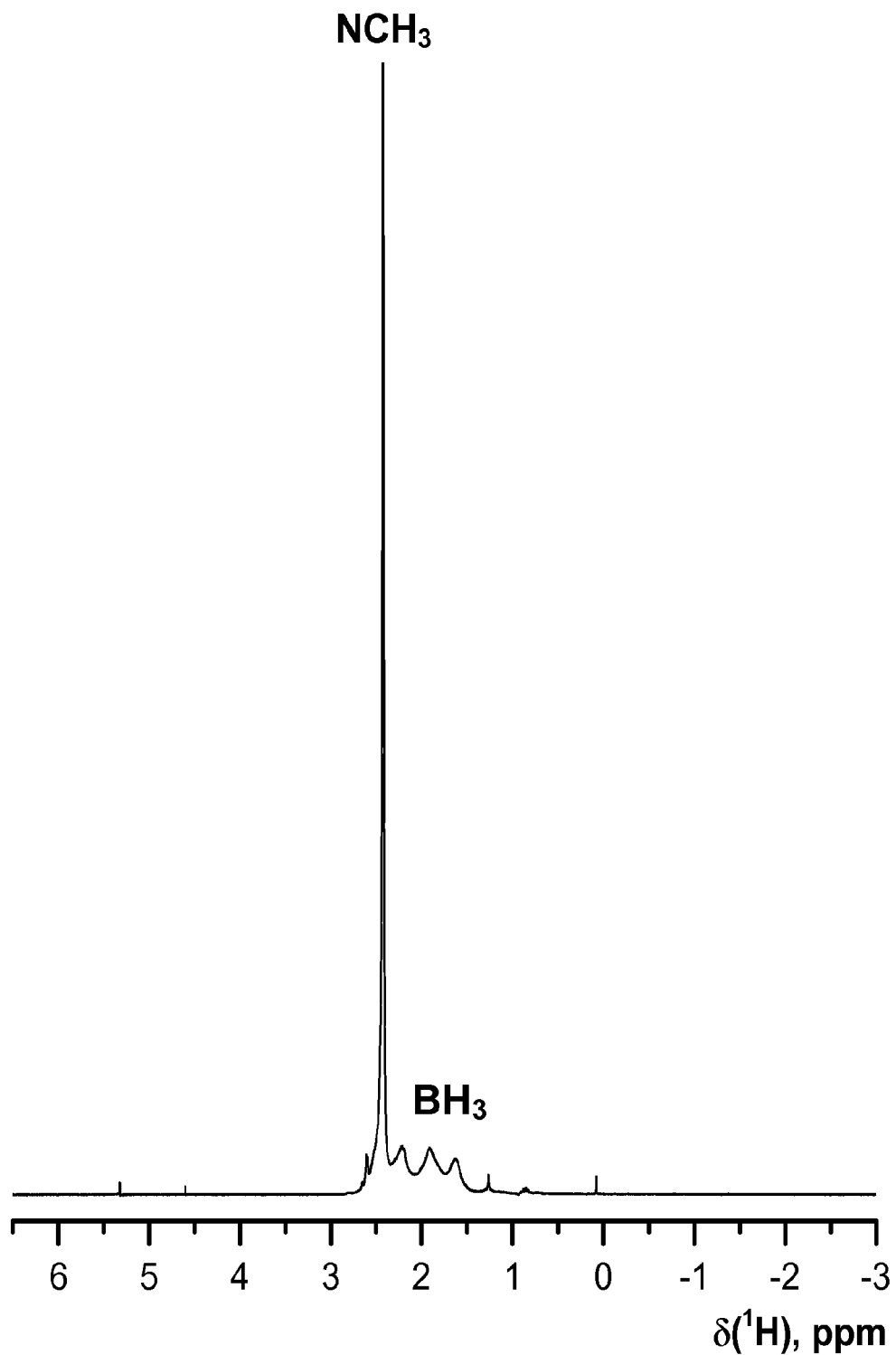
FIG. 12. $^1$H NMR spectrum of Y$_2$(H$_3$BNMe$_2$BH$_3$)$_6$, 1, in CD$_2$Cl$_2$ at 20° C.

The $^1H$ NMR spectrum of the yttrium complex 1 in $CD_2Cl_2$ at 20° C. shows two signals, a singlet at δ 2.42 for the $NMe_2$ group and a broad 1:1:1:1 quartet ($J_{BH}$=84 Hz) at δ 2.06 for the $BH_3$ groups (FIG. 12). The complex exhibits one signal for the $NMe_2$ groups in its $^{13}C$ NMR spectrum, and one signal at δ 50.8 in its $^{11}B$ NMR spectrum. At −80° C., the $^1H$ NMR spectrum exhibits a singlet for the $NMe_2$ groups and a broad unresolved signal for the $BH_3$ groups; the latter are broadened by rapid spin-lattice relaxation caused by the quadrupolar $^{11}B$ and $^{10}B$ nuclei. The presence of only one environment for the diboranamide ligands contrasts with the presence of two different environments in the solid state (see below). Evidently, the complex either dissociates to monomers in solution, or the terminal and bridging diboranamide groups are rapidly exchanging with one another even at −80° C. For the paramagnetic dysprosium complex 2, the room-temperature $^1H$ NMR spectrum exhibits a paramagnetically shifted and broadened resonance for the $NMe_2$ group at δ 97.5 (fwhm=250 Hz) but no signals for the $BH_3$ groups; the resonances for the latter must be very broad and shifted by their proximity to the paramagnetic center.

Figure 13:
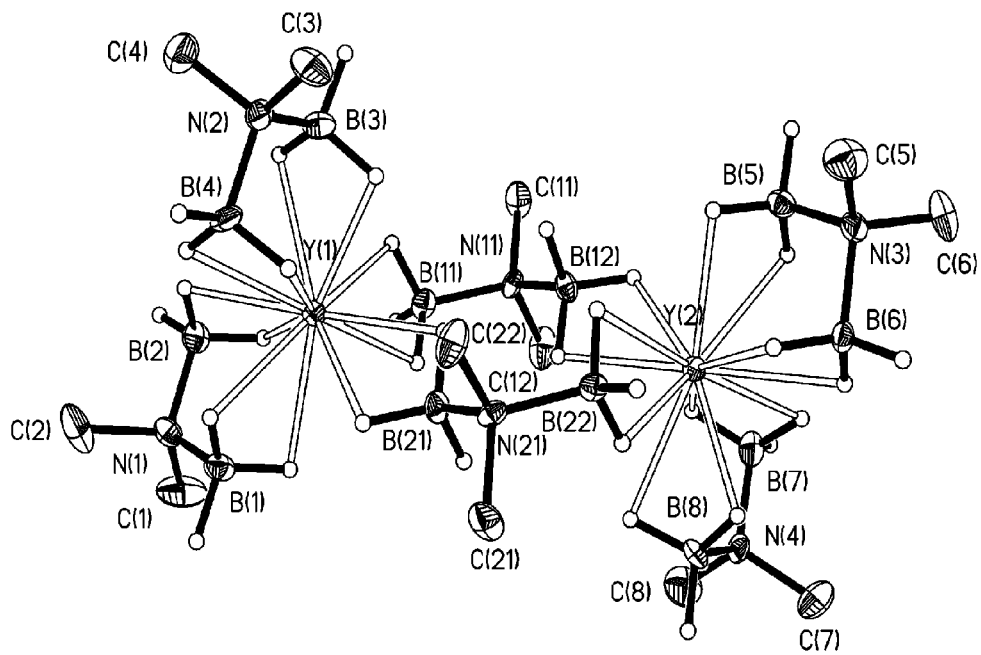
FIG. 13. a) Molecular structure of Y$_2$(H$_3$BNMe$_2$BH$_3$)$_6$, 1. Ellipsoids are drawn at the 35% probability level, except for hydrogen atoms, which are represented as arbitrarily sized spheres. Methyl hydrogen atoms have been deleted for clarity. b) Top view of 1 showing the unsymmetrical binding mode of the bridging diboranamide ligands.
Figure 13:
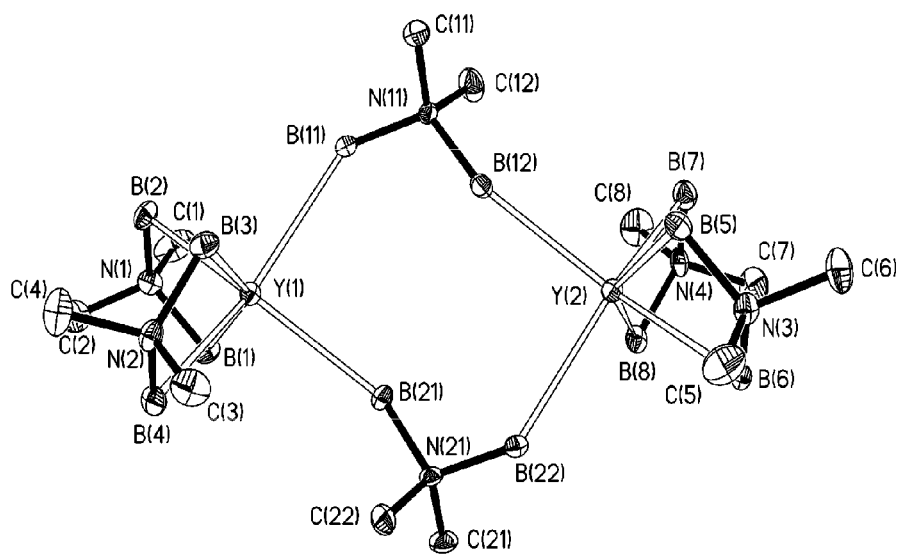
Figure 14:
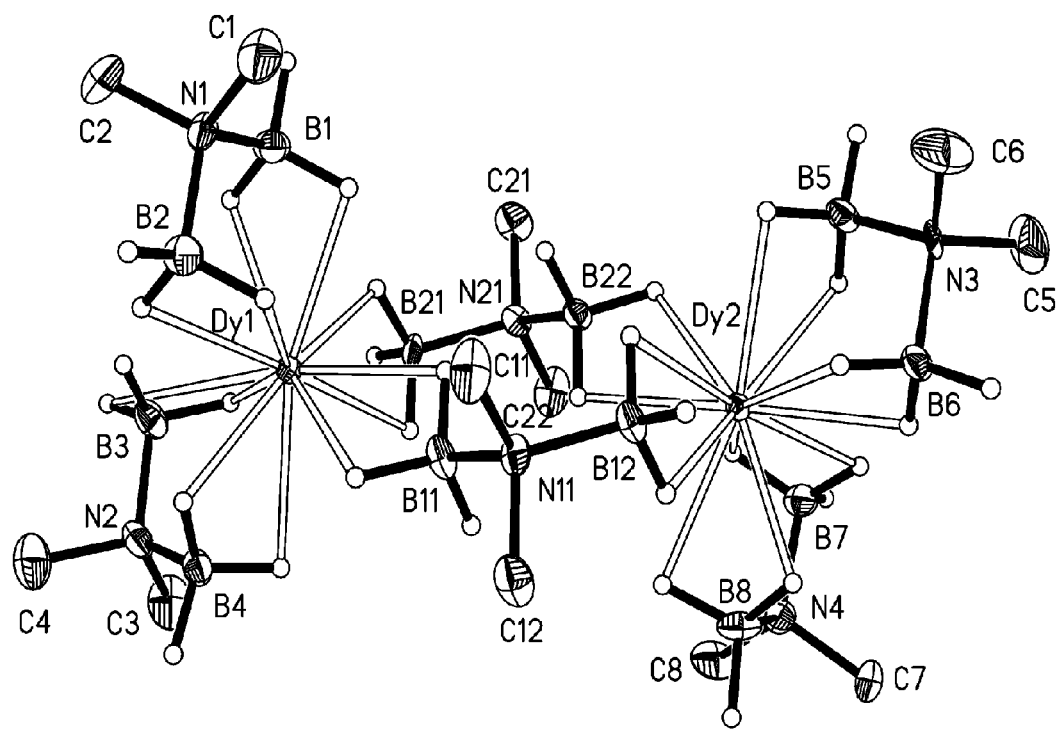
FIG. 14. Molecular structure of Dy$_2$(H$_3$BNMe$_2$BH$_3$)$_6$, 2. Ellipsoids are drawn at the 35% probability level, except for hydrogen atoms, which are represented as arbitrarily sized spheres. Methyl hydrogen atoms have been deleted for clarity.

Crystal Structures of $Y_2(H_3BNMe_2BH_3)_6$ and $Dy_2(H_3BNMe_2BH_3)_6$. The molecular structures of 1 and 2 are presented in FIGS. 13 and 14; crystallographic data and selected bond distances and angles are listed in Tables 1-3. The yttrium complex 1 adopts a dimeric structure in which two yttrium centers are connected by two bridging $H_3BNMe_2BH_3$ ligands; each yttrium center also bears two terminal diboranamide groups, which are chelating. The only other complex in which diboranamide ligands can be said to bridge between two metal centers is $[Na(H_3BNMe_2BH_3)]_5$·thf, but in this salt the diboranamide ligands actually interact in a complex way with two or three sodium cations.[38] The Y . . . Y separation in 1 is 6.03 Å. If each $BH_3$ group is considered as occupying one coordination site, each yttrium center is six-coordinate and adopts a distorted octahedral geometry. Two hydrogen atoms from each boron atom are bonded to the yttrium center, so that there are a total of 12 Y—H interactions.

The Y . . . B distances to the terminal diboranamide groups lie in the range 2.701(7)-2.763(7) Å and average 2.731(20) Å. For each of these ligands, the four-membered Y—B—N—B rings are essentially planar, as seen in other diboranamide complexes in which the $BH_3$ groups bind to the metal centers by means of two hydrogen bridges.[37] Interestingly, the bridging diboranamide ligands are not bound symmetrically to two yttrium centers: there are two short Y . . . B distances of 2.672(7) and 2.734(7) Å (Y2 . . . B12 and Y1 . . . B21) and two longer Y . . . B distances of 2.837(7) and 2.853(7) Å (Y1 . . . B11 and Y2 . . . B22). The B—N—B planes of the bridging diboranamide groups are not parallel to Y-Y axis and instead pass more closely to one yttrium center than the other: Y1 and Y2 are displaced 0.49 and 1.32 Å, respectively from the B11-N11-B12 plane, whereas they 1.44 and 0.43 Å, respectively, from the B22-N21-B22 plane. The Y—B—N angles of 145.12 and 147.56° for the longer Y . . . B distances are more obtuse by about 10° than those of 134.39 and 134.82° for the shorter Y . . . B distances.

The average B—Y—B angle of 55.6(4)° within each of the two terminal diboranamide ligands is significantly smaller than all the other B—Y—B angles, as expected for a chelating ligand with a small bite. In particular, the B—Y—B angle between the two bridging diboranamide ligands are 90.7(2) and 91.192)°, which suggest that the $BH_3$ "ends" of the two bridging diboranamide ligands jointly occupy more steric volume than would a chelating ligand. This stereochemical effect probably is related to the reasons 1 does not adopt a monomeric structure with three chelating diboranamide ligands: such a structure would not sufficiently saturate the coordination sphere of the large yttrium center. All of the B—N—B, B—N—C, and C—N—C angles within the diboranamide groups are close to ideal tetrahedral value of 109.5°, except for the B—N—B angles within the bridging ligands, 113.7(5) and 112.1(5)°, which are somewhat more obtuse.

The structure of the dysprosium analogue 2 is identical to that of 1: each dysprosium center is coordinated to two terminal and two bridging diboranamide ligands. The Dy . . . Dy separation is 6.01 Å. The bridging ligands are again bound unsymmetrically: the shorter Dy . . . B distances are 2.68 and 2.73 Å and longer Dy . . . B distances are identical at 2.84 Å. The Dy . . . B distances for the terminal diboranamide groups lie in a range 2.70±2.76 Å and average 2.73 Å. The B—Dy—B angles for the terminal ligands average 55.6°, which is smaller than the average B—Dy—B angle of 91.0° for the bridging diboranamide ligands, as seen in 1.

Synthesis and Characterization of $M(H_3BNMe_2BH_3)_3$ (thf) Complexes. Treatment of $YCl_3$ with $Na(H_3BNMe_2BH_3)$ in tetrahydrofuran affords the monomeric thf adduct $Y(H_3BNMe_2BH_3)_3$(thf), 3, which can be isolated as white crystals by sublimation at 90° C. and 0.05 Torr. Carrying out a similar reaction with $DyCl_3$ in thf yields the dysprosium analogue $Dy(H_3BNMe_2BH_3)_3$(thf)$_4$. Both complexes are air- and water-sensitive.

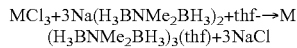

The infrared spectrum of 3 shows two strong bands in the B—H stretch region: a strong terminal B—H stretch at 2399 cm$^{-1}$ and three strong bridging B—H stretches at 2294, 2227, and 2177 cm$^{-1}$. Similar strong bands are observed in the IR spectrum of 4 at 2410, 2280, 2223 and 2176 cm$^{-1}$. The $^1$H NMR spectrum of 3 at 20° C. shows a singlet at δ 2.37 for the NMe$_2$ group, a 1:1:1:1 quartet at δ 2.00 for the BH$_3$ group, and characteristic resonances for the α and β protons of the thf ligand at δ 3.98 and 1.90. The variable temperature $^1$H{$^{11}$B} NMR spectrum between −80 and 20° C. shows no evidence of dynamic behavior. The paramagnetic dysprosium(III) complex 4 shows shifted and broadened signals for the NMe$_2$ groups at δ −19.50 (fwhm=250 Hz) and for the β-CH$_2$ protons of the thf molecule at δ −29.07 (fwhm=150 Hz). No resonances for the BH$_3$ groups or the α-CH$_2$ protons of thf could be located.

Figure 15:
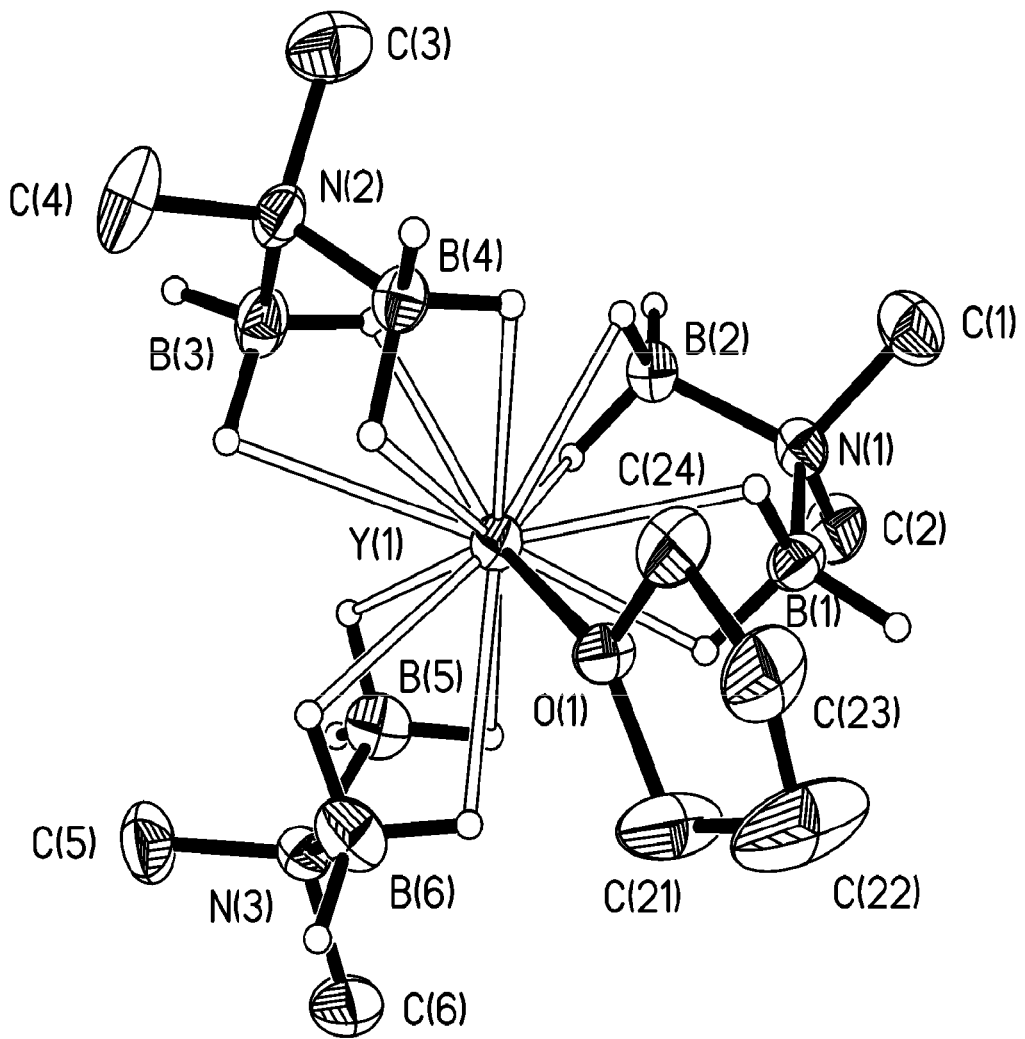
FIG. 15. Molecular structure of Y(H$_3$BNMe$_2$BH$_3$)$_3$(thf), 3. Molecule 1 is shown; molecule 2 adopts essentially same structure. Ellipsoids are drawn at the 35% probability level, except for hydrogen atoms, which are represented as arbitrarily-sized spheres. Methyl and methylene hydrogen atoms have been deleted for clarity.
Figure 16:
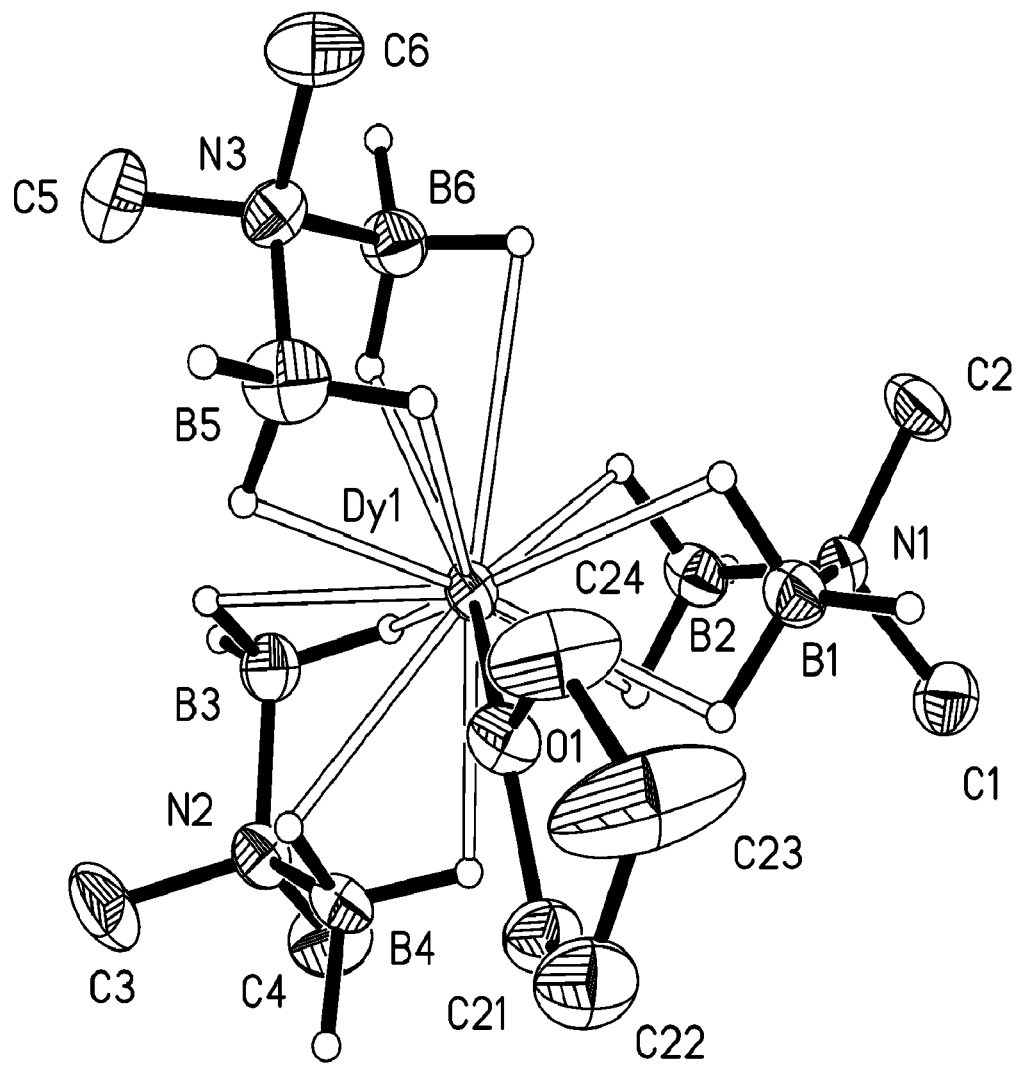
FIG. 16. Molecular structure of Dy(H$_3$BNMe$_2$BH$_3$)$_3$(thf), 4. Molecule 1 is shown; molecule 2 adopts essentially same structure. Ellipsoids are drawn at the 35% probability level, except for hydrogen atoms, which are represented as arbitrarily-sized spheres. Methyl and methylene hydrogen atoms have been deleted for clarity.

Crystal Structures of $Y(H_3BNMe_2BH_3)_3$(thf) and $Dy(H_3BNMe_2BH_3)_3$(thf). The molecular structure of 3 and 4 are illustrated in FIGS. 15 and 16; crystallographic data and selected bond distances and angles are listed in Tables 1, 4, and 5. For the yttrium complex 3, there are two crystallographically independent molecules in the unit cell and they have very similar bond lengths and angles. The yttrium center is coordinated to three chelating H$_3$BNMe$_2$BH$_3$ ligands and one thf molecule; if we consider each BH$_3$ group to occupy one coordination site, the metal center is 7-coordinate. Each BH$_3$ group is bound to the yttrium center by means of two hydrogen bridges, thus forming a total of twelve Y—H contracts. The Y—H distances fall in the range 2.23(4)-2.58(6) Å and average 2.39(16) Å. The Y . . . B distances average 2.82(2) Å, which is about 0.1 Å longer than the corresponding distances to the chelating diboranamide ligands in unsolvated 1. The average B—Y—B angle of 53.4(3)° within each diboranamide ligand is 3° smaller than that of 56.5° in 1. The longer Y . . . B distances and smaller B—Y—B angles in 3 vs. 1 probably reflect the steric crowding caused by the additional thf ligand.

The Y—H and Y . . . B distances in 1 and 3 can be compared with those in yttrium tetrahydroborate (BH$_4$) complexes; among these are $Y(BH_4)_3$(thf)$_3$,[39] $(C_5H_4CH_2CH_2OMe)_2Y(BH^4)$,[40] $(C_5Me_4Et)_2Y(BH_4)$(thf),[41] and $(MeOCH_2$ $CH_2$ $C_9H_6)_2Y(BH_4)$.[42] The average Y—H distance of 2.39(16) Å in 3 is somewhat longer than that of 2.31(19) Å for these yttrium tetrahydroborates. Moreover, the Y . . . B distances of 2.672(7)-2.853(7) Å in 1 and 2.82(2) Å in 3 are longer than those of 2.669(4)-2.693(8) Å observed for yttrium complexes containing bidentate BH$_4$ groups. Presumably, steric crowding cause by the high coordination numbers are responsible for the longer distances seen in 1 and 3, whose metal centers are bound to twelve and thirteen atoms, respectively, vs. 8 to 10 for the reference compounds above.

The structure of the dysprosium complex 4 is identical to that of yttrium complex 3: the dysprosium center is ligated by three chelating diboranamide ligands and one thf molecule. The Dy . . . B distances in 4, which average 2.821(16) Å, are longer than the same distances in 2 by nearly 0.09 Å. The three B—Dy—B angles are nearly identical and average 53.4 (3)°, which is smaller than that of 55.6° in 2. The bond length and angle differences seen for 4 vs 2 again reflect the higher degree of steric congestion caused by the presence of the additional thf ligand and higher effective coordination number in 4.

Experimental Section

All experiments were carried out under vacuum or under argon by using standard Schlenk techniques. Solvents were distilled under nitrogen from sodium/benzophenone immediately before use. The starting material $Na(H_3BNMe_2BH_3)$ was prepared by a literature procedure.[38] YCl$_3$ and DyCl$_3$ were used as received from Aldrich. Microanalyses were performed by the University of Illinois Microanalytical Laboratory. The IR spectra were recorded on a Nicolet Impact 410 instrument as Nujol mulls between KBr plates. The $^1$H and $^{13}$C NMR data were collected on Varian Gemini 500 instrument at 499.699 MHz and 125.663 MHz, respectively. The $^{11}$B NMR data were collected on General Electric GN300WB instrument at 300 MHz. Chemical shifts are reported in δ units (positive shifts to high frequency) relative to tetramethylsilane ($^1$H, $^{13}$C) or BF$_3$.Et$_2$O ($^{11}$B). Field ionization (FI) mass spectra were recorded on a Micromass 70-VSE mass spectrometer. The shapes of all peak envelops correspond with those calculated from the natural abundance isotopic distributions.

Hexakis(N,N-dimethyldiboranamido)diyttrium(III), $Y_2(H_3BNMe_2BH_3)_6$, 1. Solid YCl$_3$ (0.73 g, 3.8 mmol) and Na(H$_3$BNMe$_2$BH$_3$) (1.26 g, 13.3 mmol) were ground together briefly in a mortar and pestle. The dry solid mixture was transferred to a 100 mL round-bottom Schlenk flask, and 30-40 steel balls (4.5-mm diameter) were added. The flask was gently agitated for 30 min. Sublimation at 100° C. in vacuum afforded white crystals. Yield: 0.22 g (19%). $^1$H NMR (CD$_2$Cl$_2$, 20° C.): δ 2.42 (s, 36H, NMe$_2$), 2.06 (q, $J_{BH}$=84 Hz, 36H, BH$_3$). $^{13}$C{$^1$H} NMR (CD$_2$Cl$_2$, 20° C.): δ 51.1 (s). $^{11}$B{$^1$H} NMR (CD$_2$Cl$_2$, 20° C.): δ 50.8 (s). Anal. Calcd for C$_6$H$_{36}$N$_3$B$_6$Y: C, 23.7; H, 11.9; N, 12.8; B, 21.3; Y, 29.2. Found: C, 22.9; H, 11.1; N, 12.8; B, 19.5; Y, 28.0. IR (cm$^{-1}$): 2424 vs, 2336 m, 2273 m, 2220 s, 2166 s, 2058 sh, 1399 w, 1335 s, 1286 s, 1237 w, 1212 w, 1170 s, 1015 s, 969 m, 927 m, 902 m, 841 m, 814 s, 464 s.

Hexakis(N,N-dimethyldiboranamido)didysprosium(III), Dy$_2$(H$_3$BNMe$_2$BH$_3$)$_6$, 2. Solid DyCl$_3$ (0.56 g, 2.1 mmol) and solid Na(H$_3$BNMe$_2$BH$_3$) (0.65 g, 6.7 mmol) and were ground together briefly in a mortar and pestle. The dry solid mixture was transferred to a 100 mL round-bottom Schlenk flask, and 30-40 steel balls (4.5-mm diameter) were added. The flask was gently agitated by hand for 30 min. Sublimation at 95° C. in vacuum afforded white crystals. Yield: 0.19 g (24%). Anal. Calcd for $C_6H_{36}N_3B_6Dy$: C, 19.1; H, 9.61; N, 11.1. Found: C, 19.0; H, 9.62; N, 10.8. MS (FI): m/z 377.3 (M/2-1)$^+$. $^1$H NMR($C_6D_6$, 20 (C): δ 97.5 (s, fwhm=250 Hz, $NMe_2$). IR (cm$^{-1}$): 2416 vs, 2334 m, 2272 m, 2216 s, 2170 s, 2061 w, 1282 vs, 1237 s, 1218 m, 1183 m, 1162 vs, 1130 m, 1031 w, 1020 s, 973 w, 925 m, 904 m, 844 w, 814 w, 463 s.

Tris(N,N-dimethyldiboranamido)(tetrahydrofuran)yttrium(III), $Y(H_3BNMe_2BH_3)_3$ thf), 3. To a solution of $YCl_3$ (1.07 g, 5.5 mmol) in tetrahydrofuran (30 mL) at room temperature was added a solution of $Na(H_3BNMe_2BH_3)$ (1.56 g, 16.5 mmol) in tetrahydrofuran (30 mL). After the reaction mixture had been stirred for 10 h at room temperature, the solvent was removed in vacuum. Sublimation at 90° C. and at 0.05 Torr afforded white crystals. Yield: 0.76 g (37%). $^1$H NMR ($CD_2Cl_2$, 20° C.): δ 3.98 (m, 4H, $OCH_2$), 2.37 (s, 18H, $NMe_2$), 2.00 (q, $J_{BH}$=84 Hz, 18H, $8H_3$), 1.90 (m, 4H, $CH_2$). Anal. Calcd for $C_{10}H_{44}N_3B_6OY$: C, 31.9; H, 11.8; N, 11.2. Found: C, 30.1; H, 11.8; N, 11.5. IR (cm$^{-1}$): 2399 vs, 2294 m, 2227 s, 2177 w, 2060 sh, 1283 s, 1241 s, 1217 s, 1189 w, 1171 s, 1137 s, 1020 s, 924 m, 904 w, 856 m, 837 w, 819 w, 666 w.

Tris(N,N-dimethyldiboranamido)(tetrahydrofuran)dysprosium(III), $Dy(H_3BNMe_2BH_3)_3$(thf), 4. To a solution of $DyCl_3$ (0.50 g, 1.9 mmol) in tetrahydrofuran (30 mL) at −78° C. was added a solution of $Na(H_3BNMe_2BH_3)$ (0.60 g, 6.3 mmol) in tetrahydrofuran (30 mL). The reaction mixture was stirred at −78° C. for 30 min and then was allowed to warm slowly to room temperature. After the reaction mixture had been refluxed at 75° C. for 24 h, the solvent was removed in vacuum. The white residue was extracted with pentane (2×50 mL), and the extract was filtered and concentrated to ca. 10 mL. Crystallization at −20° C. afforded white crystals. Yield: 0.47 g (63%). $^1$H NMR ($C_6D_6$, 20° C.): δ −19.50 (s, fwhm=250 Hz, 18H, $NMe_2$); −29.07 (s, fwhm=150 Hz, 4H, β-$CH_2$). Anal. Calcd for $C_{10}H_{44}N_3B_6ODy$: C, 26.7; H, 9.86; N, 9.34; B, 14.4; Dy, 36.1. Found: C, 26.1; H, 10.1; N, 8.73; B, 15.0; Dy, 33.8. IR (cm$^{-1}$): 2410 vs, 2280 m, 2223 s, 2178 w, 2064 w, 1279 vs, 1238 m, 1217 w, 1168 s, 1139 s, 1017 vs, 927 s 902 w, 836 s, 817 w, 666 w. Single crystals for the X-ray diffraction study were grown by sublimation at 90° C. and at 0.05 Torr.

X-ray Structure Determinations.[43] Single crystals of all four compounds, grown by sublimation, were mounted on glass fibers with Krytox oil (DuPont), and immediately cooled to −80° C. in a cold nitrogen gas stream on the diffractometer. Data for 1-4 were collected with an area detector by using the measurement parameters listed in Table 1. The measured intensities were reduced to structure factor amplitudes and their esd's by correction for background, and Lorentz and polarization effects. Systematically absent reflections were deleted and symmetry-equivalent reflections were averaged to yield the sets of unique data. The analytical approximations to the scattering factors were used, and all structure factors were corrected for both real and imaginary components of anomalous dispersion. All structures were solved using direct methods (SHELXTL). The correct positions for all non-hydrogen atoms of 1-4 were deduced from E-maps. The analytical approximations to the scattering factors were used, and all structure factors were corrected for both the real and imaginary components of anomalous dispersion. In the final cycle of least squares, independent anisotropic displacement factors were refined for the non-hydrogen atoms. Final refinement parameters for 1-4 are given in Table 1. A final analysis of variance between observed and calculated structure factors showed no apparent errors. Subsequent discussions for 1-4 will be divided into individual paragraphs.

$Y_2(H_3BNMe_2BH_3)_6$, 1. Systematic absences for 0kl (k+l≠2n) and h0l (h≠2n) were consistent with space groups Pna2$_1$ and Pnma; the non-centrosymmetric Pna2$_1$ was shown to be the correct choice by successful refinement of the proposed model. All 9025 unique reflections were used in the least squares refinement. Although corrections for crystal decay were unnecessary, a face-indexed absorption correction was applied. The quantity minimized by the least-squares program was $\Sigma w(F_o^2-F_c^2)^2$, where $w=\{[\sigma(F_o^2)]^2+(0.0168 P)^2\}^{-1}$ and $P=(F_o^2+2F_c^2)/3$. Hydrogen atoms were placed in idealized positions; hydrogen atoms attached to boron and methyl hydrogen atoms were placed in idealized tetrahedral locations with B—H=1.15 Å and C—H=0.98 Å, respectively; the $BH_3$ and $CH_3$ groups were allowed to rotate about the B—N and the C—N bonds, respectively, to find the best least-squares positions. Displacement parameters for the hydrogen atoms were set equal to 1.5 times $U_{eq}$ for the attached carbon or boron atom. No correction for isotropic extinction was necessary. Analysis of the diffraction intensities suggested that the crystal was twinned by inversion; therefore, the intensities were calculated from the equation $I_{calc}=xI_{hkl}+(1-x)I_{\bar{h}\bar{k}\bar{l}}$, where x is a scale factor that relates the volumes of the inversion-related twin components. The scale factor refined to a value of 0.83(1). Successful convergence was indicated by the maximum shift/error of 0.001 for the last cycle. Final refinement parameters are given in Table 1. The largest peak in the final Fourier difference map (1.40 eÅ$^{-3}$) was located 1.80 Å from H(2A). A final analysis of variance between observed and calculated structure factors showed no apparent errors.

$Dy_2(H_3BNMe_2BH_3)_6$, 2. Systematic absences for 0kl (k+l≠2n) and h0l (h≠2n) were consistent with space groups Pna2$_1$ and Pnma; the non-centrosymmetric Pna2$_1$ was shown to be the correct choice by successful refinement of the proposed model. Systematically absent reflections were deleted and symmetry equivalent reflections were averaged; the 2 0 0 reflection was obscured by the beamstop and was deleted to yield the set of 9596 unique data. No corrections for absorption or crystal decay were applied.

Hydrogen atoms were placed in idealized positions; hydrogen atoms attached to boron and methyl hydrogen atoms were placed in idealized tetrahedral locations with B—H=1.15 Å and C—H=0.98 Å, respectively; the $BH_3$ and $CH_3$ groups were allowed to rotate about the B—N and the C—N bonds, respectively, to find the best least-squares positions. Displacement parameters for the hydrogen atoms were set equal to 1.5 times $U_{eq}$ for the attached boron or carbon atom. Despite these efforts, however, the weighted R-factor remained unacceptably high (>0.2), two unusually large peaks (±17 e/Å$^3$) remained in the difference map that appeared to be "ghosts" related to the two dysprosium atoms by the transformation (x+0.33333, 0.5−y, z), and reflections of the form hkl (h=3n) were systematically far more intense than calculated, especially but not exclusively when l=2n and h+k=2n. A reinspection of the original data frames ruled out the possibility that the crystal was a pseudo-merohedral twin in which only the h=3n reflections were affected by overlap. We concluded that the crystal was probably affected by a kind of stacking fault; the molecules are lined up in columns along the x-axis, with their Dy-Dy vectors aligned along this direction also. It seemed possible that, part of the time, the molecules in one column could be displaced by a fractional cell distance along the x-axis and still pack well. As a last measure, we deleted all reflections with h=3n, leaving 6464 unique data. Immediately, $wR^2$ decreased to ~0.15 and the sizes of the ghost peaks decreased to ±7 e/Å$^3$. A stacking fault model was constructed in which a second molecule was added that was related to the first by the transformation (x+0.33333, 0.5−y, z). This second molecule was treated as a rigid group in which all the non-hydrogen atoms were assigned a common isotropic displacement parameter and a common partial site occupancy factor. The site occupancy factors for the major and minor locations were constrained to sum to 1; the SOF for the major site refined to 0.927(1). Note that this model did not afford intensities for the h=3n reflections that agreed with the observed values.

The quantity minimized by the least-squares program was $\Sigma w(F_o^2-F_c^2)^2$, where $w=\{[\sigma(F_o^2)]^2+(0.043P)^2\}^{-1}$ and $P=(F_o^2+2F_c^2)/3$. No correction for isotropic extinction was necessary. The analytical approximations to the scattering factors were used, and all structure factors were corrected for both real and imaginary components of anomalous dispersion. Analysis of the diffraction intensities suggested that the crystal was twinned by inversion; therefore, the intensities were calculated from the equation $l_{calc}=xl_{hkl}+(1-x)l_{h'k'l'}$, where x is a scale factor that relates the volumes of the inversion-related twin components. The scale factor refined to a value of 0.62(3). Successful convergence was indicated by the maximum shift/error of 0.002 for the last cycle. Final refinement parameters are given in Table 1. The largest peak in the final Fourier difference map (1.12 eÅ$^{-3}$) was located 0.60 from Dy(2). A final analysis of variance between observed and calculated structure factors showed no apparent errors.

Y(H$_3$BNMe$_2$BH$_3$)$_3$(thf), 3. Systematic absences for 0kl (k+l≠2n) and h0l (l≠2n) were consistent with space groups Pca2$_1$ and Pbcm; the non-centrosymmetric Pca2$_1$ was shown to be the correct choice by successful refinement of the proposed model. All 8605 unique reflections were used in the least squares refinement. Although corrections for crystal decay were unnecessary, a face-indexed absorption correction was applied. The quantity minimized by the least-squares program was $\Sigma w(F_o^2-F_c^2)^2$ where $w=\{[\sigma(F_o^2)]^2+(0.0191P)^2+2.000P\}^{-1}$ and $P=(F_o^2+2F2)/3$. Hydrogen atoms attached to boron were located in the difference maps, and their positions were refined with independent isotropic displacement parameters. The B—H distances to bridging hydrogen were constrained to equal within 0.05 Å; similar constraints were applied for chemically related B—H distances to the terminal hydrogen atoms. The methyl hydrogen atoms were placed in idealized locations with C—H=0.98 Å and their displacement parameters were set equal to 1.5 times U$_{eq}$ for the attached carbon atom; the CH$_3$ groups were allowed to rotate about the C—N axis to find the best least-squares positions. Methylene hydrogen atoms were also placed in idealized locations with C—H=0.99 Å and displacement parameters set equal to 1.2 times U$_{eq}$ for the attached carbon atom. No correction for isotropic extinction was necessary. Analysis of the diffraction intensities suggested that the crystal was twinned by inversion; therefore, the intensities were calculated from the equation $l_{calc}=xl_{hkl}+(1-x)l_{h'k'l'}$, where x is a scale factor that relates the volumes of the inversion-related twin components. The scale factor refined to a value of 0.879(6). Successful convergence was indicated by the maximum shift/error of 0.002 for the last cycle. Final refinement parameters are given in Table 1. The largest peak in the final Fourier difference map (0.42 eÅ$^{-3}$) was located 1.18 Å from C(22). A final analysis of variance between observed and calculated structure factors showed no apparent errors.

Dy(H$_3$BNMe$_2$BH$_3$)$_3$(thf), 4. Systematic absences for 0kl (k+l≠2n) and h0l (l≠2n) were consistent with space groups Pca2$_1$ and Pbcm; the non-centrosymmetric Pca2$_1$ was shown to be the correct choice by successful refinement of the proposed model. All 10934 unique reflections were used in the least squares refinement. Although corrections for crystal decay were unnecessary, a face-indexed absorption correction was applied. The quantity minimized by the least-squares program was $\Sigma w(F_o^2-F_c^2)^2$, where $w=\{[\sigma(F_o^2)]^2+(0.0316P)^2\}^{-1}$ and $P=(F_o^2+2F_c^2)/3$. Hydrogen atoms attached to boron were placed in idealized tetrahedral locations, constraining the B—H distances to the bridging hydrogen to be equal within 0.005 Å; similar constraints were applied for chemically related B—H distances to the terminal hydrogen atoms. The BH$_3$ groups were allowed to rotate about the B—N bonds to find the best least-squares positions. The methyl hydrogen atoms were placed in idealized tetrahedral locations with C—H=0.98 Å; the CH$_3$ groups were allowed to rotate about the C—N bonds to find the best least-squares positions. Displacement parameters for the methyl and borane hydrogen atoms were set equal to 1.5 times U$_{eq}$ for the attached carbon or boron atom. Methylene hydrogen atoms were placed in idealized locations with C—H=0.99 Å and their displacement parameters set equal to 1.2 times U$_{eq}$ for the attached carbon atom. No correction for isotropic extinction was necessary. Analysis of the diffraction intensities suggested that the crystal was twinned by inversion; therefore, the intensities were calculated from the equation $l_{calc}=xl_{hkl}+(1-x)l_{h'k'l'}$, where x is a scale factor that relates the volumes of the inversion-related twin components. The scale factor refined to a value of 0.63(1). Successful convergence was indicated by the maximum shift/error of 0.002 for the last cycle. Final refinement parameters are given in Table 1. The largest peak in the final Fourier difference map (1.02 eÅ$^{-3}$) was located 1.21 Å from Dy(1). A final analysis of variance between observed and calculated structure factors showed no apparent errors.

REFERENCES

1. Roy, P. K.; Moon, A.; Mima, K.; Nakai, S.; Fujita, M.; Imasaki, K.; Yamanaka, C.; Yasuda, E.; Watanabe, T.; Ohigashi, N.; Okuda, Y.; Tsunawaki, Y. *Rev. Sci. Instrum.* 1996, 67, 4098-4102.
2. Tennant, D. M.; Swanson, L. W. J. *Vac. Sci. Technol., B* 1989, 7, 93-97.
3. Yamabe, M.; Furukawa, Y.; Inagaki, T. *J. Vac. Sci. Technol., A* 1984, 2, 1361-1364.
4. Doy, T. K.; Kasai, T.; Ohmori, H. *J. Ceram. Soc. Jpn.* 1999, 107, 502.
5. Schmidt, P. H.; Longinotti, L. D.; Joy, D. C.; Ferris, S. D.; Leamy, H. J.; Fisk, Z. *J. Vac. Sci. Technol.* 1978, 15, 1554-1560.
6. Verhoeven, J. D.; Gibson, E. D.; Noack, M. A. *J. Appl. Phys.* 1976, 47, 5105-5106.
7. Gesley, M.; Swanson, L. W. *Surf. Sci.* 1984, 146, 583-599.
8. Lafferty, J. M. *J. Appl. Phys.* 1951, 22, 299-309.
9. Samsonov, G. V. *Plenum Press Handbooks of High Temperature Materials, No. 2. Properties Index,* 1964.
10. Schelm, S.; Smith, G. B.; Garrett, P. D.; Fisher, W. K. *J. Appl. Phys.* 2005, 97, 124314-8.
11. Rinzler, A. G.; Hafner, J. H.; Nikolaev, P.; Lou, L.; Kim, S. G.; Tomanek, D.; Nordlander, P.; Colbert, D. T.; Smalley, R. E. *Science* 1995, 269, 1550-1553.
12. Wong, K. W.; Zhou, X. T.; Au, F. C. K.; Lai, H. L.; Lee, C. S.; Lee, S. T. *Appl. Phys. Lett.* 1999, 75, 2918-2920.
13. Lee, Y. H.; Choi, C. H.; Jang, Y. T.; Kim, E. K.; Ju, B. K.; Min, N. K.; Ahn, J. H. *Appl. Phys. Lett.* 2002, 81, 745-747.

14. L₁, Y. B.; Bando, Y.; Golberg, D.; Kurashima, K. *Appl. Phys. Lett.* 2002, 81, 5048-5050.
15. Late, D. J.; More, M. A.; Joag, D. S.; Misra, P.; Singh, B. N.; Kukreja, L. M. *Appl. Phys. Lett.* 2006, 89.
16. Nakamoto, M.; Fukuda, K. *Appl. Surf. Sci.* 2002, 202, 289-294.
17. Waldhauser, W.; Mitterer, C.; Laimer, J.; Stori, H. *Surf. Coat. Technol.* 1998, 98, 1315-1323.
18. Mroczkowski, S. J. *J. Vac. Sci. Technol. A* 1991, 9, 586-590.
19. Yutani, A.; Kobayashi, A.; Kinbara, A. *Appl. Surf. Sci.* 1993, 70-1, 737-741.
20. Okamoto, Y.; Aida, T.; Shinada, S. *Jpn. J. Appl. Phys. 1* 1987, 26, 1722-1726.
21. Zhang, H.; Zhang, Q.; Tang, J.; Qin, L. C. *J. Am. Chem. Soc.* 2005, 127, 8002-8003.
22. Zhang, H.; Zhang, Q.; Zhao, G.; Tang, J.; Zhou, O.; Qin, L. C. *J. Am. Chem. Soc.* 2005, 127, 13120-13121.
23. Zhang, H.; Tang, J.; Zhang, Q.; Zhao, G.; Yang, G.; Zhang, J.; Zhou, O.; Qin, L. C. *Adv. Mater.* 2006, 18, 87-91.
24. Zhang, H.; Zhang, Q.; Tang, J.; Qin, L. C. *J. Am. Chem. Soc.* 2005, 127, 2862-2863.
25. Kher, S. S.; Spencer, J. T. *J. Phys. Chem. Solids* 1998, 59, 1343-1351.
26. Hagimura, A.; Kato, A. *Nippon Kagaku Kaishi* 1980, 1108-1113.
27. Ephritikhine, M. *Chem. Rev.* 1997, 97, 2193-2242.
28. Tiitta, M.; Niinisto, L. *Chem. Vap. Deposition* 1997, 3, 167-182.
29. Edleman, N. L.; Wang, A.; Belot, J. A.; Metz, A. W.; Babcock, J. R.; Kawaoka, A. M.; Ni, J.; Metz, M. V.; Flaschenriem, C. J.; Stern, C. L.; Liable-Sands, L. M.; Rheingold, A. L.; Markworth, P. R.; Chang, R. P. H.; Chudzik, M. P.; Kannewurf, C. R.; Marks, T. J. *Inorg. Chem.* 2002, 41, 5005-5023.
30. Lo Nigro, R.; Malandrino, G.; Toro, R. G.; Fragala, I. L. *Chem. Vap. Deposition* 2006, 12, 109-124.
31. Weber, A.; Suhr, H.; Schumann, H.; Kohn, R. D. *Appl. Phys. A: Mater. Sci. Process.* 1990, 51, 520-525.
32. Paivasaari, J.; Niinisto, J.; Arstila, K.; Kukli, K.; Putkonen, M.; Niinisto, L. *Chem. Vap. Deposition* 2005, 11, 415-419.
33. Niinisto, J.; Putkonen, M.; Niinisto, L. *Chem. Mater.* 2004, 16, 2953-2958.
34. Gordon, R. G.; Becker, J.; Hausmann, D.; Suh, S. *Chem. Mater.* 2001, 13, 2463-2464.
35. Just, O.; Rees, W. S. *Adv. Mater. Opt. Electr.* 2000, 10, 213-221.
36. Rees, W. S.; Just, O.; Van Derveer, D. S. *J. Mater. Chem.* 1999, 9, 249-252.
37. See Example 13.
38. Noth, H.; Thomas, S. *Eur. J. Inorg. Chem.* 1999, 1373-1379.
39. Segal, B. G.; Lippard, S. *J. Inorg. Chem.* 1978, 17, 844-850.
40. Laske, D. A.; Duchateau, R.; Teuben, J. H.; Spek, A. L. *J. Organomet. Chem.* 1993, 462, 149-153.
41. Herbert Schumann, M. R. K. J. D. S. M. Z. *Anorg. Allg. Chem.* 1998, 624, 1811-1818.
42. Qian, C.-T.; Zou, G.; Nie, W.-L.; Sun, J.; Lemenovskii, D. A.; Borzov, M. V. *Polyhedron* 2000, 19, 1955-1959.
43. For details of the crystallographic methods used see: Brumaghim, J. L.; Priepot, J. G.; Girolami, G. S. *Organometallics* 1999, 18, 2139-2144.

Example 15

Catalyzed Chemical Vapor Deposition of Titanium-Doped Magnesium Diboride Thin Films from $Mg(H_3BNMe_2BH_3)_2$ Introduction The incorporation of superconductors into integrated circuits is the subject of considerable interest due to the promise of creating ultrafast digital logic devices:[1,2] rapid single-flux quantum logic circuits made of niobium have shown that the clock speeds of the superconducting devices can reach up to 770 GHz.[3,4] Josephson junctions, which are the core elements of these superconducting circuits, are typically constructed from thin films of niobium-based materials owing to their reliable properties at 4.2 K. Cuprate superconductors, whose higher critical temperatures would enable cooling with liquid nitrogen rather than liquid helium, have proven difficult to incorporate into integrated circuits owing to their short coherence lengths, their electrical anisotropy, and the complexities associated with depositing stoichiometric thin films containing four or more different chemical elements.[5,7]

Cuprate materials aside, the superconductor with the highest known critical temperature is magnesium diboride ($MgB_2$), which has a superconducting transition temperature of 39 K,[8] a long coherence length of ~5 nm,[9] and a large energy gap.[10] In combination with the simple stoichiometry, these properties strongly suggest that superconducting integrated circuits made of $MgB_2$ should operate faster at higher temperatures than current devices based on niobium.

The deposition of $MgB_2$ thin films is complicated by one major challenge: loss of Mg from the $MgB_2$ phase at growth temperatures above ca. 400° C.[11] If enough Mg is lost, the $MgB_2$ films become non-superconducting. Several strategies to overcome this problem have been reported. Kang and co-workers have produced $MgB_2$ films by depositing amorphous boron followed by reaction with Mg vapor at 900° C.[12] Although this method has produced high-quality $MgB_2$ films with a critical temperature $T_c$ of 39 K, the ex-situ high temperature annealing process must be conducted in a sealed tantalum tube, which makes this method less attractive for producing multilayer thin films on a large scale. Ueda et al. have produced $MgB_2$ thin films with a $T_c$ of ca. 38 K by co-evaporation of Mg and B at 240 to 270° C.[13] Zeng et al. have grown $MgB_2$ thin films by an in situ hybrid physical-chemical vapor deposition (HP-CVD) method in which $B_2H_6$ reacts with Mg vapor generated from Mg chips placed near the substrate.[14] The main drawback to employing this latter approach in the fabrication of multilayer devices is the high deposition temperature of ca. 750° C., which will promote undesirable interfacial reactions.

There is a compelling need to develop a method for depositing $MgB_2$ thin films that produces crystalline, conformal deposits below 400° C. via an in situ deposition process, without the need for subsequent annealing at elevated temperatures. To date, only the co-evaporation method comes close to this requirement, but this method cannot afford conformal films on topologically complex substrates. A CVD method to $MgB_2$ films would be far more useful. It is known that metal borohydrides such as $Zr(BH_4)_4$, $Hf(BH_4)_4$, and $Cr(B_3H_8)_2$ are excellent CVD precursors for $MB_2$ thin films at temperatures as low as 150° C.[15-17] The structure of $MgB_2$ is identical with that of these transition metal diborides, but no low-temperature CVD methods for depositing $MgB_2$ thin films have been described, largely due to the absence of suitable precursors. To address this lack, we report herein the synthesis of highly volatile magnesium hydroborate complexes, $Mg(H_3BNMe_2BH_3)_2$[18] and $Mg(B_3H_8)_2L_2$ ($L=Et_2O$ or $Me_2O$).[19] Initial attempts to use the latter molecules as precursors for the CVD of $MgB_2$ afforded boron-rich non-stoichiometric films, principally because the onset temperatures for deposition were high ($\geq 400°$ C.), thus leading to significant evaporative loss of Mg during growth.

We now describe the successful chemical vapor deposition of doped $MgB_2$ phases from the precursor $Mg(H_3BNMe_2BH_3)_2$ at lower temperatures by conducting the depositions in the presence of a catalyst that accelerates the surface reaction rate of the $MgB_2$ precursor. The phases are doped because metal atoms from the catalyst are partly incorporated into the films by substitution into the Mg sites. We find that several molecules can serve as effective catalysts for the CVD growth of the doped $MgB_2$ phase, of which $Ti(H_3BNMe_2BH_3)_2$ is the most attractive so far because it leads to the lowest level of Mg site substitution. This is the first successful low-temperature CVD method for the deposition of doped $MgB_2$ thin films. The doping levels are high enough to render the films non-superconducting above 4 K, but the results described herein clearly point the way to the development of technologically-attractive CVD processes to grow superconducting $MgB_2$ thin films at temperatures below 400° C.

Results and Discussion

Catalyzed Chemical Vapor Deposition of $Mg_{0.8}Ti_{0.2}B_2$. Bis(N,N-dimethyl-diboranamido)magnesium(II), $Mg(H_3BNMe_2BH_3)_2$, is highly volatile; its vapor pressure of 800 mTorr at 20° C.[18] is the highest among all known magnesium compounds. When gaseous $Mg(H_3BNMe_2BH_3)_2$ is passed over heated substrates in vacuum, no deposition occurs up to 500° C., except for the formation of traces of magnesium oxide, which results from reactions of the precursor with background water in the chamber. Interestingly, bulk $Mg(H_3BNMe_2BH_3)_2$ begins to decompose at 120° C. with evolution of gas.[18] We did not explore deposition temperatures above 500 C, owing to the known propensity of $MgB_2$ to undergo magnesium loss above 400° C.[11] The low reactivity of $Mg(H_3BNMe_2BH_3)_2$ at surface temperatures below 500° C. suggests that there is a kinetic barrier associated with the nucleation and growth from this precursor. If so, then it might be possible to induce growth under these conditions by adding a suitable growth catalyst.

We have found that addition of small amounts of the titanium compound $Ti(H_3BNMe_2BH_3)_2$ to the $Mg(H_3BNMe_2BH_3)_2$ precursor flux results in the deposition of a titanium-doped $MgB_2$ phase on Si(100) at temperatures as low as 250° C. The ratio between the partial pressures of $Mg(H_3BNMe_2BH_3)_2$ and $Ti(H_3BNMe_2BH_3)_2$ in the growth stream was approximately 10. The best films were grown between 300 and 400° C.; below 250° C. the films contain ~10% carbon, and at 600° C. the films are significantly depleted in magnesium (~3 at. %).

Figure 17:
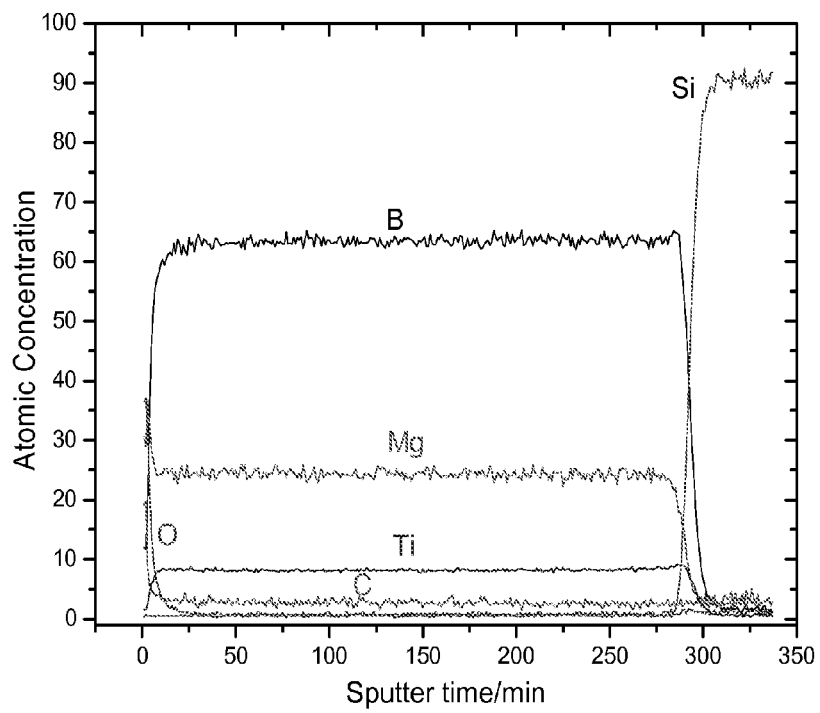
FIG. 17. Auger depth profile of a Mg$_{0.8}$Ti$_{0.2}$B$_2$ film grown from Mg(H$_3$BNMe$_2$BH$_3$)$_2$ and Ti(H$_3$BNMe$_2$BH$_3$)$_2$ on Si(100) at 350° C.
Figure 18:
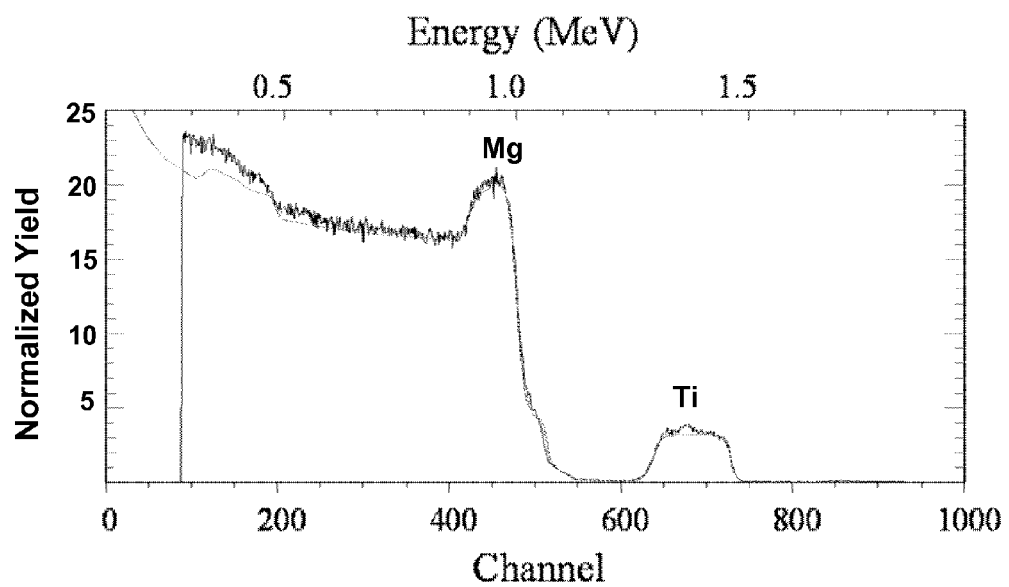
FIG. 18. RBS spectrum of a Mg$_{0.8}$Ti$_{0.2}$B$_2$ film grown from Mg(H$_3$BNMe$_2$BH$_3$)$_2$ and Ti(H$_3$BNMe$_2$BH$_3$)$_2$ on Si(100) at 350° C. The red line is the curve fit used to calculate the magnesium and titanium contents.

At 350° C., simultaneous passage of $Mg(H_3BNMe_2BH_3)_2$ and 10% of $Ti(H_3BNMe_2BH_3)_2$ over a Si(100) substrate affords silvery, mirror-bright deposits. Identical results were obtained on $SiO_2$ and sapphire substrates. The AES depth profiles (FIG. 17) reveal that the boron to metal ratio, B/(Mg+Ti), is very close to 2, and that the Mg to Ti ratio is approximately 3. Negligible amounts of carbon (<2%) and nitrogen (<1%) are present. Because lighter elements can often be preferentially sputtered out during the collection of AES depth profiles, the film stoichiometry was assessed independently by a non-destructive technique, Rutherford backscattering spectroscopy (RBS). Well separated Mg and Ti peaks are seen, with the Mg peak overlapping partly with the tail of the silicon substrate signal (FIG. 18). The Mg to Ti ratio from the RBS data is 4; consequently, we conclude that the film stoichiometry is $Mg_{0.8}Ti_{0.2}B_2$.

Figure 19:
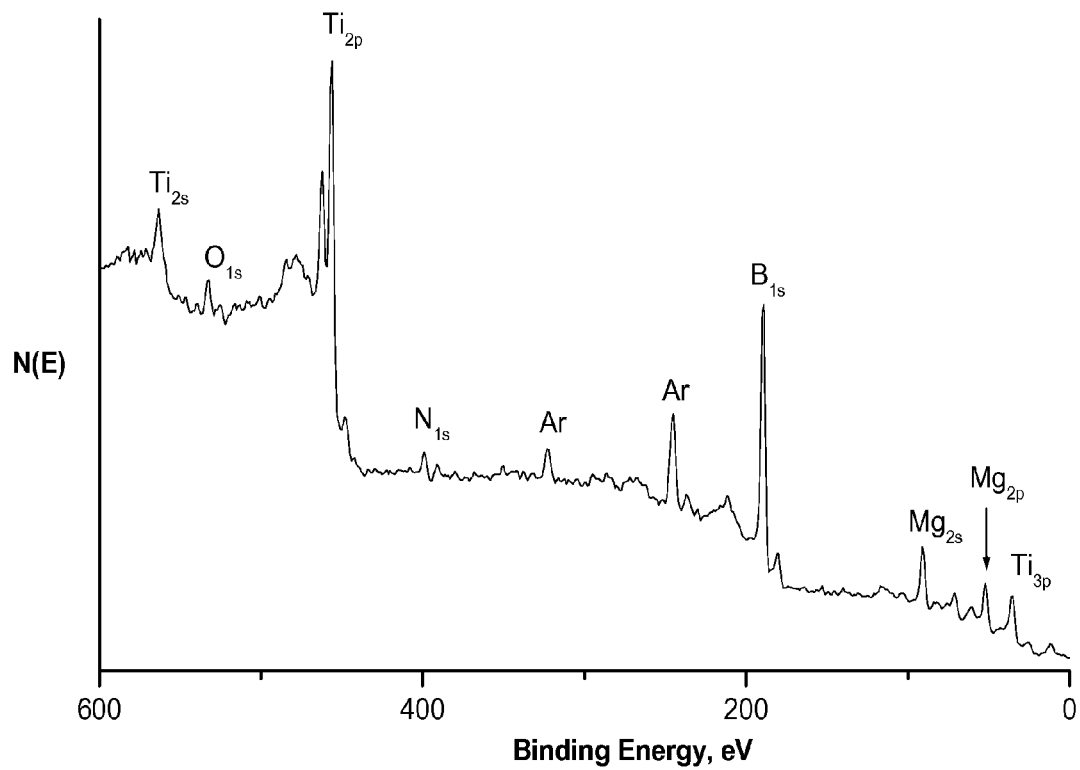
FIG. 19. XPS survey spectrum of a Mg$_{0.8}$Ti$_{0.2}$B$_2$ film grown from Mg(H$_3$BNMe$_2$BH$_3$)$_2$ and Ti(H$_3$BNMe$_2$BH$_3$)$_2$ on Si(100) at 350° C. after sputtering away the surface coat.
Figure 20:
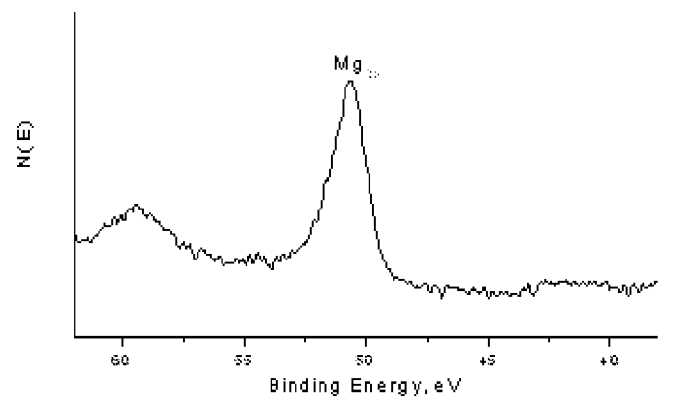
FIG. 20. XPS spectra in the Mg 2 p (top), Ti 2 p (middle), and B 1s (bottom) regions of a Mg$_{0.8}$Ti$_{0.2}$B$_2$ film grown from Mg(H$_3$BNMe$_2$BH$_3$)$_2$ and Ti(H$_3$BNMe$_2$BH$_3$)$_2$ on Si(100) at 350° C.
Figure 20:
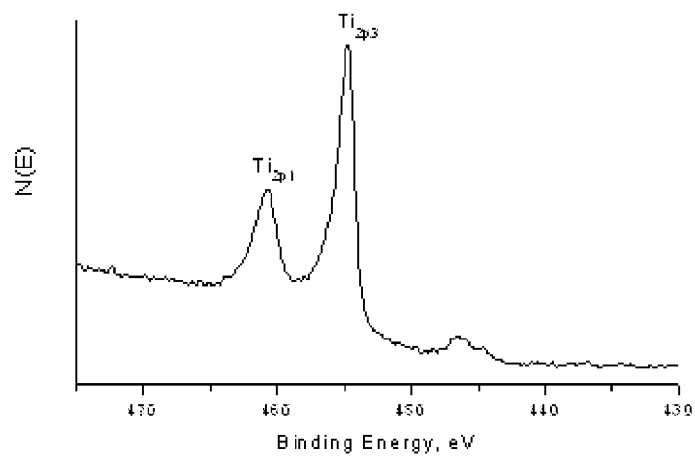
Figure 20:
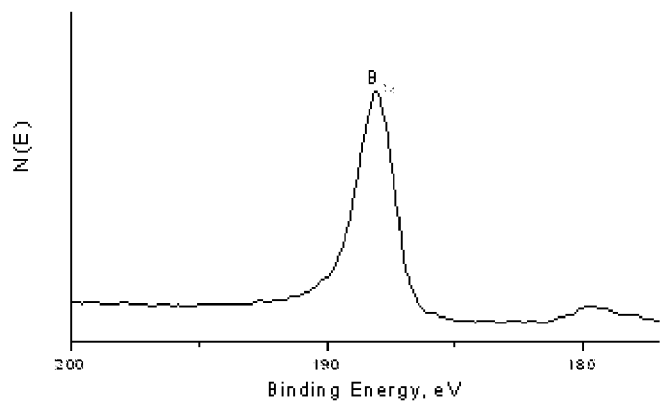

X-ray photoelectron spectra (XPS) of the deposits grown on Si(100) at 350° C. show that significant amounts of oxygen are present on the surface of the films due to the air-oxidation during the sample transport from the growth chamber to the XPS chamber. Upon sputtering surface layers away, the oxides signals become negligible (FIG. 19). An XPS spectrum obtained after sputtering into the interior of the film exhibited a Mg 2 p binding energy of 50.65 eV (FIG. 20); this value lies between the reported values ~49.5 and ~51.3 eV for bulk and thin films of $MgB_2$, respectively.[20-23] The Mg 2 p binding energy of our films may be affected by the presence of titanium. The B 1s peak of 188.1 eV lies in the observed range of 186.55 eV-188.2 eV for $MgB_2$.[20-23] The Ti 2 p binding energy of 454.8 eV is close to the value of 454.3 eV observed for $TiB_2$.[24,25] XPS signal for N 1s and C 1s were near background levels.

Figure 21:
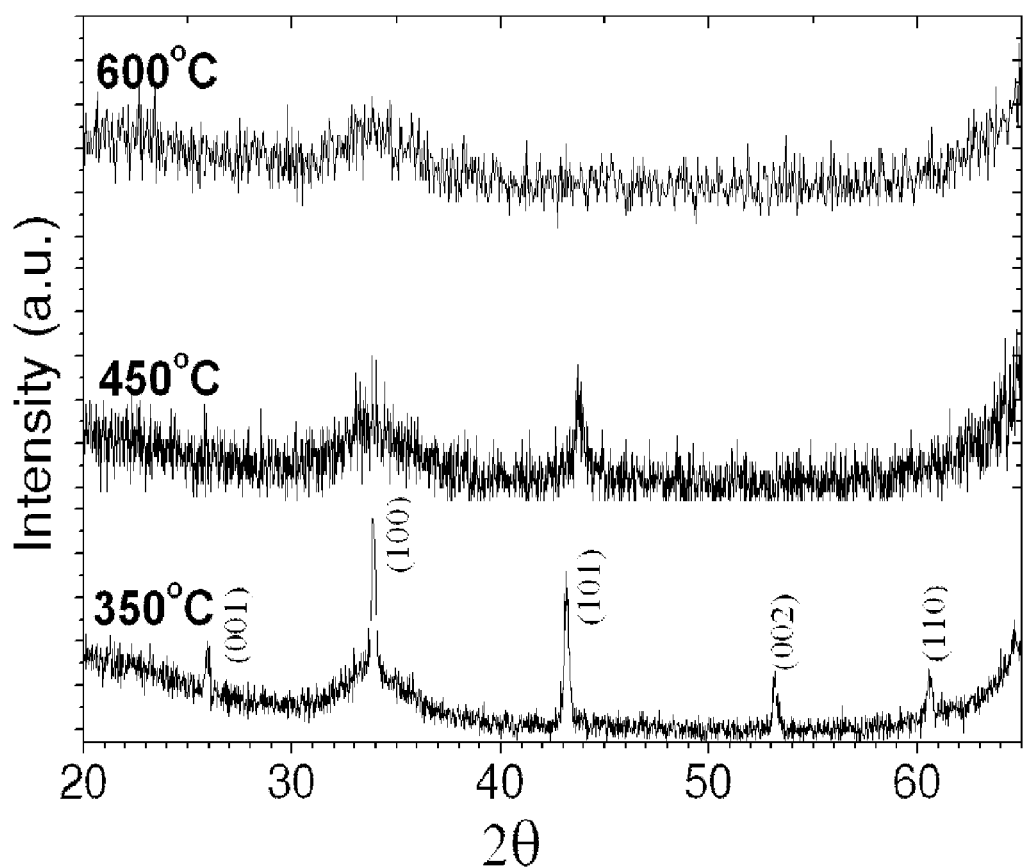
FIG. 21. The XRD profiles of Mg$_{1-x}$Ti$_x$B$_2$ films grown from Mg(H$_3$BNMe$_2$BH$_3$)$_2$ and Ti(H$_3$BNMe$_2$BH$_3$)$_2$ on Si(100) at various temperatures.
Figure 22:
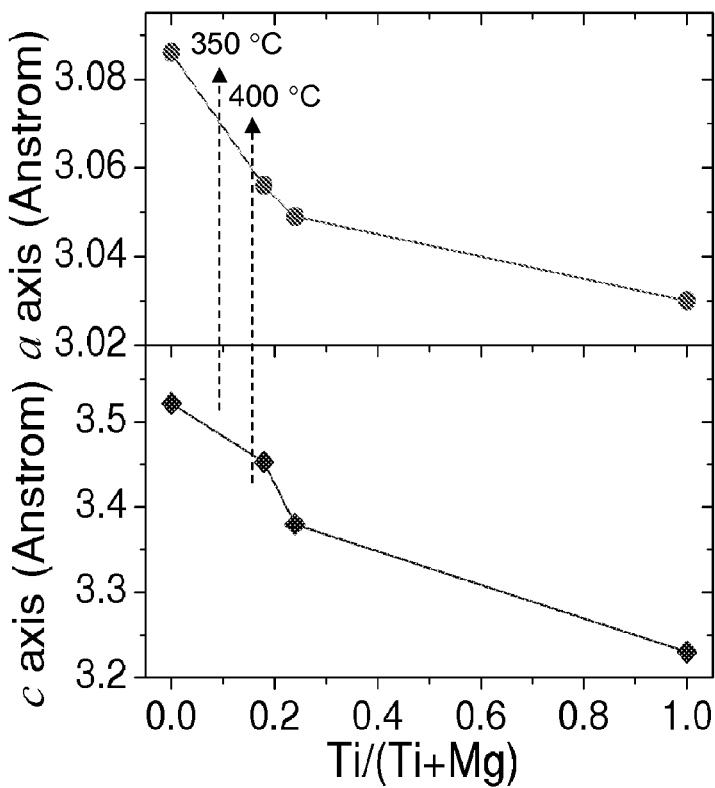
FIG. 22. Lattice constants a and c of the Mg$_{1-x}$Ti$_x$B$_2$ films grown from Mg(H$_3$BNMe$_2$BH$_3$)$_2$ and Ti(H$_3$BNMe$_2$BH$_3$)$_2$ on Si(100) at 350 and 400° C. The lattice constants are calculated from the XRD profiles.

The X-ray diffraction (XRD) profile shows that the films are polycrystalline, and that the lattice parameters are those of a $MB_2$ phase (FIG. 21). The cell constants (a=3.056 and c=3.432 Å) differ slightly from those for bulk $MgB_2$, and lie between those for pure $MgB_2$ (a=3.086 and c=3.522 Å) and for pure $TiB_2$ (a=3.03 and c=3.23 Å). The cell parameters more closely resemble those of pure $MgB_2$ (FIG. 22), as expected from the $Mg_{0.8}Ti_{0.2}B_2$ stoichiometry. No preferential orientation of the crystallites is noted on the Si(100) substrate. Magnesium-depleted films grown at 450 and 600° C. are non-crystalline.

Figure 23:
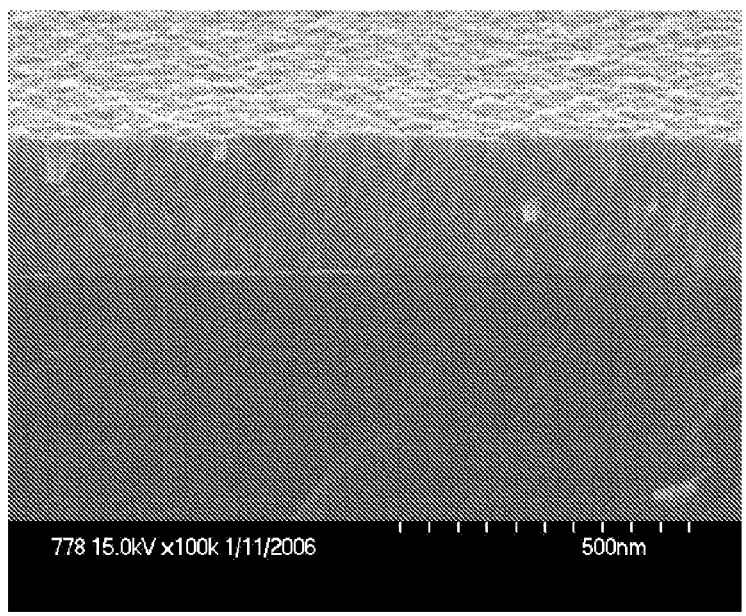
FIG. 23. Cross sectional SEM micrograph of a Mg$_{0.8}$Ti$_{0.2}$B$_2$ film grown from Mg(H$_3$BNMe$_2$BH$_3$)$_2$ and Ti(H$_3$BNMe$_2$BH$_3$)$_2$ on Si(100) at 350° C.
Figure 24:
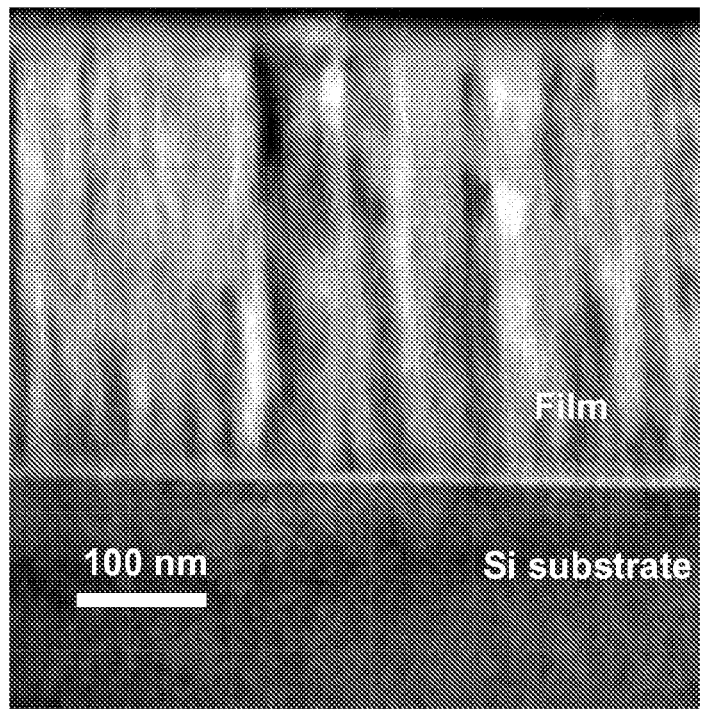
FIG. 24. Cross sectional TEM image (top) and high resolution TME image showing lattice fringes (bottom) of a Mg$_{0.8}$Ti$_{0.2}$B$_2$ film grown from Mg(H$_3$BNMe$_2$BH$_3$)$_2$ and Ti(H$_3$BNMe$_2$BH$_3$)$_2$ on Si(100) at 350° C.
Figure 24:
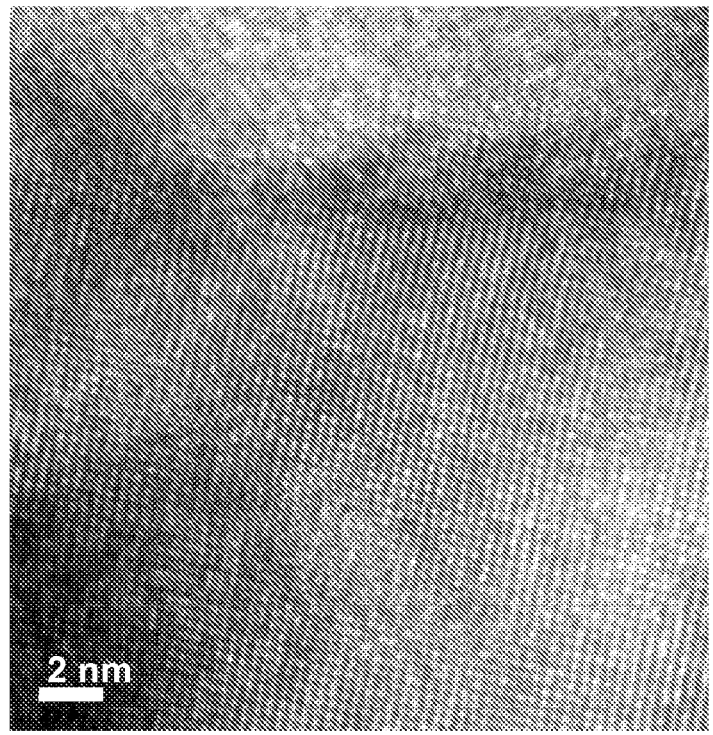

Scanning electron micrographs of fracture cross-sections show that the films are essentially columnar (FIG. 23), which is a consequence of the low surface diffusion rates of the adatoms at the 350° C. growth temperature. For similar reasons, a columnar growth morphology has been seen for $HfB_2$ films grown from $Hf(BH_4)_4$ at 400° C.[16] Transmission electron micrographs of the $Mg_{0.8}Ti_{0.2}B_2$ films confirm the columnar growth morphology and reveal the presence of polycrystals with non-uniform orientations (FIG. 24).

Electron energy loss spectroscopy (EELS) shows that the titanium atoms are homogeneously distributed throughout the deposits (the B/Mg/Ti ratios are the same in all locations). The formation of a homogeneously mixed material and the absence of segregation into separate $MgB_2$ and $TiB_2$ phases can be ascribed to slow diffusion rates of metal atoms at the low deposition temperature of 350° C.

The electrical resistivity of the crystalline $Mg_{0.8}Ti_{0.2}B_2$ films on sapphire gradually decreases upon cooling from room temperature to 4 K, but no superconducting transition was observed. The absence of a superconducting transition strongly suggests that titanium substitutes into the magnesium sites in the $MgB_2$ phase (see below).

Dependence of the Properties of $Mg_{1-x}Ti_xB_2$ on the Film Microstructure. Our results differ from another study of the effect of adding $TiB_2$ to $Mg B_2$.[26-29] Specifically, Zhao et al. have reported that the solid state reaction of magnesium, boron, and titanium powders at 900° C. affords a material composed of 90% $MgB_2$ and 10% $TiB_2$ that has a critical current density about 10 times greater than that of pure $MgB_2$. Interestingly, samples prepared by mixing 40% $MgB_2$ with 60% $TiB_2$ still exhibited a superconducting transition.[26] The authors ascribed the high critical current density to improvements in intergranular contacts between $MgB_2$ grains, and to strong vortex pinning by a second phase (probably $TiB_2$), rather than to the replacement of Ti for Mg in the $MgB_2$ phase.

The absence of a superconducting transition for our CVD-deposited $Mg_{0.8}Ti_{0.2}B_2$ films can be ascribed to the direct substitution of Ti for Mg atoms in the $MB_2$ lattice; our samples are not intimate mixtures of largely separate $TiB_2$ and $MgB_2$ phases as in the study by Zhao et al. It is known that replacement of Mg with Al,[30] Sc,[31] Mn,[32,33] Co,[34] and Cu[35] leads to a drop in the superconducting transition temperature. Similar drops in the critical temperature are also seen when carbon is substituted into the boron sites.[36,37] The addition of enough electrons to $MgB_2$ by substitutional replacement moves the Fermi level to a lower density of state region where superconductivity disappears.

Another factor that can disrupt the superconducting transition in our mixed $Mg_{0.8}Ti_{0.2}B_2$ films is the magnetic moment of the titanium atoms. Exchange interactions between conduction electrons and the magnetic moments of substituted ions are known to weaken Cooper pairing and to suppress superconductivity.[38] This effect is sufficiently large that replacing only 2% of the Mg atoms in $MgB_2$ with Mn renders the material non-superconductive.[33] It is therefore not surprising that our $Mg_{0.8}Ti_{0.2}B_2$ films, in which 20% of Mg sites are substituted by Ti, are not superconducting.

Static Vacuum Deposition and Analyses of the Gaseous Byproducts. In order to investigate the chemical mechanism by which the $Mg_{0.8}Ti_{0.2}B_2$ films are deposited from $Mg(H_3BNMe_2BH_3)_2$ and $Ti(H_3BNMe_2BH_3)_2$, we have analyzed the gaseous byproducts that are generated during deposition. Under a static vacuum (0.05 Torr), $Mg(H_3BNMe_2BH_3)_2$ and $Ti(H_3BNMe_2BH_3)_2$ were sublimed into a deposition zone maintained at 300° C. After the deposition was complete, the gaseous byproducts were collected, dissolved in $C_6D_6$, and analyzed by $^1H$ and $^{13}C$ NMR spectroscopy. The principal byproducts are $H_2$ and $[Me_2NBH_2]_2$. The formation of $[Me_2NBH_2]_2$ from amino-borane compounds is known to be catalyzed by certain transition-metal compounds.[39-43] These findings suggests that the mass balance for the deposition of $MgB_2$ is $Mg(H_3BNMe_2BH_3)_2 \longrightarrow MgB_2 + [Me_2NBH_2]_2 + H_2$.

Survey of Other Potential Catalysts for the Deposition of $MgB_2$ from $Mg(H_3BNMe_2BH_3)_2$. We have shown above that the deposition of thin films by CVD can be catalyzed by addition of small amounts of a co-reactant. Specifically, $Mg(H_3BNMe_2BH_3)_2$ by itself does not afford any deposits even at temperatures as high as 500° C. In contrast, addition of small amounts of $Ti(H_3BNMe_2BH_3)_2$ results in the deposition of Mg-containing thin films at temperatures as low as 300° C.

We conducted a survey to determine whether other compounds could catalyze the growth of thin films from the $Mg(H_3BNMe_2BH_3)_2$ precursor; we were particularly interested in discovering catalysts that would generate undoped (and thus superconducting) $MgB_2$ thin films. The results are summarized in Table 1; all the depositions were conducted at 350° C. The hydroborate complexes $Ti(BH_4)_3(dme)$, $Zr(BH_4)_4$, $Hf(BH_4)_4$, and $Cr(H_3BNMe_2BH_3)_2$ all can serve as catalysts, but all afford deposits in which the transition metal substitutes for some of the Mg atoms, and films of approximate composition $Mg_{0.8}M_{0.2}B_2$. The yttrium complex $Y(H_3BNMe_2BH_3)_3(thf)$ also catalyzes the growth of Mg-containing deposits, but the film stoichiometry is approximately $Mg_{0.45}Y_{0.55}B_{3.5}$ and no $MgB_2$ phase is present as shown by XRD. The deposits obtained from $Mg(H_3BNMe_2BH_3)_2$ in the presence of the transition metal complexes $Ti(NMe_2)_4$, $CpPd(allyl)$, and $Fe(CO)_5$ all contain significant amounts of carbon, but no $MB_2$ phase. Other compounds tested—including the titanium alkyl $Ti(neo\text{-}pentyl)_4$, the metallocene $Ni(C_5H_4Me)_2$, and the halo compounds ethyl iodide[44] and iodine were unable to initiate the film growth.

Few examples of catalyzed CVD growth have been described. Transition metal catalysts have been shown to lower the deposition temperature,[45,46] initiate the film growth,[47] or facilitate the removal of the ligands from the precursors.[48,49] For example, Puddephatt and co-workers reported that the deposition of yttrium oxide from $Y(thd)_3$ (thd=2,2,6,6-tetramethyl-3,5-heptanedionate) and oxygen could be significantly accelerated by the presence of small amounts of a palladium catalyst.[46] The palladium content in the deposited film was nearly undetectable by XPS. They proposed that the palladium migrates through $Y_2O_3$ as $Pd(thd)_2$, which is generated from the reaction of metallic palladium with the CVD reaction product Hthd. We believe that the idea of catalyzing CVD reactions constitutes a fascinating new direction for CVD research.

Experimental Section

General Methods. $^1H$ NMR spectra were recorded on a Varian Unity 400 instrument at 400 MHz. Chemical shifts are reported in δ units (positive shifts to high frequency) relative to tetramethylsilane. A HP 6980 Series gas chromatograph equipped with a 30 m AT™-WAX (polyethylene glycol, 0.25 mm i.d., Alltech) column and a HP 5973 mass selective detector was used to obtain the GC/MS data. Auger spectra were recorded on a Physical Electronics PHI 660 system with a beam energy of 5 kV and a base pressure of ca. $1 \times 10^{-10}$ Torr. X-ray photoelectron spectra were recorded on a Physical Electronics PHI 5400 system with a 15 kV, 300 W Mg Kα radiation source (1253.6 eV). AES and XPS spectra were collected after the samples had been argon-sputtered to remove contaminants on the surface. X-ray diffraction data were recorded on a Phillips Xpert system with Cu Kα radiation. Scanning electron micrographs were recorded on a Hitachi S4700 instrument. Rutherford back scattering data were recorded on 3-MeV Van de Graaff accelerator. Electrical resistivities were measured by the four-point probe method.[50]

Reagents. $Mg(H_3BNMe_2BH_3)_2$,[18] $Cp^*Mg(H_3BNMe_2BH_3)(thf)$,[18] $Ti(H_3BNMe_2BH_3)_2$,[51] $Cr(H_3BNMe_2BH_3)_2$,[51] $Y_2(H_3BNMe_2BH_3)_6$,[52] $CpPd(allyl)$,[53] $Ti(neo\text{-}pentyl)_4$,[54] $Ti(BH_4)_3(dme)$,[55] $Cu(hfac)(VTMS)$,[56] $Zr(BH_4)_4$, and $Hf(BH_4)_4$[57] were prepared as described in the literature. Ethyl iodide, iodine, methylhydrazine, $Ni(C_5H_4Me)_2$, $Fe(CO)_5$, and $Ti(NMe_2)_4$ were purchased from Aldrich and used without further purification.

CVD of $Mg_{1-x}Ti_xB_2$. Deposition of thin films was carried out in an ultra high vacuum (UHV) chamber equipped with a turbomolecular pump; the base pressure was $5 \times 10^{-9}$ Torr.[58] The reactants were delivered to the film growth surface without the use of a carrier gas. The stainless steel reservoir was kept at room temperature for $Mg(H_3BNMe_2BH_3)_2$, $Cp^*Mg(H_3BNMe_2BH_3)(thf)$, $CpPd(allyl)$, $Ti(neo\text{-}pentyl)_4$, $Cu(hfac)(VTMS)$, $Ni(C_5H_4Me)_2$, $Fe(CO)_5$, ethyl iodide, iodine, and methylhydrazine. The reservoir was kept at 30° C. for $Ti(H_3BNMe_2BH_3)_2$, $Cr(H_3BNMe_2BH_3)_2$, and $Ti(BH_4)_3$ (dme); at 100° C. for $Y_2(H_3BNMe_2BH_3)_6$; and at −5° C. for $Zr(BH_4)_4$ and $Hf(BH_4)_4$. The fluxes of highly volatile ethyl iodide, methylhydrazine, $Fe(CO)_5$, $Zr(BH_4)_4$ and $Hf(BH_4)_4$ were regulated by a needle valve. Reactants were delivered to the growth surface through two independent 0.25 inch (6.35 mm) o.d. stainless steel tubes, one for the $MgB_2$ source and one for the other co-reactant. The line pressure of the $Mg(H_3BNMe_2BH_3)_2$ precursor was maintained at 120-150 mTorr during the growth run. The silicon substrates were degreased by successive sonications in acetone, tetrachloroethylene, isopropanol, and deionized water for 10 min each. To remove the native oxide on the surface, the degreased silicon substrates were immersed in a 10% HF solution and then rinsed with deionized water. Silicon substrates were heated by passing an electric current through the substrate, and the surface temperature was determined by means of an infrared pyrometer. An in situ spectroscopic ellipsometer was used to monitor the film thickness in real time. The magnesium atomic density was calculated by dividing the magnesium areal density (determined by RBS) by the film thickness (measured by SEM).

Analysis of Byproducts of CVD Growth. To collect and analyze the gaseous products from the reaction of $Mg(H_3BNMe_2BH_3)_2$ with $Ti(H_3BNMe_2BH_3)_2$ under the CVD conditions, CVD experiments was carried out in a closed static vacuum system. Two small glass vials that contain $Mg(H_3BNMe_2BH_3)_2$ and $Ti(H_3BNMe_2BH_3)_2$ separately were placed in a standard Schlenk (250 mL) tube, the middle of which was wrapped with an electric heating tape (Thermolyne Briskheat). The apparatus was evacuated to 0.05 Torr and the electric heating tape was heated up to 300° C., forming a deposition hot zone. The stopcock between the apparatus and the vacuum pump was closed during the deposition. After the deposition was complete, the gaseous byproducts were analyzed by GC/MS and by NMR methods (the gaseous products were condensed in a liquid $N_2$ cooled NMR tube). A similar apparatus has been described.[59] The principal byproducts are $H_2$ (singlet at δ 4.46) and $[Me_2NBH_2]_2$ ($^1$H NMR: δ 3.06 (1:1:1:1 quartet, $J_{BH}$=110 Hz, $BH_2$) δ 2.22 (s, $NMe_2$). $^{13}C\{^1H\}$ NMR: δ 52.0 (s, $NMe_2$). The chemical shifts and the splitting patterns for $[Me_2NBH_2]_2$ in $C_6D_6$ are consistent with those reported.[43,69] GC-MS analysis of the byproducts shows that dimethylamine is the only detectable species. Boron-containing products are not seen in the GC-MS assay suggests because they react with the polyethylene glycol stationary phase.

REFERENCES

1. Abelson, L. A.; Kerber, G. L. *P. IEEE.* 2004, 92, 1517-1533.
2. Brock, D. K.; Track, E. K.; Rowell, J. M. *IEEE Spectrum* 2000, 37, 40-46.
3. Chen, W.; Rylyakov, A. V.; Patel, V.; Lukens, J. E.; Likharev, K. K. *Appl. Supercon. IEEE Trans.* 1999, 9, 3212-3215.
4. Likharev, K. K.; Semenov, V. K. *Appl. Supercon. IEEE Trans.* 1991, 1, 3-28.
5. Tonouchi, M.; Fujimaki, A.; Tanabe, K.; Enpuku, K.; Nikawa, K.; Kobayashi, T. *Jpn. J. Appl. Phys. 1* 2005, 44, 7735-7749.
6. Klein, N. *Rep. Prog. Phys.* 2002, 65, 1387-1425.
7. Claeson, T.; Ivanov, Z.; Winkler, D. *Curr. Opin. Solid St. M.* 1999, 4, 45-52.
8. Nagamatsu, J.; Nakagawa, N.; Muranaka, T.; Zenitani, Y.; Akimitsu, J. *Nature* 2001, 410, 63-64.
9. Xu, M.; Kitazawa, H.; Takano, Y.; Ye, J.; Nishida, K.; Abe, H.; Matsushita, A.; Tsujii, N.; Kido, G. *Appl. Phys. Lett.* 2001, 79, 2779-2781.
10. Tsuda, S.; Yokoya, T.; Kiss, T.; Takano, Y.; Togano, K.; Kito, H.; Ihara, H.; Shin, S. *Phys. Rev. Lett.* 2001, 8717.
11. Fan, Z. Y.; Hinks, D. G.; Newman, N.; Rowell, J. M. *Appl. Phys. Lett.* 2001, 79, 87-89.
12. Kang, W. N.; Kim, H. J.; Choi, E. M.; Jung, C. U.; Lee, S. L. *Science* 2001, 292, 1521-1523.
13. Ueda, K.; Naito, M. *J. Appl. Phys.* 2003, 93, 2113-2120.
14. Zeng, X. H.; Pogrebnyakov, A. V.; Kotcharov, A.; Jones, J. E.; Xi, X. X.; Lysczek, E. M.; Redwing, J. M.; Xu, S. Y.; Lettieri, J.; Schlom, D. G.; Tian, W.; Pan, X. Q.; Liu, Z. K. *Nat. Mater.* 2002, 1, 35-38.
15. Sung, J. W.; Goedde, D. M.; Girolami, G. S.; Abelson, J. R. *J. Appl. Phys.* 2002, 91, 3904-3911.
16. Jayaraman, S.; Yang, Y.; Kim, D. Y.; Girolami, G. S.; Abelson, J. R. *J. Vac. Sci. Technol., A* 2005, 23, 1619-1625.
17. Jayaraman, S.; Klein, E. J.; Yang, Y.; Kim, D. Y.; Girolami, G. S.; Abelson, J. R. *J. Vac. Sci. Technol., A* 2005, 23, 631-633.
18. See Example 13.
19. See Example 12.
20. Ueda, K.; Yamamoto, H.; Naito, M. *Physica C* 2002, 378, 225-228.
21. Talapatra, A.; Bandyopadhyay, S. K.; Sen, P.; Barat, P.; Mukherjee, S.; Mukherjee, M. *Physica C* 2005, 419, 141-147.
22. Garg, K. B.; Chatterji, T.; Dalela, S.; Heinormen, M.; Leiro, J.; Dalela, B.; Singhal, R. K. *Solid State Commun.* 2004, 131, 343-347.
23. Vasquez, R. P.; Jung, C. U.; Park, M. S.; Kim, H. J.; Kim, J. Y.; Lee, S. I. *Phys. Rev. B* 2001, 6405.
24. Aouadi, S. M.; Debessai, M.; Namavar, E.; Wong, K. C.; Mitchell, K. A. R. *Surf. Coat. Technol.* 2004, 183, 369-377.
25. Baker, M. A.; Steiner, A.; Haupt, J.; Gissler, W. *J. Vac. Sci. Technol., A* 1995, 13, 1633-1638.
26. Zhao, Y.; Feng, Y.; Cheng, C. H.; Zhou, L.; Wu, Y.; Machi, T.; Fudamoto, Y.; Koshizuka, N.; Murakami, M. *Appl. Phys. Lett.* 2001, 79, 1154-1156.
27. Wilke, R. H. T.; Bud'ko, S. L.; Canfield, P. C.; Kramer, M. J.; Wu, Y. Q.; Finnemore, D. K.; Suplinskas, R. J.; Marzik, J. V.; Hannahs, S. T. *Physica C* 2005, 418, 160-167.
28. Wang, J.; Bugoslaysky, Y.; Berenov, A.; Cowey, L.; Caplin, A. D.; Cohen, L. F.; Driscoll, J. L. M.; Cooley, L. D.; Song, X.; Larbalestier, D. C. *Appl. Phys. Lett.* 2002, 81, 2026-2028.
29. Kitaguchi, H.; Matsumoto, A.; Kumakura, H.; Doi, T.; Yamamoto, H.; Saitoh, K.; Sosiati, H.; Hata, S. *Appl. Phys. Lett.* 2004, 85, 2842-2844.
30. Slusky, J. S.; Rogado, N.; Regan, K. A.; Hayward, M. A.; Khalifah, P.; He, T.; Inumaru, K.; Loureiro, S. M.; Haas, M. K.; Zandbergen, H. W.; Cava, R. J. *Nature* 2001, 410, 343-345.
31. Agrestini, S.; Metallo, C.; Filippi, M.; Simonelli, L.; Campi, G.; Sanipoli, C.; Liarokapis, E.; De Negri, S.; Giovannini, M.; Saccone, A.; Latini, A.; Bianconi, A. *Phys. Rev. B* 2004, 70.
32. Xu, S.; Moritomo, Y.; Kato, K.; Nakamura, A. *J. Phys. Soc. Jpn.* 2001, 70, 1889-1891.
33. Rogacki, K.; Batlogg, B.; Karpinski, J.; Zhigadlo, N. D.; Schuck, G.; Kazakov, S. M.; Wagli, P.; Puzniak, R.; Wisniewski, A.; Carbone, F.; Brinkman, A.; van der Marel, D. *Phy. Rev. B (Condensed Matter and Materials Physics)* 2006, 73, 174520-8.
34. Kuhberger, M.; Gritzner, G. *Physica C* 2002, 370, 39-43.
35. Tampieri, A.; Celotti, G.; Sprio, S.; Rinaldi, D.; Barucca, G.; Caciuffo, R. *Solid State Commun.* 2002, 121, 497-500.
36. de la Peña, O.; Aguayo, A.; de Coss, R. *Phys. Rev. B* 2002, 66, 012511.
37. Klie, R. F.; Zheng, J. C.; Zhu, Y.; Zambano, A. J.; Cooley, L. D. *Phys. Rev. B (Condensed Matter and Materials Physics)* 2006, 73, 014513-10.
38. Moca, C. P.; Horea, C. *Phys. Rev. B* 2002, 66, 052501.
39. Clark, T. J.; Russell, C. A.; Manners, I. *J. Am. Chem. Soc.* 2006, 128, 9582-9583.
40. Jaska, C. A.; Manners, I. *J. Am. Chem. Soc.* 2004, 126, 1334-1335.
41. Jaska, C. A.; Manners, I. *J. Am. Chem. Soc.* 2004, 126, 9776-9785.
42. Jaska, C. A.; Temple, K.; Lough, A. J.; Manners, I. *J. Am. Chem. Soc.* 2003, 125, 9424-9434.
43. Jaska, C. A.; Temple, K.; Lough, A. J.; Manners, I. *Chem. Commun.* 2001, 962-963.

44. Shim, K. C.; Lee, H. B.; Kwon, O. K.; Park, H. S.; Koh, W.; Kang, S. W. *J. Electrochem. Soc.* 2002, 149, G109-G113.
45. Zhang, Y.; Choi, S. W. K.; Puddephatt, R. J. *J. Am. Chem. Soc.* 1997, 119, 9295-9296.
46. Zhang, Y.; Puddephatt, R. *J. Chem. Mater.* 1999, 11, 148-153.
47. R. H. W. Au, R. J. P. *Chem. Vap. Deposition* 2007, 13, 20-22.
48. Alfred Zinn, B. N. H. D. K. *Adv. Mater.* 1992, 4, 375-378.
49. Niemer, B.; Zinn, A. A.; Stovall, W. K.; Gee, P. E.; Hicks, R. F.; Kaesz, H. D. *Appl. Phys. Lett.* 1992, 61, 1793-1795.
50. Schroder, D. K. *Semiconductor Materials and Device Characterization*, 2nd Ed.; Wiley-Interscience 1998.
51. See Example 13.
52. See Example 14.
53. Tatsuno, Y.; Yoshida, T.; Otsuka, S. *Inorg. Synth.* 1979, 19, 220-3.
54. Girolami, G. S.; Jensen, J. A.; Pollina, D. M.; Williams, W. S.; Kaloyeros, A. E.; Allocca, C. M. *J. Am. Chem. Soc.* 1987, 109, 1579-1580.
55. Jensen, J. A.; Girolami, G. S. *Inorg. Chem.* 1989, 28, 2107-2113.
56. Chi, K. M.; Shin, H. K.; Hampden-Smith, M. J.; Kodas, T. T. *Inorg. Synth.* 1997, 31, 289-294.
57. Goedde, D. M. Ph.D. Thesis, University of Illinois at Urbana-Champaign, 2001.
58. For the details of the growth condition, see: J., Sreenivas; Yang, Y.; Kim, D. Y.; Girolami, G. S.; Abelson, J. R. *J. Vac. Sci. Technol., A* 2005, 23, 1619-1625.
59. Jeffries, P. M.; Dubois, L. H.; Girolami, G. S. *Chem. Mater.* 1992, 4, 1169-1175.
60. Srivastava, D. K.; Krannich, L. K.; Watkins, C. L. *Inorg. Chem.* 1991, 30, 2441-2444.

Example 16

Chemical Vapor Deposition of Metal Oxide Thin films from Metal N,N,-dimethlydiboranamide compounds and Water Introduction Metal oxides have many interesting applications including High-$T_c$ superconductors, ion conductors, dielectrics in microelectronics, optical widows, passive and protective layers. Chemical vapor deposition is an important method to grow metal oxide thin films, which usually involves the reaction of metal containing precursors, including metal halides, alkyls, alkoxides, beta-diketonates, and sometimes alkylaminate, with oxygen sources such as water and $O_2$. In this example, we show the first time that metal oxide films can be deposited from borohdride-bonded precursors. The deposition of MgO for $Mg(H_3BNMe_2BH_3)_2$ is of particular interest and is therefore reported in details, because it is superior to any other CVD processes in that it affords high quality, rapid growing and conformal MgO films at low deposition temperatures.

MgO is a refractory oxide with a melting point of 2852° C. It has a relative dielectrics constant of 9.8. It's optically transparent to a wide spectrum due to its large band gap (7.2 eV). Its low sputtering rate and high second electron emission coefficient make it a suitable protective material in plasma display panels,[1,2] MgO has a NaCl type crystal structure and has a lattice constant of 4.211 Å. It is closely lattice-matched to a range of materials including the high Tc superconductor oxide[3], ferroelectric oxide[4,5], conductive transparent oxide[6], metals[7-10] and metal nitrides[11-13], therefore Single crystal MgO has been the choice of substrate for the epitaxial growth of these materials. In addition, MgO thin films has been used as buffer layers for eptaixial and highly oriented overgrowth of them on single crystal silicon[14-18], GaAs[19-21], sapphire[22], and glass[23] substrates. The epitaxial MgO has also been used as an insulation layer for the magnetoresistance junction[25,26].

MgO thin films can be deposited by PVD and CVD methods. Comparing to PVD the advantages of CVD include the simplicity of the process and the high growth conformality, however, it also have disadvantages such as high growth temperature, relatively high impurity level, and limited growth rate. Unfortunately, so far the reported CVD growths of MgO did not fully demonstrate their advantages but suffered a great deal from disadvantages: The growth rates are usually only a few nm/min; growth temperature above 400° C. is required; impurities like carbon and halogen has been detected. Such issues can be attributed to the Mg containing precursors being used for deposition. In Table 1 we summarized the Mg precursors that have been employed for CVD growth of MgO. These precursors generally have very low vapor pressure, and have to be delivered with the assistance of a carrier gas at an elevated temperature. The low precursor feeding rate limits the film growth rate. Most of these precursors use oxygen as a co-reactant and the ligands attached to Mg are removed by complete oxidation, leaving issues such as high reaction temperature and impurity level.

We have developed a completely new type of Mg precursor, bis(dimethyldiboranamido)magnesium $(Mg(H_3BNMe_2BH_3)_2)$. The structure and preparation of this precursor is reported herein. The vapor pressure of this precursor is ~0.8 Torr at room temperature, which is more than an order of magnitude higher that those listed in Table 1. The precursor is thermally stable. However, when supplied with water, it produces MgO films at temperatures as low as 225° C. The high vapor pressure of the precursor can either allow us to achieve extremely conformal growth, or film growth at a rate of a few hundred nm/min. Below we report the CVD growth kinetics, the microstructure, crystallinity, electric and optical properties of the MgO films for $Mg(H_3BNMe_2BH_3)_2$ and $H_2O$.

Experiment

Figure 25:
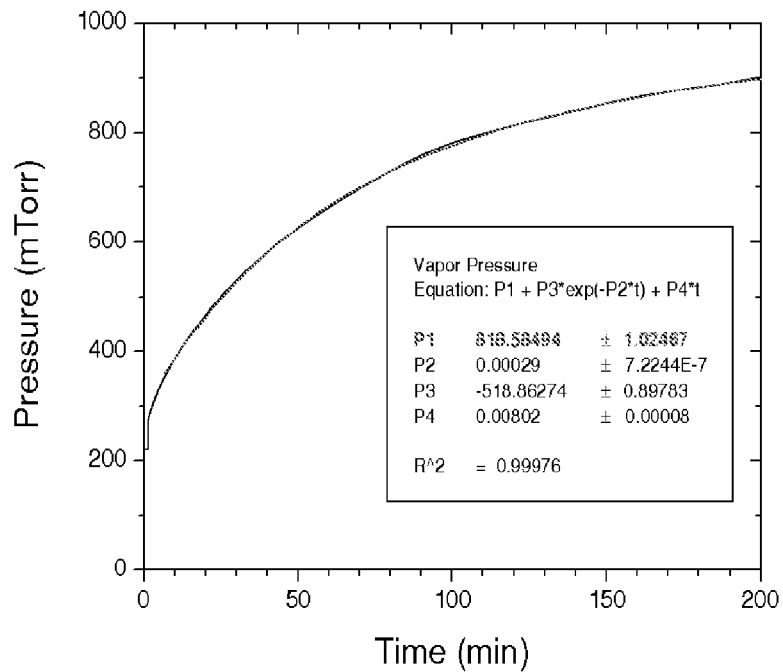
FIG. 25. Pressure rise of Mg(H$_3$BNMe$_2$BH$_3$)$_2$ as a function of time in a sealed container.

The vapor pressure of $Mg(H_3BNMe_2BH_3)_2$ was measured using a similar method as described in ref [28]. The precursor container is directly connected to a capacitance manometer. After the vapor is pumped into vacuum, the pressure rise as a function of time is recorded, as shown in FIG. 25. The vapor pressure of $Mg(H_3BNMe_2BH_3)_2$ at 30° C. is 0.82 Torr. The high vapor pressure of this precursor allows it to flow into the growth chamber with considerable feed rate without any carrier gas. During growth, both $H_2O$ and $Mg(H_3BNMe_2BH_3)_2$ were maintained at room temperature and were conducted to the chamber through a ¼" O.D. stainless steel tube. Their partial pressure in the chamber was controlled by regulating the corresponding inline metering valves. A steady state partial pressure as high as $10^{-2}$ Torr could be established for $Mg(H_3BNMe_2BH_3)_2$.

The CVD growth has been carried out in an UHV chamber with base pressure of $5\times10^{-9}$ Torr which has been described in detail elsewhere [29]. The substrates used for this work are Si(100) and Corning 7059 glass. Both substrates were degreased thoroughly with organic solvents before being loaded into the growth chamber. The silicon substrates were dipped into 10% HF solution for 10 seconds to remove native oxide. The silicon substrates were heated directly by passing current though, whereas the glass substrates were heated indirectly by a backed conductive silicon piece. A k-type thermocouple was placed onto the substrate for temperature measurement.

In-situ SE studies were carried out with a J.A. Woollam M-2000FI™ rotating compensator system with its accompanying software EASE™. The incident angle was fixed at 70°. The photon energies used for SE measurements spanned from the infra-red to the ultra-violet (0.75-5.05 eV). For dynamic studies of growth, a spectroscopic scan was acquired every 2-10 seconds. A standard multilayer model is employed to describe the MgO film, which consists of a substrate layer (silicon or glass) and a dielectric film layer simulated by a Cauchy model.

Film thickness and microstructure were determined by examining the fracture cross-sections in a scanning electron microscope (SEM). Film stoichiometry was measured by Auger electron spectrometer (AES) and Rutherford backscattering spectrometry (RBS). RBS also measured the area density of the Mg atom in the film, which was used to calculate the film density. The surface morphology of the film was studied by atomic force microscopy (AFM). The film crystallinity was analyzed by X-ray diffraction (Rigaku DMAX). For electrical characterization, a gold film was evaporated onto MgO/Si and the C—V and I—V measurements were carried out on this MOS structure. Optical transmission of the film grown on glass substrates were measured by a UV-VIS-NIR spectrophotometer (Varian Cary 5 G).

Results and Discussions
Growth Kinetics

The spectroscopic ellipsometer has a very high precision and sensitivity in the MgO film thickness measurement. Film thickness values are in very good agreement with the value measured by SEM, whereas film thickness change in angstrom level can be detected. The spectrometer was able to acquire a full spectrum scan in less than a second, thus a powerful tool to monitor the film growth rate in real-time.

Figure 26:
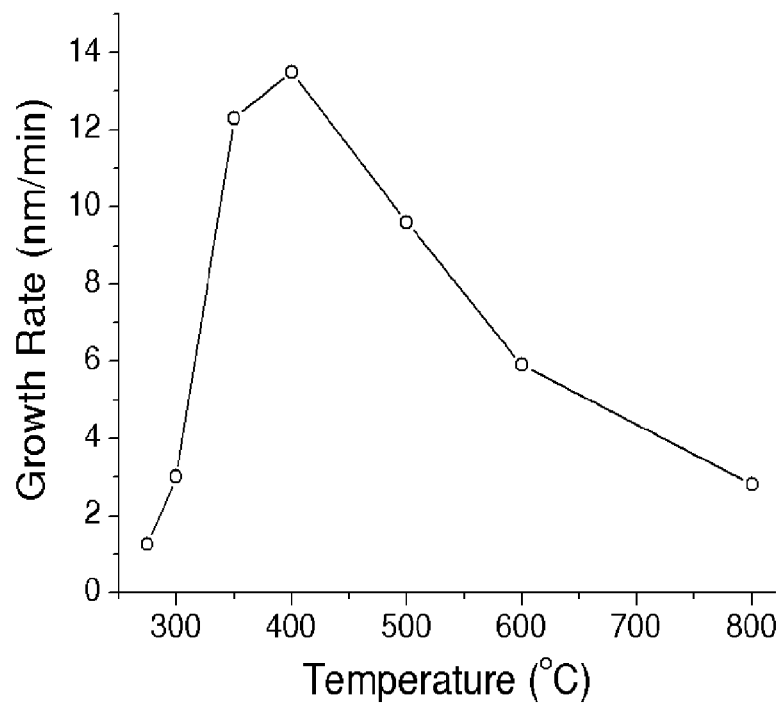
FIG. 26. Growth rates of MgO films as a function of substrate temperatures. The Mg(H$_3$BNMe$_2$BH$_3$)$_2$ and H$_2$O pressures were kept at 2×10$^{-5}$ Torr and 3×10$^{-5}$ Torr, respectively.

FIG. 26 shows the MgO film growth rate as a function of substrate temperature with a $Mg(H_3BNMe_2BH_3)_2$ pressure of $2\times10^{-5}$ Torr and $H_2O$ pressure of $3\times10^{-5}$ Torr at substrate temperature ranging from 275° C. to 800° C. At 275° C.<T<400° C., the growth rapidly increases with T, which is a clear indication of reaction-limited growth. However, at T≧400° C. the growth rate decreases with temperature, inconsistent with the conventional knowledge of a flux-limited growth where the growth rate is supposed to be invariant of temperature. There are two possible reasons for this growth rate decreasing. First, the growth is carried out in a cold wall reactor, and the sample is the only heat source. At higher growth temperature, the surface surrounding the sample will be heated substantially, reaching a temperature above the CVD growth threshold, which is ~250° C. in this case. Therefore, at a constant feed rate growth condition, these hot surface acts as a sink to the precursor and reduces the precursor partial pressure inside the chamber, which in turn decreases the growth rate on the substrate. Clearly, the higher the substrate temperature is, the larger this effect. We have observed similar growth rate reduction at higher growth temperature for the $HfB_2$ CVD growth in the same reactor.[29] The reaction rate drop at higher growth temperatures is also possibly due to the decrease of the hydroxyl group density on the surface which reduces the sticking coefficient of the metal containing precursor, as suggested by Matero et al. in their study of the ALD growth of $Al_2O_3$.[30]

Figure 27:
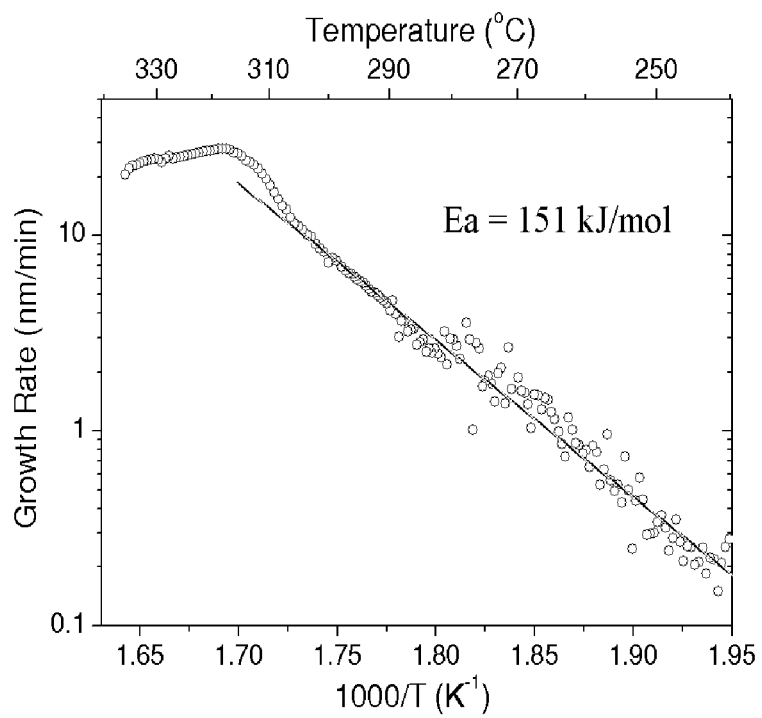
FIG. 27. a) Growth rate variation as monitored by real-time spectroscopic ellipsometry along a linear increase of substrate temperature. The Mg(H$_3$BNMe$_2$BH$_3$)$_2$ and H$_2$O pressures were kept at 2×10$^{-5}$ Torr and 3×10$^{-5}$ Torr, respectively. b) Growth rate as a function of Mg(H$_3$BNMe$_2$BH$_3$)$_2$ pressure at 225° C. and a H$_2$O pressure of 3 mTorr.
Figure 27:
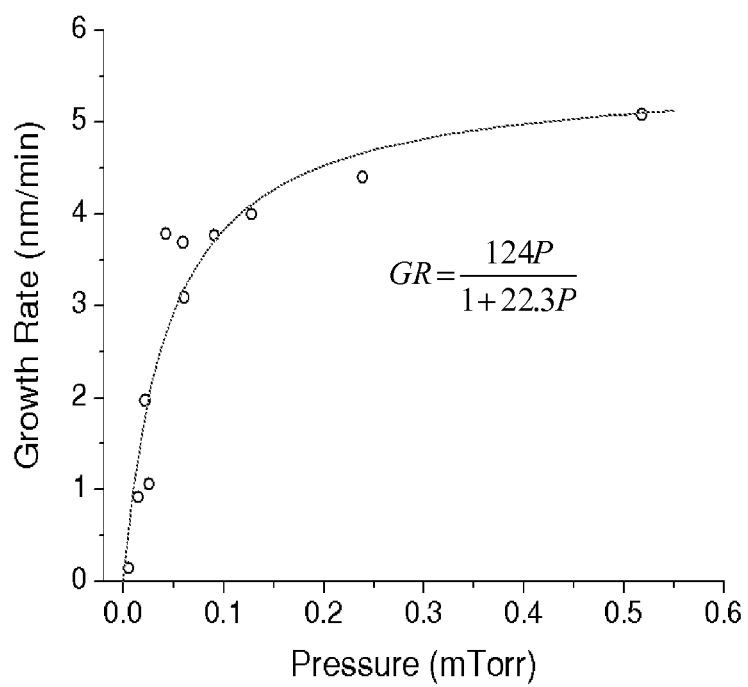

FIG. 27a presents a higher resolution study of the reaction limited regime. In this experiment the substrate temperature was ramped up linearly with a rate of 0.05° C./sec, with the film thickness monitored in real-time. The growth rate as a function of temperature was obtained by taking the first derivative of the thickness profile, and was shown in an Arrhenius plot. (FIG. 27a) The flux and reaction limited growth regimes are clearly separated. The apparent activation energy calculated from the slope of the plot at the reaction limited regime is 151 kJ/mol. Note that this energy is an apparent value for the reaction mechanism containing multiple reaction steps. It is likely to correspond to the activation energy of the rate limiting step; however, under a different precursor pressure the competition among various reaction steps may lead to a different value.

Figure 28:
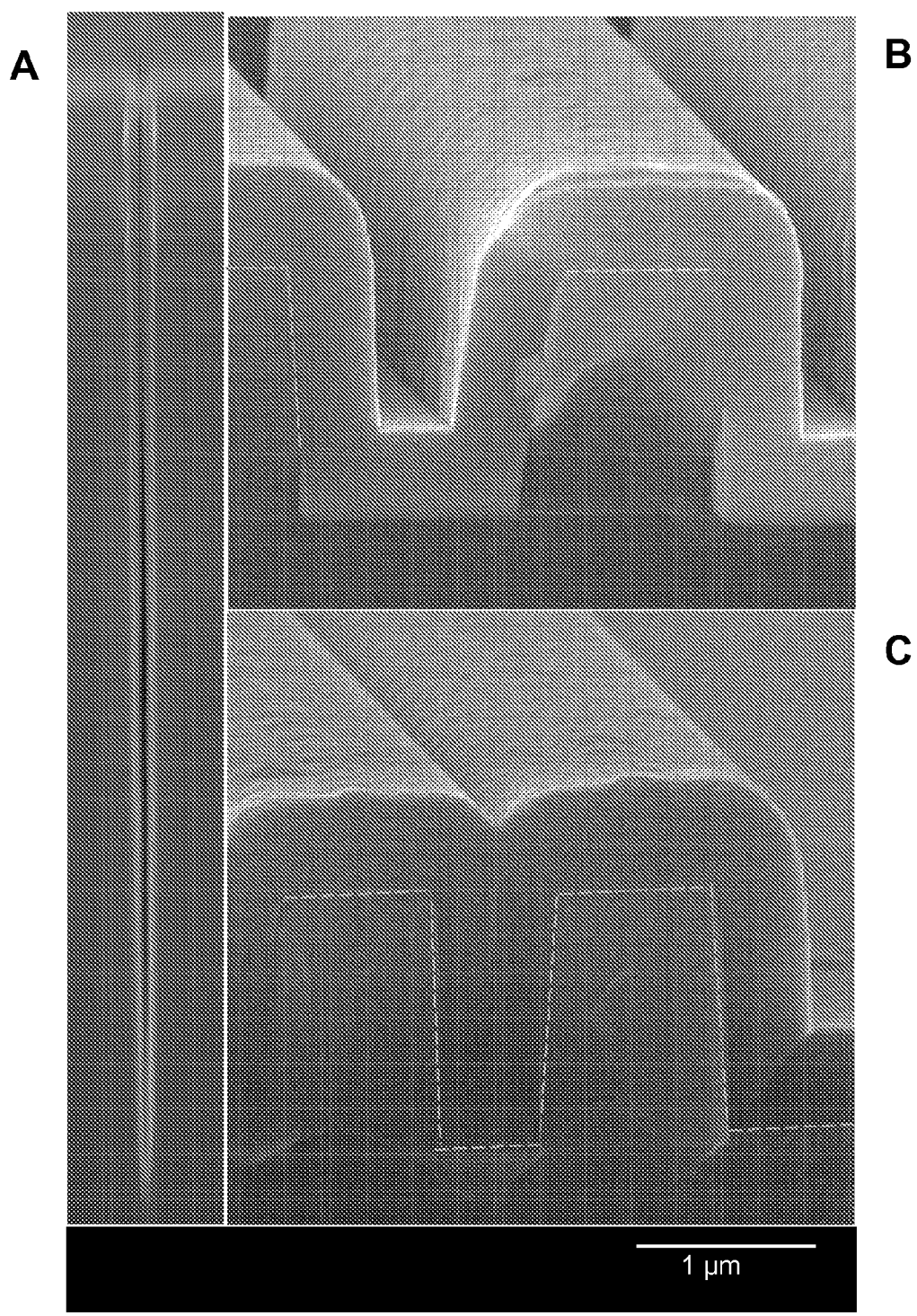
FIG. 28. SEM images of the conformal MgO films grown on trenches. The trench shown in a) has a depth to width ratio of 30:1.

The growth rate as a function of Mg precursor pressure is presented in FIG. 27b. The water pressure was kept at 3 mTorr, which is significantly higher than the Mg pressure. The growth rate saturates at high $Mg(H_3BNMe_2BH_3)_2$ pressure, which could be attributed to a "site-blocking" mechanism: the surface sites are all occupied by the precursor molecules that have not complete the surface reaction, and thus is unavailable to the incoming precursor molecules. The consequence is that the reaction probability decreases as precursor pressure increases. The growth at this regime is highly desired for coating of complex features, because lower precursor reaction probability leads to better growth conformality [31]. FIG. 28a shows an example of an ultra-conformal MgO film grown on a deep trench structure with depth to width ratio equal to 30:1. In this growth experiment, the substrate temperature was 225° C., and the $Mg(H_3BNMe_2BH_3)_2$ and $H_2O$ pressures were 6 mTorr and 15 mTorr, respectively. The film growth rate was 2 nm/min, and the reaction probability of the precursor is calculated to be $6\times10^{-5}$, which in theory is capable of coating a 50:1 aspect ratio trench according to simulation study.[31] Note that for CVD growth with more than one reactant, the grown conformality is limited by the reactant with lowest process pressure, in this case $Mg(H_3BNMe_2BH_3)_2$.

The growth conformality shown in FIG. 28a is comparable to that of atomic layer deposition (ALD). However, ALD suffers from its low growth rate, whereas CVD has the possibility of trading off the conformality with growth rate by varying the deposition conditions, demonstrated by the MgO growth shown in FIGS. 28b and 28c. Here, a higher substrate temperature of 285° C. was used to enhance the growth rate by an order of magnitude, while still maintaining excellent growth conformality on lower aspect ratio trenches. The growth rate could be further boosted up to hundreds of nm/min with a requirement on conformality. The growths with high growth rate or high conformality require high precursor pressures, therefore the capability of this CVD MgO process is attributed to the unique high vapor pressure of the $Mg(H_3BNMe_2BH_3)_2$ precursor.

Film Stoichiometry

Figure 29:
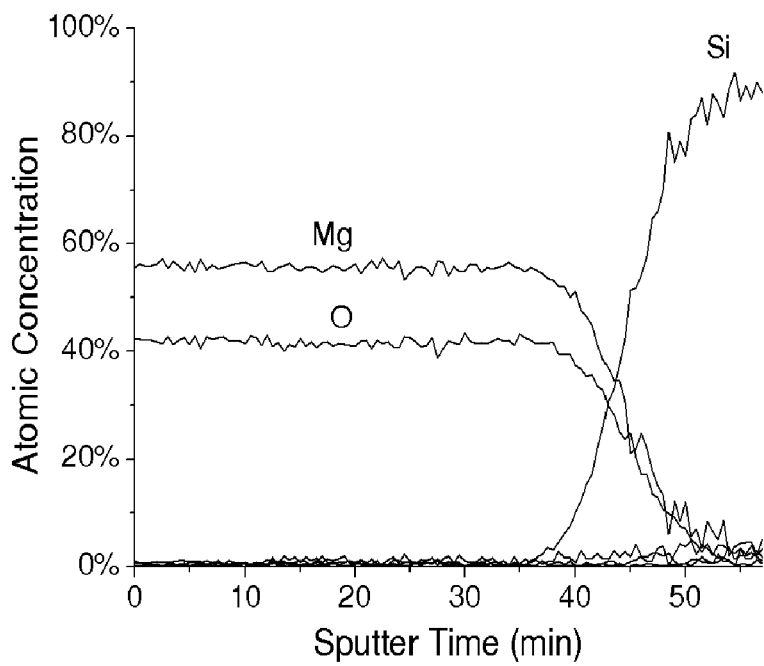
FIG. 29. AES depth profiling of the MgO films on silicon substrate deposited at a) 275° C. and b) 400° C.
Figure 29:
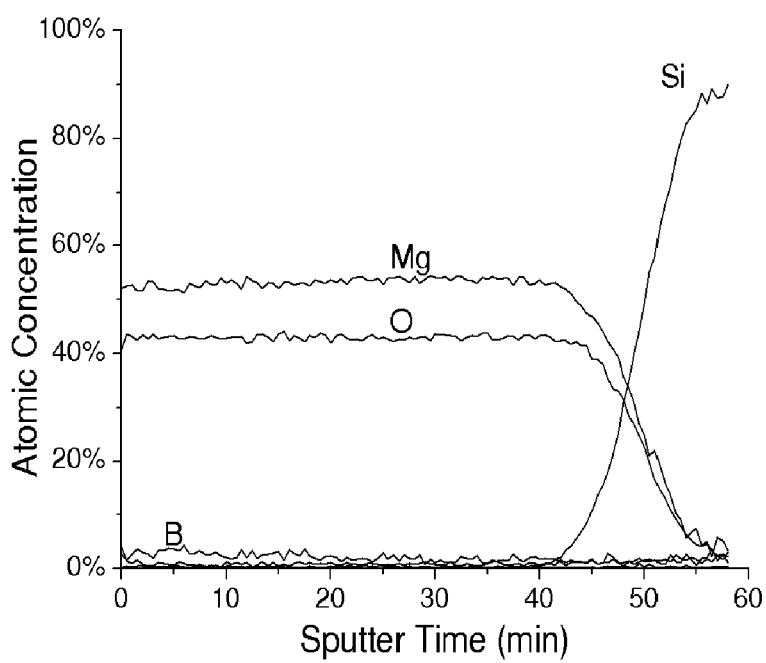
Figure 30:
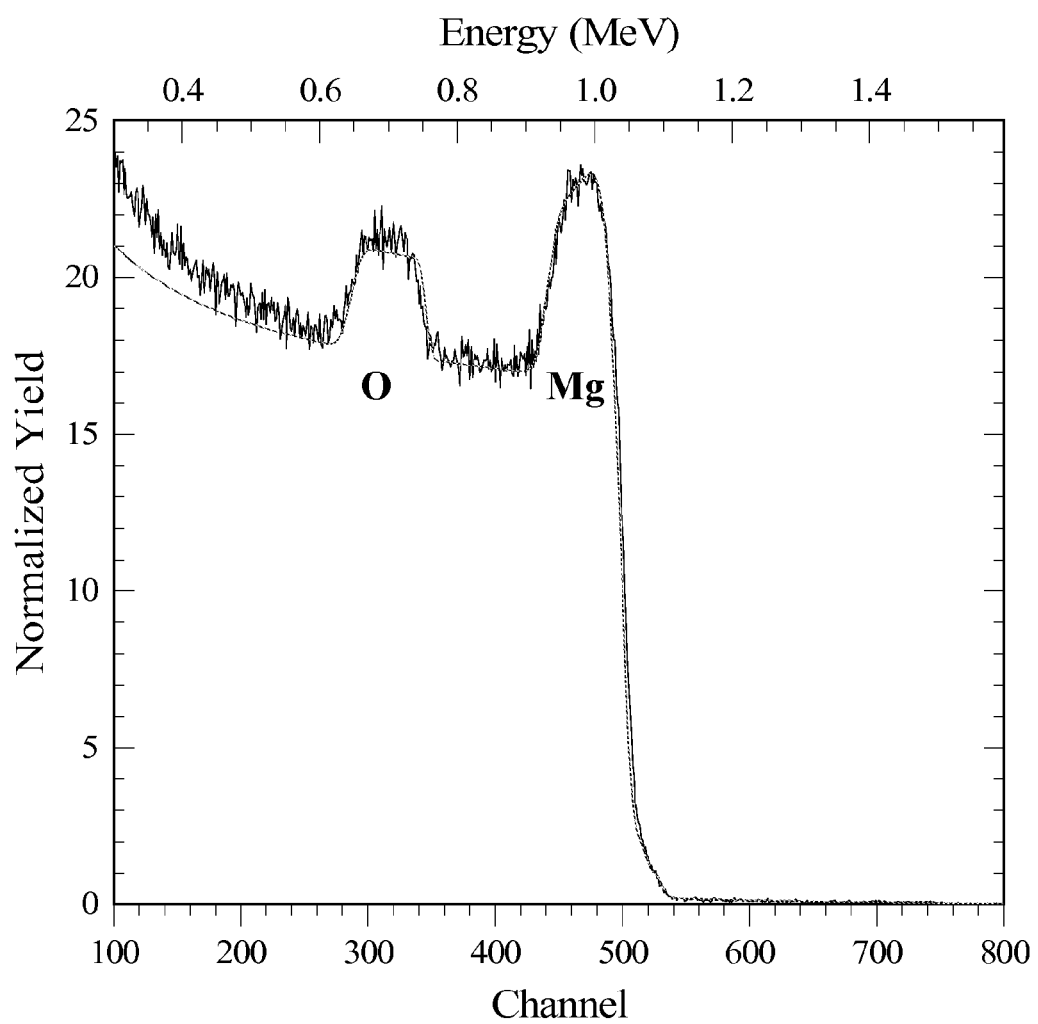
FIG. 30. RBS of a MgO film grown at 500° C. on silicon substrate. The noised and smooth lines are the measured and fitted spectra, respectively.

The composition of the MgO films grown at various temperatures are characterized by AES, as shown FIG. 29. The impurities may be expected from the precursor molecules including carbon, boron, and nitrogen. The intensity of these elements are essentially below the instrument detection limit for all the films being characterized, except the one grown at 400° C. which contains a few percent of boron. The atomic concentration in the Auger electron spectroscopy are calculated from the standard sensitivity factors provided by the software, therefore the consistent magnesium to oxygen ratio of 4:3 found by AES, as shown in FIG. 29, may not correspond to the actually film stoichiometry. To obtain a more accurate film stoichiometry, RBS was employed to measure the number per area of the magnesium and oxygen atoms in the film. A typical RBS spectrum of a film grown at 500° C. is shown in FIG. 30, where the Mg to O ratio is 0.9:1. While the MgO films deposited at most other temperatures has similar Mg to O ratio, the 400° C. film has Mg/O=0.7. The higher oxygen content in all the CVD MgO films could be explained by an incomplete decomposition or a post-growth adsorption of water into the film, given that the alkaline-earth metal oxide has a strong affinity to water. Excessive oxygen content due to water adsorption is reported in an ALD growth of $Y_2O_3$ thin film [32].

From atomic density per area measurement by RBS, we could further calculate the atomic density per volume of the film by dividing the atomic density per area with the film thickness. The Mg density of our films are mostly 80-90% of that of a perfect MgO crystal, except that the film grown at 400° C. has a lower density of 70%. Such film density values are reasonable considering that most of our films are amorphous or weakly crystallized. Clearly, the film grown at 400° C. has poorer quality than those grown at lower or higher temperatures.

Film Surface Morphology, Microstructure and Crystallinity

Figure 31:
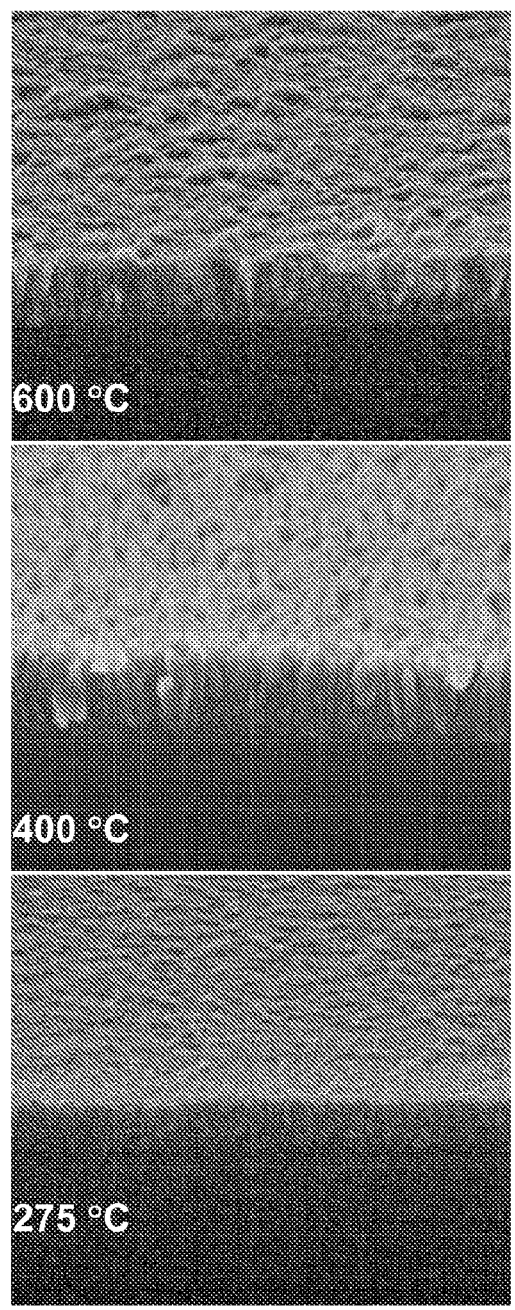
FIG. 31. Cross sectional SEM images of the MgO films on silicon substrates deposited at 275, 400, and 600° C.
Figure 32:
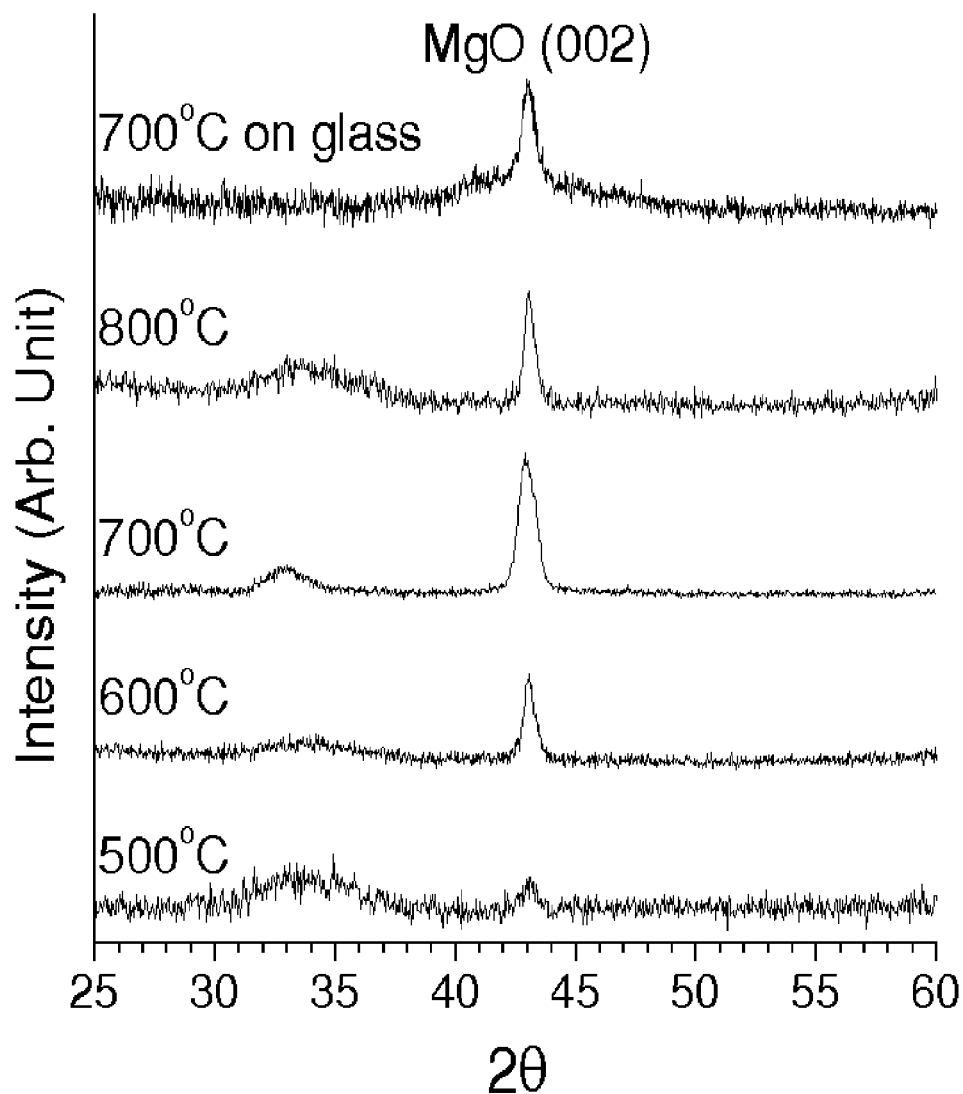
FIG. 32. XRD results of the MgO films deposited at various temperatures on silicon substrates except for the top profile where a glass substrate was used.

The cross sectional SEM images of the MgO films grown at 275° C., 400° C., and 600° C. with a $Mg(H_3BNMe_2BH_3)_2$ pressure of $2 \times 10^{-5}$ Torr and $H_2O$ pressure of $3 \times 10^{-5}$ Torr are shown in FIG. 31. The film grown at high temperatures are clearly columnar, owing to the high reaction probability of the precursor. Films grown at T<300° C. are very smooth, even at a large thickness (FIG. 28*b*). X-ray diffraction spectra (FIG. 32) suggest that the film start to crystallize at 500° C. The x-ray peak is sharper at higher growth temperature, indicating an increased crystallinity with growth temperature. Films grown on Si(100) substrate at all growth temperatures are universally (002) textured, partially attributed to a registration with the substrate symmetry. However, a film grown on glass substrate at 700° C. also shows (002) texture, indicating that (002) texture is inherently favored, agreed with reported MgO growth by CVD [33, 34].

Optical and Electrical Properties

Figure 33:
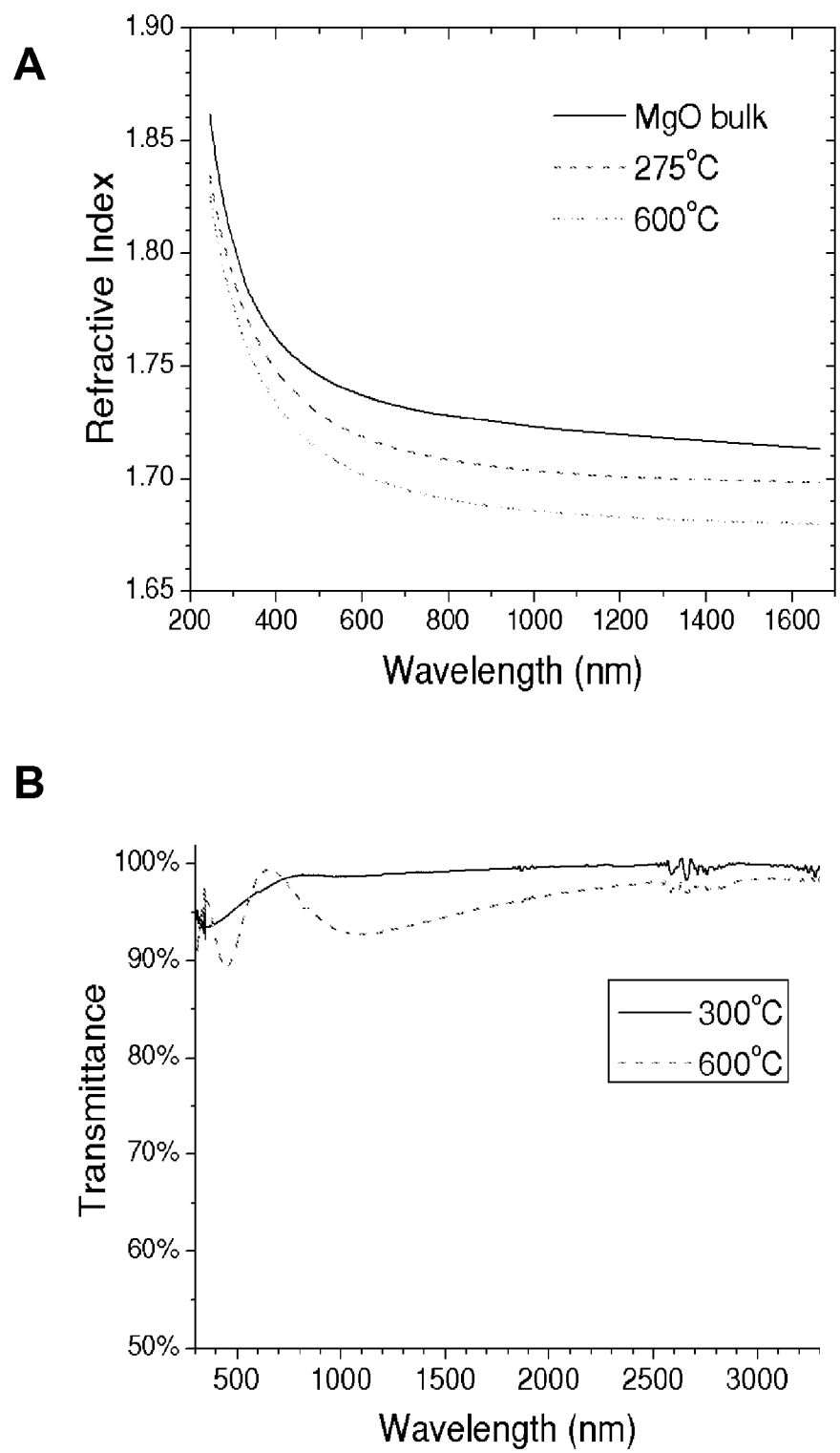
FIG. 33. a) Refractive index of the MgO films deposited at 275 and 600° C. compare to that of the bulk MgO. b) Transmittance spectra of the MgO films deposited at 275 and 600° C.

By modeling the ellipsometry spectrum with Cauchy equation, the refractive index of the MgO film grown at 275° C. and 600° C. as a function of wavelength are shown in FIG. 33*a*. The refractive index of bulk MgO, is present in the same figure for comparison. The CVD MgO films have a slightly smaller refractive index, which could be explained by their lower density comparing with bulk MgO. Both films have excellent transparency. As shown in the transmittance spectrum (FIG. 33*b*), the 250 nm thick films grown at both 275° C. and 600° C. on glass substrates have a transmittance >90% in spectrum ranging from near UV to near IR. The dielectric constant of the MgO film grown on Si substrate is 9.5 by a C—V measurement, slightly lower than the bulk MgO value of 9.8, which could also be attributed to the film density.

CVD of Other Metal Oxide Thin Films $Y_2O_3$ and $TiO_2$ are the other two metal oxide thin films that have been successfully deposited from the corresponding diboronaminde compound $Y(H_3BNMe_2BH_3)_3$ and $Ti(H_3BNMe_2BH_3)_2$ precursors using water as a co-reactant. Both of them are also very useful materials. $Y_2O_3$ has a high permittivity, and thus is a candidate for the high K gate dielectric material for next generation microelectronics [32]. It has a very small lattice mismatch with Si and can serve as an epitaxial buffer layer for ferroelectrics and superconductor oxides [35]. $TiO_2$ is known to be a good photo-catalyst [36].

Figure 34:
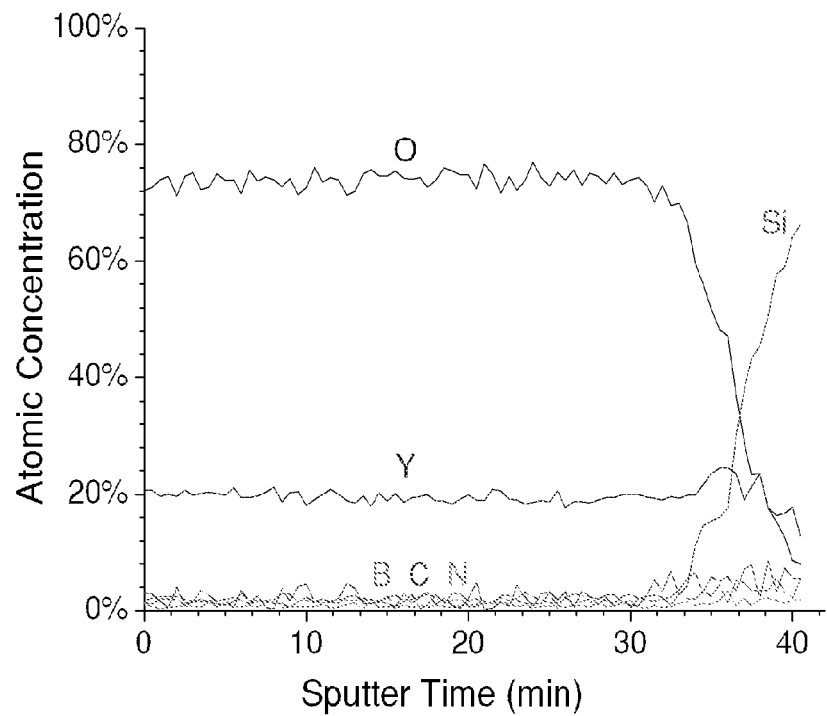
FIG. 34. AES depth profiling of a Y$_2$O$_3$ and a TiO$_2$ film deposited on silicon substrates at 300° C.
Figure 34:
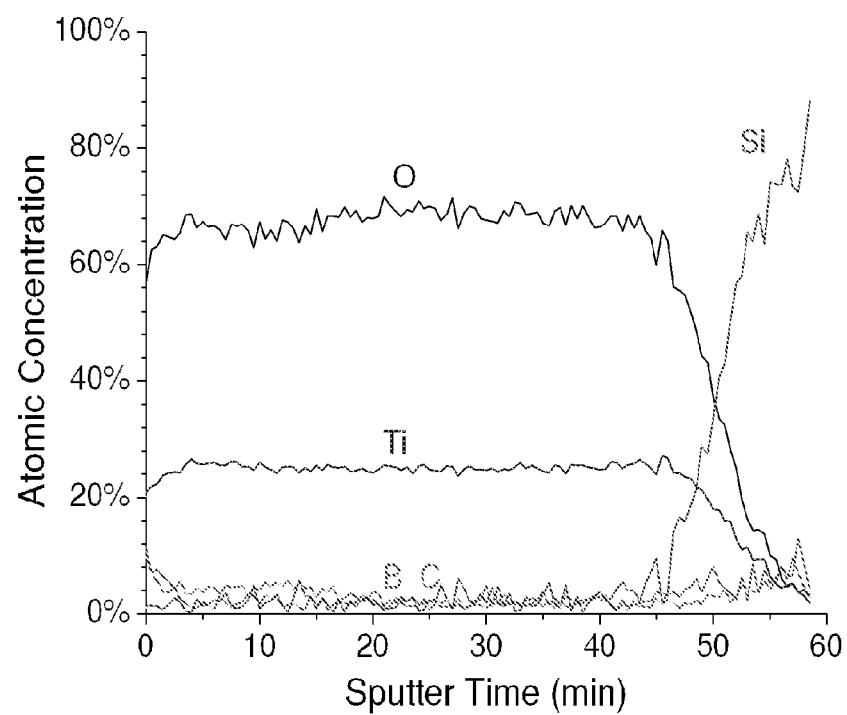
Figure 35:
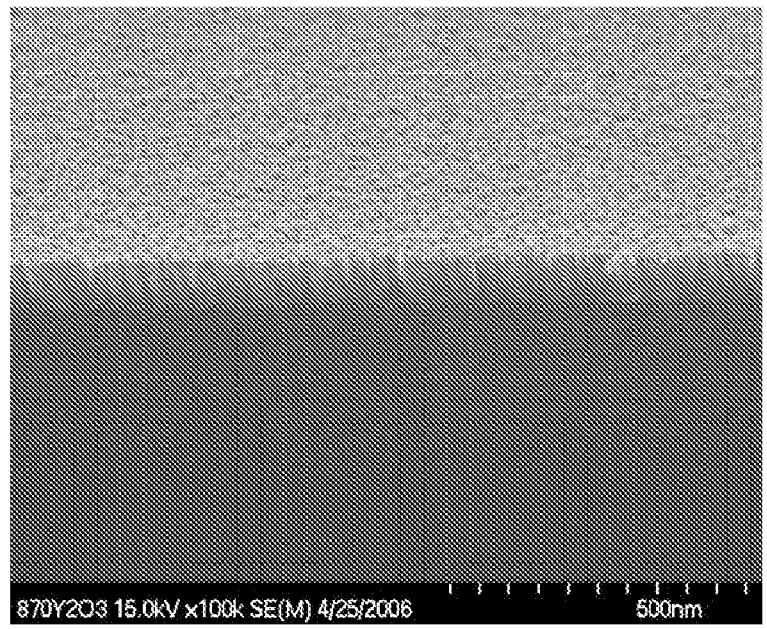
FIG. 35. Cross sectional SEM images of the Y$_2$O$_3$ and TiO$_2$ films deposited on silicon substrates by CVD.
Figure 35:
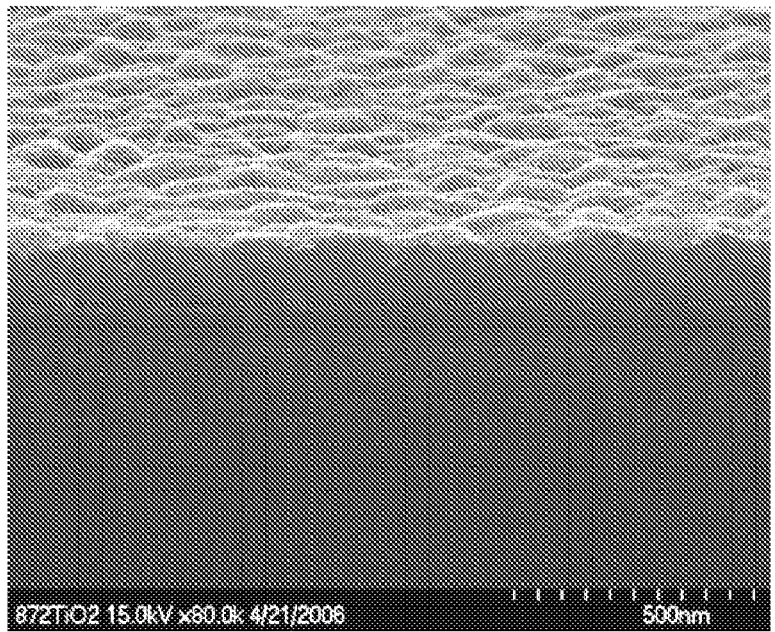
Figure 36:
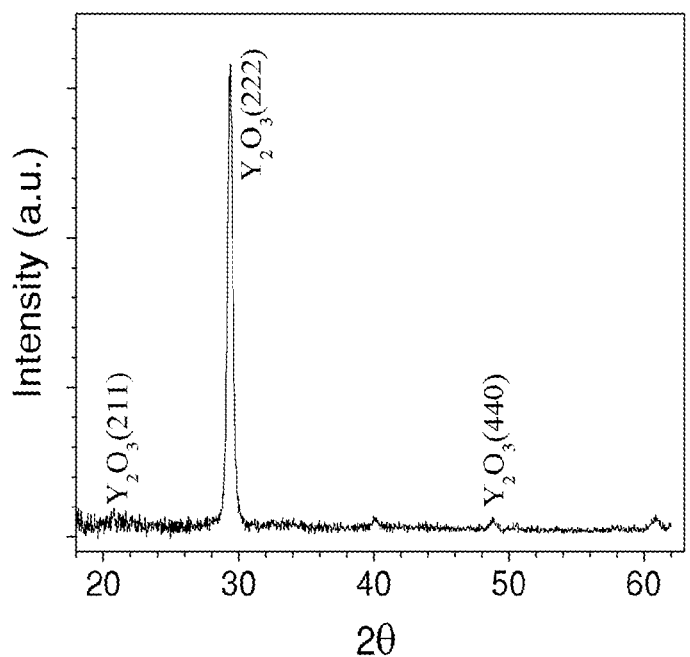
FIG. 36. XRD profile of a Y$_2$O$_3$ film deposited on a Si(100) substrate at 800° C.

FIG. 34 shows the AES depth profiling of the $TiO_2$ and $Y_2O_3$ thin films deposited from the diboranamide precursors. Similar to the AES analysis of MgO film, the oxygen to metal ratio does not exactly match with the bulk material stoichiometry, which can also be explain by the inappropriate use of the standard AES sensitivity factors for the oxide films. However, carbon, nitrogen, and boron levels are below the AES detection limit, indicating that the films are free of impurities. The films are dense, but columnar, similar to the MgO film deposited at low pressure. The vapor pressure of $Ti(H_3BNMe_2BH_3)_2$ and $Y(H_3BNMe_2BH_3)_3$ are much lower than $Mg(H_3BNMe_2BH_3)_2$, thus only low precursor pressure can be used. This explains the columnar microstructure of the films, as shown in FIG. 35. It is very similar to the MgO film deposited at low pressure conditions (FIG. 31). FIG. 36 shows the XRD profile of a $Y_2O_3$ film deposited at 800° C. on a Si(100) substrate, which is actually an unsuccessful epitaxial growth attempt. In spite of the close lattice match between Si(100) and $Y_2O_3$(100), the film is strongly (111) textured. This is because at high temperature, silicon tends to react with the oxygen source ($H_2O$ here) to form an amorphous $SiO_2$ film on top, which blocks the direct contact of the crystalline silicon with the oxide film. The texture observed in FIG. 31 is in fact a film texture formed on silicon oxide. The epitaxial growth of oxide on silicon substrate should be carried out at conditions where $SiO_2$ formation is not preferred or the oxygen source is strictly controlled [37], both of which are not trivial for simple thermal CVD.

Figure 37:
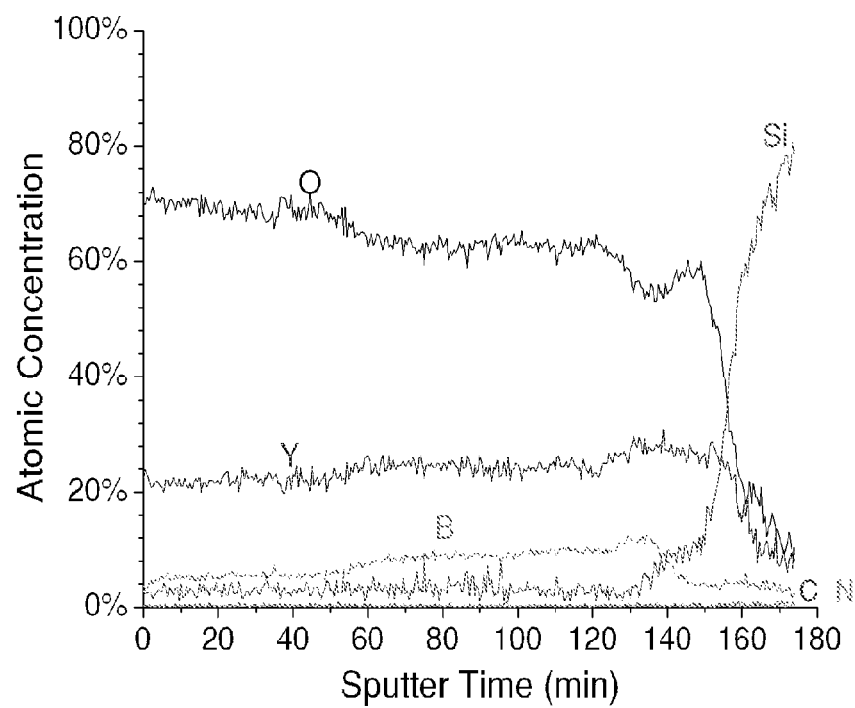
FIG. 37. AES depth profiling of a Y$_2$O$_3$ film deposited on a silicon substrate at low H$_2$O pressure.
Figure 38:
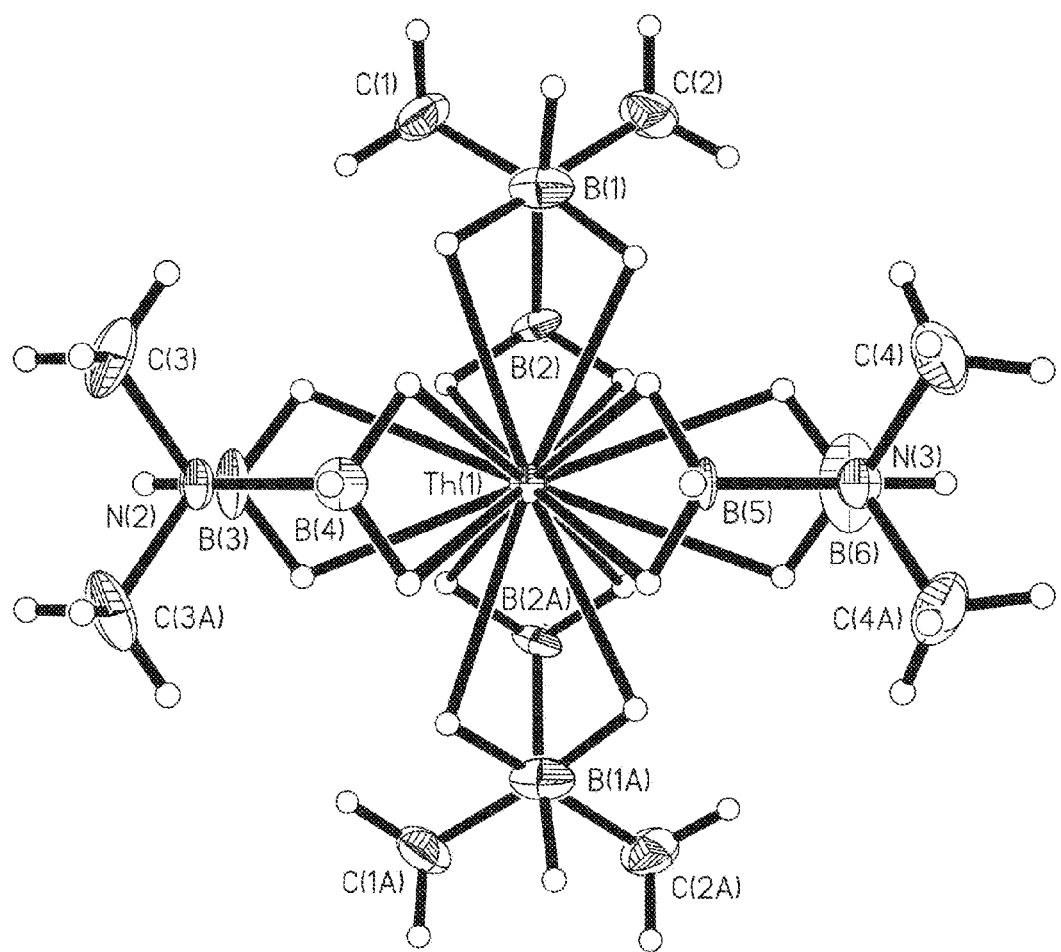
FIG. 38. Molecular structure of Th(H$_3$BNMe$_2$BH$_3$)$_4$. Ellipsoids are drawn at the 35% probability level, except for the hydrogen atoms, which are represented as arbitrarily-sized spheres.
Figure 39:
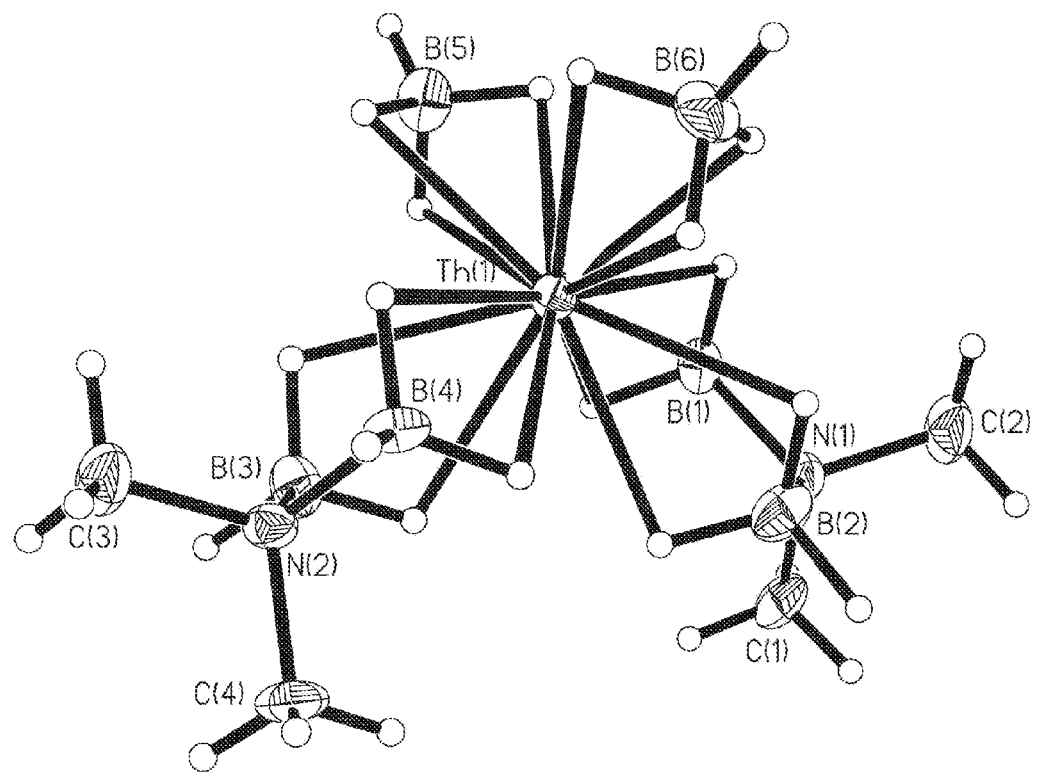
FIG. 39. Molecular structure of Th(H$_3$BNMe$_2$BH$_3$)$_2$(BH$_4$)$_2$. Ellipsoids are drawn at the 35% probability level, except for the hydrogen atoms, which are represented as arbitrarily-sized spheres.
Figure 40:
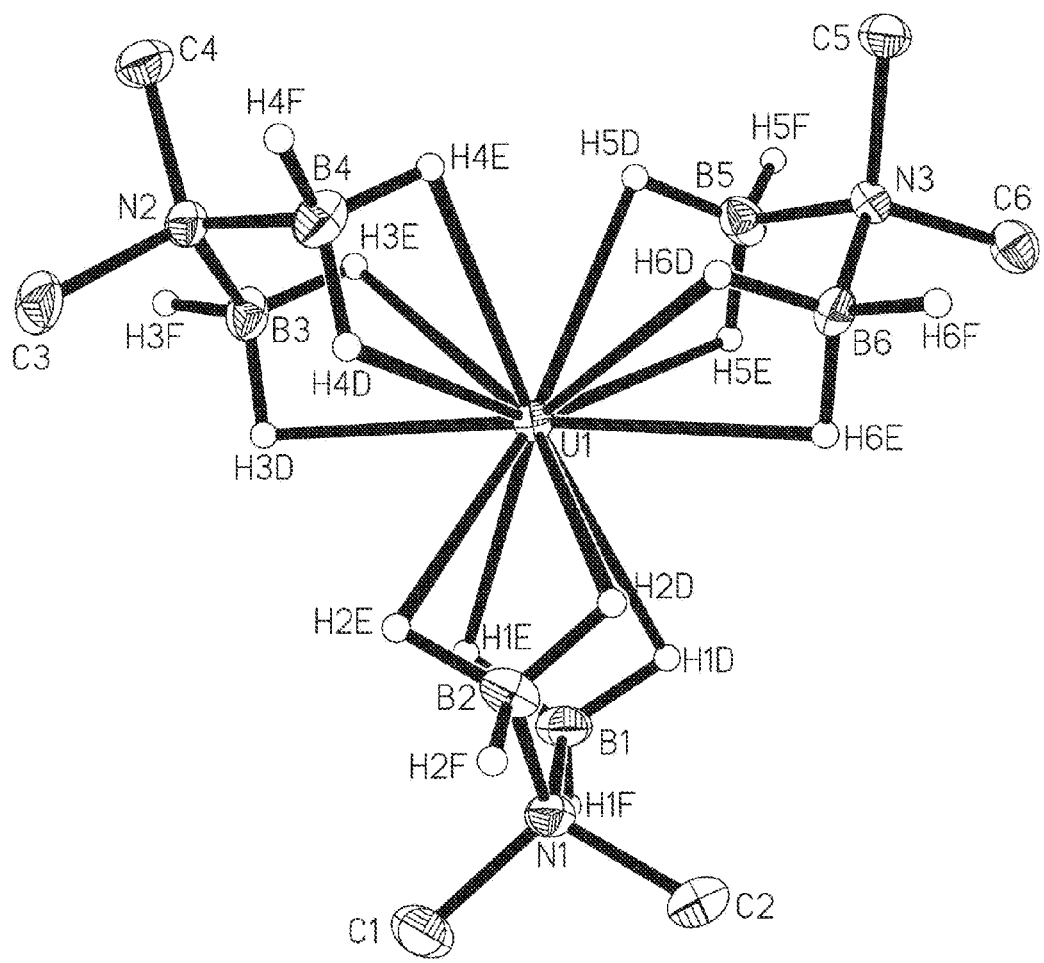
FIG. 40. Molecular structure of U(H$_3$BNMe$_2$BH$_3$)$_3$, structural isomer A. Ellipsoids are drawn at the 35% probability level, except for the hydrogen atoms, which are represented as arbitrarily-sized spheres. Methyl and methylene hydrogen atoms have been deleted for clarity.
Figure 41:
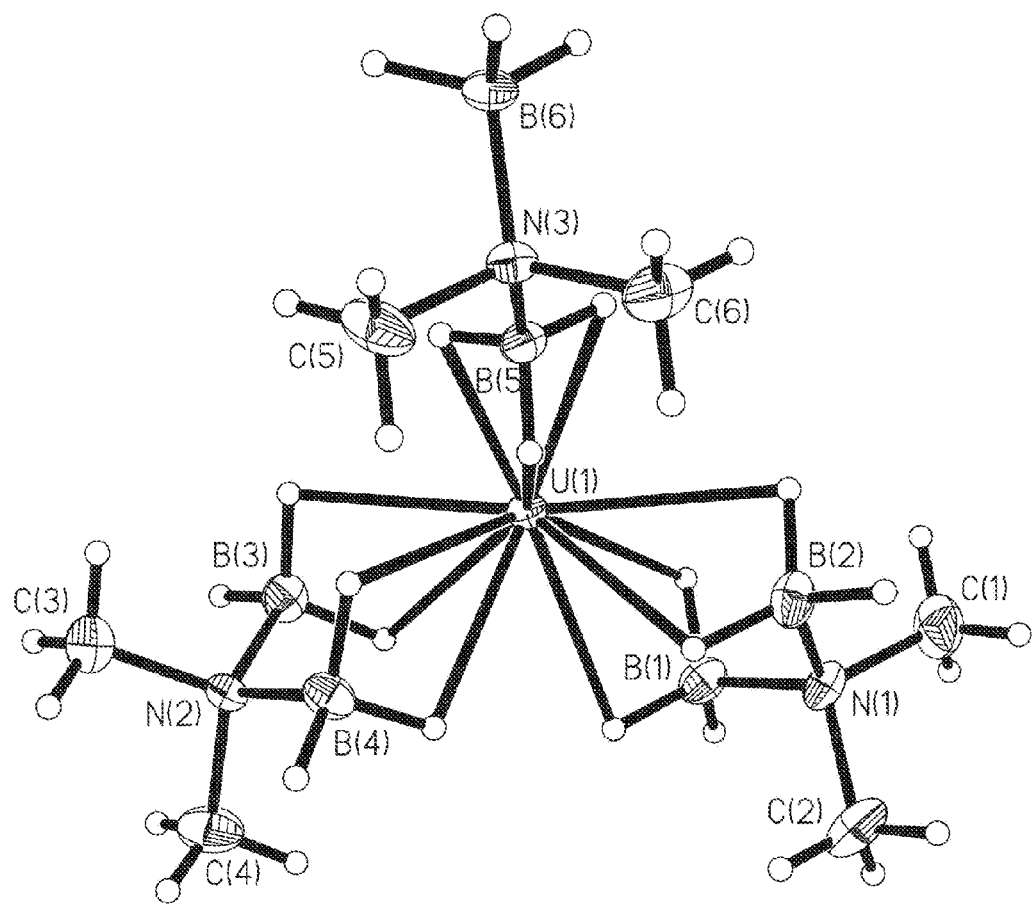
FIG. 41. Molecular structure of U(H$_3$BNMe$_2$BH$_3$)$_3$, structural isomer B. Ellipsoids are drawn at the 35% probability level, except for the hydrogen atoms, which are represented as arbitrarily-sized spheres.
Figure 42:
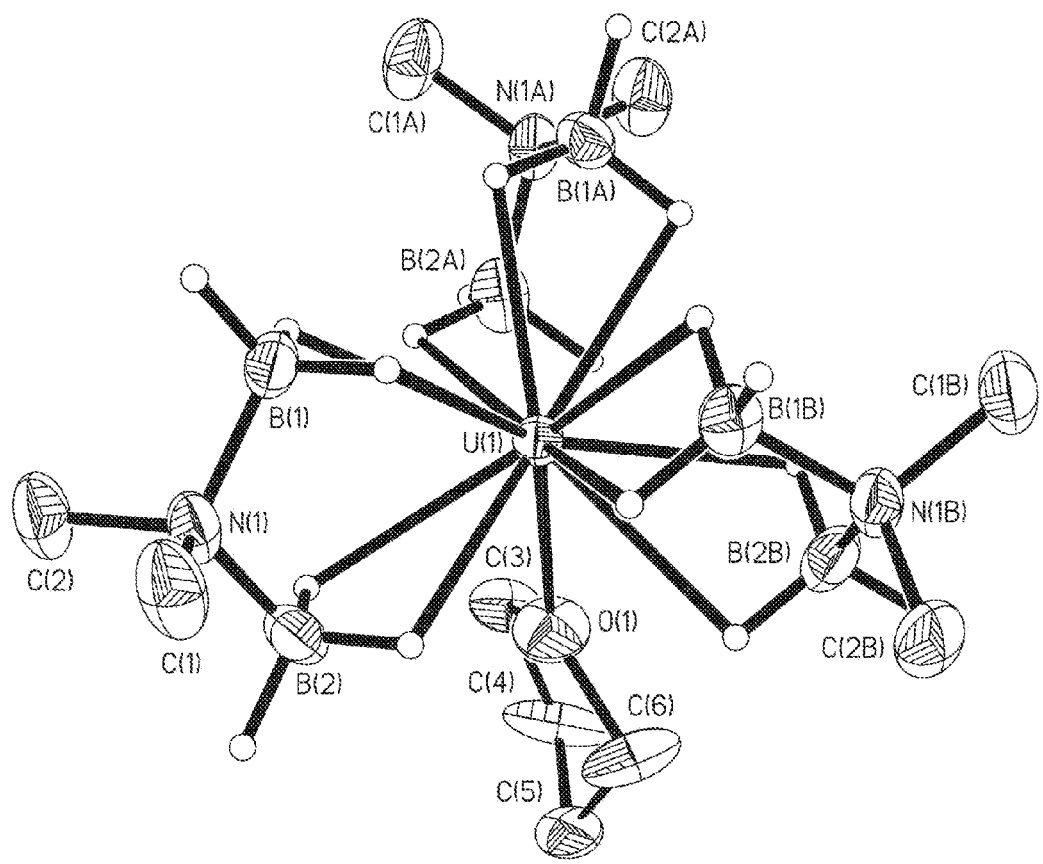
FIG. 42. Molecular structure of U(H$_3$BNMe$_2$BH$_3$)$_3$(thf). Ellipsoids are drawn at the 35% probability level, except for the hydrogen atoms, which are represented as arbitrarily-sized spheres. Methyl and methylene hydrogen atoms have been deleted for clarity.
Figure 43:
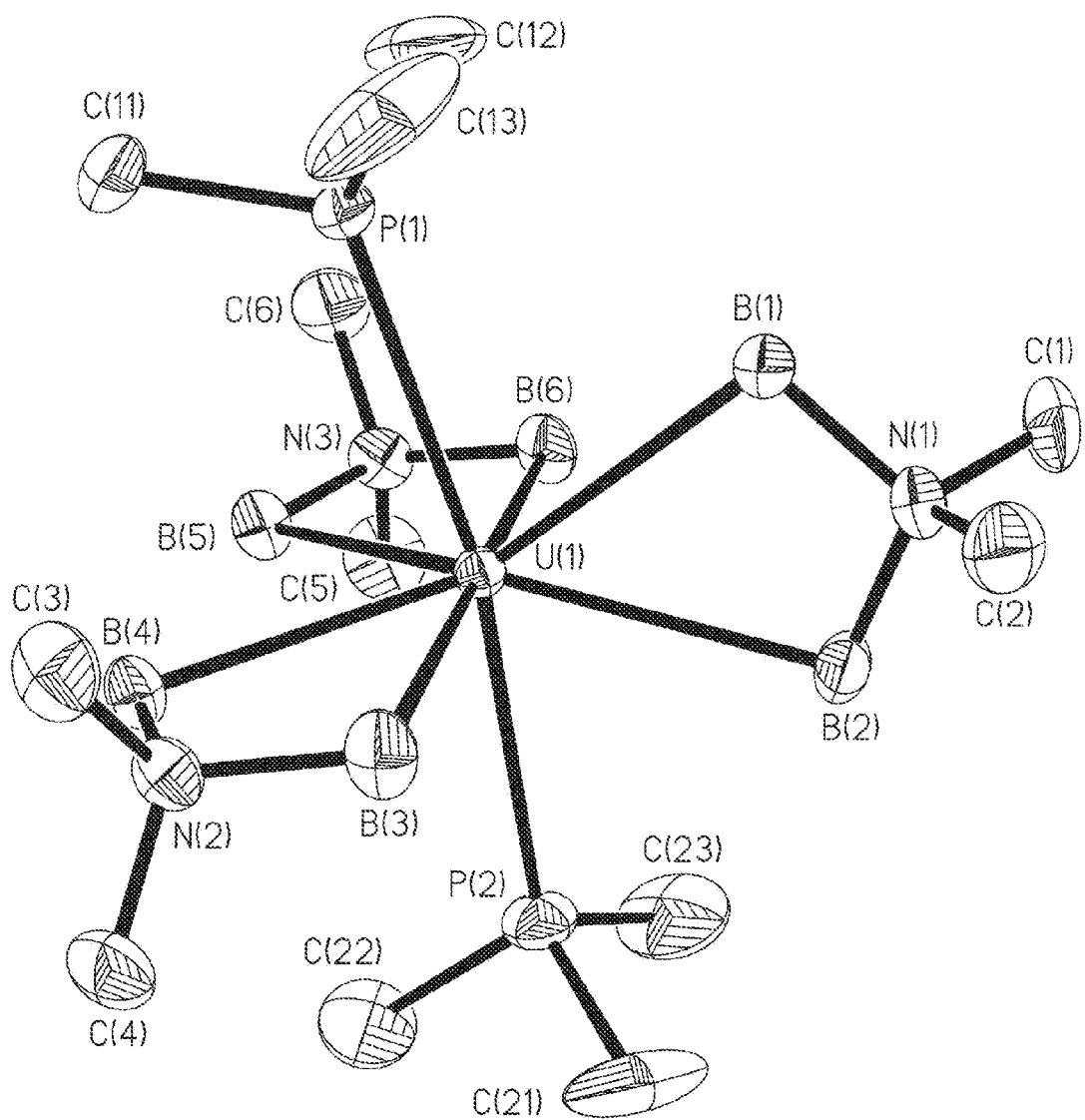
FIG. 43. Molecular structure of U(H$_3$BNMe$_2$BH$_3$)$_3$(PMe$_3$)$_2$. Ellipsoids are drawn at the 35% probability level. Hydrogen atoms have been deleted for clarity.
Figure 44:
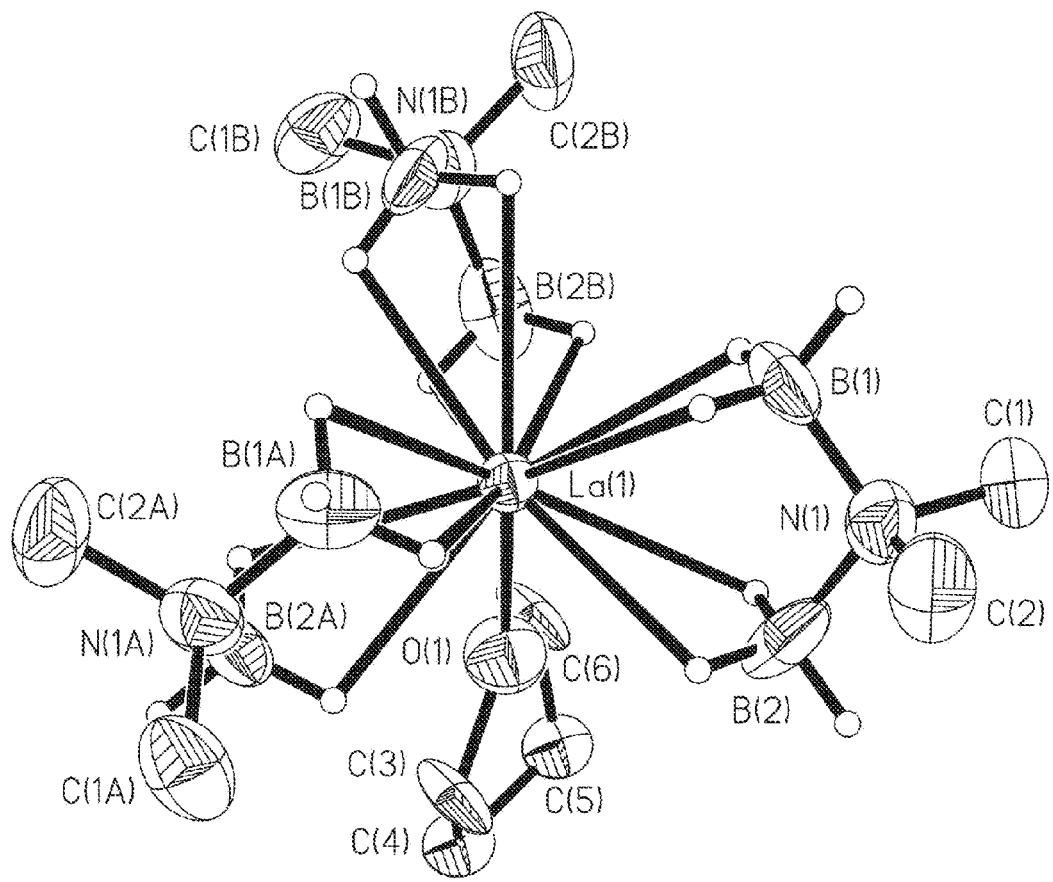
FIG. 44. Molecular structure of La(H$_3$BNMe$_2$BH$_3$)$_3$(thf). Ellipsoids are drawn at the 35% probability level, except for the hydrogen atoms, which are represented as arbitrarily-sized spheres. Methyl and methylene hydrogen atoms have been deleted for clarity.
Figure 45:
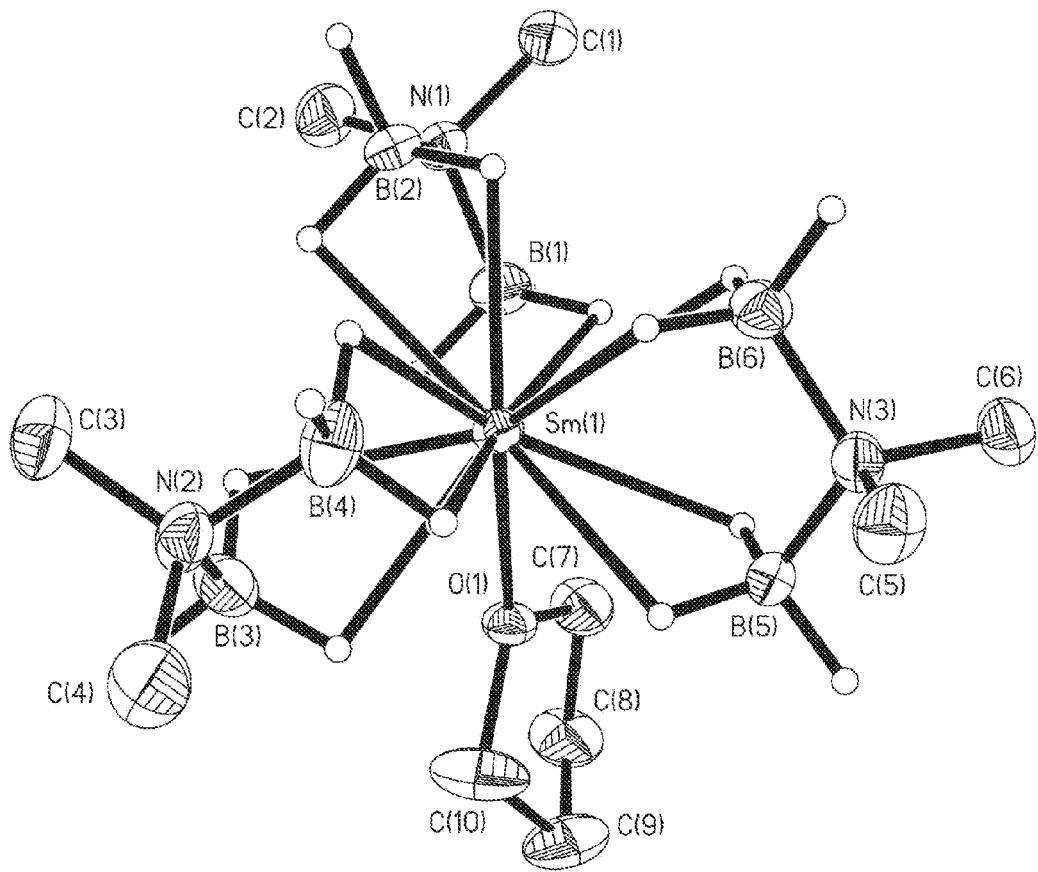
FIG. 45. Molecular structure of Sm(H$_3$BNMe$_2$BH$_3$)$_3$(thf). Ellipsoids are drawn at the 35% probability level, except for the hydrogen atoms, which are represented as arbitrarily-sized spheres. Methyl and methylene hydrogen atoms have been deleted for clarity.
Figure 46:
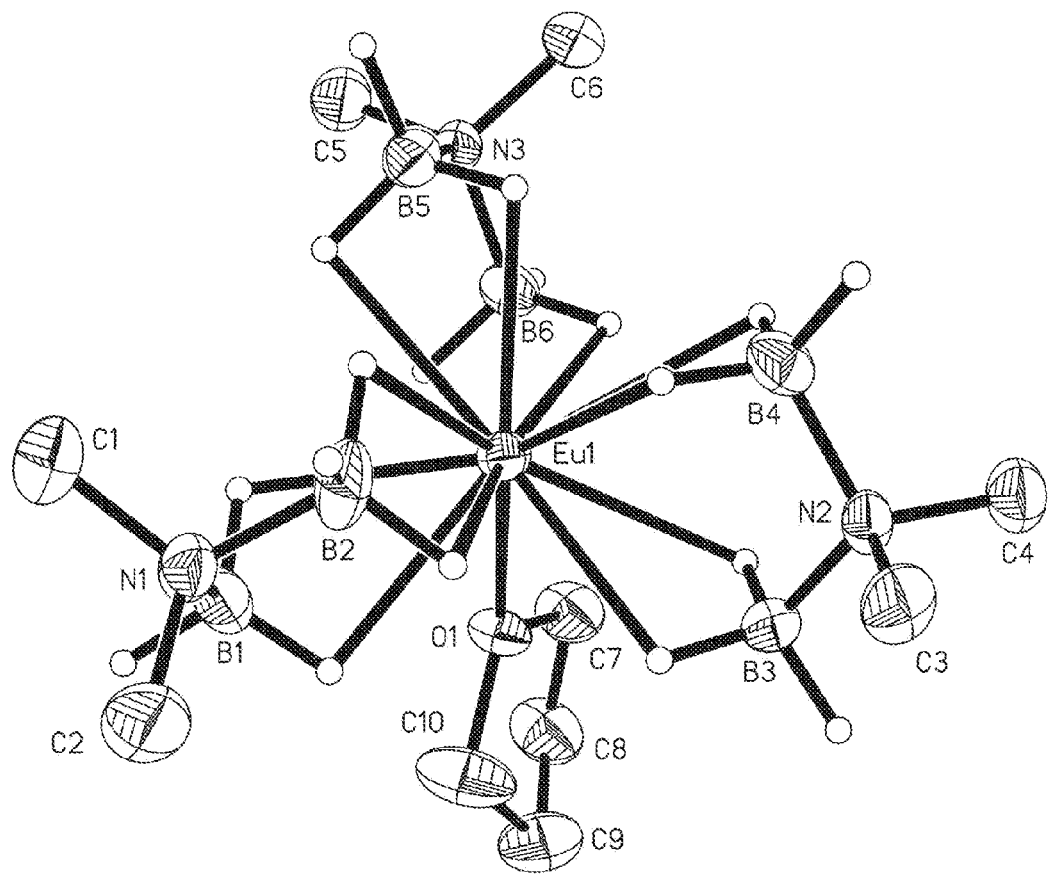
FIG. 46. Molecular structure of Eu(H$_3$BNMe$_2$BH$_3$)$_3$(thf). Ellipsoids are drawn at the 35% probability level, except for the hydrogen atoms, which are represented as arbitrarily-sized spheres. Methyl and methylene hydrogen atoms have been deleted for clarity.
Figure 47:
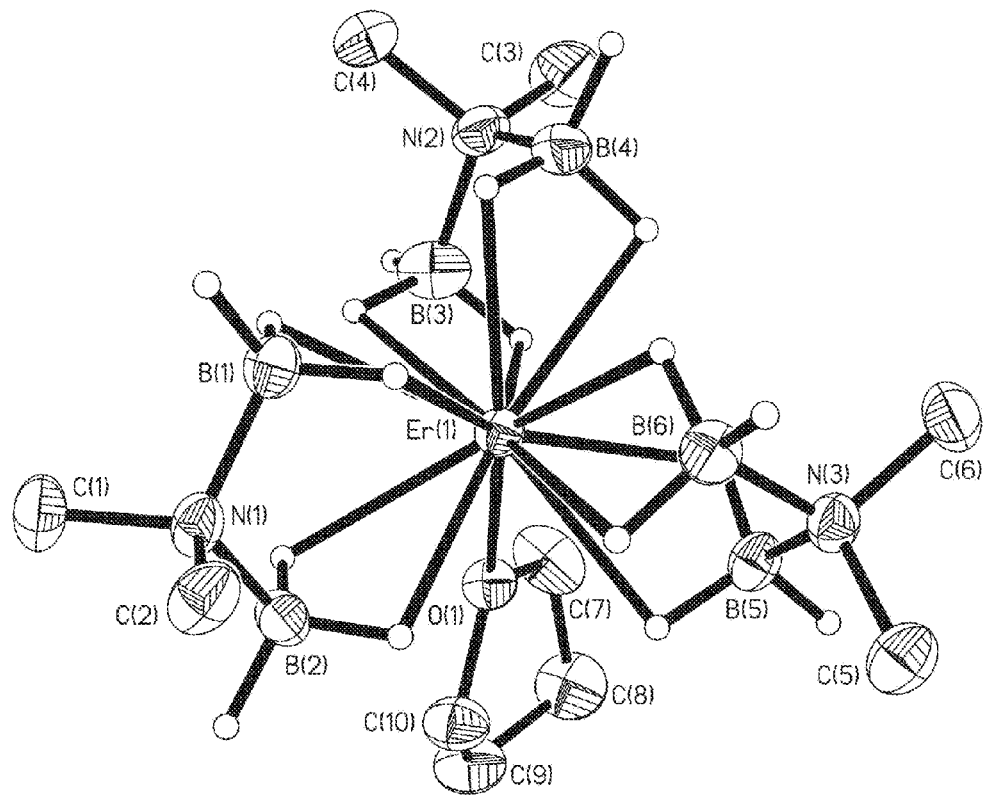
FIG. 47. Molecular structure of Er(H$_3$BNMe$_2$BH$_3$)$_3$(thf). Ellipsoids are drawn at the 35% probability level, except for the hydrogen atoms, which are represented as arbitrarily-sized spheres. Methyl and methylene hydrogen atoms have been deleted for clarity.
Figure 48:
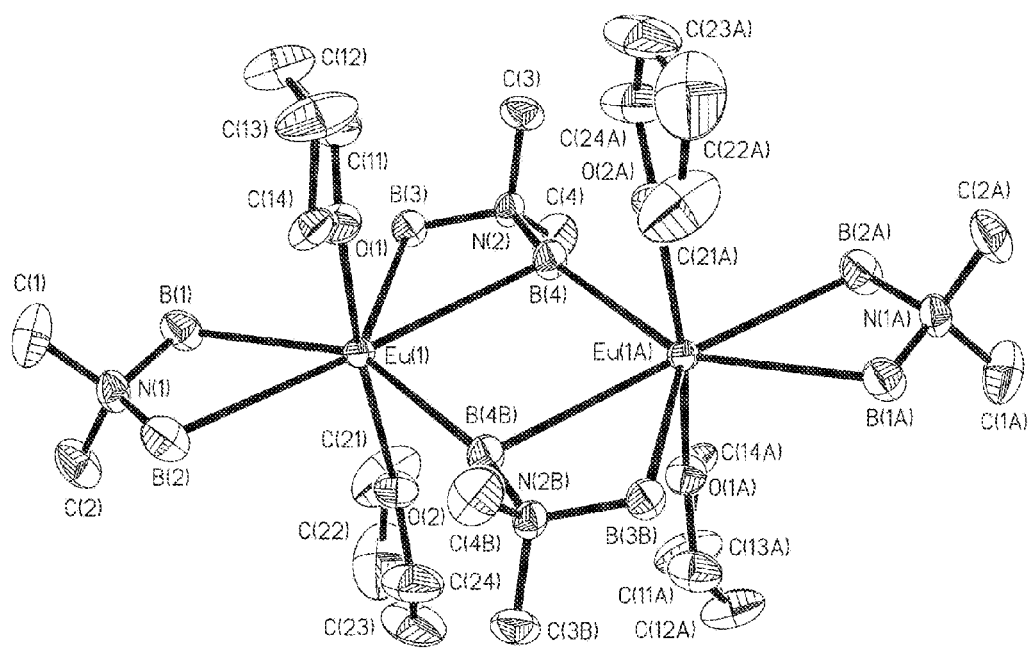
FIG. 48. Molecular structure of Eu$_2$(H$_3$BNMe$_2$BH$_3$)$_4$(thf)$_4$. Ellipsoids are drawn at the 35% probability level. Hydrogen atoms have been omitted for clarity.

Besides their vapor pressure, one other important difference between $Y(H_3BNMe_2BH_3)_3/Ti(H_3BNMe_2BH_3)_2$ and $Mg(H_3BNMe_2BH_3)_2$ is that the former generally decompose at T>300° C. as single source precursors. The thermal decomposition of $Ti(H_3BNMe_2BH_3)_2$ has been described herein, and $Y(H_3BNMe_2BH_3)_3$ has a similar behavior. The afforded films contain significant amount of metal, boron, carbon, and nitrogen. Therefore, in the oxide growth if the water supply is insufficient, it should be expected that the boron, carbon, and nitrogen level in the film will be elevated. However, as shown in FIG. 37, one growth of $Y_2O_3$ with lower water pressure only shows boron as the impurity. This result is interesting and actually provides us with some hint to the growth mechanism. There decomposition of the diboranamide ligand may involve two steps. The fraction containing dimethylamino group, which is likely to be converted to the stable molecule bis-μ-(dimethylamino)-diborane ($H_2B=NMe_2$) leaves the surface earlier than the other borohydride group.

SUMMARY

We demonstrate a simple CVD route toward high quality MgO, $TiO_2$ and $Y_2O_3$ films from the dimethyldiboranamide precursors and $H_2O$. Compared to the reported CVD of MgO, our methods has the merit of low deposition temperature (≧225° C.), excellent conformality (conformally coated a 35:1 trench), and high growth rate (>100 nm/min), which is mainly attributed to their remarkable volatility (Pv=0.82 mTorr at 30° C.) of $Mg(H_3BNMe_2BH_3)_2$ and its high reactivity with $H_2O$. The growth rate increases with temperature, while it saturates under high $Mg(H_3BNMe_2BH_3)_2$ pressure At low growth temperatures (<300° C.), indicating a Langmurian surface reaction mechanism. The film crystallizes at T>500° C. with a (002) texture on (100) oriented single crystal silicon and glass substrates. Films grown at T>400° C. are columnar, whereas the films grown a lower temperatures are dense and smooth. The refractive index of the film is 1.69-1.72 and the dielectric constant is 9.5, both of which are very close to bulk MgO. The combination of the high process capability and excellent film quality makes the CVD growth of MgO from $Mg(H_3BNMe_2BH_3)_2$ very attractive for a variety of technical applications.

REFERENCES

[1] G. Auday, P. Guillot, J. Galy, J. Appl. Phys. 88 (2000) 4871.

[2] J. P. Boeuf, J. of Phys. D-Applied Physics 36 (2003) R53.
[3] R. Ramesh, et al., Appl. Phys. Lett. 56 (1990) 2243.
[4] Y. Gao, G. Bai, K. L. Merkle, Y. Shi, H. L. M. Chang, Z. Shen, D. J. Lam, J. of Mater. Res. 8 (1993) 145.
[5] C. M. Foster, et al., J. Appl. Phys. 78 (1995) 2607.
[6] M. Yan, M. Lane, C. R. Kannewurf, R. P. H. Chang, Appl. Phys. Lett. 78 (2001) 2342.
[7] B. M. Lairson, M. R. Visokay, R. Sinclair, B. M. Clemens, Appl. Phys. Lett. 62 (1993) 639.
[8] J. W. He, P. J. Moller, Surf. Sci. 178 (1986) 934.
[9] B. M. Lairson, M. R. Visokay, R. Sinclair, S. Hagstrom, B. M. Clemens, Appl. Phys. Lett. 61 (1992) 1390.
[10] P. Sandstrom, E. B. Svedberg, J. Birch, J. E. Sundgren, J. Cryst. Growth 197 (1999) 849.
[11] K. Inumaru, T. Ohara, S. Yamanaka, Appl. Surf. Sci. 158 (2000) 375.
[12] C. S. Shin, S. Rudenja, D. Gall, N. Hellgren, T. Y. Lee, I. Petrov, J. E. Greene, J. Appl. Phys. 95 (2004) 356.
[13] H. S. Seo, T. Y. Lee, I. Petrov, J. E. Greene, D. Gall, J. Appl. Phys. 97 (2005).
[14] B. S. Kwak, E. P. Boyd, K. Zhang, A. Erbil, B. Wilkins, Appl. Phys. Lett. 54 (1989) 2542.
[15] B. H. Moeckly, S. E. Russek, D. K. Lathrop, R. A. Buhrman, J. Li, J. W. Mayer, Appl. Phys. Lett. 57 (1990) 1687.
[16] M. M. Sung, C. Kim, C. G. Kim, Y. Kim, J. Cryst. Growth 210 (2000) 651.
[17] F. Niu, B. H. Hoerman, B. W. Wessels, J. Vac. Sci. Technol. B 18 (2000) 2146.
[18] A. K. Sharma, A. Kvit, J. Narayan, J. Vac. Sci. Technol. A 17 (1999) 3393.
[19] L. S. Hung, L. R. Zheng, T. N. Blanton, Appl. Phys. Lett. 60 (1992) 3129.
[20] K. Nashimoto, D. K. Fork, T. H. Geballe, Appl. Phys. Lett. 60 (1992) 1199.
[21] J. Musolf, E. Boeke, E. Waffenschmidt, X. He, M. Heuken, K. Heime, J Alloy Compd 195 (1993) 295.
[22] W. I. Park, D. H. Kim, G. C. Yi, C. Kim, Jpn. J. Appl. Phys. 41 (2002) 6919.
[23] L. A. Wang, Y. Yang, S. Jin, T. J. Marks, Appl. Phys. Lett. 88 (2006).
[24] M. Bauer, R. Semerad, H. Kinder, Ieee Transactions on Applied Superconductivity 9 (1999) 1502.
[25] J. Mathon, A. Umerski, Phys. Rev. B 6322 (2001).
[26] S. Yuasa, A. Fukushima, T. Nagahama, K. Ando, Y. Suzuki, Japan. J. of Appl. Phys. Part 2-Letters & Express Letters 43 (2004) L588.
[27] D. Y. Kim, G. S. Girolami, see herein.
[28] T. Ohta, F. Cicoira, P. Doppelt, L. Beitone, P. Hofmann, Chem. Vapor Depos. 7 (2001) 33.
[29] S. Jayaraman, Y. Yang, D. Y. Kim, G. S. Girolami, J. R. Abelson, J. Vac. Sci. Technol. A 23 (2005) 1619.
[30] R. Matero, A. Rahtu, M. Ritala, M. Leskela, T. Sajavaara, Thin Solid Films 368 (2000) 1.
[31] Y. Yang, J. R. Abelson, See herein.
[32] P. de Rouffignac, J. S. Park, R. G. Gordon, Chem. Mater. 17 (2005) 4808.
[33] L. Wang, Y. Yang, J. Ni, C. L. Stern, T. J. Marks, Chem. Mater. 17 (2005) 5697.
[34] M. M. Sung, C. G. Kim, J. Kim, Y. Kim, Chem. Mater. 14 (2002) 826.
[35] S. C. Choi, M. H. Cho, S. W. Whangbo, C. N. Whang, S. B. Kang, S. I. Lee, M. Y. Lee, Appl. Phys. Lett. 71 (1997) 903.
[36] A. Mills, N. Elliott, I. P. Parkin, S. A. O'Neill, R. J. Clark, J. of Photochem. and Photobio. a 151 (2002) 171.
[37] J. Lettieri, J. H. Haeni, D. G. Schlom, J. Vac. Sci. Technol. A 20 (2002) 1332.
[38] Y. W. Zhao, H. Suhr, Appl. Phys. A-Materials Science & Processing 54 (1992) 451.
[39] Z. Lu, R. S. Feigelson, R. K. Route, S. A. Dicarolis, R. Hiskes, R. D. Jacowitz, J. Cryst. Growth 128 (1993) 788.
[40] E. Fujii, A. Tomozawa, S. Fujii, H. Torii, R. Takayama, T. Hirao, Jpn. J. Appl. Phys. 33 (1994) 6331.
[41] J. H. Boo, K. S. Yu, W. Koh, Y. Kim, Mater. Lett. 26 (1996) 233.
[42] J. M. Zeng, H. Wang, S. X. Shang, Z. Wang, M. Wang, J. Cryst. Growth 169 (1996) 474.
[43] J. H. Boo, S. B. Lee, K. S. Yu, W. Koh, Y. Kim, Thin Solid Films 341 (1999) 63.
[44] E. Fujii, A. Tomozawa, H. Torii, R. Takayama, M. Nagaki, T. Narusawa, Thin Solid Films 352 (1999) 85.
[45] T. Hatanpaa, J. Ihanus, J. Kansikas, I. Mutikainen, M. Ritala, M. Leskela, Chem. Mater. 11 (1999) 1846.
[46] J. S. Matthews, O. Just, B. Obi-Johnson, W. S. Rees, Chem. Vapor Depos. 6 (2000) 129.
[47] W. Fan, P. R. Markworth, T. J. Marks, R. P. H. Chang, Mater. Chem. Phys. 70 (2001) 191.
[48] J. R. Babcock, D. D. Benson, A. G. Wang, N. L. Edleman, J. A. Belot, M. V. Metz, T. J. Marks, Chem. Vapor Depos. 6 (2000) 180.
[49] R. Huang, A. H. Kitai, Appl. Phys. Lett. 61 (1992) 1450.
[50] R. Huang, A. H. Kitai, J. of Elec. Mater. 22 (1993) 215.
[51] M. Putkonen, T. Sajavaara, L. Niinisto, J. Mater. Chem. 10 (2000) 1857.
[52] M. Putkonen, M. Nieminen, L. Niinisto, Thin Solid Films 466 (2004) 103.

EXAMPLE 12 TABLE 1

|  | 2 | 3 |
|---|---|---|
| Formula | $MgB_6C_8H_{36}O_2$ | $MgB_6C_4H_{28}O_2$ |
| formula weight | 253.54 | 197.43 |
| T, °C. | −80 | −80 |
| space group | $P2_12_12$ | $Pca2_1$ |
| a, Å | 7.337(4) | 13.9644(19) |
| b, Å | 15.586(8) | 6.9088(10) |
| c, Å | 8.332(4) | 16.034(2) |
| V, Å$^3$ | 952.7(9) | 1546.9(4) |
| Z | 2 | 4 |
| $\rho_{calcd}$, g cm$^{-3}$ | 0.884 | 0.848 |
| λ, Å | 0.71073 | 0.71073 |
| $\mu_{calcd}$, cm$^{-1}$ | 0.81 | 0.86 |
| transmissn coeff | 0.956-0.966 | 0.954-0.991 |
| unique reflns | 1750 | 2837 |
| Parameters | 151 | 186 |
| $R_1{}^a$ | 0.0726 | 0.0347 |
| $wR_2{}^b$ | 0.1579 | 0.0796 |

$^a R_1 = \Sigma ||F_o| - |F_c||/\Sigma |F_o|$ for reflections with $F_o{}^2 > 2\sigma(F_o{}^2)$.
$^b wR_2 = [\Sigma w(F_o{}^2 - F_c{}^2)^2/\Sigma w(F_o{}^2)^2]^{1/2}$ for all reflections.

EXAMPLE 12 TABLE 2

| Bond Lengths (Å) | | | |
|---|---|---|---|
| Mg—O | 2.025(3) | B(1)—H(12) | 1.12(3) |
| Mg—B(1) | 2.575(5) | B(1)—H(13) | 1.02(4) |
| Mg—B(2) | 2.591(5) | B(2)—H(21) | 1.17(2) |
| Mg—H(11) | 1.99(3) | B(2)—H(22) | 1.11(3) |
| Mg—H(21) | 2.01(4) | B(2)—H(23) | 1.02(4) |
| B(1)—B(2) | 1.779(7) | B(3)—H(13) | 1.43(4) |
| B(1)—B(3) | 1.795(10) | B(3)—H(23) | 1.43(4) |
| B(2)—B(3) | 1.809(7) | B(3)—H(31) | 1.02(3) |
| B(1)—H(11) | 1.17(2) | B(3)—H(32) | 1.02(3) |

EXAMPLE 12 TABLE 2-continued

Bond Angles (deg)

| | | | |
|---|---|---|---|
| O'—Mg—O | 93.66(16) | Mg—B(2)—H(21) | 48(2) |
| O'—Mg—H(11) | 92.9(8) | B(1)—B(2)—H(22) | 112(2) |
| O—Mg—H(11) | 172.8(9) | B(3)—B(2)—H(22) | 126(2) |
| O'—Mg—H(21) | 100.8(10) | Mg—B(2)—H(22) | 123(2) |
| O—Mg—H(21) | 85.8(8) | H(21)—B(2)—H(22) | 109(3) |
| H(11)—Mg—H(21) | 90.0(15) | B(1)—B(2)—H(23) | 112(2) |
| B(2)—B(1)—B(3) | 60.8(3) | B(3)—B(2)—H(23) | 52(2) |
| B(2)—B(1)—Mg | 70.3(2) | Mg—B(2)—H(23) | 126(3) |
| B(3)—B(1)—Mg | 105.2(3) | H(21)—B(2)—H(23) | 99(3) |
| B(2)—B(1)—H(11) | 116.7(15) | H(22)—B(2)—H(23) | 107(4) |
| B(3)—B(1)—H(11) | 117.5(15) | B(1)—B(3)—B(2) | 59.2(3) |
| Mg—B(1)—H(11) | 48.1(15) | B(1)—B(3)—H(13) | 34.6(18) |
| B(2)—B(1)—H(12) | 114(2) | B(2)—B(3)—H(13) | 93.8(19) |
| B(3)—B(1)—H(12) | 133(2) | B(1)—B(3)—H(23) | 93.5(18) |
| Mg—B(1)—H(12) | 116(2) | B(2)—B(3)—H(23) | 34.3(17) |
| H(11)—B(1)—H(12) | 106(3) | H(13)—B(3)—H(23) | 128(4) |
| B(2)—B(1)—H(13) | 113(2) | B(1)—B(3)—H(31) | 107(3) |
| B(3)—B(1)—H(13) | 53(2) | B(2)—B(3)—H(31) | 113(3) |
| Mg—B(1)—H(13) | 127(4) | H(13)—B(3)—H(31) | 96(4) |
| H(11)—B(1)—H(13) | 96(4) | H(23)—B(3)—H(31) | 106(4) |
| H(12)—B(1)—H(13) | 109(4) | B(1)—B(3)—H(32) | 111(3) |
| B(1)—B(2)—B(3) | 60.0(3) | B(2)—B(3)—H(32) | 118(3) |
| B(1)—B(2)—Mg | 69.4(2) | H(13)—B(3)—H(32) | 96(4) |
| B(3)—B(2)—Mg | 104.2(3) | H(23)—B(3)—H(32) | 107(3) |
| B(1)—B(2)—H(21) | 117(2) | H(31)—B(3)—H(32) | 127(4) |
| B(3)—B(2)—H(21) | 121.7(18) | H(21)—B(2)—H(23) | 99(3) |

EXAMPLE 12 TABLE 3

Bond Lengths (Å)

| | | | |
|---|---|---|---|
| Mg(1)—O(2) | 2.0181(15) | B(1)—H(13) | 1.10(2) |
| Mg(1)—O(1) | 2.0279(14) | B(2)—H(21) | 1.167(19) |
| Mg(1)—B(2) | 2.557(3) | B(2)—H(22) | 1.144(19) |
| Mg(1)—B(4) | 2.559(3) | B(2)—H(23) | 1.11(2) |
| Mg(1)—B(1) | 2.570(3) | B(3)—H(13) | 1.38(2) |
| Mg(1)—B(5) | 2.572(3) | B(3)—H(23) | 1.45(2) |
| Mg(1)—H(11) | 1.967(19) | B(3)—H(31) | 1.06(2) |
| Mg(1)—H(21) | 1.973(16) | B(3)—H(32) | 1.06(2) |
| Mg(1)—H(41) | 1.91(2) | B(4)—H(41) | 1.19(2) |
| Mg(1)—H(51) | 1.98(2) | B(4)—H(42) | 1.08(2) |
| B(1)—B(2) | 1.795(4) | B(4)—H(43) | 1.17(3) |
| B(1)—B(3) | 1.802(4) | B(5)—H(51) | 1.14(2) |
| B(2)—B(3) | 1.803(5) | B(5)—H(52) | 1.10(2) |
| B(4)—B(5) | 1.777(4) | B(5)—H(53) | 1.15(2) |
| B(4)—B(6) | 1.804(5) | B(6)—H(43) | 1.45(2) |
| B(5)—B(6) | 1.780(4) | B(6)—H(53) | 1.39(2) |
| B(1)—H(11) | 1.140(19) | B(6)—H(61) | 1.11(2) |
| B(1)—H(12) | 1.13(2) | B(6)—H(62) | 1.17(2) |

Bond Angles (deg)

| | | | |
|---|---|---|---|
| O(2)—Mg(1)—O(1) | 91.80(6) | B(1)—B(3)—B(2) | 59.72(16) |
| O(2)—Mg(1)—H(11) | 172.8(6) | B(1)—B(3)—H(13) | 37.5(10) |
| O(1)—Mg(1)—H(11) | 90.3(6) | B(2)—B(3)—H(13) | 97.2(11) |
| B(2)—Mg(1)—H(11) | 65.3(6) | B(1)—B(3)—H(23) | 97.6(10) |
| B(4)—Mg(1)—H(11) | 90.2(6) | B(2)—B(3)—H(23) | 37.9(10) |
| B(1)—Mg(1)—H(11) | 24.8(6) | H(13)—B(3)—H(23) | 135.1(15) |
| B(5)—Mg(1)—H(11) | 94.8(6) | B(1)—B(3)—H(31) | 117.5(12) |
| O(2)—Mg(1)—H(21) | 83.2(6) | B(2)—B(3)—H(31) | 116.5(11) |
| O(1)—Mg(1)—H(21) | 91.9(5) | H(13)—B(3)—H(31) | 102.5(16) |
| B(2)—Mg(1)—H(21) | 26.0(6) | H(23)—B(3)—H(31) | 100.7(15) |
| B(4)—Mg(1)—H(21) | 158.2(5) | B(1)—B(3)—H(32) | 116.5(12) |
| B(1)—Mg(1)—H(21) | 66.4(6) | B(2)—B(3)—H(32) | 115.2(12) |
| B(5)—Mg(1)—H(21) | 117.8(5) | H(13)—B(3)—H(32) | 102.1(15) |
| H(11)—Mg(1)—H(21) | 89.9(8) | H(23)—B(3)—H(32) | 99.9(15) |
| O(2)—Mg(1)—H(41) | 106.2(6) | H(31)—B(3)—H(32) | 118.2(17) |
| O(1)—Mg(1)—H(41) | 85.8(7) | B(5)—B(4)—B(6) | 59.60(17) |
| B(2)—Mg(1)—H(41) | 145.6(6) | B(5)—B(4)—H(41) | 113.4(10) |
| B(4)—Mg(1)—H(41) | 25.9(7) | B(6)—B(4)—H(41) | 120.2(9) |
| B(1)—Mg(1)—H(41) | 104.7(6) | Mg(1)—B(4)—H(41) | 44.6(10) |
| B(5)—Mg(1)—H(41) | 65.8(7) | B(5)—B(4)—H(42) | 114.7(12) |
| H(11)—Mg(1)—H(41) | 80.8(8) | B(6)—B(4)—H(42) | 129.4(13) |
| H(21)—Mg(1)—H(41) | 170.3(8) | Mg(1)—B(4)—H(42) | 118.9(13) |
| O(2)—Mg(1)—H(51) | 89.1(5) | H(41)—B(4)—H(42) | 108.1(16) |
| O(1)—Mg(1)—H(51) | 174.6(6) | B(5)—B(4)—H(43) | 113.0(13) |
| B(2)—Mg(1)—H(51) | 85.0(6) | B(6)—B(4)—H(43) | 53.4(12) |
| B(4)—Mg(1)—H(51) | 64.6(6) | Mg(1)—B(4)—H(43) | 129.4(13) |
| B(1)—Mg(1)—H(51) | 83.4(6) | H(41)—B(4)—H(43) | 101.0(16) |
| B(5)—Mg(1)—H(51) | 24.9(6) | H(42)—B(4)—H(43) | 105.5(19) |
| H(11)—Mg(1)—H(51) | 89.4(8) | B(4)—B(5)—B(6) | 60.97(18) |
| H(21)—Mg(1)—H(51) | 93.6(8) | B(4)—B(5)—Mg(1) | 69.35(12) |
| H(41)—Mg(1)—H(51) | 88.8(9) | B(6)—B(5)—Mg(1) | 106.48(17) |
| B(2)—B(1)—B(3) | 60.15(18) | B(4)—B(5)—H(51) | 114.7(10) |
| B(2)—B(1)—H(11) | 114.4(9) | B(6)—B(5)—H(51) | 118.4(10) |
| B(3)—B(1)—H(11) | 120.9(10) | Mg(1)—B(5)—H(51) | 47.3(10) |
| Mg(1)—B(1)—H(11) | 46.5(9) | B(4)—B(5)—H(52) | 110.4(12) |
| B(2)—B(1)—H(12) | 110.3(10) | B(6)—B(5)—H(52) | 127.3(12) |
| B(3)—B(1)—H(12) | 125.7(11) | Mg(1)—B(5)—H(52) | 118.7(12) |
| Mg(1)—B(1)—H(12) | 120.8(12) | H(51)—B(5)—H(52) | 112.1(15) |

EXAMPLE 12 TABLE 3-continued

| | | | |
|---|---|---|---|
| H(11)—B(1)—H(12) | 111.5(14) | B(4)—B(5)—H(53) | 112.4(11) |
| B(2)—B(1)—H(13) | 110.2(12) | B(6)—B(5)—H(53) | 51.5(11) |
| B(3)—B(1)—H(13) | 50.0(12) | Mg(1)—B(5)—H(53) | 129.1(12) |
| Mg(1)—B(1)—H(13) | 127.5(12) | H(51)—B(5)—H(53) | 98.4(15) |
| H(11)—B(1)—H(13) | 101.1(15) | H(52)—B(5)—H(53) | 108.2(16) |
| H(12)—B(1)—H(13) | 108.8(17) | B(5)—B(6)—B(4) | 59.43(17) |
| B(1)—B(2)—B(3) | 60.14(17) | B(5)—B(6)—H(43) | 99.6(11) |
| B(1)—B(2)—Mg(1) | 69.90(13) | B(4)—B(6)—H(43) | 40.2(11) |
| B(3)—B(2)—Mg(1) | 106.10(17) | B(5)—B(6)—H(53) | 40.3(10) |
| B(1)—B(2)—H(21) | 116.3(8) | B(4)—B(6)—H(53) | 99.8(10) |
| B(3)—B(2)—H(21) | 120.5(9) | H(43)—B(6)—H(53) | 139.9(15) |
| Mg(1)—B(2)—H(21) | 47.8(8) | B(5)—B(6)—H(61) | 116.2(10) |
| B(1)—B(2)—H(22) | 110.4(9) | B(4)—B(6)—H(61) | 118.2(11) |
| B(3)—B(2)—H(22) | 123.1(10) | H(43)—B(6)—H(61) | 103.3(14) |
| Mg(1)—B(2)—H(22) | 123.4(10) | H(53)—B(6)—H(61) | 99.4(13) |
| H(21)—B(2)—H(22) | 113.4(12) | B(5)—B(6)—H(62) | 119.3(11) |
| B(1)—B(2)—H(23) | 113.7(12) | B(4)—B(6)—H(62) | 119.3(11) |
| B(3)—B(2)—H(23) | 53.6(12) | H(43)—B(6)—H(62) | 100.1(15) |
| Mg(1)—B(2)—H(23) | 127.7(12) | H(53)—B(6)—H(62) | 100.3(15) |
| H(21)—B(2)—H(23) | 97.1(15) | H(61)—B(6)—H(62) | 113.9(15) |
| H(22)—B(2)—H(23) | 104.7(15) | | |

EXAMPLE 13 TABLE 1

| | 1 | 2 | 3 | 4 |
|---|---|---|---|---|
| formula | $C_4H_{24}B_4N_2Mg$ | $C_8H_{32}B_4N_2OMg$ | $C_8H_{34}B_4N_2O_2Mg$ | $C_{16}H_{35}B_2NOMg$ |
| formula weight | 167.80 | 239.91 | 257.92 | 303.38 |
| T, °C. | −80 | −80 | −80 | −80 |
| space group | $I\bar{4}2d$ | Cc | C2/c | $P2_1/n$ |
| a, Å | 11.3649(19) | 10.0103(8) | 22.5822(17) | 11.309(3) |
| b, Å | 11.3649(19) | 17.5686(15) | 13.6560(10) | 14.569(3) |
| c, Å | 19.183(7) | 10.5611(8) | 14.700(2) | 12.255(3) |
| β, deg | 90 | 111.412(5) | 125.324(3) | 90.397(X) |
| V, Å$^3$ | 2477.6(10) | 1729.2(2) | 3698.6(7) | 2019.1(8) |
| Z | 8 | 4 | 8 | 4 |
| $\rho_{calcd}$, g cm$^{-3}$ | 0.900 | 0.922 | 0.926 | 0.998 |
| λ, Å | 0.71073 | 0.71073 | 0.71073 | 0.71073 |
| $\mu_{calcd}$, cm$^{-1}$ | 0.94 | 0.87 | 0.88 | 0.86 |
| transmissn coeff | 0.963-0.979 | 0.982-0.994 | 0.970-0.989 | 0.985-0.997 |
| unique reflns | 1542 | 2576 | 3840 | 3827 |
| parameters | 161 | 197 | 268 | 222 |
| $R_1{}^a$ | 0.0297 | 0.0455 | 0.0349 | 0.0679 |
| $wR_2{}^b$ | 0.0688 | 0.1196 | 0.0883 | 0.1393 |

$^a$R1 = Σ||F$_o$| − |F$_c$||/Σ|F$_o$| for reflections with F$_o{}^2$ > 2 σ(F$_o{}^2$).
$^b$wR$_2$ = [Σw(F$_o{}^2$ − F$_c{}^2$)$^2$/Σ w(F$_o{}^2$)$^2$]$^{1/2}$ for all reflections.

EXAMPLE 13 TABLE 2

| Bond Lengths (Å) | | | |
|---|---|---|---|
| Mg(1)—H(11) | 1.990(15) | B(1)—H(13) | 1.033(16) |
| Mg(1)—H(12) | 2.021(11) | B(2)—H(21) | 1.110(16) |
| Mg(1)—H(21) | 2.058(16) | B(2)—H(22) | 1.166(18) |
| Mg(1)—H(22) | 1.998(15) | B(2)—H(23) | 1.072(12) |
| Mg(1)—B(1) | 2.3690(14) | B(1)—N(1) | 1.5847(13) |
| Mg(1)—B(2) | 2.3859(13) | B(2)—N(2) | 1.5810(13) |
| B(1)—H(11) | 1.126(15) | N(1)—C(1) | 1.4884(15) |
| B(1)—H(12) | 1.151(13) | N(2)—C(2) | 1.4869(14) |
| Bond Angles (deg) | | | |
| H(11)—Mg(1)—H(12) | 54.1(6) | N(1)—B(1)—Mg(1) | 91.63(7) |
| H(11)—Mg(1)—H(21) | 86.2(6) | N(2)—B(2)—Mg(1) | 92.48(6) |
| H(11)—Mg(1)—H(22) | 91.8(7) | B(1)—N(1)—B(1)' | 110.20(11) |
| H(12)—Mg(1)—H(21) | 92.6(5) | B(2)—N(2)—B(2)' | 109.52(11) |
| H(12)—Mg(1)—H(22) | 135.6(6) | C(1)—N(1)—B(1) | 109.52(9) |
| H(21)—Mg(1)—H(22) | 53.6(6) | C(1)—N(1)—B(1)' | 109.36(9) |
| B(1)—Mg(1)—B(1)' | 66.55(6) | C(2)—N(2)—B(2) | 109.80(9) |
| B(1)—Mg(1)—B(2) | 119.96(5) | C(2)—N(2)—B(2)' | 109.62(10) |
| B(1)—Mg(1)—B(2)' | 155.05(6) | C(1)'—N(1)—C(1) | 108.85(16) |
| B(2)—Mg(1)—B(2)' | 65.53(6) | C(2)—N(2)—C(2)' | 108.47(13) |
| H(11)—B(1)—H(12) | 106.5(10) | N(1)—B(1)—H(11) | 106.1(8) |
| H(11)—B(1)—H(13) | 113.5(13) | N(1)—B(1)—H(12) | 106.7(7) |
| H(12)—B(1)—H(13) | 110.3(12) | N(1)—B(1)—H(13) | 113.3(8) |
| H(21)—B(2)—H(22) | 107.0(10) | N(2)—B(2)—H(21) | 106.6(8) |
| H(21)—B(2)—H(23) | 111.0(13) | N(2)—B(2)—H(22) | 107.6(7) |
| H(22)—B(2)—H(23) | 111.1(11) | N(2)—B(2)—H(23) | 113.2(6) |

$^a$Symmetry transformations used to generate equivalent atoms: ' = x, −y + 1/2, −z + 1/4

EXAMPLE 13 TABLE 3

| Bond Lengths (Å) | | | |
|---|---|---|---|
| Mg(1)—H(11) | 2.14(3) | B(2)—H(22) | 1.08(3) |
| Mg(1)—H(12) | 2.10(3) | B(2)—H(23) | 1.15(3) |
| Mg(1)—H(21) | 2.29(6) | B(3)—H(31) | 1.12(2) |
| Mg(1)—H(22) | 1.98(4) | B(3)—H(32) | 1.06(3) |

EXAMPLE 13 TABLE 3-continued

| | | | |
|---|---|---|---|
| Mg(1)—H(31) | 2.20(3) | B(3)—H(33) | 1.06(3) |
| Mg(1)—H(32) | 2.11(3) | B(4)—H(41) | 1.13(2) |
| Mg(1)—H(41) | 2.28(3) | B(4)—H(42) | 1.16(3) |
| Mg(1)—H(42) | 1.94(3) | B(4)—H(43) | 1.07(3) |
| Mg(1)—B(1) | 2.487(4) | B(1)—N(1) | 1.565(5) |
| Mg(1)—B(2) | 2.553(5) | B(2)—N(1) | 1.532(6) |
| Mg(1)—B(3) | 2.484(4) | B(3)—N(2) | 1.576(5) |
| Mg(1)—B(4) | 2.503(4) | B(4)—N(2) | 1.562(4) |
| Mg(1)—O(1) | 2.063(2) | N(1)—C(1) | 1.460(4) |
| B(1)—H(11) | 1.09(3) | N(1)—C(2) | 1.479(4) |
| B(1)—H(12) | 1.11(3) | N(2)—C(3) | 1.477(4) |
| B(1)—H(13) | 1.12(3) | N(2)—C(4) | 1.483(4) |
| B(2)—H(21) | 1.14(3) | | |
| Bond Angles (deg) | | | |
| H(11)—Mg(1)—H(12) | 49.7(11) | H(11)—B(1)—H(13) | 114(3) |
| H(11)—Mg(1)—H(21) | 58.5(16) | H(12)—B(1)—H(13) | 104(3) |
| H(11)—Mg(1)—H(22) | 89.6(12) | H(21)—B(2)—H(22) | 99(3) |
| H(11)—Mg(1)—H(31) | 92.3(11) | H(21)—B(2)—H(23) | 118(4) |
| H(11)—Mg(1)—H(32) | 140.4(10) | H(22)—B(2)—H(23) | 107(3) |
| H(11)—Mg(1)—H(41) | 65.3(11) | H(31)—B(3)—H(32) | 107(2) |
| H(11)—Mg(1)—H(42) | 103.8(12) | H(31)—B(3)—H(33) | 109(2) |
| H(12)—Mg(1)—H(21) | 86.0(15) | H(32)—B(3)—H(33) | 102(2) |
| H(12)—Mg(1)—H(22) | 81.0(14) | H(41)—B(4)—H(42) | 105(2) |
| H(12)—Mg(1)—H(31) | 141.9(10) | H(41)—B(4)—H(43) | 112(2) |
| H(12)—Mg(1)—H(32) | 169.9(11) | H(42)—B(4)—H(43) | 114(2) |
| H(12)—Mg(1)—H(41) | 96.1(11) | N(2)—B(4)—Mg(1) | 94.25(19) |
| H(12)—Mg(1)—H(42) | 98.6(13) | N(1)—B(1)—Mg(1) | 96.0(2) |
| H(21)—Mg(1)—H(22) | 46.0(13) | N(1)—B(2)—Mg(1) | 94.3(3) |
| H(21)—Mg(1)—H(31) | 68.2(13) | N(2)—B(3)—Mg(1) | 94.6(2) |
| H(21)—Mg(1)—H(32) | 99.8(16) | B(2)—N(1)—B(1) | 108.8(3) |
| H(21)—Mg(1)—H(41) | 101.6(13) | B(4)—N(2)—B(3) | 109.0(2) |
| H(21)—Mg(1)—H(42) | 151.7(13) | C(1)—N(1)—B(1) | 110.0(3) |
| H(22)—Mg(1)—H(31) | 98.4(13) | C(1)—N(1)—B(2) | 114.4(5) |
| H(22)—Mg(1)—H(32) | 97.0(13) | C(2)—N(1)—B(1) | 110.1(3) |
| H(22)—Mg(1)—H(41) | 147.5(10) | C(2)—N(1)—B(2) | 107.5(4) |
| H(22)—Mg(1)—H(42) | 162.2(12) | C(3)—N(2)—B(3) | 110.1(3) |
| H(31)—Mg(1)—H(32) | 48.1(10) | C(3)—N(2)—B(4) | 109.7(3) |
| H(31)—Mg(1)—H(41) | 64.3(11) | C(4)—N(2)—B(3) | 109.5(2) |
| H(31)—Mg(1)—H(42) | 92.7(12) | C(1)—N(1)—C(2) | 106.0(3) |
| H(32)—Mg(1)—H(41) | 90.9(11) | C(3)—N(2)—C(4) | 108.3(3) |
| H(32)—Mg(1)—H(42) | 80.2(13) | C(4)—N(2)—B(4) | 110.3(3) |
| H(41)—Mg(1)—H(42) | 50.3(11) | N(1)—B(1)—H(11) | 106.9(17) |
| B(1)—Mg(1)—B(2) | 59.91(16) | N(1)—B(1)—H(12) | 107.6(17) |
| B(1)—Mg(1)—B(4) | 106.80(13) | N(1)—B(1)—H(13) | 116(2) |
| B(3)—Mg(1)—B(1) | 141.87(15) | N(1)—B(2)—H(21) | 100(3) |
| B(3)—Mg(1)—B(2) | 111.21(19) | N(1)—B(2)—H(22) | 119(2) |
| B(3)—Mg(1)—B(4) | 61.62(12) | N(1)—B(2)—H(23) | 113(2) |
| B(4)—Mg(1)—B(2) | 151.0(2) | N(2)—B(3)—H(31) | 107.4(15) |
| O(1)—Mg(1)—B(1) | 110.65(12) | N(2)—B(3)—H(32) | 114.7(18) |
| O(1)—Mg(1)—B(2) | 103.2(2) | N(2)—B(3)—H(33) | 116.4(16) |
| O(1)—Mg(1)—B(3) | 107.48(13) | N(2)—B(4)—H(41) | 104.5(16) |
| O(1)—Mg(1)—B(4) | 105.79(12) | N(2)—B(4)—H(42) | 110.0(17) |
| H(11)—B(1)—H(12) | 109(2) | N(2)—B(4)—H(43) | 110.5(16) |

EXAMPLE 13 TABLE 4

| Bond Lengths (Å) | | | |
|---|---|---|---|
| Mg(1)—H(11) | 1.984(13) | B(2)—H(22) | 1.137(13) |
| Mg(1)—H(21) | 2.010(13) | B(2)—H(23) | 1.147(14) |
| Mg(1)—H(31) | 2.119(13) | B(3)—H(31) | 1.162(14) |
| Mg(1)—H(32) | 2.395(13) | B(3)—H(32) | 1.127(13) |
| Mg(1)—H(41) | 2.157(14) | B(3)—H(33) | 1.112(14) |
| Mg(1)—H(42) | 2.199(13) | B(4)—H(41) | 1.154(12) |
| Mg(1)—B(1) | 2.6077(18) | B(4)—H(42) | 1.177(14) |
| Mg(1)—B(2) | 2.8680(19) | B(4)—H(43) | 1.114(14) |
| Mg(1)—B(3) | 2.6333(18) | B(1)—N(1) | 1.576(2) |
| Mg(1)—B(4) | 2.5621(18) | B(2)—N(1) | 1.588(2) |
| Mg(1)—O(1) | 2.1118(10) | B(3)—N(2) | 1.581(2) |
| Mg(1)—O(2) | 2.0865(9) | B(4)—N(2) | 1.5776(19) |
| B(1)—H(11) | 1.164(13) | N(1)—C(1) | 1.484(2) |
| B(1)—H(12) | 1.130(13) | N(1)—C(2) | 1.4807(19) |
| B(1)—H(13) | 1.091(15) | N(2)—C(3) | 1.4847(19) |
| B(2)—H(21) | 1.187(13) | N(2)—C(4) | 1.483(2) |

EXAMPLE 13 TABLE 4-continued

| Bond Angles (deg) | | | |
|---|---|---|---|
| H(11)—Mg(1)—H(21) | 78.0(5) | H(21)—B(2)—H(22) | 109.0(9) |
| H(11)—Mg(1)—H(31) | 77.7(5) | H(21)—B(2)—H(23) | 108.9(9) |
| H(11)—Mg(1)—H(32) | 75.0(5) | H(22)—B(2)—H(23) | 111.8(9) |
| H(11)—Mg(1)—H(41) | 148.9(5) | H(31)—B(3)—H(32) | 108.8(9) |
| H(11)—Mg(1)—H(42) | 134.2(5) | H(31)—B(3)—H(33) | 107.9(9) |
| H(21)—Mg(1)—H(31) | 117.6(5) | H(32)—B(3)—H(33) | 113.5(9) |
| H(21)—Mg(1)—H(32) | 70.2(5) | H(41)—B(4)—H(42) | 108.3(9) |
| H(21)—Mg(1)—H(41) | 120.9(5) | H(41)—B(4)—H(43) | 108.7(10) |
| H(21)—Mg(1)—H(42) | 69.9(6) | H(42)—B(4)—H(43) | 110.0(10) |
| H(31)—Mg(1)—H(32) | 48.2(5) | B(1)—N(1)—B(2) | 109.61(11) |
| H(31)—Mg(1)—H(41) | 71.6(5) | B(4)—N(2)—B(3) | 109.11(11) |
| H(31)—Mg(1)—H(42) | 89.1(5) | N(1)—B(1)—Mg(1) | 100.28(9) |
| H(32)—Mg(1)—H(41) | 88.0(5) | N(1)—B(2)—Mg(1) | 90.02(8) |
| H(32)—Mg(1)—H(42) | 64.1(5) | N(2)—B(3)—Mg(1) | 94.10(8) |
| H(41)—Mg(1)—H(42) | 51.4(5) | N(2)—B(4)—Mg(1) | 96.93(9) |
| B(1)—Mg(1)—B(2) | 56.11(5) | C(1)—N(1)—B(1) | 110.46(13) |
| B(1)—Mg(1)—B(3) | 107.59(6) | C(1)—N(1)—B(2) | 108.26(12) |
| B(3)—Mg(1)—B(2) | 111.14(6) | C(2)—N(1)—B(1) | 109.50(12) |
| B(4)—Mg(1)—B(1) | 161.98(6) | C(2)—N(1)—B(2) | 110.71(13) |
| B(4)—Mg(1)—B(2) | 114.43(6) | C(3)—N(2)—B(3) | 109.85(12) |
| B(4)—Mg(1)—B(3) | 59.36(5) | C(3)—N(2)—B(4) | 109.90(12) |
| O(1)—Mg(1)—B(1) | 88.65(5) | C(4)—N(2)—B(3) | 110.11(12) |
| O(1)—Mg(1)—B(2) | 136.33(5) | C(4)—N(2)—B(4) | 109.40(12) |
| O(1)—Mg(1)—B(3) | 103.16(5) | C(2)—N(1)—C(1) | 108.29(13) |
| O(1)—Mg(1)—B(4) | 105.91(5) | C(4)—N(2)—C(3) | 108.46(13) |
| O(2)—Mg(1)—B(1) | 103.57(5) | N(1)—B(2)—H(21) | 108.4(6) |
| O(2)—Mg(1)—B(2) | 86.22(5) | N(1)—B(2)—H(22) | 108.7(7) |
| O(2)—Mg(1)—B(3) | 148.83(5) | N(1)—B(2)—H(23) | 109.8(7) |
| O(2)—Mg(1)—B(4) | 90.19(5) | N(2)—B(3)—H(31) | 107.0(7) |
| O(2)—Mg(1)—O(1) | 77.38(4) | N(2)—B(3)—H(32) | 107.3(7) |
| H(11)—B(1)—H(12) | 108.7(9) | N(2)—B(3)—H(33) | 112.1(7) |
| H(11)—B(1)—H(13) | 108.4(10) | N(2)—B(4)—H(41) | 107.1(7) |
| H(12)—B(1)—H(13) | 111.8(10) | N(2)—B(4)—H(42) | 108.5(7) |

EXAMPLE 13 TABLE 5

| Bond Lengths (Å) | | | |
|---|---|---|---|
| Mg(1)—H(11) | 2.30(4) | Mg(1)—O(1) | 2.055(3) |
| Mg(1)—H(12) | 2.18(4) | B(1)—H(11) | 1.22(4) |
| Mg(1)—H(21) | 2.17(4) | B(1)—H(12) | 1.05(3) |
| Mg(1)—H(22) | 2.21(4) | B(1)—H(13) | 1.15(3) |
| Mg(1)—B(1) | 2.534(7) | B(2)—H(21) | 1.18(4) |
| Mg(1)—B(2) | 2.554(8) | B(2)—H(22) | 1.05(4) |
| Mg(1)—C(1) | 2.374(5) | B(2)—H(23) | 1.07(4) |
| Mg(1)—C(2) | 2.386(5) | N(1)—B(1) | 1.570(7) |
| Mg(1)—C(3) | 2.414(6) | N(1)—B(2) | 1.564(7) |
| Mg(1)—C(4) | 2.393(5) | N(1)—C(11) | 1.476(5) |
| Mg(1)—C(5) | 2.360(5) | N(1)—C(12) | 1.484(5) |
| Bond Angles (deg) | | | |
| H(11)—Mg(1)—H(12) | 49.8(13) | B(2)—N(1)—B(1) | 110.1(4) |
| H(11)—Mg(1)—H(21) | 69.6(14) | N(1)—B(1)—Mg(1) | 94.9(4) |
| H(11)—Mg(1)—H(22) | 91.8(14) | N(1)—B(2)—Mg(1) | 94.3(4) |
| H(12)—Mg(1)—H(21) | 90.1(15) | C(11)—N(1)—B(1) | 110.8(5) |
| H(12)—Mg(1)—H(22) | 72.4(13) | C(11)—N(1)—B(2) | 110.0(5) |
| H(21)—Mg(1)—H(22) | 48.1(14) | C(12)—N(1)—B(1) | 109.0(4) |
| B(1)—Mg(1)—B(2) | 60.6(2) | C(12)—N(1)—B(2) | 108.2(5) |
| O(1)—Mg(1)—B(1) | 103.9(2) | C(11)—N(1)—C(12) | 108.7(4) |
| O(1)—Mg(1)—B(2) | 101.0(2) | N(1)—B(1)—H(11) | 109.8(19) |
| H(11)—B(1)—H(12) | 113(3) | N(1)—B(1)—H(12) | 109(2) |
| H(11)—B(1)—H(13) | 109(3) | N(1)—B(1)—H(13) | 110.8(18) |
| H(12)—B(1)—H(13) | 106(3) | N(1)—B(2)—H(21) | 108(2) |
| H(21)—B(2)—H(22) | 106(3) | N(1)—B(2)—H(22) | 111(2) |
| H(21)—B(2)—H(23) | 107(3) | N(1)—B(2)—H(23) | 114(2) |
| H(22)—B(2)—H(23) | 110(3) | | |

EXAMPLE 14 TABLE 1

| | 1 | 2 | 3 | 4 |
|---|---|---|---|---|
| formula | $C_{12}H_{72}B_{12}N_6Y_2$ | $C_{12}H_{72}B_{12}N_6Dy_2$ | $C_{10}H_{44}B_6N_3OY$ | $C_{10}H_{44}B_6N_3ODy$ |
| formula weight | 608.30 | 755.48 | 376.25 | 449.84 |
| T, °C. | −80 | −80 | −80 | −80 |
| space group | $Pna2_1$ | $Pna2_1$ | $Pca2_1$ | $Pca2_1$ |
| a, Å | 28.546(3) | 28.4566(15) | 21.868(7) | 21.8439(11) |
| b, Å | 14.0655(14) | 14.0202(7) | 10.395(4) | 10.4025(5) |
| c, Å | 9.4086(7) | 9.3884(5) | 20.630(7) | 20.6450(11) |
| V, Å³ | 3777.6(6) | 3745.5(3) | 4689(3) | 4691.2(4) |
| Z | 4 | 4 | 8 | 8 |
| $\rho_{calcd}$, g cm$^{-3}$ | 1.070 | 1.340 | 1.066 | 1.274 |
| λ, Å | 0.71073 | 0.71073 | 0.71073 | 0.71073 |
| $\mu_{calcd}$, cm$^{-1}$ | 30.69 | 39.71 | 24.86 | 31.84 |
| transmissn coeff | 0.685-0.838 | N/A | 0.400-0.512 | 0.503-0.798 |
| unique reflns | 9025 | 9596 | 8605 | 10934 |
| parameters | 314 | 322 | 536 | 500 |
| $R_1{}^a$ | 0.0462 | 0.0436 | 0.0539 | 0.0364 |
| $wR_2{}^b$ | 0.0852 | 0.1022 | 0.0877 | 0.0724 |

$^aR_1 = \Sigma||F_o| - |F_c||/\Sigma|F_o|$ for reflections with $F_o{}^2 > 2\sigma(F_o{}^2)$.
$^bwR_2 = [\Sigma w(F_o{}^2 - F_c{}^2)^2/\Sigma w(F_o{}^2)^2]^{1/2}$ for all reflections.

EXAMPLE 14 TABLE 2

Bond Lengths (Å)

| | | | |
|---|---|---|---|
| Y(1)—B(1) | 2.701(7) | B(7)—N(4) | 1.578(9) |
| Y(1)—B(2) | 2.739(7) | B(8)—N(4) | 1.563(8) |
| Y(1)—B(3) | 2.718(7) | B(11)—N(11) | 1.545(8) |
| Y(1)—B(4) | 2.756(7) | B(12)—N(11) | 1.609(7) |
| Y(2)—B(5) | 2.719(8) | B(21)—N(21) | 1.576(7) |
| Y(2)—B(6) | 2.763(7) | B(22)—N(21) | 1.551(8) |
| Y(2)—B(7) | 2.732(7) | N(1)—C(1) | 1.492(7) |
| Y(2)—B(8) | 2.717(7) | N(1)—C(2) | 1.481(8) |
| Y(1)—B(11) | 2.837(7) | N(2)—C(3) | 1.490(7) |
| Y(1)—B(12) | 2.672(7) | N(2)—C(4) | 1.458(7) |
| Y(1)—B(21) | 2.734(7) | N(3)—C(5) | 1.477(7) |
| Y(2)—B(22) | 2.853(7) | N(3)—C(6) | 1.476(8) |
| B(1)—N(1) | 1.562(8) | N(4)—C(7) | 1.469(7) |
| B(2)—N(1) | 1.565(9) | N(4)—C(8) | 1.508(7) |
| B(3)—N(2) | 1.554(8) | N(11)—C(11) | 1.478(7) |
| B(4)—N(2) | 1.558(8) | N(11)—C(12) | 1.515(7) |
| B(5)—N(3) | 1.561(8) | N(21)—C(21) | 1.496(7) |
| B(6)—N(3) | 1.580(8) | N(21)—C(22) | 1.463(7) |

Bond Angles (deg)

| | | | |
|---|---|---|---|
| B(1)—Y(1)—B(2) | 56.1(2) | C(4)—N(2)—C(3) | 108.2(5) |
| B(3)—Y(1)—B(4) | 55.2(2) | C(5)—N(3)—B(5) | 109.9(5) |
| B(11)—Y(1)—B(21) | 90.7(2) | C(5)—N(3)—B(6) | 109.0(5) |
| B(5)—Y(2)—B(6) | 55.7(2) | C(6)—N(3)—B(5) | 110.9(5) |
| B(7)—Y(2)—B(8) | 55.6(2) | C(6)—N(3)—B(6) | 107.8(5) |
| B(12)—Y(1)—B(22) | 91.1(2) | C(6)—N(3)—C(5) | 110.0(5) |
| B(1)—N(1)—B(2) | 109.7(5) | C(7)—N(4)—B(7) | 111.9(5) |
| B(3)—N(2)—B(4) | 109.2(5) | C(7)—N(4)—B(8) | 109.7(5) |
| B(5)—N(3)—B(6) | 109.3(5) | C(7)—N(4)—C(8) | 108.8(5) |
| B(7)—N(4)—B(8) | 107.9(5) | C(8)—N(4)—B(7) | 109.2(5) |
| B(11)—N(11)—B(12) | 113.7(5) | C(8)—N(4)—B(8) | 109.3(5) |
| B(22)—N(21)—B(21) | 112.1(5) | C(11)—N(11)—B(11) | 108.3(5) |
| C(1)—N(1)—B(1) | 109.1(5) | C(11)—N(11)—B(12) | 109.3(4) |
| C(1)—N(1)—B(2) | 110.6(5) | C(11)—N(11)—C(12) | 107.2(5) |
| C(2)—N(1)—B(1) | 110.5(5) | C(12)—N(11)—B(11) | 108.6(5) |
| C(2)—N(1)—B(2) | 107.4(5) | C(12)—N(11)—B(12) | 109.5(4) |
| C(2)—N(1)—C(1) | 109.5(6) | C(21)—N(21)—B(21) | 108.5(5) |
| C(3)—N(2)—B(3) | 110.1(5) | C(21)—N(21)—B(22) | 108.8(5) |
| C(3)—N(2)—B(4) | 109.3(5) | C(22)—N(21)—B(21) | 109.7(5) |
| C(4)—N(2)—B(3) | 111.0(5) | C(22)—N(21)—B(22) | 109.2(5) |
| C(4)—N(2)—B(4) | 109.0(5) | C(22)—N(21)—C(21) | 108.5(5) |

EXAMPLE 14 TABLE 3

Bond Lengths (Å)

| | | | |
|---|---|---|---|
| Dy(1)—B(1) | 2.73 | B(7)—N(4) | 1.568(14) |
| Dy(1)—B(2) | 2.73 | B(8)—N(4) | 1.542(16) |
| Dy(1)—B(3) | 2.76 | B(11)—N(11) | 1.588(16) |
| Dy(1)—B(4) | 2.70 | B(12)—N(11) | 1.532(14) |
| Dy(2)—B(5) | 2.72 | B(21)—N(21) | 1.573(13) |
| Dy(2)—B(6) | 2.75 | B(22)—N(21) | 1.584(13) |
| Dy(2)—B(7) | 2.74 | N(1)—C(1) | 1.493(18) |
| Dy(2)—B(8) | 2.72 | N(1)—C(2) | 1.481(15) |
| Dy(1)—B(11) | 2.68 | N(2)—C(3) | 1.485(16) |
| Dy(2)—B(12) | 2.84 | N(2)—C(4) | 1.518(14) |
| Dy(1)—B(21) | 2.84 | N(3)—C(5) | 1.503(16) |
| Dy(2)—B(22) | 2.73 | N(3)—C(6) | 1.44(2) |
| B(1)—N(1) | 1.547(19) | N(4)—C(7) | 1.485(13) |
| B(2)—N(1) | 1.587(17) | N(4)—C(8) | 1.452(14) |
| B(3)—N(2) | 1.580(14) | N(11)—C(11) | 1.461(17) |
| B(4)—N(2) | 1.511(15) | N(11)—C(12) | 1.520(15) |
| B(5)—N(3) | 1.579(17) | N(21)—C(21) | 1.471(11) |
| B(6)—N(3) | 1.577(18) | N(21)—C(22) | 1.446(13) |

Bond Angles (deg)

| | | | |
|---|---|---|---|
| B(1)—Dy(1)—B(2) | 55.3 | C(4)—N(2)—B(3) | 107.7(10) |
| B(3)—Dy(1)—B(4) | 55.6 | C(4)—N(2)—B(4) | 110.5(10) |
| B(11)—Dy(1)—B(21) | 91.8 | C(5)—N(3)—B(5) | 106.8(12) |
| B(5)—Dy(2)—B(6) | 55.8 | C(5)—N(3)—B(6) | 108.3(11) |
| B(7)—Dy(2)—B(8) | 55.7 | C(6)—N(3)—B(5) | 110.5(12) |
| B(12)—Dy(2)—B(22) | 90.2 | C(6)—N(3)—B(6) | 111.9(13) |
| B(1)—N(1)—B(2) | 107.9(11) | C(6)—N(3)—C(5) | 110.9(11) |
| B(3)—N(2)—B(4) | 110.8(9) | C(7)—N(4)—B(7) | 110.8(9) |
| B(5)—N(3)—B(6) | 108.4(9) | C(7)—N(4)—B(8) | 107.9(10) |
| B(7)—N(4)—B(8) | 110.2(9) | C(7)—N(4)—C(8) | 111.3(10) |
| B(11)—N(11)—B(12) | 113.2(10) | C(8)—N(4)—B(8) | 111.2(9) |
| B(21)—N(21)—B(22) | 109.4(8) | C(8)—N(4)—C(7) | 105.4(9) |
| B(1)—N(1)—B(2) | 107.9(11) | C(11)—N(11)—B(11) | 110.8(8) |
| C(1)—N(1)—B(1) | 111.1(9) | C(11)—N(11)—B(12) | 108.9(11) |
| C(1)—N(1)—B(2) | 108.7(12) | C(11)—N(11)—C(12) | 108.5(11) |
| C(2)—N(1)—B(1) | 110.4(12) | C(12)—N(11)—B(11) | 107.7(10) |
| C(2)—N(1)—B(2) | 107.3(10) | C(12)—N(11)—B(12) | 107.6(8) |
| C(2)—N(1)—C(1) | 111.3(12) | C(21)—N(21)—B(21) | 107.8(8) |
| C(3)—N(2)—B(3) | 109.3(10) | C(21)—N(21)—B(22) | 110.6(7) |
| C(3)—N(2)—B(4) | 112.1(10) | C(22)—N(21)—B(21) | 108.6(9) |
| C(3)—N(2)—C(4) | 106.3(10) | C(22)—N(21)—B(22) | 112.9(8) |

EXAMPLE 14 TABLE 4

Bond Lengths (Å)

| | | | |
|---|---|---|---|
| Y(1)—H(11) | 2.41(5) | B(3)—H(31) | 1.13(3) |
| Y(1)—H(12) | 2.23(4) | B(3)—H(32) | 1.11(3) |
| Y(1)—H(21) | 2.37(4) | B(3)—H(33) | 1.11(3) |
| Y(1)—H(22) | 2.44(4) | B(4)—H(41) | 1.12(3) |
| Y(1)—H(31) | 2.37(4) | B(4)—H(42) | 1.10(3) |
| Y(1)—H(32) | 2.60(5) | B(4)—H(43) | 1.10(3) |

EXAMPLE 14 TABLE 4-continued

| | | | |
|---|---|---|---|
| Y(1)—H(41) | 2.41(4) | B(5)—H(51) | 1.11(3) |
| Y(1)—H(42) | 2.30(4) | B(5)—H(52) | 1.13(3) |
| Y(1)—H(51) | 2.58(6) | B(5)—H(53) | 1.11(3) |
| Y(1)—H(52) | 2.27(5) | B(6)—H(61) | 1.12(3) |
| Y(1)—H(61) | 2.29(5) | B(6)—H(62) | 1.07(3) |
| Y(1)—H(62) | 2.36(5) | B(6)—H(63) | 1.08(3) |
| Y(1)—B(1) | 2.807(8) | B(1)—N(1) | 1.557(8) |
| Y(1)—B(2) | 2.836(8) | B(2)—N(1) | 1.593(8) |
| Y(1)—B(3) | 2.867(7) | B(3)—N(2) | 1.580(9) |
| Y(1)—B(4) | 2.773(7) | B(4)—N(2) | 1.541(9) |
| Y(1)—B(5) | 2.891(9) | B(5)—N(3) | 1.559(9) |
| Y(1)—B(6) | 2.765(8) | B(6)—N(3) | 1.572(9) |
| Y(1)—O(1) | 2.441(4) | N(1)—C(1) | 1.491(7) |
| B(1)—H(11) | 1.12(3) | N(1)—C(2) | 1.477(7) |
| B(1)—H(12) | 1.14(3) | N(2)—C(3) | 1.499(7) |
| B(1)—H(13) | 1.11(3) | N(2)—C(4) | 1.472(7) |
| B(2)—H(21) | 1.11(3) | N(3)—C(5) | 1.476(7) |
| B(2)—H(22) | 1.14(3) | N(3)—C(6) | 1.473(7) |
| B(2)—H(23) | 1.08(3) | | |
| Bond Angles (deg) | | | |
| B(1)—Y(1)—B(2) | 53.7(2) | O(1)—Y(1)—B(6) | 76.9(2) |
| B(3)—Y(1)—B(4) | 53.6(2) | C(2)—N(1)—C(1) | 108.5(4) |
| B(5)—Y(1)—B(6) | 53.0(2) | C(2)—N(1)—B(1) | 111.7(5) |
| B(1)—Y(1)—B(3) | 139.9(2) | C(1)—N(1)—B(1) | 108.9(5) |
| B(1)—Y(1)—B(5) | 104.5(3) | C(2)—N(1)—B(2) | 109.8(5) |
| B(2)—Y(1)—B(3) | 88.8(2) | C(1)—N(1)—B(2) | 109.8(5) |
| B(2)—Y(1)—B(5) | 91.9(2) | B(1)—N(1)—B(2) | 108.2(5) |
| B(3)—Y(1)—B(5) | 88.9(2) | C(4)—N(2)—C(3) | 108.3(5) |
| B(4)—Y(1)—B(1) | 115.6(2) | C(4)—N(2)—B(4) | 109.8(5) |
| B(4)—Y(1)—B(2) | 103.1(2) | C(3)—N(2)—B(4) | 110.0(5) |
| B(6)—Y(1)—B(1) | 115.8(3) | C(4)—N(2)—B(3) | 110.3(5) |
| B(6)—Y(1)—B(2) | 142.1(2) | C(3)—N(2)—B(3) | 109.3(5) |
| B(6)—Y(1)—B(3) | 102.6(3) | B(4)—N(2)—B(3) | 109.2(5) |
| B(6)—Y(1)—B(4) | 112.8(2) | C(6)—N(3)—C(5) | 108.0(5) |
| O(1)—Y(1)—B(1) | 74.71(18) | C(6)—N(3)—B(5) | 110.3(5) |
| O(1)—Y(1)—B(2) | 123.71(18) | C(5)—N(3)—B(5) | 111.7(5) |
| O(1)—Y(1)—B(3) | 127.86(18) | C(6)—N(3)—B(6) | 109.6(5) |
| O(1)—Y(1)—B(4) | 78.08(19) | C(5)—N(3)—B(6) | 109.7(5) |
| O(1)—Y(1)—B(5) | 124.57(19) | B(5)—N(3)—B(6) | 107.6(5) |

EXAMPLE 14 TABLE 5

| | | | |
|---|---|---|---|
| Bond Lengths (Å) | | | |
| Dy(1)—B(1) | 2.803(7) | B(6)—N(3) | 1.591(8) |
| Dy(1)—B(2) | 2.830(6) | C(1)—N(1) | 1.492(7) |
| Dy(1)—B(3) | 2.847(7) | C(2)—N(1) | 1.475(6) |
| Dy(1)—B(4) | 2.784(6) | C(5)—N(3) | 1.463(8) |
| Dy(1)—B(5) | 2.768(7) | C(6)—N(3) | 1.481(7) |
| Dy(1)—B(6) | 2.894(7) | N(2)—C(3) | 1.479(8) |
| Dy(1)—O(1) | 2.449(4) | N(2)—C(4) | 1.490(7) |
| B(1)—N(1) | 1.582(8) | N(4)—B(7) | 1.583(8) |
| B(2)—N(1) | 1.575(8) | N(4)—B(8) | 1.564(7) |
| B(3)—N(2) | 1.580(9) | N(4)—C(7) | 1.491(7) |
| B(4)—N(2) | 1.566(10) | N(4)—C(8) | 1.504(7) |
| B(5)—N(3) | 1.589(9) | | |
| Bond Angles (deg) | | | |
| B(1)—Dy(1)—B(2) | 53.6(2) | C(3)—N(2)—B(4) | 109.1(5) |
| B(3)—Dy(1)—B(4) | 53.0(2) | C(3)—N(2)—C(4) | 108.4(5) |
| B(5)—Dy(1)—B(6) | 53.7(2) | C(4)—N(2)—B(3) | 111.4(5) |
| B(2)—N(1)—B(1) | 107.2(4) | C(4)—N(2)—B(4) | 109.8(5) |
| C(1)—N(1)—B(1) | 108.2(4) | B(5)—N(3)—B(6) | 107.2(5) |
| C(1)—N(1)—B(2) | 110.4(5) | C(5)—N(3)—B(5) | 110.0(5) |
| C(2)—N(1)—B(1) | 111.6(4) | C(5)—N(3)—B(6) | 111.2(5) |
| C(2)—N(1)—B(2) | 110.5(5) | C(5)—N(3)—C(6) | 108.6(5) |
| C(2)—N(1)—C(1) | 108.9(4) | C(6)—N(3)—B(5) | 108.6(5) |
| B(4)—N(2)—B(3) | 108.7(4) | C(6)—N(3)—B(6) | 111.1(5) |
| C(3)—N(2)—B(3) | 109.4(5) | | |

EXAMPLE 15 TABLE 1

| Catalyst | Film Composition |
|---|---|
| Ti(H$_3$BNMe$_2$BH$_3$)$_2$ | Mg$_{0.8}$Ti$_{0.2}$B$_2$ |
| Ti(BH$_4$)$_3$(dme) | Mg$_{0.8}$Ti$_{0.2}$B$_2$ |
| Zr(BH$_4$)$_4$ | Mg$_{0.75}$Zr$_{0.25}$B$_2$ |
| Hf(BH$_4$)$_4$ | Mg$_{0.75}$Hf$_{0.25}$B$_2$ |
| Cr(H$_3$BNMe$_2$BH$_3$)$_2$ | Mg$_{0.7}$Cr$_{0.3}$B$_2$ |
| Y(DMDBA)$_3$(thf) | Mg$_{0.45}$Y$_{0.55}$B$_{3.5}$ |
| Ti(NMe$_2$)$_4$ | Mg$_3$Ti$_2$B$_3$C$_5$N$_7$ |
| CpPd(allyl) | MgPdBC$_2$ |
| TiNp$_4$ | no growth |
| Ni(MeCp)$_2$ | no growth |
| Cp*Mg(DMDBA)(thf) | no growth |
| EtI | no growth |
| I$_2$ | no growth |
| MeNHNH$_2$ | no growth |

EXAMPLE 16 TABLE 1

| Precursors | Precursor delivery | Co-reactant | Ref. |
|---|---|---|---|
| Mg diketonate (thd, hfac, dpm) | >150° C., with carrier gas | O$_2$ | [14, 38-47] |
| Mg(dpm)$_2$(TMEDA) | >100° C., with carrier gas | O$_2$ | [48] |
| Mg(hfca)$_2$L | 40° C., with carrier gas | O$_2$ | [33] |
| MethylMg tert-Butoxide | 140° C., with carrier gas | — | [16, 34] |
| Bis-cyclopentadienyl Mg | 40° C., with carrier gas | H$_2$O, O$_2$ | [21, 22, 49-52] |
| Mg(DMDBA)$_2$ | RT, no carrier gas needed | H$_2$O | this work |

REFERENCES (1) Pierson, J. F.; Bertran, F.; Bauer, J. P.; Jolly, J. *Surface & Coatings Technology* 2001, 142, 906-910.
(2) Kelesoglu, E.; Mitterer, C.; Kazmanli, M. K.; Urgen, M. *Surface and Coatings Technology* 1999, 116-119, 133-140.
(3) Bazhin, A. I.; Goncharov, A. A.; Petukhov, V. V.; Radjabov, T. D.; Stupak, V. A.; Konovalov, V. A. *Vacuum* 2006, 80, 918-922.
(4) Lin, S. T.; Lee, C. *Journal of the Electrochemical Society* 2003, 150, G607-G611.
(5) Dahm, K. L.; Jordan, L. R.; Haase, J.; Dearnley, P. A. *Surface & Coatings Technology* 1998, 109, 413-418.
(6) Beckloff, B. N.; Lackey, W. J. *Journal of the American Ceramic Society* 1999, 82, 503-512
(7) Motojima, S.; Funahashi, K.; Kurosawa, K. *Thin Solid Films* 1990, 189, 73-79.
(8) Mukaida, M.; Goto, T.; Hirai, T. *Journal of Materials Science* 1990, 25, 1069-1075.
(9) Randich, E. *Thin Solid Films* 1980, 72, 517-522.
(10) Sung, J. W.; Goedde, D. M.; Girolami, G. S.; Abelson, J. R. *Journal of Applied Physics* 2002, 91, 3904-3911.
(11) Jayaraman, S.; Yang, Y.; Kim, D. Y.; Girolami, G. S.; Abelson, J. R. *Journal of Vacuum Science & Technology A* 2005, 23, 1619-1625.
(12) Jayaraman, S.; Klein, E. J.; Yang, Y.; Kim, D. Y.; Girolami, G. S.; Abelson, J. R. *Journal of Vacuum Science & Technology A* 2005, 23, 631-633.
(13) Goedde, D. M.; Girolami, G. S. *Journal of the American Chemical Society* 2004, 126, 12230-12231.
(14) Liu, Z. K.; Schlom, D. G.; Li, Q.; Xi, X. X. *Applied Physics Letters* 2001, 78, 3678-3680.

(15) Kang, W. N.; Kim, H. J.; Choi, E. M.; Jung, C. U.; Lee, S. L. *Science* 2001, 292, 1521-1523.
(16) Ueda, K.; Makimoto, T. *Japanese Journal of Applied Physics Part 1-Regular Papers Brief Communications & Review Papers* 2006, 45, 5738-5741.
(17) Ueda, K.; Naito, M. *Journal of Applied Physics* 2003, 93, 2113-2120.
(18) Zeng, X. H.; Pogrebnyakov, A. V.; Kotcharov, A.; Jones, J. E.; Xi, X. X.; Lysczek, E. M.; Redwing, J. M.; Xu, S. Y.; Lettieri, J.; Schlom, D. G.; Tian, W.; Pan, X. Q.; Liu, Z. K. *Nature Materials* 2002, 1, 35-38.
(19) Zeng, X.; Pogrebnyakov, A.; Xi, X.; Redwing, J. M.; Lui, Z.-K.; Schlom, D. G. In *PCT Int. Appl.*; (Penn State Research Foundation, USA). Wo, 2003.

Example 17

Synthesis of Actinide Boranamide Complexes

Experimental Section. All operations were carried out in vacuum or under argon using standard Schlenk techniques. Diethyl ether, tetrahydrofuran, pentane, and toluene were distilled under nitrogen from sodium/benzophenone immediately before use. Anhydrous $LnCl_3$ (Ln=La, Ce, Pr, Nd, Sm, Eu, Er) and $ThCl_4$ (Cerac) was used as received. The starting materials $Na(H_3BNMe_2BH_3)$,[1] $UCl_4$,[2] and $PMe_3$[3] were prepared by literature routes.

Elemental analyses were carried out by the University of Illinois Microanalytical Laboratory. The IR spectra were recorded on a Nicolet Impact 410 infrared spectrometer as Nujol mulls between KBr plates. The $^1H$ data were obtained on a Varian Unity 400 instrument at 399.951 MHz or on a Varian Unity Inova 600 at 599.765 MHz. The $^{11}B$ NMR data were collected on a General Electric GN300WB instrument at 96.289 MHz or on a Varian Unity Inova 600 instrument at 192.425 MHz. Chemical shifts are reported in $\delta$ units (positive shifts to high frequency) relative to tetramethylsilane ($^1H$) or $BF_3.Et_2O$ ($^{11}B$). Field ionization (FI) mass spectra were recorded on a Micromass 70-VSE mass spectrometer. Melting points and decomposition temperatures were determined in closed capillaries under argon on a Thomas-Hoover Unimelt apparatus.

Tetrakis(N,N-dimethyldiboranamido)thorium(IV), $Th(H_3BNMe_2BH_3)_4$. To a suspension of $ThCl_4$ (0.47 g, 1.3 mmol) in tetrahydrofuran (15 mL) at −78° C. was added a solution of sodium N,N-dimethyldiboranamide (0.47 g, 5.0 mmol) in tetrahydrofuran (15 mL). The reaction mixture was allowed to warm to room temperature and stirred for 36 h. After several hours the mixture consisted of a gray-white precipitate and a clear solution. The solution was filtered and the clear filtrate was evaporated to dryness under vacuum. The residue was extracted with toluene (3×15 mL). The extract was filtered and evaporated to dryness under vacuum to afford a white powder. Most of the white powder was dissolved in diethyl ether (60 mL). The resulting solution was filtered, concentrated to ca. 40 mL and cooled to −20° C. to yield 0.20 g of colorless, block-shaped crystals. Another 30 mL of diethyl ether was added to the remaining toluene extract and this fraction was combined with the mother liquor. The solution was concentrated to ca. 30 mL and cooled to −20° C. to yield an additional 0.08 g of crystals. Yield: 0.28 g (42%). Mp: 152° C. Anal. Calcd for $C_8H_{48}B8N4Th$: C, 18.51; H, 9.32; N, 10.80. Found: C, 18.51; H, 9.42; N, 10.45. $^1H$ NMR($C_6D_6$, 20° C.): $\delta$ 4.24 (br q, $BH_3$, 24H), 2.11 (s, fwhm=4 Hz, $NMe_2$, 24H). $^{11}B$ NMR($C_6D_6$, 20° C.): $\delta$ −2.77 (q, $J_{BH}$=91 Hz, $BH_3$). MS (FI) [fragment ion, relative abundance]: m/z 391 [$Th(H_3BNMe_2BH_3)_2(BH_4)^+$, 25], 405 [Th$(H_3BNMe_2BH_3)_2(BH_4)(BH_3)^+$, 85], 448 [Th$(H_3BNMe_2BH_3)_3^+$, 100], 462 [Th$(H_3BNMe_2BH_3)_3(BH_3)^+$, 75], 796 Th$_2(H_3BNMe_2BH_3)_4(BH_4)_3$, 25], 853 [Th$_2$$(H_3BNMe_2BH_3)_5(BH_4)_2^+$, 40], 910 [Th$_2(H_3BNMe_2BH_3)_6$$(BH_4)^+$, 30], 967 [Th$_2(H_3BNMe_2BH_3)_7^+$, 20]. IR (cm$^{-1}$): 2420 s, 2330 m, 2264 s, 2208 vs, 2069 sh, 1400 w, 1275 s, 1240 s, 1186 m, 1161 s, 1132 s, 1036 m, 1011 s, 926 m, 903 w, 827 w, 806 w, 455 m.

Crystallographic Studies. Single crystals of $Th(H_3BNMe_2BH_3)_4$, crystallized from diethyl ether, were mounted on glass fibers with Paratone-N oil (Exxon) and immediately cooled to −80° C. in a cold nitrogen gas stream on the diffractometer. Standard peak search and indexing procedures gave rough cell dimensions, and least squares refinement using 9601 reflections yielded the cell dimensions.

The orthorhombic lattice and systematic absences for 0kl (k+l≠2n) and h0l (h≠2n) were consistent with space groups Pna2$_1$ and Pnma; the centrosymmetric group Pnma was shown to be the correct choice by successful refinement of the proposed model. The measured intensities were reduced to structure factor amplitudes and their esd's by correction for background, scan speed, and Lorentz and polarization effects. No corrections for crystal decay were necessary, but a face-indexed absorption correction was applied, the minimum and maximum transmission factors being 0.486 and 0.845. Systematically absent reflections were deleted and symmetry equivalent reflections were averaged to yield the set of unique data. The reflection 020 was found to be a statistical outlier and was deleted; the remaining 2436 unique data were used in the least squares refinement.

The structure was solved using direct methods (SHELXTL). The correct position for the thorium atom was deduced from an E-map. Subsequent least-squares refinement and difference Fourier calculations revealed the positions of the remaining non-hydrogen atoms. The quantity minimized by the least-squares program was $\Sigma w(F_o^2-F_c^2)^2$, where $w=\{[(F_o^2)]^2+(0.117P)^2\}^{-1}$ and $P=(F_o^2+2F_c^2)/3$. The analytical approximations to the scattering factors were used, and all structure factors were corrected for both real and imaginary components of anomalous dispersion. In the final cycle of least squares, independent anisotropic displacement factors were refined for the non-hydrogen atoms. The boranyl hydrogen atoms were located in the difference maps, and their positions were refined with independent isotropic displacement parameters. The chemically equivalent B—H and H...H distances within the $BH_3$ units were constrained to be equal within an esd of 0.01 Å. The remaining hydrogen atoms were placed in idealized positions; the methyl groups were allowed to rotate about the N—C axis to find the best least-squares positions. The displacement parameters for boranyl hydrogens were set equal to 1.2 times $U_{eq}$ for the attached boron; those for methyl hydrogens were set to 1.5 times $U_{eq}$ for the attached carbon. Successful convergence was indicated by the maximum shift/error of 0.000 for the last cycle. The largest peak in the final Fourier difference map (1.47 eÅ$^{-3}$) was located 1.04 Å from Th1. A final analysis of variance between observed and calculated structure factors showed no apparent errors.

Bis(N,N-dimethyldiboranamido)bis(tetrahydroborato)thorium(IV), $Th(H_3BNMe_2BH_3)_2(BH_4)_2$ Method A. Sublimation of $Th(H_3BNMe_2BH_3)_4$ (0.15 g, 0.33 mmol) at 100° C. at $10^{-2}$ Torr afforded white microcrystals. Yield: 0.11 g (82%). Note: A small amount of Th(H$_3$BNMe$_2$BH$_3$)$_3$(BH$_4$), an intermediate in the thermal conversion of Th(H$_3$BNMe$_2$BH$_3$)$_4$ to Th(H$_3$BNMe$_2$BH$_3$)$_2$(BH$_4$)$_2$, is present.

Method B. Th(H$_3$BNMe$_2$BH$_3$)$_4$ (12 mg, 0.023 mmol) in C$_7$D$_8$ (1.9 mL) was heated at 80° C. The reaction was monitored by $^{11}$B NMR spectroscopy. Quantitative conversion to 2 was complete after 7 hours. Anal. Calcd for C$_8$H$_{48}$B8N4Th: C, 11.86; H, 7.96; N, 6.91. Found: C, 12.63; H, 7.86; N, 7.34. $^1$H{$^{11}$B} NMR(C$_6$D$_6$, 20° C.): δ 1.85 (s, fwhm=2 Hz, NMe$_2$, 12H), 4.29 (s, fwhm=2 Hz, BH$_4$, 8H), 4.35 (s, fwhm=2 Hz, BH$_3$, 12H). $^{11}$B NMR(C$_6$D$_6$, 20° C.): δ −2.34 (quintet, J$_{BH}$=89 Hz, BH$_4$, 2B), 0.88 (q, J$_{BH}$=92 Hz, BH$_3$, 4B). IR (cm$^{-1}$): 2522 m, 2497 sh, 2453 s, 2428 sh, 2328 m, 2258 m, 2204 vs, 2168 s, 1277 s, 1238 s, 1217 vs, 1196 s, 1184 s, 1163 s, 1126 m, 1101 w, 1014 vs, 928 m, 899 w, 847 w, 438 m.

Crystallographic Studies. Single crystals of Th(H$_3$BNMe$_2$BH$_3$)$_2$(BH$_4$)$_2$, grown by sublimation, were mounted on glass fibers with Krytox oil (Dupont) and immediately cooled to −80° C. in a cold nitrogen gas stream on the diffractometer. Standard peak search and indexing procedures gave rough cell dimensions, and least squares refinement using 5156 reflections yielded the cell dimensions.

The monoclinic lattice and systematic absences 0k0 (k≠2n) and h0l (l≠2n) were uniquely consistent with the space group P2$_1$/c, which was confirmed by the success of the subsequent refinement. The measured intensities were reduced to structure factor amplitudes and their esd's by correction for background, scan speed, and Lorentz and polarization effects. No corrections for crystal decay were necessary, but a face-indexed absorption correction was applied, the minimum and maximum transmission factors being 0.323 and 0.690. Systematically absent reflections were deleted and symmetry equivalent reflections were averaged to yield the set of unique data. All 4133 unique data were used in the least squares refinement.

The structure was solved using direct methods (SHELXTL). The correct position for the thorium atom was deduced from an E-map. Subsequent least-squares refinement and difference Fourier calculations revealed the positions of the remaining non-hydrogen atoms. The quantity minimized by the least-squares program was Σw(F$_o$$^2$−F$_c$$^2$)$^2$, where w=[σ$^2$(F$_o$$^2$)]$^{-1}$. The analytical approximations to the scattering factors were used, and all structure factors were corrected for both real and imaginary components of anomalous dispersion. In the final cycle of least squares, independent anisotropic displacement factors were refined for the non-hydrogen atoms. Hydrogen atoms bonded to boron were located in the difference maps, and their positions were refined with independent isotropic displacement parameters. The chemically equivalent B—H and Th—H distances within the BH$_3$ units of the diboranamide ligands and the BH$_4$ units were constrained to be equal within an esd of 0.01 Å. The remaining hydrogen atoms were placed in idealized positions; the methyl groups were allowed to rotate about the N—C axis to find the best least-squares positions. The displacement parameters for the boron bound hydrogens were set equal to 1.2 times U$_{eq}$ for the attached boron; those for methyl hydrogens were set to 1.5 times U$_{eq}$ for the attached carbon. No correction for isotropic extinction was necessary. Successful convergence was indicated by the maximum shift/error of 0.000 for the last cycle. The largest peak in the final Fourier difference map (1.93 eÅ$^{-3}$) was located 0.46 Å from Th1. A final analysis of variance between observed and calculated structure factors showed no apparent errors.

Tris(N,N-dimethyldiboranamido)uranium(III), U(H$_3$BNMe$_2$BH$_3$)$_3$. To a suspension of UCl$_4$ in diethyl ether at −78° C. was added a solution of sodium N,N-dimethyldiboranamide in diethyl ether. The reaction mixture was allowed to warm to room temperature and stirred for 18 hours. Gas slowly evolved and the bright green solution gradually turned dark brown. The solution was filtered and the brown filtrate was evaporated to dryness under vacuum. The residue was extracted with toluene (2×25 mL). The dark red extract was filtered, concentrated to 20 mL, and cooled to −20° C. to yield red microcrystals. Yield: 0.14 g (26%). MP: 156° C. (dec). Anal. Calcd for C$_6$H$_{36}$B$_6$N$_3$U: C, 15.90; H, 8.01; N, 9.27. Found: C, 15.69; H, 7.50; N, 9.06. $^1$H NMR (C$_7$D$_8$, 20° C.): δ 3.76 (br s, fwhm=2210 Hz, NMe$_2$, 36H). $^{11}$B NMR(C$_7$D$_8$, 20° C.): δ 163.36 (br s, fwhm=510 Hz, BH$_3$). IR (cm$^{-1}$): 2399 vs, 2331 m, 2270 s, 2202 vs, 2168 s, 2094 sh, 1402 w, 1327 sh, 1265 s, 1238 s, 1215 s, 1182 m, 1166 s, 1161 s, 1132 m, 1032 m, 928 m, 902 w, 810 w, 760 w, 451 m.

Crystallographic Studies, Structural Isomer A. Single crystals of U(H$_3$BNMe$_2$BH$_3$)$_3$, crystallized from pentane, were mounted on glass fibers with Paratone-N oil (Exxon) and immediately cooled to −80° C. in a cold nitrogen gas stream on the diffractometer. Standard peak search and indexing procedures gave rough cell dimensions, and least squares refinement using 7463 reflections yielded the cell dimensions.

The monoclinic lattice and systematic absences 0k0 (k≠2n) and h0l (l≠2n) were uniquely consistent with the space group P2$_1$/c, which was confirmed by the success of the subsequent refinement. The measured intensities were reduced to structure factor amplitudes and their esd's by correction for background, scan speed, and Lorentz and polarization effects. No corrections for crystal decay were necessary, but a face-indexed absorption correction was applied, the minimum and maximum transmission factors being 0.190 and 0.843. Systematically absent reflections were deleted and symmetry equivalent reflections were averaged to yield the set of unique data. All 4251 unique data were used in the least squares refinement.

The structure was solved using direct methods (SHELXTL). Correct position for the uranium atom was deduced from an E-map. Subsequent least-squares refinement and difference Fourier calculations revealed the positions of the remaining non-hydrogen atoms. The quantity minimized by the least-squares program was Σw(F$_o$$^2$−F$_c$$^2$)$^2$, where w={[σ(F$_o$$^2$)]$^2$+(0.0318P)$^2$}$^{-1}$ and P=(F$_o$$^2$+2F$_c$$^2$)/3. The analytical approximations to the scattering factors were used, and all structure factors were corrected for both real and imaginary components of anomalous dispersion. In the final cycle of least squares, independent anisotropic displacement factors were refined for the non-hydrogen atoms. Hydrogen atoms were placed in idealized positions with C—H and B—H distances fixed at 0.98 and 1.15 Å, respectively; the methyl and boranyl groups were allowed to rotate about the C—N axis and the B—N axis, respectively, to find the best least-squares positions. The displacement parameters for methyl hydrogens were set to 1.5 times U$_{eq}$ for the attached carbon atoms and the boranyl hydrogens were set to 1.2 times U$_{eq}$ for the attached boron atoms. No correction for isotropic extinction was necessary. Successful convergence was indicated by the maximum shift/error of 0.000 for the last cycle. The largest peak in the final Fourier difference map (2.90 eÅ$^{-3}$) was located 0.96 Å from U1. A final analysis of variance between observed and calculated structure factors showed no apparent errors.

Crystallographic Studies, Structural Isomer B. Single crystals of U(H$_3$BNMe$_2$BH$_3$)$_3$, crystallized from toluene, were mounted on glass fibers with Paratone-N oil (Exxon) and immediately cooled to −80° C. in a cold nitrogen gas stream on the diffractometer. Standard peak search and indexing procedures gave rough cell dimensions, and least squares refinement using 14808 reflections yielded the cell dimensions.

The monoclinic lattice and systematic absences 0k0 (k≠2n) and h0l (l≠2n) were uniquely consistent with the space group P2₁/c, which was confirmed by the success of the subsequent refinement. The measured intensities were reduced to structure factor amplitudes and their esd's by correction for background, scan speed, and Lorentz and polarization effects. No corrections for crystal decay were necessary but a face-indexed absorption correction was applied, the minimum and maximum transmission factors being 0.456 and 0.754. Systematically absent reflections were deleted and symmetry equivalent reflections were averaged to yield the set of unique data. All 5035 unique data were used in the least squares refinement.

The structure was solved using direct methods (SHELXTL). Correct position for the uranium atom was deduced from an E-map. Subsequent least-squares refinement and difference Fourier calculations revealed the positions of the remaining non-hydrogen atoms. The quantity minimized by the least-squares program was $\Sigma w(F_o^2-F_c^2)^2$, where $w=\{[\sigma(F_o^2)]^2+(0.374P)^2\}^{-1}$ and $P=(F_o^2+2F_c^2)/3$. The analytical approximations to the scattering factors were used, and all structure factors were corrected for both real and imaginary components of anomalous dispersion. In the final cycle of least squares, independent anisotropic displacement factors were refined for the non-hydrogen atoms. The boranyl hydrogen atoms were located in the difference maps, and their positions were refined with independent isotropic displacement parameters. The chemically equivalent B—H distances within the BH₃ units were constrained to be equal within an esd of 0.01 Å. The remaining hydrogen atoms were placed in idealized positions; the methyl groups were allowed to rotate about the N—C axis to find the best least-squares positions. No correction for isotropic extinction was necessary. Successful convergence was indicated by the maximum shift/error of 0.000 for the last cycle. The largest peak in the final Fourier difference map (4.18 eÅ⁻³) was located 0.96 Å from U1. A final analysis of variance between observed and calculated structure factors showed no apparent errors.

Tris(N,N-dimethyldiboranamido)(tetrahydrofuran)uranium(III), U(H₃BNMe₂BH₃)₃(thf). To a suspension of UCl₄ (0.46 g, 1.2 mmol) in tetrahydrofuran (25 mL) at −78° C. was added a solution of sodium N,N-dimethyldiboranamide (0.45 g, 4.8 mmol) in tetrahydrofuran (25 mL). The reaction mixture was allowed to warm to room temperature and stirred for 68 h. Gas slowly evolved and after several hours the mixture consisted of a white precipitate and a green solution. The green solution was filtered and the filtrate was evaporated to dryness under vacuum to afford a sticky, dark brown solid. The residue was extracted with pentane (2×20 mL). The filtered extract was concentrated to ca. 7 mL and cooled to −20° C. to yield 0.11 g of round, brown crystals. The mother liquor was concentrated to 4 mL and cooled to −20° C. to yield an additional 0.03 g of brown crystals. Yield: 0.14 g (22%). MP: 135° C. Anal. Calcd for C₁₀H₄₄B₆N₃OU: C, 22.86; H, 8.44; N, 7.99. Found: C, 22.84; H, 8.25; N, 7.66. ¹H NMR(C₆D₆, 20° C.): δ −5.56 (b, fwhm=125 Hz, OCH₂, 4H), −1.89 (b, fwhm=38 Hz, OCH₂CH₂, 4H), 3.36 (s, fwhm=4 Hz, CH₃, 18H), 104.40 (br q, $J_{BH}$=90 Hz, BH₃, 18H). ¹¹B NMR (C₆D₆, 20° C.): δ 152.77 (br s, fwhm=180 Hz, BH₃). MS (FI) [fragment ion, relative abundance]: m/z 453 [U(H₃BNMe₂BH₃)₃⁺, 100]. IR (cm⁻¹): 2390 vs, 2335 m, 2278 s, 2210 vs, 2173 sh, 2064 sh, 1400 w, 1236 s, 1217 s, 1186 s, 1169 s, 1136 s, 930 m, 903 w, 856 m, 837 m, 812 w, 451 m.

Crystallographic Studies. Single crystals of U(H₃BNMe₂BH₃)₃(thf), crystallized from pentane, were mounted on glass fibers with Paratone-N oil (Exxon) and immediately cooled to −80° C. in a cold nitrogen gas stream on the diffractometer. Standard peak search and indexing procedures gave rough cell dimensions, and least squares refinement using 8026 reflections yielded the cell dimensions.

The cubic lattice and systematic absences hkl (h+k+l≠2n) were consistent with space groups Im-3, I23, I2₁3, Im-3m, I-43m, and I432; the non-centrosymmetric group I23 was shown to be the correct choice by successful refinement of the proposed model. The measured intensities were reduced to structure factor amplitudes and their esd's by correction for background, scan speed, and Lorentz and polarization effects. No corrections for crystal decay were necessary, but a face-indexed absorption correction was applied, the minimum and maximum transmission factors being 0.162 and 0.306. The reflections 011 and 103 were found to be statistical outliers and were deleted; the remaining 1799 unique data were used in the least squares refinement.

The structure was solved using direct methods (SHELXTL). Correct position for the uranium atom was deduced from an E-map. Subsequent least-squares refinement and difference Fourier calculations revealed the positions of the remaining non-hydrogen atoms. The quantity minimized by the least-squares program was $\Sigma w(F_o^2-F_c^2)^2$, where $w=\{[\sigma(F_o^2)]^2+(0.0201P)^2\}^{-1}$ and $P=(F_o^2+2F_c^2)/3$. The analytical approximations to the scattering factors were used, and all structure factors were corrected for both real and imaginary components of anomalous dispersion. In the final cycle of least squares, independent anisotropic displacement factors were refined for the non-hydrogen atoms. The tetrahydrofuran molecule is disordered about a three-fold axis and its C—O and C—C bond distances were fixed at 1.48±0.01 and 1.52±0.01 Å, respectively. Hydrogen atoms on the diboranamide ligands were placed in idealized positions with C—H=0.98 Å and B—H=1.15 Å; the methyl and boranyl groups were allowed to rotate about their respective axis to find the best least-squares positions. The displacement parameters for the methylene and boranyl hydrogens were set equal to 1.2 times $U_{eq}$ for the attached carbon and boron, respectively; those for methyl hydrogens were set to 1.5 times $U_{eq}$ for the attached carbon. No correction for isotropic extinction was necessary. Successful convergence was indicated by the maximum shift/error of 0.000 for the last cycle. The largest peak in the final Fourier difference map (0.58 eÅ⁻³) was located 0.72 Å from U1. A final analysis of variance between observed and calculated structure factors showed no apparent errors.

Tris(N,N-dimethyldiboranamido)bis(trimethylphosphine) uranium(III), U(H₃BNMe₂BH₃)₃(PMe₃)₂. To U(H₃BNMe₂BH₃)₃(thf) (0.18 g, 0.34 mmol) in pentane (20 mL) was added trimethylphosphine (0.14 mL, 1.4 mmol). The brown solution immediately turned dark red. The solution was stirred for 20 minutes, concentrated to 10 mL, and cooled to −20° C. to yield dark crystals. Yield: 0.13 g (64%). MP: 173° C. (dec). Anal. Calcd for C₁₂H₅₄B₆N₃P₂U: C, 23.80; H, 8.99; N, 6.94. Found: C, 23.73; H, 9.30; N, 6.80. ¹H NMR(C₆D₆, 20° C.): δ −1.56 (br s, fwhm=110 Hz, PMe₃, 18H), 4.03 (s, fwhm=4 Hz, NMe₂, 36H), 98.32 (br s, fwhm=330 Hz, BH₃, 36H). ¹¹B NMR(C₆D₆, 20° C.): δ 152.45 (br s, fwhm=190 Hz, BH₃). MS (FI) [fragment ion, relative abundance]: m/z 454 [U(H₃BNMe₂BH₃)₃⁺, 83], 530 [U(H₃BNMe₂BH₃)₃(PMe₃)⁺, 100], 601 [U(H₃BNMe₂BH₃)₄ (PMe₃)⁺, 75]. IR (cm⁻¹): 2357 vs, 2341 sh, 2276 m, 2214 vs, 2094 w, 1303 w, 1284 w, 1228 s, 1213 m, 1182 sh, 1163 vs, 1136 s, 947 m, 923 sh, 904 sh, 812 w, 459 m.

Crystallographic Studies. Single crystals of U(H$_3$BNMe$_2$BH$_3$)$_3$(PMe$_3$)$_2$, crystallized from pentane, were mounted on glass fibers with Paratone-N oil (Exxon) and immediately cooled to −80° C. in a cold nitrogen gas stream on the diffractometer. Standard peak search and indexing procedures gave rough cell dimensions, and least squares refinement using 9378 reflections yielded the cell dimensions.

The orthorhombic lattice and the systematic absences 0kl (k≠2n), h0l (l≠2n), and hk0 (h≠2n) were uniquely consistent with the space group Pbca, which was confirmed by the success of the subsequent refinement. The measured intensities were reduced to structure factor amplitudes and their esd's by correction for background, scan speed, and Lorentz and polarization effects. No corrections for crystal decay were necessary, but a face-indexed absorption correction was applied, the minimum and maximum transmission factors being 0.272 and 0.799. Systematically absent reflections were deleted and symmetry equivalent reflections were averaged to yield the set of unique data. The reflections 104, 202, 002, 106, and 102 were statistical outliers and were deleted. The remaining 6684 reflections were used in the least squares refinement.

The structure was solved using direct methods (SHELXTL). Correct position for the uranium atom was deduced from an E-map. Subsequent least-squares refinement and difference Fourier calculations revealed the positions of the remaining non-hydrogen atoms. The quantity minimized by the least-squares program was $\Sigma w(F_o^2-F_c^2)^2$, where $w=\{[\sigma(F_o^2)]^2+(0.0238P)^2\}^{-1}$ and $P=(F_o^2+2F_c^2)/3$. The analytical approximations to the scattering factors were used, and all structure factors were corrected for both real and imaginary components of anomalous dispersion. In the final cycle of least squares, independent anisotropic displacement factors were refined for the non-hydrogen atoms. Hydrogen atoms were placed in idealized positions with C—H and B—H distances fixed at 0.98 and 1.15 Å, respectively; the methyl and boranyl groups were allowed to rotate about the C—N axis and the B—N axis, respectively, to find the best least-squares positions. The displacement parameters for the boranyl hydrogens were set equal to 1.2 times $U_{eq}$ for the attached boron; those for methyl hydrogens were set to 1.5 times $U_{eq}$ for the attached carbon. No correction for isotropic extinction was necessary. Successful convergence was indicated by the maximum shift/error of 0.000 for the last cycle. The largest peak in the final Fourier difference map (0.75 eÅ$^{-3}$) was located 1.01 Å from U1. A final analysis of variance between observed and calculated structure factors showed no apparent errors.

Tris(N,N-dimethyldiboranamido)(tetrahydrofuran)lanthanum(III), La(H$_3$BNMe$_2$BH$_3$)$_3$(thf). Solid LaCl$_3$ (0.52 g, 2.1 mmol) and solid Na(H$_3$BNMe$_2$BH$_3$) (0.56 g, 5.9 mmol) were added to a 100 mL Schlenk tube with 30-40 steel balls (4.5 mm diameter). To the solid mixture was added 2 mL tetrahydrofuran. The residue was evaporated to dryness under vacuum and the flask was gently agitated by hand for 30 min. Sublimation at 105° C. at 10$^{-2}$ Torr afforded white microcrystals. Yield: 33 mg (4%). $^1$H NMR(CH$_2$Cl$_2$, 20° C.): δ 1.87 (m, OCH$_2$CH$_2$, 4H), 2.36 (s, fwhm=4 Hz, NMe$_2$, 18H), 3.85 (m, OC$\overline{H}_2$, 4H). $^{11}$B NMR(CH$_2$Cl$_2$, 20° C.): δ −4.27 (br q, $J_{BH}$=90 Hz, BH$_3$).

Crystallographic Studies. Single crystals of La(H$_3$BNMe$_2$BH$_3$)$_3$(thf), grown by sublimation, were mounted on glass fibers with Paratone-N oil (Exxon) and immediately cooled to −80° C. in a cold nitrogen gas stream on the diffractometer. Standard peak search and indexing procedures gave rough cell dimensions, and least squares refinement using 11511 reflections yielded the cell dimensions.

The cubic lattice and systematic absences hkl (h+k+l≠2n) were consistent with space groups Im-3, I23, I2$_1$3, Im-3m, I-43m, I432, and I4$_1$32 the non-centrosymmetric group I23 was shown to be the correct choice by successful refinement of the proposed model. The measured intensities were reduced to structure factor amplitudes and their esd's by correction for background, scan speed, and Lorentz and polarization effects. No corrections for crystal decay were necessary, but a face-indexed absorption correction was applied, the minimum and maximum transmission factors being 0.756 and 0.869. The reflections 011 and 013 were found to be statistical outliers and were deleted; the remaining 1514 unique data were used in the least squares refinement.

The structure was solved using direct methods (SHELXTL). Correct position for the lanthanum atom was deduced from an E-map. Subsequent least-squares refinement and difference Fourier calculations revealed the positions of the remaining non-hydrogen atoms. The quantity minimized by the least-squares program was $\Sigma w(F_o^2-F_c^2)^2$, where $w=\{[\sigma^2(F_o^2)]\}^{-1}$. The analytical approximations to the scattering factors were used, and all structure factors were corrected for both real and imaginary components of anomalous dispersion. In the final cycle of least squares, independent anisotropic displacement factors were refined for the non-hydrogen atoms. The tetrahydrofuran molecule is disordered about a three-fold axis and its C—O and C—C bond distances were fixed at 1.48±0.01 and 1.52±0.01 Å, respectively. Hydrogen atoms on the diboranamide ligands were placed in idealized positions with C—H=0.98 Å and B—H=1.15 Å; the methyl and boranyl groups were allowed to rotate about their respective axis to find the best least-squares positions. The displacement parameters for all hydrogen atoms were set to 1.5 times $U_{eq}$ for the attached carbon and 1.2 times for the attached boron atom, except for those on the disordered tetrahydrofuran molecule, which were not included in the model. An isotropic extinction parameter was refined to a final value of x=1.36(3)×10$^{-3}$ where $F_c$ is multiplied by the factor k[1+$F_c^2$×λ$^3$/sin 2θ]$^{-1/4}$ with k being the overall scale factor. Analysis of the diffraction intensities suggested slight inversion twinning; therefore, the intensities were calculated from the equation I=xI$_a$+(1−x)I$_b$, where x is a scale factor that relates the volumes of the inversion-related twin components. The scale factor refined to a value of 0.67 (7). Successful convergence was indicated by the maximum shift/error of 0.000 for the last cycle. The largest peak in the final Fourier difference map (1.17 eÅ$^{-3}$) was located 1.12 Å from H2A. A final analysis of variance between observed and calculated structure factors showed no apparent errors.

Tris(N,N-dimethyldiboranamido)(tetrahydrofuran)cerium(III), Ce(H$_3$BNMe$_2$BH$_3$)$_3$(thf). To a suspension of CeCl$_3$ (0.27 g, 1.1 mmol) in tetrahydrofuran (15 mL) at 0° C. was added a solution of sodium N,N-dimethyldiboranamide (0.30 g, 3.2 mmol) in tetrahydrofuran (12 mL). The white reaction mixture was stirred at 0° C. for 10 minutes before being allowed to warm to room temperature. The resulting white mixture was stirred for 15 h and then evaporated to dryness under vacuum to afford a sticky, white solid. The residue was extracted with pentane (2×25 mL). The filtered extract was concentrated to ca. 5 mL and cooled to −20° C. to yield large, white crystals. Yield: 41 mg (9%). MP: 132° C. Anal. Calcd for C$_{10}$H$_{44}$B$_6$N$_3$OCe: C, 28.10; H, 10.38; N, 9.83. Found: C, 28.41; H, 11.23; N, 10.28. $^1$H NMR(C$_6$D$_6$, 20° C.): δ 0.79 (s, fwhm=6 Hz, NMe$_2$, 18H), 3.84 (s, fwhm=12 Hz, OCH$_2$CH$_2$, 4H), 7.11 (s, fwhm=22 Hz, OCH$_2$, 4H), 20.39 (br q, J$_{BH}$=92 Hz, BH$_3$, 18H). $^{11}$B NMR(C$_6$D$_6$, 20° C.): δ 23.14 (br s, fwhm=49 Hz, BH$_3$). IR (cm$^{-1}$): 2390 s, 2340 w, 2285 m, 2255 sh, 2216 vs, 2168 sh, 2064 w, 1235 s, 1216 s, 1186 s, 1169 vs, 1138 s, 929 w, 901 w, 855 m, 836 w, 809 w, 449 m.

Tris(N,N-dimethyldiboranamido)(tetrahydrofuran) praseodymium(III), Pr(H$_3$BNMe$_2$BH$_3$)$_3$(thf). To a suspension of PrCl$_3$ (0.26 g, 1.0 mmol) in tetrahydrofuran (10 mL) at 0° C. was added a solution of sodium N,N-dimethyldiboranamide (0.30 g, 3.2 mmol) in tetrahydrofuran (10 mL). The pale green reaction mixture was stirred at 0° C. for 15 minutes before being allowed to warm to room temperature. The resulting white mixture was stirred for 17 h and then evaporated to dryness under vacuum to afford a sticky solid. The residue was extracted with pentane (2×10 mL). The filtered pale green extract was concentrated to ca. 10 mL and cooled to −20° C. to yield large, pale green crystals. Yield: 0.14 g (31%). MP: 134° C. Anal. Calcd for C$_{10}$H$_{44}$B6N3OPr: C, 28.05; H, 10.36; N, 9.81. Found: C, 27.46; H, 10.76; N, 9.50. $^1$H NMR(C$_6$D$_6$, 20° C.): δ 0.02 (s, fwhm=7 Hz, NMe$_2$, 18H), 6.48 (s, fwhm=13 Hz, OCH$_2$CH$_2$, 4H), 9.93 (s, fwhm=22 Hz, OCH$_2$, 4H), 58.06 (br d, J$_{BH}$=98 Hz, BH$_3$, 18H). $^{11}$B NMR (C$_6$D$_6$, 20° C.): δ 75.13 (br s, fwhm=200 Hz, BH$_3$). IR (cm$^{-1}$): 2390 vs, 2340 m, 2284 s, 2250 sh, 2213 vs, 2169 sh, 2066 w, 1262 s, 1237 s, 1216 s, 1185 m, 1170 s, 1137 s, 929 m, 901 w, 856 m, 812 w.

Tris(N,N-dimethyldiboranamido)(tetrahydrofuran) neodymium(III), Nd(H$_3$BNMe$_2$BH$_3$)$_3$(thf). To a suspension of NdCl$_3$ (0.26 g, 1.0 mmol) in tetrahydrofuran (10 mL) at 0° C. was added a solution of sodium N,N-dimethyldiboranamide (0.30 g, 3.2 mmol) in tetrahydrofuran (10 mL). The pale green reaction mixture was stirred at 0° C. for 10 minutes before being allowed to warm to room temperature. The resulting white mixture was stirred for 13 h and then evaporated to dryness under vacuum to afford a sticky solid. The residue was extracted with pentane (12 mL). The filtered lavender extract was concentrated to ca. 8 mL and cooled to −20° C. to yield 0.17 g of large, lavender crystals. The mother liquor was concentrated to 4 mL and cooled to −20° C. to yield an additional 0.03 g of lavender crystals. Yield: 0.20 g (45%). MP: 133° C. Anal. Calcd for C$_{10}$H$_{44}$B6N3ONd: C, 27.83; H, 10.28; N, 9.74. Found: C, 27.80; H, 10.86; N, 10.00. $^1$H NMR(C$_6$D$_6$, 20° C.): δ 0.66 (s, fwhm=21 Hz, OCH$_2$, 4H) 0.95 (s, fwhm=9 Hz, OCH$_2$CH$_2$, 4H), 3.06 (s, fwhm=7 Hz, NMe$_2$, 18H), 82.86 (br s, fwhm=330 Hz, BH$_3$, 18H). $^{11}$B NMR(C$_6$D$_6$, 20° C.): δ 104.77 (br s, fwhm=170 Hz, BH$_3$). MS (FI) [fragment ion, relative abundance]: m/z 358 [Nd (H$_3$BNMe$_2$BH$_3$)$_3$$^+$, 100], 645 [Nd$_2$(H$_3$BNMe$_2$BH$_3$)$_5$$^+$, 60], 1003 [Nd$_3$(H$_3$BNMe$_2$BH$_3$)$_8$$^+$, 10]. IR (cm$^{-1}$): 2392 s, 2342 m, 2285 s, 2252 sh, 2216 vs, 2173 sh, 2066 w, 1264 s, 1238 s, 1216 s, 1186 s, 1170 s, 1137 s, 926 m, 902 w, 857 m, 813 w.

Tris(N,N-dimethyldiboranamido)(tetrahydrofuran)samarium(III), Sm(H$_3$BNMe$_2$BH$_3$)$_3$(thf). To a suspension of SmCl$_3$ (0.30 g, 1.2 mmol) in tetrahydrofuran (18 mL) at −78° C. was added a solution of sodium N,N-dimethyldiboranamide (0.33 g, 3.5 mmol) in tetrahydrofuran (10 mL). The pale green reaction mixture was stirred at −78° C. for 25 minutes before being allowed to warm to room temperature. The white suspension slowly turned to a hazy yellow solution after several hours at room temperature. The mixture was stirred for 14 h at room temperature and then evaporated to dryness under vacuum to afford a sticky, ivory solid. The residue was extracted with pentane (2×15 mL). The filtered extract was concentrated to ca. 15 mL and cooled to −20° C. to yield 0.18 g of large, pale yellow crystals. The mother liquor was concentrated to 7 mL and cooled to −20° C. to yield an additional 0.11 g of pale yellow crystals. Yield: 0.29 g (57%). MP: 134° C. Anal. Calcd for C$_{10}$H$_{44}$B$_6$N$_3$OSm: C, 27.44; H, 10.13; N, 9.60. Found: C, 27.62; H, 11.02; N, 9.46. $^1$H NMR(C$_6$D$_6$, 20° C.): δ −1.86 (br q, J$_{BH}$=104 Hz, BH$_3$, 18H), 1.29 (s, fwhm=10 Hz, OCH$_2$CH$_2$, 4H), 3.80 (s, fwhm=14 Hz, OCH$_2$, 4H), 2.25 (s, fwhm=4 Hz, NMe$_2$, 18H). $^{11}$B NMR(C$_6$D$_6$, 20° C.): δ −9.79 (br q, J$_{BH}$=87 Hz, BH$_3$). MS (FI) [fragment ion, relative abundance]: m/z 362 [Sm(H$_3$BNMe$_2$BH$_3$)$_3$$^+$, 100], 660 [Sm$_2$ (H$_3$BNMe$_2$BH$_3$)$_5$$^+$, 80]. IR (cm$^{-1}$): 2496 sh, 2392 vs, 2344 m, 2286 s, 2255 m, 2218 vs, 2173 m, 2067 w, 1268 s, 1238 s, 1216 s, 1187 m, 1170 s, 1137 s, 1019 s, 924 m, 902 w, 856 m, 814 w, 457 m.

Crystallographic Studies. Single crystals of Sm(H$_3$BNMe$_2$BH$_3$)$_3$(thf), crystallized from pentane, were mounted on glass fibers with Paratone-N oil (Exxon) and immediately cooled to −80° C. in a cold nitrogen gas stream on the diffractometer. Standard peak search and indexing procedures gave rough cell dimensions, and least squares refinement using 33620 reflections yielded the cell dimensions.

The orthorhombic lattice and systematic absences 0kl (l≠2n) and h0l (h≠2n) were consistent with the space groups Pca2$_1$ and Pbcm; the non-centrosymmetric space group Pca2$_1$ was shown to be the correct choice by successful refinement of the proposed model. The measured intensities were reduced to structure factor amplitudes and their esd's by correction for background, scan speed, and Lorentz and polarization effects. No corrections for crystal decay were necessary but a face-indexed absorption correction was applied, the minimum and maximum transmission factors being 0.530 and 0.633. Systematically absent reflections were deleted and symmetry equivalent reflections were averaged to yield the set of unique data. All 15617 unique data were used in the least squares refinement.

The structure was solved using direct methods (SHELXTL). Correct positions for the samarium atoms were deduced from an E-map. Subsequent least-squares refinement and difference Fourier calculations revealed the positions of the remaining non-hydrogen atoms. The quantity minimized by the least-squares program was $\Sigma w(F_o^2-F_c^2)^2$, where $w=\{[\sigma(F_o^2)]^2+(0.0208P)^2\}^{-1}$ and $P=(F_o^2+2F_c^2)/3$. The analytical approximations to the scattering factors were used, and all structure factors were corrected for both real and imaginary components of anomalous dispersion. In the final cycle of least squares, independent anisotropic displacement factors were refined for the non-hydrogen atoms. The C—O and C—C bond distances of the tetrahydrofuran molecule were fixed at 1.48±0.001 and 1.52±0.001 Å, respectively. Hydrogen atoms were placed in idealized positions with C—H=0.98 Å and B—H=1.15 Å; the methyl and boranyl groups were allowed to rotate about their respective axis to find the best least-squares positions. The displacement parameters for the methylene and boranyl hydrogens were set equal to 1.2 times U$_{eq}$ for the attached carbon and boron, respectively; those for methyl hydrogens were set to 1.5 times U$_{eq}$ for the attached carbon. No correction for isotropic extinction was necessary. Successful convergence was indicated by the maximum shift/error of 0.000 for the last cycle. The largest peak in the final Fourier difference map (0.84 eÅ$^{-3}$) was located 0.86 Å from Sm2. A final analysis of variance between observed and calculated structure factors showed no apparent errors.

Tris(N,N-dimethyldiboranamido)(tetrahydrofuran)europium(III), Eu(H$_3$BNMe$_2$BH$_3$)$_3$(thf). To a suspension of EuCl$_3$ (0.26 g, 1.0 mmol) in tetrahydrofuran (15 mL) at 0° C. was added a solution of sodium N,N-dimethyldiboranamide (0.29 g, 3.1 mmol) in tetrahydrofuran (15 mL). The grey reaction mixture was stirred at 0° C. for 25 minutes before being allowed to warm to room temperature. The grey suspension slowly gained a yellow solution after several hours at room temperature. The mixture was stirred for 43 h at room temperature and then evaporated to dryness under vacuum to afford a sticky, yellow solid. The residue was extracted with pentane (3×5 mL). The yellow extract was filtered, concentrated to ca. 5 mL, and cooled to −20° C. to yield large, bright yellow crystals. Yield: 0.24 g (55%). $^{11}$B NMR ($C_6D_6$, 20° C.): δ −176.8 (br s, $J_{BH}$=2140 Hz, $BH_3$).

Crystallographic Studies. Single crystals of $Eu(H_3BNMe_2BH_3)_3$(thf), crystallized from pentane, were mounted on glass fibers with Paratone-N oil (Exxon) and immediately cooled to −80° C. in a cold nitrogen gas stream on the diffractometer. Standard peak search and indexing procedures gave rough cell dimensions, and least squares refinement using 14459 reflections yielded the cell dimensions.

The orthorhombic lattice and systematic absences 0kl (l≠2n) and h0l (h≠2n) were consistent with the space groups $Pca2_1$ and Pbcm; the non-centrosymmetric space group $Pca2_1$ was shown to be the correct choice by successful refinement of the proposed model. The measured intensities were reduced to structure factor amplitudes and their esd's by correction for background, scan speed, and Lorentz and polarization effects. No corrections for crystal decay were necessary but a face-indexed absorption correction was applied, the minimum and maximum transmission factors being 0.485 and 0.705. Systematically absent reflections were deleted and symmetry equivalent reflections were averaged to yield the set of unique data. The reflections 014, 413, and 403 were found to be statistical outliers and were deleted; the remaining 8672 unique data were used in the least squares refinement.

The structure was solved using direct methods (SHELXTL). Correct positions for the europium atoms were deduced from an E-map. Subsequent least-squares refinement and difference Fourier calculations revealed the positions of the remaining non-hydrogen atoms. The C28 atom in the tetrahydrofuran ring of molecule 2 was disordered; to produce satisfactory ellipsoids, the atom was partitioned over two positions and the site occupancy factors of these positions were refined independently so that the sum of these SOF's was equal to one. The quantity minimized by the least-squares program was $\Sigma w(F_o^2-F_c^2)^2$, where $w=\{[\sigma(F_o^2)]^2+(0.0137P)^2\}^{-1}$ and $P=(F_o^2+2F_c^2)/3$. The analytical approximations to the scattering factors were used, and all structure factors were corrected for both real and imaginary components of anomalous dispersion. In the final cycle of least squares, independent anisotropic displacement factors were refined for the non-hydrogen atoms. Hydrogen atoms were placed in idealized positions with C—H=0.98 Å and B—H=1.15 Å; the methyl and boranyl groups were allowed to rotate about their respective axis to find the best least-squares positions. The displacement parameters for the methylene and boranyl hydrogens were set equal to 1.2 times $U_{eq}$ for the attached carbon and boron, respectively; those for methyl hydrogens were set to 1.5 times $U_{eq}$ for the attached carbon. No correction for isotropic extinction was necessary. Successful convergence was indicated by the maximum shift/error of 0.000 for the last cycle. The largest peak in the final Fourier difference map (0.68 eÅ$^{-3}$) was located 1.02 Å from Eu2. A final analysis of variance between observed and calculated structure factors showed no apparent errors.

Tris(N,N-dimethyldiboranamido)(tetrahydrofuran)erbium(III), $Er(H_3BNMe_2BH_3)_3$(thf). To a suspension of $ErCl_3$ (2.11 g, 7.71 mmol) in tetrahydrofuran (125 mL) at 0° C. was added a solution of sodium N,N-dimethyldiboranamide (2.27 g, 24.0 mmol) in tetrahydrofuran (50 mL). The pale pink reaction mixture was stirred at 0° C. for 15 minutes before being allowed to warm to room temperature. The pink suspension slowly turned to a hazy pink solution after several hours at room temperature. The mixture was stirred for 42 h at room temperature and then evaporated to dryness under vacuum to afford a sticky, pink solid. The residue was extracted with pentane (3×40 mL). The filtered extract was concentrated to ca. 50 mL and cooled to −20° C. to yield 1.89 g of large, pale pink crystals. The mother liquor was concentrated to 8 mL and cooled to −20° C. to yield an additional 0.61 g of pale pink crystals. Yield: 2.50 g (71%). MP: 114° C. Anal. Calcd for $C_{10}H_{44}B_6N_3OU$: C, 26.42; H, 9.76; N, 9.24. Found: C, 26.43; H, 9.96; N, 9.17. $^1$H NMR($C_6D_6$, 20° C.): δ −43.14 (br s, fwhm=250 Hz, $OCH_2$, 4H), −28.57 (s, fwhm=87 Hz, $OCH_2CH_2$, 4H), 14.79 (s, fwhm=110 Hz, $NMe_2$, 18H), 108.45 (br s, fwhm=2380 Hz, $BH_3$). $^{11}$B NMR($C_6D_6$, 20° C.): δ −171.46 (s, fwhm=180 Hz, $BH_3$). MS (FI) [fragment ion, relative abundance]: m/z 381 [$Er(H_3BNMe_2BH_3)_3^+$, 100]. IR (cm$^{-1}$): 2405 s, 2355 sh, 2297 m, 2293 m, 2230 vs, 2185 s, 2087 sh, 1286 s, 1242 s, 1219 m, 1173 vs, 1140 s, 926 w, 856 m, 849 w, 825 sh, 468 m.

Crystallographic Studies. Single crystals of $Er(H_3BNMe_2BH_3)_3$(thf), crystallized from pentane, were mounted on glass fibers with Paratone-N oil (Exxon) and immediately cooled to −80° C. in a cold nitrogen gas stream on the diffractometer. Standard peak search and indexing procedures gave rough cell dimensions, and least squares refinement using 14237 reflections yielded the cell dimensions.

The orthorhombic lattice and systematic absences 0kl (l≠2n) and h0l (h≠2n) were consistent with the space groups $Pca2_1$, and Pbcm; the non-centrosymmetric space group $Pca2_1$ was shown to be the correct choice by successful refinement of the proposed model. The measured intensities were reduced to structure factor amplitudes and their esd's by correction for background, scan speed, and Lorentz and polarization effects. No corrections for crystal decay were necessary but a face-indexed absorption correction was applied, the minimum and maximum transmission factors being 0.251 and 0.480. Systematically absent reflections were deleted and symmetry equivalent reflections were averaged to yield the set of unique data. The reflections 010, 110, and 11-2 were found to be statistical outliers and were deleted; the remaining 8542 unique data were used in the least squares refinement.

The structure was solved using direct methods (SHELXTL). Correct positions for the erbium atoms were deduced from an E-map. Subsequent least-squares refinement and difference Fourier calculations revealed the positions of the remaining non-hydrogen atoms. The C29 atom in the tetrahydrofuran ring of molecule 2 was disordered; to produce satisfactory ellipsoids, the atom was partitioned over two positions and the site occupancy factors of these positions were refined independently so that the sum of these SOF's was equal to one. The quantity minimized by the least-squares program was $\Sigma w(F_o^2-F_c^2)^2$, where $w=\{[\sigma^2(F_o^2)]+(0.0181P)^2\}^{-1}$ and $P=(F_o^2+2F_c^2)/3$. The analytical approximations to the scattering factors were used, and all structure factors were corrected for both real and imaginary components of anomalous dispersion. In the final cycle of least squares, independent anisotropic displacement factors were refined for the non-hydrogen atoms. Hydrogen atoms were placed in idealized positions with C—H=0.98 Å and B—H=1.15 Å; the methyl and boranyl groups were allowed to rotate about their respective axis to find the best least-squares positions. The displacement parameters for the methylene and boranyl hydrogens were set equal to 1.2 times $U_{eq}$ for the attached carbon and boron, respectively; those for methyl hydrogens were set to 1.5 times $U_{eq}$ for the attached carbon. No correction for isotropic extinction was necessary. Successful convergence was indicated by the maximum shift/error of 0.000 for the last cycle. The largest peak in the final Fourier difference map (0.87 eÅ$^{-3}$) was located 0.83 Å from Er2. A final analysis of variance between observed and calculated structure factors showed no apparent errors.

Hexakis(N,N-dimethyldiboranamido)dilanthanum(III), $La_2(H_3BNMe_2BH_3)_6$. Solid $LaCl_3$ (0.51 g, 2.1 mmol) and solid $Na(H_3BNMe_2BH_3)$ (0.58 g, 6.1 mmol) were added to a 100 mL Schlenk tube with 30-40 steel balls (4.5 mm diameter). The flask was gently agitated by hand for 20 min and the powdery solid slowly became sticky. Sublimation at 125° C. at $10^{-2}$ Torr afforded white microcrystals. Yield: 0.11 g (15%). Anal. Calcd for $C_{12}H_{72}B_{12}N_6La_2$: C, 20.35; H, 10.25; N, 11.87. Found: C, 20.56; H, 11.19; N, 11.93. $^1$H NMR ($C_6D_6$, 20° C.): δ 2.22 (s, fwhm=40 Hz, $NMe_2$, 36), 2.78 (br q, $J_{BH}$=110 Hz, $BH_3$, 36). $^{11}$B NMR($C_6D_6$, 20° C.): δ −2.82 (br q, $J_{BH}$=79 Hz, $BH_3$).

Hexakis(N,N-dimethyldiboranamido)dicerium(III), $Ce_2(H_3BNMe_2BH_3)_6$. Solid $CeCl_3$ (0.53 g, 2.2 mmol) and solid $Na(H_3BNMe_2BH_3)$ (0.66 g, 7.0 mmol) were added to a 250 mL round bottom flask with 30-40 steel balls (4.5 mm diameter). The flask was gently agitated by hand for 30 min and the powdery solid slowly became sticky. Sublimation at 110° C. at $10^{-2}$ Torr afforded white microcrystals. Yield: 0.25 g (33%). MP: 183° C. (dec). Anal. Calcd for $C_{12}H_{72}B_{12}N_6Ce_2$: C, 20.28; H, 10.21; N, 11.82. Found: C, 20.60; H, 11.06; N, 11.67. $^1$H NMR($C_6D_6$, 20° C.): δ 4.23 (s, fwhm=40 Hz, $NMe_2$, 36), 26.39 (br s, fwhm=330 Hz, $BH_3$, 36). $^{11}$B NMR ($C_6D_6$, 20° C.): δ 39.83 (s, fwhm=190 Hz, $BH_3$). MS (FI) [fragment ion, relative abundance]: m/z 356 [Ce$(H_3BNMe_2BH_3)_3^+$, 100], 639 [$Ce_2(H_3BNMe_2BH_3)_6^+$, 35], 995 [$Ce_3(H_3BNMe_2BH_3)_8^+$, 5].

Hexakis(N,N-dimethyldiboranamido)dierbium(III), $Er_2(H_3BNMe_2BH_3)_6$. Sublimation of $Er(H_3BNMe_2BH_3)_3(thf)$ (0.15 g, 0.33 mmol) at 75° C. at $10^{-2}$ Torr afforded pink microcrystals. Yield: 92 mg (73%). Anal. Calcd for $C_{12}H_{72}B_{12}N_6Er_2$: C, 18.84; H, 9.49; N, 10.99. Found: C, 19.55; H, 9.61; N, 10.97. $^1$H NMR($C_6D_6$, 20° C.): δ −32.50 (s, fwhm=150 Hz, $NMe_2$). $^{11}$B NMR($C_6D_6$, 20° C.): δ −324.43 (s, fwhm=240 Hz, $BH_3$). MS (FI) [fragment ion, relative abundance]: m/z 381 [$Er(H_3BNMe_2BH_3)_3^+$, 100], 693 [$Er_2(H_3BNMe_2BH_3)_6^+$, 15].

Tetrakis(N,N-dimethyldiboranamido)tetrakis(tetrahydrofuran)dieuropium(II), $Eu_2(H_3BNMe_2BH_3)_4(thf)_4$. To a suspension of $EuCl_3$ (0.50 g, 1.9 mmol) in tetrahydrofuran (20 mL) at 0° C. was added a solution of sodium N,N-dimethyldiboranamide (0.56 g, 5.9 mmol) in tetrahydrofuran (20 mL). The grey reaction mixture was stirred at 0° C. for 15 minutes before being allowed to warm to room temperature. The grey suspension slowly gained a yellow hue after several hours at room temperature. The mixture was stirred for 40 h at room temperature and then evaporated to dryness under vacuum to afford a sticky, yellow solid. The residue was extracted with pentane (2×20 mL). The pale yellow extract was filtered, concentrated to ca. 15 mL, and cooled to −20° C. to yield pale yellow crystals. Yield: 0.39 g (47%).

Crystallographic Studies. Single crystals of $Eu_2(H_3BNMe_2BH_3)_4(thf)_4$, crystallized from pentane, were mounted on glass fibers with Paratone-N oil (Exxon) and immediately cooled to −80° C. in a cold nitrogen gas stream on the diffractometer. Standard peak search and indexing procedures gave rough cell dimensions, and least squares refinement using 7317 reflections yielded the cell dimensions.

The monoclinic lattice and systematic absences 0k0 (k≠2n) and h0l (l≠2n) were uniquely consistent with the space group $P2_1/c$, which was confirmed by the success of the subsequent refinement. The measured intensities were reduced to structure factor amplitudes and their esd's by correction for background, scan speed, and Lorentz and polarization effects. No corrections for crystal decay were necessary, but a face-indexed absorption correction was applied, the minimum and maximum transmission factors being 0.594 and 0.734. Systematically absent reflections were deleted and symmetry equivalent reflections were averaged to yield the set of unique data. All 4865 unique data were used in the least squares refinement.

The structure was solved using direct methods (SHELXTL). Correct positions for europium atoms were deduced from an E-map. Subsequent least-squares refinement and difference Fourier calculations revealed the positions of the remaining non-hydrogen atoms. The europium centers and the bridging diboranamide ligands are disordered over two positions related by a pseudo two-fold axis running along the length of the molecule and passing approximately through the nitrogen atoms of the two terminal diboranamide ligands. The terminal diboranamides and the tetrahydrofuran molecules of the two disordered components are essentially superimposed and could be refined as full occupancy groups. The site occupancy factors for these two disordered components were constrained to sum one; the S.O.F. for the major occupancy component refined to 0.690. The tetrahydrofuran molecules show further disorder; one is disordered over two positions at the α-carbons while the other is disordered over a two-fold rotation. The site occupancy factors for the disordered components were also constrained to the sum of one; the S.O.F. for the major occupancy components refined to 0.512 and 0.563, respectively. The quantity minimized by the least-squares program was $\Sigma w(F_o^2-F_c^2)^2$, where $w=\{[\sigma(F_o)]^2+(0.421P)^2\}^{-1}$ and $P=(F_o^2+2F_c^2)/3$. The analytical approximations to the scattering factors were used, and all structure factors were corrected for both real and imaginary components of anomalous dispersion. In the final cycle of least squares, independent anisotropic displacement factors were refined for the non-hydrogen atoms. The chemically equivalent C—N, B—N, B . . . C, and C . . . C distances within the diboranamide ligands were constrained to be equal within an esd of 0.005 Å. The C—O and C—C distances in the tetrahydrofuran molecules were constrained to be 1.48±0.005 and 1.52±0.005 Å, respectively. Hydrogen atoms were placed in idealized positions; the methyl groups were allowed to rotate about the C—C axis to find the best least-squares positions. The displacement parameters for methylene and boranyl hydrogens were set equal to 1.2 times $U_{eq}$ for the attached carbon and boron; those for methyl hydrogens were set to 1.5 times $U_{eq}$ for the attached carbon. No correction for isotropic extinction was necessary. Successful convergence was indicated by the maximum shift/error of 0.000 for the last cycle. The largest peak in the final Fourier difference map (0.65 eÅ$^{-3}$) was located 0.95 Å from Eu1. A final analysis of variance between observed and calculated structure factors showed no apparent errors.

REFERENCES

1. Noth, H.; Thomas, S., Metal tetrahydridoborates and tetrahydroboratometalates. Part 24. Solvates of sodium bis(borane)dimethylamide. *Eur. J. Inorg. Chem.* 1999, (8), 1373-1379.

2. Hermann, J. A.; Suttle, J. F., *Inorg. Synth.* 1978, 5, 143-145.

3. Leutkens, M. L.; Sattelberger, A. P.; Murray, H. H.; Basil, J. D.; Fackler, J. P., *Inorg. Synth.* 1989, 26, 7-12.

TABLE 1

Selected Bond Lengths and Angles for Th(H$_3$BNMe$_2$BH$_3$)$_4$[a]

Bond Lengths (Å)

| | | | |
|---|---|---|---|
| Th(1)—B(1) | 2.978(8) | B(3)—N(2) | 1.588(12) |
| Th(1)—B(2) | 2.881(8) | B(4)—N(2) | 1.544(12) |
| Th(1)—B(3) | 2.950(11) | B(5)—N(3) | 1.547(11) |
| Th(1)—B(4) | 2.866(10) | B(6)—N(3) | 1.591(12) |
| Th(1)—B(5) | 2.860(12) | N(1)—C(1) | 1.486(8) |
| Th(1)—B(6) | 3.193(14) | N(1)—C(2) | 1.481(7) |
| B(1)—N(1) | 1.566(9) | N(2)—C(3) | 1.484(7) |
| B(2)—N(1) | 1.570(9) | N(2)—C(4) | 1.469(8) |

Bond Angles (deg)

| | | | |
|---|---|---|---|
| B(1)—Th(1)—B(2) | 51.2(2) | C(2)—N(1)—B(2) | 111.1(5) |
| B(3)—Th(1)—B(4) | 51.7(3) | C(3)—N(2)—B(3) | 109.6(5) |
| B(5)—Th(1)—B(6) | 49.6(3) | C(3)—N(2)—B(4) | 110.4(5) |
| B(1)—N(1)—B(2) | 107.6(5) | C(4)—N(3)—B(5) | 109.8(5) |
| B(3)—N(2)—B(4) | 107.7(7) | C(4)—N(3)—B(6) | 110.6(5) |
| B(5)—N(3)—B(6) | 109.0(8) | C(1)—N(1)—C(2) | 108.4(5) |
| C(1)—N(1)—B(1) | 110.1(6) | C(3)—N(2)—C(3)' | 109.1(8) |
| C(1)—N(1)—B(2) | 110.0(6) | C(4)—N(3)—C(4)' | 107.0(8) |
| C(2)—N(1)—B(1) | 109.6(6) | | |

[a]Symmetry transformations used to generate equivalent atoms: ' = x, −y + ½, z

TABLE 2

Selected Bond Lengths and Angles for Th(H$_3$BNMe$_2$BH$_3$)$_2$(BH$_4$)$_2$

Bond Lengths (Å)

| | | | |
|---|---|---|---|
| Th(1)—B(1) | 2.862(10) | B(2)—N(1) | 1.575(10) |
| Th(1)—B(2) | 2.862(10) | B(3)—N(2) | 1.597(10) |
| Th(1)—B(3) | 2.882(9) | B(4)—N(2) | 1.569(10) |
| Th(1)—B(4) | 2.848(9) | N(1)—C(1) | 1.489(8) |
| Th(1)—B(5) | 2.608(9) | N(1)—C(2) | 1.494(9) |
| Th(1)—B(6) | 2.583(10) | N(2)—C(3) | 1.483(9) |
| B(1)—N(1) | 1.546(10) | N(2)—C(4) | 1.500(7) |

Bond Angles (deg)

| | | | |
|---|---|---|---|
| B(1)—Th(1)—B(2) | 53.0(3) | B(4)—Th(1)—B(5) | 118.6(3) |
| B(3)—Th(1)—B(4) | 53.6(2) | B(4)—Th(1)—B(6) | 88.3(3) |
| B(5)—Th(1)—B(6) | 96.6(3) | B(1)—N(1)—B(2) | 109.7(6) |
| B(2)—Th(1)—B(3) | 100.1(3) | B(3)—N(2)—B(4) | 109.5(6) |
| B(1)—Th(1)—B(3) | 104.8(3) | C(1)—N(1)—B(1) | 109.1(6) |
| B(1)—Th(1)—B(4) | 143.5(2) | C(1)—N(1)—B(2) | 110.7(6) |
| B(1)—Th(1)—B(5) | 88.2(3) | C(2)—N(1)—B(1) | 110.0(6) |
| B(1)—Th(1)—B(6) | 114.2(3) | C(2)—N(1)—B(2) | 109.9(6) |
| B(2)—Th(1)—B(4) | 98.2(3) | C(3)—N(2)—B(3) | 109.6(6) |
| B(2)—Th(1)—B(5) | 141.0(3) | C(3)—N(2)—B(4) | 108.9(5) |
| B(2)—Th(1)—B(6) | 96.8(3) | C(1)—N(1)—C(2) | 107.4(6) |
| B(3)—Th(1)—B(5) | 92.6(3) | C(3)—N(2)—C(4) | 109.6(5) |
| B(3)—Th(1)—B(6) | 140.1(3) | | |

TABLE 3

Selected Bond Lengths and Angles for U(H$_3$BNMe$_2$BH$_3$)$_3$, Structural Isomer A Bond Lengths (Å)

| | | | |
|---|---|---|---|
| U(1)—B(1) | 2.953(4) | U(1)—H(6D) | 2.478(1) |
| U(1)—B(2) | 2.957(3) | U(1)—H(6E) | 2.599(1) |
| U(1)—B(3) | 2.939(4) | U(1A)—H(6F) | 2.496(1) |
| U(1)—B(4) | 2.943(3) | B(1)—N(1) | 1.569(8) |
| U(1)—B(5) | 2.944(3) | B(2)—N(1) | 1.583(7) |
| U(1)—B(6) | 2.949(4) | B(3)—N(2) | 1.581(7) |
| U(1)—H(1D) | 2.569(1) | B(4)—N(2) | 1.562(8) |
| U(1)—H(1E) | 2.368(1) | B(5)—N(3) | 1.576(7) |
| U(1)—H(2D) | 2.424(1) | B(6)—N(3) | 1.562(7) |

TABLE 3-continued

Selected Bond Lengths and Angles for U(H$_3$BNMe$_2$BH$_3$)$_3$, Structural Isomer A

| | | | |
|---|---|---|---|
| U(1)—H(2E) | 2.531(1) | N(1)—C(1) | 1.483(7) |
| U(1)—H(3D) | 2.459(1) | N(1)—C(2) | 1.477(7) |
| U(1)—H(3E) | 2.438(1) | N(2)—C(3) | 1.491(7) |
| U(1)—H(4D) | 2.500(1) | N(2)—C(4) | 1.486(7) |
| U(1)—H(4E) | 2.563(1) | N(3)—C(5) | 1.487(7) |
| U(1)—H(5D) | 2.518(1) | N(3)—C(6) | 1.490(6) |
| U(1)—H(5E) | 2.476(1) | | |

Bond Angles (deg)

| | | | |
|---|---|---|---|
| B(1)—U(1)—B(2) | 53.4(2) | C(3)—N(2)—B(4) | 109.9(5) |
| B(3)—U(1)—B(4) | 53.0(2) | C(4)—N(2)—B(3) | 109.4(4) |
| B(5)—U(1)—B(6) | 51.9(2) | C(4)—N(2)—B(4) | 110.1(4) |
| B(1)—N(1)—B(2) | 109.4(4) | C(5)—N(3)—B(5) | 110.1(4) |
| B(3)—N(2)—B(4) | 109.8(4) | C(5)—N(3)—B(6) | 110.7(4) |
| B(5)—N(3)—B(6) | 108.8(4) | C(6)—N(3)—B(5) | 108.8(4) |
| C(1)—N(1)—B(1) | 109.1(5) | C(6)—N(3)—B(6) | 110.3(4) |
| C(1)—N(1)—B(2) | 109.3(2) | C(1)—N(1)—C(2) | 108.3(4) |
| C(2)—N(1)—B(1) | 110.8(4) | C(3)—N(2)—C(4) | 108.4(4) |
| C(2)—N(1)—B(2) | 109.9(5) | C(5)—N(3)—C(6) | 108.2(4) |
| C(3)—N(2)—B(3) | 109.2(4) | | |

TABLE 4

Selected Bond Lengths and Angles for U(H$_3$BNMe$_2$BH$_3$)$_3$, Structural Isomer B[a]

Bond Lengths (Å)

| | | | |
|---|---|---|---|
| U(1)—B(1) | 2.902(6) | U(1)—H(52) | 2.51(5) |
| U(1)—B(2) | 2.862(7) | U(1)—H(53) | 2.46(5) |
| U(1)—B(3) | 2.861(7) | B(1)—N(1) | 1.581(8) |
| U(1)—B(4) | 2.889(6) | B(2)—N(1) | 1.583(8) |
| U(1)—B(5) | 2.670(6) | B(3)—N(2) | 1.593(8) |
| U(1)—B(6)' | 2.665(6) | B(4)—N(2) | 1.572(7) |
| U(1)—H(11) | 2.59(5) | B(5)—N(3) | 1.540(7) |
| U(1)—H(12) | 2.46(7) | B(6)—N(3) | 1.553(7) |
| U(1)—H(21) | 2.57(6) | N(1)—C(1) | 1.495(7) |
| U(1)—H(22) | 2.48(6) | N(1)—C(2) | 1.480(7) |
| U(1)—H(31) | 2.46(5) | N(2)—C(3) | 1.484(7) |
| U(1)—H(32) | 2.47(5) | N(2)—C(4) | 1.473(7) |
| U(1)—H(41) | 2.47(6) | N(3)—C(5) | 1.491(7) |
| U(1)—H(42) | 2.40(5) | N(3)—C(6) | 1.484(7) |
| U(1)—H(51) | 2.31(5) | | |

Bond Angles (deg)

| | | | |
|---|---|---|---|
| B(1)—U(1)—B(2) | 53.2(2) | C(2)—N(1)—B(2) | 110.2(5) |
| B(3)—U(1)—B(4) | 53.0(2) | C(3)—N(2)—B(3) | 109.4(5) |
| B(1)—U(1)—B(4) | 104.0(2) | C(3)—N(2)—B(4) | 109.4(5) |
| B(1)—U(1)—B(5) | 139.1(2) | C(4)—N(2)—B(3) | 110.2(5) |
| B(2)—U(1)—B(5) | 86.2(2) | C(4)—N(2)—B(4) | 110.3(5) |
| B(3)—U(1)—B(5) | 118.3(2) | C(5)—N(3)—B(5) | 108.7(4) |
| B(4)—U(1)—B(5) | 89.8(2) | C(5)—N(3)—B(6) | 109.1(4) |
| B(1)—N(1)—B(2) | 109.2(4) | C(6)—N(3)—B(5) | 108.2(4) |
| B(3)—N(2)—B(4) | 108.4(4) | C(6)—N(3)—B(6) | 109.3(4) |
| B(5)—N(3)—B(6) | 112.7(4) | C(1)—N(1)—C(2) | 109.7(5) |
| C(1)—N(1)—B(1) | 109.0(5) | C(3)—N(2)—C(4) | 109.2(5) |
| C(1)—N(1)—B(2) | 109.0(5) | C(5)—N(3)—C(6) | 108.8(5) |
| C(2)—N(1)—B(1) | 109.7(5) | | |

[a]Symmetry transformations used to generate equivalent atoms: ' = −x, y + ½, −z + ½

TABLE 5

Selected Bond Lengths and Angles for U(H$_3$BNMe$_2$BH$_3$)$_3$(thf)[a]

Bond Lengths (Å)

| | | | |
|---|---|---|---|
| U(1)—B(1) | 2.895(3) | U(1)—O(1) | 2.549(4) |
| U(1)—B(2) | 2.901(3) | B(1)—N(1) | 1.582(5) |
| U(1)—H(1A) | 2.556(1) | B(2)—N(1) | 1.556(5) |
| U(1)—H(1B) | 2.446(1) | N(1)—C(1) | 1.484(4) |
| U(1)—H(2A) | 2.462(1) | N(1)—C(2) | 1.485(4) |
| U(1)—H(2B) | 2.547(1) | | |

TABLE 5-continued

Selected Bond Lengths and Angles for U(H$_3$BNMe$_2$BH$_3$)$_3$(thf)$^a$

Bond Angles (deg)

| | | | |
|---|---|---|---|
| H(1A)—U(1)—H(1B) | 44.0(1) | B(1)—N(1)—B(2) | 108.9(2) |
| H(2A)—U(1)—H(2B) | 44.0(1) | C(1)—N(1)—B(1) | 109.8(3) |
| B(1)—U(1)—B(2) | 52.3(1) | C(1)—N(1)—B(2) | 110.6(3) |
| B(1)—U(1)—B(1)' | 89.5(1) | C(2)—N(1)—B(1) | 109.2(3) |
| B(1)—U(1)—B(2)' | 138.3(1) | C(2)—N(1)—B(2) | 109.9(3) |
| B(2)—U(1)—B(1)' | 104.2(1) | C(1)—N(1)—C(2) | 108.4(3) |
| B(2)—U(1)—B(2)" | 115.4(1) | | |

$^a$Symmetry transformations used to generate equivalent atoms: ' = −y + 1, z, −x + 1 " = −z + 1, −x + 1, y

TABLE 6

Selected Bond Lengths and Angles for U(H$_3$BNMe$_2$BH$_3$)$_3$(PMe$_3$)$_2$

Bond Lengths (Å)

| | | | |
|---|---|---|---|
| U(1)—B(1) | 2.953(4) | B(3)—N(2) | 1.581(4) |
| U(1)—B(2) | 2.957(3) | B(4)—N(2) | 1.560(4) |
| U(1)—B(3) | 2.939(4) | B(5)—N(3) | 1.564(4) |
| U(1)—B(4) | 2.943(3) | B(6)—N(3) | 1.569(4) |
| U(1)—B(5) | 2.944(3) | N(1)—C(1) | 1.489(4) |
| U(1)—B(6) | 2.949(4) | N(1)—C(2) | 1.475(4) |
| U(1)—P(1) | 3.114(1) | N(2)—C(3) | 1.481(4) |
| U(1)—P(2) | 3.109(1) | N(2)—C(4) | 1.483(3) |
| B(1)—N(1) | 1.579(4) | N(3)—C(5) | 1.485(4) |
| B(2)—N(1) | 1.569(4) | N(3)—C(6) | 1.491(4) |

Bond Angles (deg)

| | | | |
|---|---|---|---|
| B(1)—U(1)—B(2) | 51.2(1) | P(2)—U(1)—B(5) | 86.6(1) |
| B(3)—U(1)—B(4) | 50.9(1) | P(2)—U(1)—B(6) | 88.0(1) |
| B(5)—U(1)—B(6) | 50.9(1) | B(1)—N(1)—B(2) | 108.4(2) |
| B(3)—U(1)—B(6) | 173.1(1) | B(3)—N(2)—B(4) | 107.1(2) |
| B(5)—U(1)—B(4) | 74.0(1) | B(5)—N(3)—B(6) | 107.9(2) |
| B(1)—U(1)—B(3) | 93.1(1) | C(1)—N(1)—B(1) | 108.9(3) |
| B(2)—U(1)—B(3) | 90.1(1) | C(1)—N(1)—B(2) | 110.3(3) |
| B(1)—U(1)—B(6) | 93.3(1) | C(2)—N(1)—B(1) | 110.3(2) |
| B(2)—U(1)—B(6) | 91.9(1) | C(2)—N(1)—B(2) | 110.5(3) |
| P(1)—U(1)—P(2) | 168.9(1) | C(3)—N(2)—B(3) | 110.0(3) |
| P(1)—U(1)—B(1) | 69.1(1) | C(3)—N(2)—B(4) | 110.1(3) |
| P(1)—U(1)—B(2) | 120.3(1) | C(4)—N(2)—B(3) | 110.6(2) |
| P(1)—U(1)—B(3) | 93.8(1) | C(4)—N(2)—B(4) | 110.2(2) |
| P(1)—U(1)—B(4) | 83.3(1) | C(5)—N(3)—B(5) | 110.2(2) |
| P(1)—U(1)—B(5) | 84.2(1) | C(5)—N(3)—B(6) | 110.8(3) |
| P(1)—U(1)—B(6) | 91.0(1) | C(6)—N(3)—B(5) | 110.1(2) |
| P(2)—U(1)—B(1) | 122.0(1) | C(6)—N(3)—B(6) | 110.3(2) |
| P(2)—U(1)—B(2) | 70.7(1) | C(1)—N(1)—C(2) | 108.4(3) |
| P(2)—U(1)—B(3) | 86.4(1) | C(3)—N(2)—C(4) | 108.8(2) |
| P(2)—U(1)—B(4) | 88.3(1) | C(5)—N(3)—C(6) | 107.7(3) |

TABLE 7

Selected Bond Lengths and Angles for La(H$_3$BNMe$_2$BH$_3$)$_3$(thf)$^a$

Bond Lengths (Å)

| | | | |
|---|---|---|---|
| La(1)—B(1) | 2.96(1) | La(1)—O(1) | 2.51(1) |
| La(1)—B(2) | 2.93(1) | B(1)—N(1) | 1.54(1) |
| La(1)—H(1A) | 2.683(1) | B(2)—N(1) | 1.57(1) |
| La(1)—H(1B) | 2.438(1) | N(1)—C(1) | 1.50(1) |
| La(1)—H(2A) | 2.583(1) | N(1)—C(2) | 1.46(1) |
| La(1)—H(2B) | 2.480(1) | | |

Bond Angles (deg)

| | | | |
|---|---|---|---|
| H(1A)—La(1)—H(1B) | 42.7(1) | B(1)—N(1)—B(2) | 109.9(7) |
| H(2A)—La(1)—H(2B) | 43.5(1) | C(1)—N(1)—B(1) | 111.2(8) |
| B(1)—La(1)—B(2) | 51.3(3) | C(1)—N(1)—B(2) | 110.6(8) |
| B(1)—La(1)—B(1)' | 89.1(3) | C(2)—N(1)—B(1) | 105.4(9) |
| B(1)—La(1)—B(2)' | 136.1(3) | C(2)—N(1)—B(2) | 112.1(9) |

TABLE 7-continued

Selected Bond Lengths and Angles for La(H$_3$BNMe$_2$BH$_3$)$_3$(thf)$^a$

| | | | |
|---|---|---|---|
| B(2)—La(1)—B(1)' | 106.0(3) | C(1)—N(1)—C(2) | 107.6(7) |
| B(2)—La(1)—B(2)" | 115.7(2) | | |

$^a$Symmetry transformations used to generate equivalent atoms: ' = −z + 1, −x + 1, y " = −y + 1, z, −x + 1

TABLE 8

Selected Bond Lengths and Angles for Sm(H$_3$BNMe$_2$BH$_3$)$_3$(thf)

Bond Lengths (Å)

| | | | |
|---|---|---|---|
| Sm(1)—O(1) | 2.468(2) | B(4)—N(2) | 1.569(6) |
| Sm(1)—B(1) | 2.843(4) | B(5)—N(3) | 1.555(5) |
| Sm(1)—B(2) | 2.842(4) | B(6)—N(3) | 1.574(5) |
| Sm(1)—B(3) | 2.851(4) | N(1)—C(1) | 1.485(4) |
| Sm(1)—B(4) | 2.853(4) | N(1)—C(2) | 1.475(4) |
| Sm(1)—B(5) | 2.833(4) | N(2)—C(3) | 1.474(4) |
| Sm(1)—B(6) | 2.876(4) | N(2)—C(4) | 1.471(5) |
| B(1)—N(1) | 1.558(5) | N(3)—C(5) | 1.491(4) |
| B(2)—N(1) | 1.567(5) | N(3)—C(6) | 1.483(4) |
| B(3)—N(2) | 1.583(6) | | |

Bond Angles (deg)

| | | | |
|---|---|---|---|
| B(1)—Sm(1)—B(2) | 53.0(1) | C(3)—N(2)—B(4) | 110.4(3) |
| B(3)—Sm(1)—B(4) | 53.0(1) | C(4)—N(2)—B(3) | 109.1(3) |
| B(5)—Sm(1)—B(6) | 52.9(1) | C(4)—N(2)—B(4) | 111.0(3) |
| B(1)—N(1)—B(2) | 108.4(2) | C(5)—N(3)—B(5) | 110.7(3) |
| B(3)—N(2)—B(4) | 107.6(3) | C(5)—N(3)—B(6) | 110.5(3) |
| B(5)—N(3)—B(6) | 108.6(2) | C(6)—N(3)—B(5) | 109.1(3) |
| C(1)—N(1)—B(1) | 110.5(3) | C(6)—N(3)—B(6) | 109.6(3) |
| C(1)—N(1)—B(2) | 109.8(3) | C(1)—N(1)—C(2) | 108.9(3) |
| C(2)—N(1)—B(1) | 109.9(3) | C(3)—N(2)—C(4) | 108.4(3) |
| C(2)—N(1)—B(2) | 109.4(3) | C(5)—N(3)—C(6) | 108.2(3) |
| C(3)—N(2)—B(3) | 110.3(3) | | |

TABLE 9

Selected Bond Lengths and Angles for Eu(H$_3$BNMe$_2$BH$_3$)$_3$(thf)

Bond Lengths (Å)

| | | | |
|---|---|---|---|
| Eu(1)—O(1) | 2.468(3) | B(4)—N(2) | 1.578(7) |
| Eu(1)—B(1) | 2.851(7) | B(5)—N(3) | 1.581(7) |
| Eu(1)—B(2) | 2.863(7) | B(6)—N(3) | 1.553(7) |
| Eu(1)—B(3) | 2.854(7) | N(1)—C(1) | 1.474(6) |
| Eu(1)—B(4) | 2.886(7) | N(1)—C(2) | 1.483(6) |
| Eu(1)—B(5) | 2.851(7) | N(2)—C(3) | 1.498(6) |
| Eu(1)—B(6) | 2.838(6) | N(2)—C(4) | 1.486(6) |
| B(1)—N(1) | 1.593(8) | N(3)—C(5) | 1.481(6) |
| B(2)—N(1) | 1.593(8) | N(3)—C(6) | 1.499(6) |
| B(3)—N(2) | 1.549(7) | | |

Bond Angles (deg)

| | | | |
|---|---|---|---|
| B(1)—Eu(1)—B(2) | 53.6(2) | C(3)—N(2)—B(4) | 111.3(4) |
| B(3)—Eu(1)—B(4) | 52.7(2) | C(4)—N(2)—B(3) | 108.9(4) |
| B(5)—Eu(1)—B(6) | 53.2(2) | C(4)—N(2)—B(4) | 109.0(5) |
| B(1)—N(1)—B(2) | 108.2(4) | C(5)—N(3)—B(5) | 109.9(4) |
| B(3)—N(2)—B(4) | 109.2(4) | C(5)—N(3)—B(6) | 110.5(4) |
| B(5)—N(3)—B(6) | 108.8(4) | C(6)—N(3)—B(5) | 109.7(4) |
| C(1)—N(1)—B(1) | 110.3(5) | C(6)—N(3)—B(6) | 110.0(4) |
| C(1)—N(1)—B(2) | 109.8(5) | C(1)—N(1)—C(2) | 107.7(5) |
| C(2)—N(1)—B(1) | 109.8(5) | C(3)—N(2)—C(4) | 108.4(4) |
| C(2)—N(1)—B(2) | 111.2(5) | C(5)—N(3)—C(6) | 108.0(4) |
| C(3)—N(2)—B(3) | 109.9(4) | | |

TABLE 10

Selected Bond Lengths and Angles for Er(H$_3$BNMe$_2$BH$_3$)$_3$(thf)

Bond Lengths (Å)

| | | | |
|---|---|---|---|
| Er(1)—O(1) | 2.417(3) | B(4)—N(2) | 1.586(8) |
| Er(1)—B(1) | 2.815(5) | B(5)—N(3) | 1.568(6) |
| Er(1)—B(2) | 2.786(6) | B(6)—N(3) | 1.592(6) |
| Er(1)—B(3) | 2.775(7) | N(1)—C(1) | 1.485(6) |
| Er(1)—B(4) | 2.820(6) | N(1)—C(2) | 1.494(6) |
| Er(1)—B(5) | 2.763(5) | N(2)—C(3) | 1.490(7) |
| Er(1)—B(6) | 2.856(6) | N(2)—C(4) | 1.489(6) |
| B(1)—N(1) | 1.572(7) | N(3)—C(5) | 1.489(6) |
| B(2)—N(1) | 1.577(6) | N(3)—C(6) | 1.489(6) |
| B(3)—N(2) | 1.570(8) | | |

Bond Angles (deg)

| | | | |
|---|---|---|---|
| B(1)—Er(1)—B(2) | 53.9(2) | C(3)—N(2)—B(4) | 110.8(5) |
| B(3)—Er(1)—B(4) | 53.7(2) | C(4)—N(2)—B(3) | 111.0(4) |
| B(5)—Er(1)—B(6) | 53.6(2) | C(4)—N(2)—B(4) | 109.6(4) |
| B(1)—N(1)—B(2) | 107.5(3) | C(5)—N(3)—B(5) | 110.0(4) |
| B(3)—N(2)—B(4) | 106.5(4) | C(5)—N(3)—B(6) | 110.1(4) |
| B(5)—N(3)—B(6) | 106.8(4) | C(6)—N(3)—B(5) | 110.3(4) |
| C(1)—N(1)—B(1) | 110.7(4) | C(6)—N(3)—B(6) | 111.2(4) |
| C(1)—N(1)—B(2) | 109.7(4) | C(1)—N(1)—C(2) | 108.6(4) |
| C(2)—N(1)—B(1) | 109.9(4) | C(3)—N(2)—C(4) | 108.1(4) |
| C(2)—N(1)—B(2) | 110.4(4) | C(5)—N(3)—C(6) | 108.5(4) |
| C(3)—N(2)—B(3) | 110.9(4) | | |

TABLE 11

Selected Bond Lengths and Angles for Eu$_2$(H$_3$BNMe$_2$BH$_3$)$_4$(thf)$_4$[a]

Bond Lengths (Å)

| | | | |
|---|---|---|---|
| Eu(1)—O(1) | 2.582(2) | B(2)—N(1) | 1.579(4) |
| Eu(1)—O(2) | 2.605(2) | B(3)—N(2) | 1.570(4) |
| Eu(1)—B(1) | 2.885(4) | B(4)—N(2) | 1.571(4) |
| Eu(1)—B(2) | 3.127(4) | N(1)—C(1) | 1.468(4) |
| Eu(1)—B(3) | 2.991(4) | N(1)—C(2) | 1.480(4) |
| Eu(1)—B(4) | 3.215(6) | N(2)—C(3) | 1.481(5) |
| Eu(1)'—B(4) | 2.975(4) | N(2)—C(4) | 1.484(5) |
| B(1)—N(1) | 1.582(4) | | |

Bond Angles (deg)

| | | | |
|---|---|---|---|
| O(1)—Eu(1)—O(2) | 167.9(1) | O(2)—Eu(1)—B(4) | 92.0(1) |
| B(2)—Eu(1)—B(4) | 173.8(1) | B(1)—N(1)—B(2) | 110.9(2) |
| B(1)—Eu(1)—B(4) | 132.0(1) | B(3)—N(2)—B(4) | 111.6(4) |
| B(2)—Eu(1)—B(3) | 133.9(1) | C(1)—N(1)—B(1) | 109.8(3) |
| B(1)—Eu(1)—B(2) | 51.1(1) | C(1)—N(1)—B(2) | 110.3(3) |
| B(3)—Eu(1)—B(4) | 49.3(1) | C(2)—N(1)—B(1) | 109.0(3) |
| O(1)—Eu(1)—B(1) | 96.1(1) | C(2)—N(1)—B(2) | 109.1(3) |
| O(1)—Eu(1)—B(2) | 87.4(1) | C(3)—N(2)—B(3) | 108.8(4) |
| O(1)—Eu(1)—B(3) | 96.2(1) | C(3)—N(2)—B(4) | 109.3(4) |
| O(1)—Eu(1)—B(4) | 87.0(1) | C(4)—N(2)—B(3) | 109.1(4) |
| O(2)—Eu(1)—B(1) | 93.5(1) | C(4)—N(2)—B(4) | 109.3(4) |
| O(2)—Eu(1)—B(2) | 93.1(1) | C(1)—N(1)—C(2) | 107.7(3) |
| O(2)—Eu(1)—B(3) | 92.2(1) | C(3)—N(2)—C(4) | 108.8(4) |

[a]Symmetry transformations used to generate equivalent atoms: ' = −x + 1, −y + 1, −z

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Many of the molecules disclosed herein contain one or more ionizable groups [groups from which a proton can be removed (e.g., —COON) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A composition of matter comprising a metal complex having the formula:

$$(ML_x)_z D_y \qquad (F1)$$

wherein the metal complex comprises one or more metal atoms, M, wherein each M, independent of other M, is a metal atom selected from the group consisting of: Be, Mg, Ca, Sr, Ba, Ra, Al, Ga, In, Sc, Y, La, Ti, Zr, Hf, V, Nb, Ta, Cr, Mo, W, Mn, Re, Fe, Ru, Os, Co, Rh, Ir, Ni, Pd, Pt, Cu, Ag, Au, Zn, Hg, Ce, Pr, Nd, Pm, Sm, Eu, Gd, Tb, Dy, Ho, Er, Tm, Yb, Lu, Ac, Th, Pa, U, Np, Pu, Am, and Cm;

wherein each D, independent of other D, is a neutral coordinating ligand;

wherein x is the oxidation state of M;

wherein y is 0, 1, 2, 3 or 4;

wherein z is equal to 1, 2 or 3;

wherein each L, independent of other L, is an anionic ligand, wherein at least one of L is a monoanionic group comprising a diboranamide or diboranaphosphide group having the formula;

(F2)

wherein: each X is independently N or P;

wherein, independently for each L, $R^1$ and $R^2$ are functional groups independently selected from the group consisting of hydrogen, alkyl, haloalkyl, aryl, heteroaryl, trialkylsilyl, alkenyl, alkynyl, halogen, fluoroalkyl, silylalkyl, alkoxy, hydroxyl, amide, boryl, and thiolate.

2. The composition of claim 1 wherein x is 2 and z is 1.

3. The composition of claim 2 wherein $ML_2$ has a formula selected from the group consisting of: $M((BH_3)_2NR_1R_2)_2$ and $M((BH_3)_2PR_1R_2)_2$.

4. The composition of claim 2 wherein $ML_2$ has a formula selected from the group consisting of:

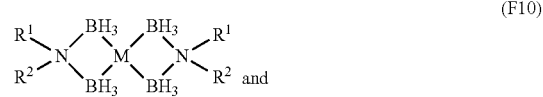

(F10)

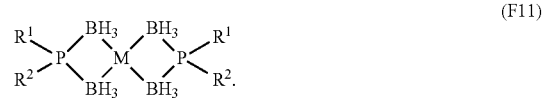

(F11)

5. The composition of claim 1 wherein M is selected from the group consisting of Be, Mg, Ca, Sr, Ra, Ti, V, Nb, Cr, Mo, Mn, Re, Fe, Eu, Yb, Sr, Ru, Os, Co, Rh, Ir, Ni, Pd, Pt, and W.

6. The composition of claim 1 wherein M is selected from the group consisting of Mg, Ti, V, Cr, Mo, and Mn.

7. The composition of claim 1 wherein $R^1$ and $R^2$ are $C_1$ to $C_{10}$ alkyl groups.

8. The composition of claim 1 wherein $R^1$ and $R^2$ are methyl groups.

9. The composition of claim 1 having a formula selected from the group consisting of: $Mg(H_3BNMe_2BH_3)_2$; $Mg(H_3BNMe_2BH_3)_2$(tetrahydrofuran); $Mg(H_3BNMe_2BH_3)_2$ (dimethoxyethane); $Ti(H_3BNMe_2BH_3)_2$; $Cr(H_3BNMe_2BH_3)_2$; $Mo(H_3BNMe_2BH_3)_2$ and; $Mn(H_3BNMe_2BH_3)_2$.

* * * * *